US010526381B2

(12) United States Patent
Roschke et al.

(10) Patent No.: US 10,526,381 B2
(45) Date of Patent: Jan. 7, 2020

(54) MULTIVALENT AND MONOVALENT MULTISPECIFIC COMPLEXES AND THEIR USES

(71) Applicant: Zyngenia, Inc., Washington, DC (US)

(72) Inventors: Viktor Roschke, Bethesda, MD (US); David Lafleur, Washington, DC (US); David M. Hilbert, Bethesda, MD (US); Peter Kiener, Potomac, MD (US)

(73) Assignee: Zygenia, Inc., Washington, DC (US)

( * ) Notice: Subject to any disclaimer, the term of this patent is extended or adjusted under 35 U.S.C. 154(b) by 0 days.

(21) Appl. No.: 15/458,079

(22) Filed: Mar. 14, 2017

(65) Prior Publication Data

US 2017/0298106 A1 Oct. 19, 2017

Related U.S. Application Data

(63) Continuation of application No. 14/481,181, filed on Sep. 9, 2014, now abandoned, which is a continuation of application No. 13/838,438, filed on Mar. 15, 2013, now abandoned, application No. 15/458,079, which is a continuation of application No. 13/838,438, filed on Mar. 15, 2013, now abandoned, which is a continuation of application No. PCT/US2012/039469, filed on May 24, 2012.

(60) Provisional application No. 61/610,831, filed on Mar. 14, 2012, provisional application No. 61/597,714, filed on Feb. 10, 2012, provisional application No. 61/489,249, filed on May 24, 2011.

(51) Int. Cl.
| | |
|---|---|
| *C07K 16/46* | (2006.01) |
| *C07K 16/24* | (2006.01) |
| *A61K 39/395* | (2006.01) |
| *A61K 45/06* | (2006.01) |
| *C07K 7/08* | (2006.01) |
| *A61K 39/00* | (2006.01) |
| *C07K 14/47* | (2006.01) |
| *C07K 16/28* | (2006.01) |
| *C07K 16/22* | (2006.01) |
| *C07K 16/32* | (2006.01) |
| *C07K 16/40* | (2006.01) |
| *C07K 14/00* | (2006.01) |

(52) U.S. Cl.
CPC .......... *C07K 14/47* (2013.01); *A61K 39/3955* (2013.01); *A61K 45/06* (2013.01); *C07K 14/00* (2013.01); *C07K 16/22* (2013.01); *C07K 16/24* (2013.01); *C07K 16/241* (2013.01); *C07K 16/2803* (2013.01); *C07K 16/2809* (2013.01); *C07K 16/2839* (2013.01); *C07K 16/2848* (2013.01); *C07K 16/2863* (2013.01); *C07K 16/32* (2013.01); *C07K 16/40* (2013.01); *C07K 16/468* (2013.01); *A61K 2039/505* (2013.01); *C07K 7/08* (2013.01); *C07K 2317/21* (2013.01); *C07K 2317/24* (2013.01); *C07K 2317/31* (2013.01); *C07K 2317/60* (2013.01); *C07K 2317/73* (2013.01); *C07K 2317/732* (2013.01); *C07K 2317/76* (2013.01); *C07K 2317/90* (2013.01); *C07K 2319/01* (2013.01); *C07K 2319/30* (2013.01); *C07K 2319/33* (2013.01); *C07K 2319/35* (2013.01); *C07K 2319/40* (2013.01); *C07K 2319/70* (2013.01); *C07K 2319/74* (2013.01)

(58) Field of Classification Search
None
See application file for complete search history.

(56) References Cited

U.S. PATENT DOCUMENTS

| | | |
|---|---|---|
| 4,599,304 A | 7/1986 | Lanier et al. |
| 5,141,736 A | 8/1992 | Iwasa et al. |
| 5,196,193 A | 3/1993 | Carroll |
| 5,637,481 A | 6/1997 | Ledbetter et al. |
| 5,677,171 A | 10/1997 | Hudziak et al. |
| 5,720,954 A | 2/1998 | Huclziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,821,337 A | 10/1998 | Carter et al. |
| 5,844,094 A | 12/1998 | Hudson et al. |
| 5,977,322 A | 2/1999 | Marks et al. |
| 5,877,289 A | 3/1999 | Thorpe et al. |
| 6,054,561 A | 4/2000 | Ring |
| 6,103,889 A | 8/2000 | Whitlow et al. |
| 6,132,992 A | 10/2000 | Ledbetter et al. |
| 6,165,464 A | 12/2000 | Hudziak et al. |
| 6,166,185 A | 12/2000 | Davis et al. |

(Continued)

FOREIGN PATENT DOCUMENTS

| | | |
|---|---|---|
| EP | 1 591 527 A1 | 11/2005 |
| EP | 1 600 459 A2 | 11/2005 |

(Continued)

OTHER PUBLICATIONS

Unpublished U.S. Appl. No. 15/589,585, inventors Roschke et al., filed on May 8, 2017 (Not Published).

(Continued)

*Primary Examiner* — Marianne P Allen

(74) *Attorney, Agent, or Firm* — Sterne, Kessler, Goldstein & Fox P.L.L.C.

(57) ABSTRACT

Compositions containing multivalent and monovalent multispecific complexes having scaffolds such as antibodies that support such binding functionalities are described. The use of and methods of compositions containing multivalent and monovalent multispecific complexes having scaffolds, such as antibodies, that support such binding functionalities are also described.

20 Claims, 27 Drawing Sheets

Specification includes a Sequence Listing.

(56) References Cited

U.S. PATENT DOCUMENTS

| | | |
|---|---|---|
| 6,194,177 B1 | 2/2001 | Campbell et al. |
| 6,235,883 B1 | 5/2001 | Jakobovits et al. |
| 6,267,958 B1 | 7/2001 | Andya et al. |
| 6,268,488 B1 | 7/2001 | Barbas, III et al. |
| 6,339,142 B1 | 1/2002 | Basey et al. |
| 6,387,371 B1 | 5/2002 | Hudziak et al. |
| 6,399,063 B1 | 6/2002 | Hudziak et al. |
| 6,413,932 B1 | 7/2002 | Cerretti et al. |
| 6,417,168 B1 | 7/2002 | Greene et al. |
| 6,458,356 B1 | 10/2002 | Arakawa et al. |
| 6,512,096 B2 | 1/2003 | Weiner et al. |
| 6,515,110 B1 | 2/2003 | Filpula et al. |
| 6,521,424 B2 | 2/2003 | Cerretti et al. |
| 6,627,196 B1 | 9/2003 | Baughman et al. |
| 6,660,843 B1 | 12/2003 | Feige |
| 6,719,971 B1 | 4/2004 | Carter et al. |
| 6,800,738 B1 | 10/2004 | Carter et al. |
| 6,818,213 B1 | 11/2004 | Thorpe et al. |
| 6,821,515 B1 | 11/2004 | Cleland et al. |
| 6,884,879 B1 | 4/2005 | Baca et al. |
| 7,063,840 B2 | 6/2006 | Davis et al. |
| 7,067,475 B2 | 6/2006 | Cerretti et al. |
| 7,074,404 B2 | 7/2006 | Basey et al. |
| 7,101,580 B2 | 9/2006 | Metzger |
| 7,112,317 B2 | 9/2006 | Thorpe et al. |
| 7,125,541 B2 | 10/2006 | Thorpe et al. |
| 7,138,370 B2 | 11/2006 | Oliner et al. |
| 7,148,321 B2 | 12/2006 | Gillies |
| 7,183,076 B2 | 2/2007 | Arathoon et al. |
| 7,189,830 B2 | 3/2007 | Gillies et al. |
| 7,205,275 B2 | 4/2007 | Oliner et al. |
| 7,211,252 B2 | 5/2007 | Mundy et a |
| 7,226,592 B2 | 6/2007 | Kreysch |
| 7,365,054 B2 | 4/2008 | Lode et al. |
| 7,371,379 B2 | 5/2008 | Baughman et al. |
| 7,449,184 B2 | 11/2008 | Allison et al. |
| 7,456,016 B2 | 11/2008 | Young et al. |
| 7,462,352 B2 | 12/2008 | Hansen et al. |
| 7,485,302 B2 | 2/2009 | Adams et al. |
| 7,521,053 B2 | 4/2009 | Oliner |
| 7,537,931 B2 | 5/2009 | Adams et al. |
| 7,541,440 B2 | 6/2009 | Goldenberg et al. |
| 7,612,181 B2 | 11/2009 | Wu et al. |
| 7,625,558 B2 | 12/2009 | Greene et al. |
| 7,638,124 B2 | 12/2009 | Reiter |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,666,832 B2 | 2/2010 | Oliner et al. |
| 7,666,839 B2 | 2/2010 | Oliner et al. |
| 7,682,609 B2 | 3/2010 | Andya et al. |
| 7,723,499 B2 | 5/2010 | Oliner et al. |
| 7,736,652 B2 | 6/2010 | Penichet et al. |
| 7,741,446 B2 | 6/2010 | Pardridge et al. |
| 7,749,501 B2 | 7/2010 | Gelfand |
| 7,750,127 B2 | 7/2010 | Gegg et al. |
| 7,750,128 B2 | 7/2010 | Gegg et al. |
| 7,786,267 B2 | 8/2010 | Zurawski et al. |
| 7,790,674 B2 | 9/2010 | Oliner et al. |
| 7,862,817 B2 | 1/2011 | Adams et al. |
| 7,951,369 B2 | 5/2011 | Goldenberg et al. |
| 7,973,140 B2 | 7/2011 | Green et al. |
| 7,981,418 B2 | 7/2011 | Amler et al. |
| 7,993,834 B2 | 8/2011 | Mass |
| 8,008,453 B2 | 8/2011 | Gegg et al. |
| 8,454,960 B2 | 6/2013 | Barbas, III |
| 8,557,242 B2 | 10/2013 | Barbas, III |
| 8,557,243 B2 | 10/2013 | Barbas, III |
| 9,676,833 B2 | 6/2017 | Roschke et al. |
| 10,150,800 B2 | 12/2018 | Roschke et al. |
| 2003/0130496 A1 | 7/2003 | Winter et al. |
| 2003/0171551 A1 | 9/2003 | Rosenblatt |
| 2003/0229023 A1 | 12/2003 | Oliner et al. |
| 2003/0236193 A1 | 12/2003 | Oliner et al. |
| 2004/0001827 A1 | 1/2004 | Dennis |
| 2004/0052785 A1 | 3/2004 | Goodman et al. |
| 2004/0057969 A1 | 3/2004 | Smith et al. |
| 2004/0106161 A1 | 6/2004 | Bossenmaier et al. |
| 2005/0136044 A1 | 6/2005 | Watkins et al. |
| 2005/0287153 A1 | 12/2005 | Dennis |
| 2006/0106203 A1 | 5/2006 | Winter et al. |
| 2006/0128944 A1 | 6/2006 | Botti et al. |
| 2006/0140936 A1 | 6/2006 | Goodman et al. |
| 2006/0222653 A1 | 10/2006 | Abel et al. |
| 2006/0269540 A1 | 11/2006 | Robert et al. |
| 2007/0031402 A1 | 2/2007 | Zhang et al. |
| 2007/0080998 A1 | 4/2007 | Morgan et al. |
| 2007/0166753 A1 | 7/2007 | Mass |
| 2007/0202041 A1 | 8/2007 | Young et al. |
| 2007/0248994 A1 | 10/2007 | Su |
| 2007/0254316 A1 | 11/2007 | Rodriguez et al. |
| 2008/0233130 A1 | 9/2008 | Tomlinson et al. |
| 2008/0241145 A1 | 10/2008 | Goldenberg et al. |
| 2008/0299120 A1 | 12/2008 | Miller et al. |
| 2009/0054323 A1 | 2/2009 | Oliner et al. |
| 2009/0087432 A1 | 4/2009 | Sliwkowski |
| 2009/0148905 A1 | 6/2009 | Ashman et al. |
| 2009/0162359 A1 | 6/2009 | Klein et al. |
| 2009/0181022 A1 | 7/2009 | Nielsen et al. |
| 2009/0191212 A1 | 7/2009 | Oliner et al. |
| 2009/0226447 A1 | 9/2009 | Boone et al. |
| 2009/0226466 A1 | 9/2009 | Fong et al. |
| 2009/0246206 A1 | 10/2009 | Nielsen et al. |
| 2009/0298195 A1 | 12/2009 | Rüker et al. |
| 2009/0304694 A1 | 12/2009 | Oliner et al. |
| 2010/0016556 A1 | 1/2010 | Carter et al. |
| 2010/0021379 A1 | 1/2010 | Lam et al. |
| 2010/0021473 A1 | 1/2010 | De Angelis et al. |
| 2010/0047239 A1 | 2/2010 | Wu et al. |
| 2010/0048877 A1 | 2/2010 | Ruker et al. |
| 2010/0056439 A1 | 3/2010 | Roland et al. |
| 2010/0104588 A1 | 4/2010 | Dennis |
| 2010/0111967 A1 | 5/2010 | Baehner et al. |
| 2010/0158926 A1 | 6/2010 | Cartilage et al. |
| 2010/0159587 A1 | 6/2010 | Brinkmann et al. |
| 2010/0166695 A1 | 7/2010 | Bundle et al. |
| 2010/0166746 A1 | 7/2010 | Chowdhury et al. |
| 2010/0178298 A1 | 7/2010 | Lindhofer |
| 2010/0233173 A1 | 9/2010 | Wu et al. |
| 2010/0286060 A1 | 11/2010 | Oliner et al. |
| 2010/0297103 A1 | 11/2010 | Murakami |
| 2010/0322934 A1 | 12/2010 | Imhof-Jung et al. |
| 2010/0330115 A1 | 12/2010 | Zurawski et al. |
| 2011/0020332 A1 | 1/2011 | Greene et al. |
| 2011/0027286 A1 | 2/2011 | Thurston et al. |
| 2011/0044998 A1 | 2/2011 | Bedian et al. |
| 2011/0046355 A1 | 2/2011 | Himmler et al. |
| 2011/0076723 A1 | 3/2011 | Min et al. |
| 2011/0097300 A1 | 4/2011 | Van Slyke et al. |
| 2011/0097321 A1 | 4/2011 | Blakey et al. |
| 2011/0110851 A1 | 5/2011 | Chang et al. |
| 2011/0129464 A1 | 6/2011 | Adams et al. |
| 2011/0150895 A1 | 6/2011 | Ryu et al. |
| 2011/0158978 A1 | 6/2011 | Kirchner et al. |
| 2011/0189206 A1 | 8/2011 | Barbas, III |
| 2012/0020966 A1 | 1/2012 | Barbas, III |
| 2012/0020967 A1 | 1/2012 | Barbas, III |
| 2012/0034211 A1 | 2/2012 | Barbas, III |
| 2012/0058114 A1 | 3/2012 | Barbas, III |
| 2012/0100166 A1 | 4/2012 | Roschke et al. |
| 2013/0303733 A1 | 11/2013 | Barbas |
| 2014/0065142 A1 | 3/2014 | Roschke et al. |
| 2014/0127200 A1 | 5/2014 | Barbas, III |
| 2015/0210765 A1 | 7/2015 | Roschke et al. |
| 2016/0046678 A1 | 2/2016 | Roschke et al. |
| 2016/0159863 A1 | 6/2016 | Barbas, III |
| 2017/0298106 A1 | 10/2017 | Roschke |

FOREIGN PATENT DOCUMENTS

| | | |
|---|---|---|
| EP | 1 517 921 B1 | 6/2006 |
| EP | 1 752 471 B9 | 11/2008 |
| EP | 2 070 944 A1 | 6/2009 |

(56) References Cited

FOREIGN PATENT DOCUMENTS

| | | |
|---|---|---|
| EP | 1 189 641 B1 | 7/2009 |
| EP | 1 210 115 B1 | 8/2009 |
| EP | 1 434 791 B1 | 10/2009 |
| EP | 2 110 138 A1 | 10/2009 |
| EP | 2 116 262 A2 | 11/2009 |
| EP | 2 272 869 A2 | 1/2011 |
| EP | 2 275 119 A1 | 1/2011 |
| EP | 2 284 194 A1 | 2/2011 |
| EP | 2 311 849 A1 | 4/2011 |
| EP | 2 316 845 A1 | 5/2011 |
| EP | 2 336 180 A1 | 6/2011 |
| JP | 2003-531588 | 10/2003 |
| JP | 2004-525630 | 8/2004 |
| JP | 2005-520853 | 8/2004 |
| JP | 2005/520853 A | 7/2005 |
| WO | WO 95/24220 A1 | 9/1995 |
| WO | WO 96/11269 A2 | 4/1996 |
| WO | WO 96/040210 A1 | 12/1996 |
| WO | WO 97/20858 A1 | 6/1997 |
| WO | WO 98/50431 A2 | 11/1998 |
| WO | WO 01/077342 A1 | 3/2001 |
| WO | WO 01/81377 A2 | 11/2001 |
| WO | WO 02/072605 A2 | 3/2002 |
| WO | WO 03/016330 A2 | 2/2003 |
| WO | WO 03/080106 A1 | 3/2003 |
| WO | WO 03/027246 A2 | 4/2003 |
| WO | WO 2004/032857 A2 | 4/2004 |
| WO | WO 2004/032961 A1 | 4/2004 |
| WO | WO 2004/092215 A2 | 10/2004 |
| WO | WO 2005/023859 A1 | 3/2005 |
| WO | WO 2005/070966 A2 | 8/2005 |
| WO | WO 2005/090407 A1 | 9/2005 |
| WO | WO 2005/117973 A2 | 12/2005 |
| WO | WO 2006/020706 A2 | 2/2006 |
| WO | WO 2006/036834 A2 | 6/2006 |
| WO | WO 2006/063150 A2 | 6/2006 |
| WO | WO 2006/078307 A1 | 7/2006 |
| WO | WO 2006/091209 A2 | 8/2006 |
| WO | WO 2007/001457 A2 | 1/2007 |
| WO | WO 2007/016185 A2 | 2/2007 |
| WO | WO 2007/019232 A2 | 2/2007 |
| WO | WO 2007/024715 A2 | 3/2007 |
| WO | WO 2007/060192 A1 | 5/2007 |
| WO | WO 2007/065635 A1 | 6/2007 |
| WO | WO 2007/066109 A1 | 6/2007 |
| WO | WO 2007/068895 A1 | 6/2007 |
| WO | WO 2007/075270 A2 | 7/2007 |
| WO | WO 2007/084181 A2 | 7/2007 |
| WO | WO 2007/136892 A2 | 11/2007 |
| WO | WO 2008/003103 A2 | 1/2008 |
| WO | WO 2008/019290 A2 | 2/2008 |
| WO | WO 2008/088658 A2 | 7/2008 |
| WO | WO 2008/116293 A1 | 10/2008 |
| WO | WO 2008/114029 A1 | 11/2008 |
| WO | WO 2008/132568 A2 | 11/2008 |
| WO | WO 2009/088805 A2 | 7/2009 |
| WO | WO 2009/097325 A1 | 8/2009 |
| WO | WO 2009/105269 A1 | 8/2009 |
| WO | WO 2009/132876 A1 | 11/2009 |
| WO | WO 2009/158432 A2 | 12/2009 |
| WO | WO 2010/010551 A2 | 1/2010 |
| WO | WO 2010/040508 A1 | 4/2010 |
| WO | WO 2010/066836 A2 | 6/2010 |
| WO | WO 2010/108153 A2 | 9/2010 |
| WO | WO 2011/014469 A1 | 2/2011 |
| WO | WO 2012/009705 A1 | 1/2012 |
| WO | WO 2012/109624 A2 | 8/2012 |
| WO | WO 2012/162561 A2 | 11/2012 |

OTHER PUBLICATIONS

Muller et al., "Targeting of Tumor Blood Vessels: A Phage-Displayed Tumor-Homing Peptide Specifically Binds to Matrix Metalloproteinase-2-Processed Collagen IV and Blocks Angiogenesis In Vivo," *Mol Canc Res.* 7(7)1078-1085, American Association for Cancer Research, United States (2009).

El-Gazzar et al., "Effects on Tumor Development and Metastatic Dissemination by the NKG2D Lymphocyte Receptor Expressed on Cancer Cells," *Oncogene* 33(41):4932-4940, Nature Publishing Group, England (2014).

Abraham, S., et al., "Synthesis of the next-generation therapeutic antibodies that combine cell targeting and antibody-catalyzed prodrug activation," PNAS USA 104(13):5584-5589, National Academy of Sciences, United States (2007).

Asano, R., et al., "Highly Effective Recombinant Format of a Humanized IgG-like Bispecific Antibody for Cancer Immunotherapy with Retargeting of Lymphocytes to Tumor Cells," *JBC* 282(38):27659-27665, The American Society for Biochemistry and Molecular Biology, Inc., United States (2007).

Bhagwat, S.S., "Kinase inhibitors for the treatment of inflammatory and autoimmune disorders," *Purinergic Signalling* 5(1):107-115, Springer, Netherlands (2009).

Connor, J.P., et al., "Ex vivo evaluation, of anti-EpCAM immunocytokine huKS-IL2 in ovarian cancer," *J. Immunother.* 27(3):211-219, Lippincott Williams & Wilkins, United States (2004).

Corte-Real, S., et al., "Intrabodies targeting the Kaposi sarcoma-associated herpesvirus latency antigen inhibit persistence in lymphoma cells," *Blood* 106:3797-3802, American Society of Hematology, United States (2005).

Dela Cruz, J.S., et al, "Recombinant Anti-Human HER2/neu IgG3-(GM-CSF) Fusion Protein Retains Antigen Specificity and Cytokine Function and Demonstates Antitumor Activity," *J. Immunol.* 165:5112-5121, The American Association of Immunologists, United States (2000).

Dennis, M.S., et al., "Albumin Binding as a General Strategy for Improving the Pharmacokinetics of Proteins," *JBC* 277(33):35035-35043, The American Society for Biochemistry and Molecular Biology, Inc., United States (2002).

Doppalapudi et al., "Chemically programmed antibodies: Endothelin receptor targeting CovX-Bodies(TM)," *Bioorganic & Medicinal Chemistry Letters* 17(2):501-506, Pergamon, Elsevier Science, Great Britain (2007).

Grzesik, W.J., et al., "Synthetic integrin-binding peptides promote adhesion and proliferation of human periodontal ligament cells in vitro," *J. Dent. Res.* 77(8):1606-1612, International & American Associations for Dental Research, United States (1998).

Helguera, G., et al., "Vaccination with novel combinations of anti-HER2/neu cytokines fusion proteins and soluble protein antigen elicits a protective immune response against HER2/neu expressing tumors," *Vaccine* 24:304-316, Elsevier Ltd., England (2005).

Huang, H., et al., "Angiopoietin-2 antagonistic CovX-BodyTM inhibits tumor growth and reduces microvessel density," *Proceedings Of The Annual Meeting Of The American Association For Cancer Research* 48:509, American Association For Cancer Research, United States (2007).

International Preliminary Report on Patentability, including the Written Opinion of the International Searching Authority, for International Application No. PCT/US2012/039469, The International Bureau of WIPO, Geneva, Switzerland, dated Nov. 26, 2013, 7 pages.

International Search Report for International Application No. PCT/US2012/039469, European Patent Office, Rijswijk, Netherlands, dated Jan. 15, 2013, 5 pages.

Kutty, G., et al., "Identification of a new member of transforming growth factor-beta superfamilt in *Drosophila*: the first invertebrate activin gene," *Biochem. Biophys. Res. Commun.* 246(3):644-649, Elsevier B.V., Netherlands (1998).

Landon, L.A. and Deutsher, S.L., "Combinatorial discovery of tumor targeting peptides using phage display," *J. Cell. Biochem.* 90(3):509-517, Wiley-Liss, United States (2003).

Li, L-S., et al., "Chemical Adaptor Immunotherapy: Design, Synthesis, and Evaluation of Novel Integrin-Targeting Devices," *J. Med. Chem.* 47:5630-5640, American Chemical Society, United States (2004).

(56) References Cited

OTHER PUBLICATIONS

Luettich, K. and Schmidt, C., "TGFβ$_1$ activates c-Jun and Erk1 cia α$_v$β$_6$ integrin," *Molecular Cancer* 2:33, BioMed Central, England, 10 pages (2003).

Niu, G. and Carter, B.W., "Human Epidermal Growth Factor Receptor 2 Regulates Angiopoietin-2 Expression in Breast Cancer via AKT and Mitogen-Activated Protein Kinase Pathways," *Cancer Res.* 67:1487-1493, American Association for Cancer Research, United States (2007).

Riemer, A.B., et al., "Matching of trastuzumab (Herceptin®) epitope mimics onto the surface of Her-2/neu—a new method of epitope definition," *Mol. Immunol.* 42(9):1121-1124, Elsevier B.V., Netherlands (2005).

Ruoslahti, E., "Integrins," *J. Clin. Invest.* 87:1-5, The American Society for Clinical Investigation, Inc., United States (1991).

Schraa, A.J., et al., "RGD-modified anti-CD3 antibodies redirect cytolytic capacity of cytotoxic T lymphocytes toward α$_v$β$_3$-expressing endothelial cells," *Int. J. Cancer* 112(2):279-285, Wiley-Liss, Inc., United States (2004).

Serini, G., et al., "Integrins and angiogenesis: A sticky business," *Exp. Cell Res.* 312(5):651-658, Academic Press, United States (2006).

Sinha, S.C., et al., "Preparation of integrin α(v)β(3)-targeting Ab 38C2 constructs," *Nature Protocols* 2(2):449-456, Nature Publishing Group, England (2007).

Stancovski, I., et al., "Mechanistic aspects of the opposing effects of monoclonal antibodies to the ERBB2 receptor on tumor growth," *Proc. Natl. Acad. Sci. USA* 88:8691-8695, United States National Academy of Sciences, United States (1991).

Taipale, J. and Keski-Oja, J., "Growth factors in the extracellular matrix," *The FASEB Journal* 11:51-59, Federation of American Societies For Experimental Biology, United States (1997).

Yu, L., et al., "Interaction between Bevavizumab and Murine VEGF-A: A Reassessment," *Invest Ophthalmol Vis Sci.* 49(2):522-527, Association for Research in Vision and Ophthalmology, United States (2008).

Zhang, J., et al., "Targeting cancer with small molecule kinase inhibitors," *Nature Reviews Cancer* 9(1):28-39, Nature Publishing Group, England (2009).

Rudikoff, S., et al, "Single amino acid substitution altering antigen-binding specificity," Proc. Nat. Acad. Sci. 79:1979-1983, National Academy of Sciences, United States (1982).

Kanakaraj, P., et al., "Simultaneous targeting of TNF and Ang2 with a novel bispecific antibody enhances efficacy in an in vivo model of arthritis," mAbs 4:5, 600-613, United States (Sep./Oct. 2012).

Lafleur, D.W., et al., "Monoclonal antibody therapeutics with up to five specificities: functional enhancement through fusion of target-specific peptides," MAbs 5(2): 208-18, United States (2013).

Pan, B., et al., "Solution structure of a phage-derived peptide antagonist in complex with vascular endothelial growth factor," J Mol Biol 16(3):769-87, Elsevier, Netherlands (2002).

Jubala, C., et al., "CD20 expression in normal canine B cells and in canine non-Hodgkin lymphoma," Vet Pathol. 42(4):468-76, SAGE Publications, United States (2005).

Golay, J., et al., "Mechanism of action of therapeutic monoclonal antibodies: promises and pitfalls of in vitro and in vivo assays," Archives of Biochemistry and Biophysics 562(2):146-153, Elsevier, Netherlands (Feb. 2012).

Colman, P., et al., "Effects of amino acid sequence changes on antibody-antigen interactions," Res Immunol. 145(1):33-6, Elsevier, Netherlands (1994).

Dufner, P., et al., "Harnessing phage and ribosome display for antibody optimization," Trends Biotechnol. 24(11):523-9, Cell Press, United States (2006).

Humira (Adalimumab), Highlights of Prescribing Information and Full Prescribing Information, Revised: Jan. 2019, https://www.rxabbvie.com/pdf/humira.pdf.

Simponi (Golimumab), Highlights of Prescribing Information and Full Prescribing Information, Revised: Dec. 2011, https://www.accessdata.fda.gov/drugsatfda_docs/label/2011/125289s00641b1.pdf.

Remicade (Infliximab), Highlights of Prescribing Information and Full Prescribing Information, Revised: Nov. 2013, https://www.accessdata.fda.gov/drugsatfda_docs/label/2013/103772s53591b1.pdf.

FIG. 17B

| Protein | Clone ID | MRD Sequence | EC50, nM | SEQ ID NO. |
|---|---|---|---|---|
| L1-7D MDD | ZC12 | PGKGGGSMGAQTNFMPM*MDD*DEQRLYEQFILQQGLE | 0.153 | 114 |
| L1-7D MQD | 1A12 | PGKGGGSMGAQTNFMPM*Q*DDEQRLYEQFILQQGLE | >100 | 115 |
| L1-7D MVD | 2A1 | PGKGGGSMGAQTNFMPM*V*DDEQRLYEQFILQQGLE | >100 | 116 |
| L1-7D MHD | 3C3 | PGKGGGSMGAQTNFMPM*H*DDEQRLYEQFILQQGLE | 17.00 | 117 |
| L1-7D MND | 4H4 | PGKGGGSMGAQTNFMPM*N*DDEQRLYEQFILQQGLE | 0.411 | 118 |
| L1-7D MKD | 5A8 | PGKGGGSMGAQTNFMPM*K*DDEQRLYEQFILQQGLE | >100 | 119 |
| L1-7D MAD | 6A3 | PGKGGGSMGAQTNFMPM*A*DDEQRLYEQFILQQGLE | >100 | 120 |
| L1-7D MSD | 7B2 | PGKGGGSMGAQTNFMPM*S*DDEQRLYEQFILQQGLE | 1.380 | 121 |
| L1-7D MRD | 8B12 | PGKGGGSMGAQTNFMPM*R*DDEQRLYEQFILQQGLE | >100 | 122 |
| L1-7D MGD | 9C7 | PGKGGGSMGAQTNFMPM*G*DDEQRLYEQFILQQGLE | 0.600 | 123 |
| L1-7D MTD | 10B12 | PGKGGGSMGAQTNFMPM*T*DDEQRLYEQFILQQGLE | 7.340 | 124 |
| L1-7D MYD | 11B10 | PGKGGGSMGAQTNFMPM*Y*DDEQRLYEQFILQQGLE | >100 | 125 |
| L1-7D MPD | 12C12 | PGKGGGSMGAQTNFMPM*P*DDEQRLYEQFILQQGLE | >100 | 126 |
| L1-7D MID | 13D5 | PGKGGGSMGAQTNFMPM*I*DDEQRLYEQFILQQGLE | >100 | 127 |
| L1-7D MFD | 14F11 | PGKGGGSMGAQTNFMPM*F*DDEQRLYEQFILQQGLE | >100 | 128 |
| L1-7D MWD | 15G12 | PGKGGGSMGAQTNFMPM*W*DDEQRLYEQFILQQGLE | >100 | 129 |
| L1-7D MLD | 16E5 | PGKGGGSMGAQTNFMPM*L*DDEQRLYEQFILQQGLE | >100 | 130 |
| L1-7D MED | 17F9 | PGKGGGSMGAQTNFMPM*E*DDEQRLYEQFILQQGLE | >100 | 131 |
| L1-7D MMD | 18E3 | PGKGGGSMGAQTNFMPM*M*DDEQRLYEQFILQQGLE | >100 | 132 |
| L1-7D MFD* | 14G4* | PGKGGGSMGAQTNFMPM*F*DDEQRLY*D*QFILQQGLE | >100 | 133 |
| Lm32 KtoS | ZC10 | PGSGGGSMGAQTNFMPMDNDELLLYEQFILQQGLE | 0.199 | 134 |
| Lm32 2X | ZC39 | PGKGGGSMGAQTNFMPMDNDELLLYEQFILQQGLEGGGSMGAQTNFMPMDNDELLLYEQFILQQGLE | 0.005 | 135 |

FIG. 17C

HER-lm32 (H)
+ FITC mouse anti-human Ig kappa

HER-lm32 (L)
+ FITC mouse anti-human Ig kappa

Ang-2-biotin/
Streptavidin-PE

Ang-2-biotin/
Streptavidin-PE + 10X Herceptin

Ang-2-biotin/
Streptavidin-PE

Ang-2-biotin/
Streptavidin-PE + 10X Herceptin

MULTIVALENT AND MONOVALENT MULTISPECIFIC COMPLEXES AND THEIR USES

REFERENCE TO RELATED APPLICATIONS

Related applications U.S. Ser. No. 14/481,181, filed Sep. 9, 2014, U.S. Ser. No. 13/838,438, filed Mar. 15, 2013, U.S. Ser. No. 61/489,249, filed May 24, 2011, U.S. Ser. No. 61/597,714, filed Feb. 10, 2012, U.S. Ser. No. 61/610,831, filed Mar. 14, 2102, and International Application No. PCT/US2012/039469, filed May 24, 2012 are herein incorporated by reference in their entireties.

REFERENCE TO A SEQUENCE LISTING SUBMITTED ELECTRONICALLY VIA EFS-WEB

The content of the electronically submitted sequence listing (Name: 2940_0230006_SeqListing.txt, Size: 52,860 bytes; and Date of Creation: Mar. 13, 2017) is herein incorporated by reference in its entirety.

BACKGROUND OF THE INVENTION

Field of the Invention

This invention relates generally to compositions containing multivalent multispecific complexes and to compositions containing multivalent and monovalent multispecific complexes having scaffolds, such as antibodies, that support such binding functionalities. The invention also generally relates to methods of making these multispecific compositions and the diagnostic and therapeutic uses of these compositions.

Background

In recent years, drug discovery efforts have primarily focused on identifying agents that modulate preselected individual targets. However, agents directed to individual targets frequently show limited efficacies and poor safety and resistance profiles, as a result of the robustness, redundancy, crosstalk, compensatory signaling networks and anti- or counter-signaling network activities associated with the therapeutic target. Consequently, drug discovery efforts have increasingly been directed toward the discovery of new multicomponent based therapies.

The development of bispecific or multi-specific molecules that target two or more targets simultaneously offers a novel and promising solution for discovering new systems-oriented multitargeted agents demonstrating improved efficacy and pharmacological properties over conventional monotherapies. Numerous attempts to develop multispecific molecules have been based on immunoglobulin-like domains or subdomains. For example, traditionally, bispecific antibodies have been prepared by chemically linking two different monoclonal antibodies or by fusing two hybridoma cell lines to produce a hybrid-hybridoma. Other immunoglobulin-like domain-based technologies that have created multispecific, and/or multivalent molecules include dAbs, diabodies, TandAbs, nanobodies, BiTEs, SMIPs, DNLs, Affibodies, Fynomers, Kunitz Domains, Albu-dabs, DARTs, DVD-IG, Covx-bodies, peptibodies, scFv-Igs, SVD-Igs, dAb-Igs, Knobs-in-Holes, DuoBodies™ and triomAbs. Although each of these molecules may bind one or more targets, they each present challenges with respect to retention of typical Ig function (e.g., half-life, effector function), production (e.g., yield, purity), valency, simultaneous target recognition, and bioavailability.

Other attempts to generate multispecific and multivalent molecules have relied on alternative scaffolds, based VASP polypeptides, Avian pancreatic polypeptide (aPP), Tetranectin (based on CTLD3), Affilin (based on γB-crystallin/ubiquitin), knottins, SH3 domains, PDZ domains, Tendamistat, Transferrin, an ankyrin consensus repeat domain (e.g., DARPins), lipocalin protein folds (e.g., Duocalins), fibronectin (see for example, US Application Publ. Nos. 2003/0170753 and 20090155275 which are herein incorporated by reference), a domain of protein A (e.g., Affibodies), thioredoxin. Other attempts have relied on alternative scaffolds fuse or associate polypeptides of interest with albumin (e.g., ALBUdAb (Domantis/GSK) and ALB-Kunitz (Dyax)), unstructured repeat sequences of 3 or 6 amino acids (e.g., PASylation® technology and XTEN® technology), and sequences containing elastin-like repeat domains (see for example, U.S. Pat. Appl. No. 61/442,106, which is herein incorporated by reference). To date, these technologies have demonstrated limited clinical potential as robust platforms for developing diverse multispecific and multivalent therapeutic compositions.

The genetic complexity of most human malignancies and other disorders strongly suggest that interfering with a single target or pathway associated with these disorders is unlikely to produce optimal or sustained therapeutic benefit. There is, therefore, a great need for developing multispecific and multivalent therapeutics such as multispecific antibodies that are capable of interfering with the activity of multiple targets and/or signaling mechanisms in or to optimize the therapeutic benefits of treatments directed towards these disorders.

BRIEF SUMMARY OF THE INVENTION

The invention relates to compositions containing multivalent as well as multivalent and monovalent, multispecific complexes having scaffolds, such as antibodies, that support such binding functionalities. The invention is based in part on the surprising discovery that multispecific and multivalent binding compositions, such as those generated using the ZYBODY™ platform (Zyngenia, Inc.; see, e.g., Intl. Pub. No. WO 2009/088805 which is herein incorporated by reference) demonstrate dramatic synergistic biological activity compared to conventional monotherapy combinations. This synergistic activity is expected to extend to novel therapies, for treating or preventing cancer, diseases or disorders of the immune system (e.g., autoimmune diseases such as, rheumatoid arthritis, and IBD), skeletal system (e.g., osteoporosis), cardiovascular system (e.g., stroke, heart disease), nervous system (e.g., Alzheimer's), infectious disease (e.g., HIV), and other diseases or disorders described herein or otherwise known in the art.

In one embodiment, the invention is directed to treating a disease or disorder by administering a therapeutically effective amount of a multivalent and monovalent multispecific composition to a patient in need thereof. In a further embodiment, the invention is directed to treating a disease or disorder by administering a therapeutically effective amount of a multivalent and multispecific MRD-containing antibody to a patient in need thereof.

In one embodiment, the multivalent and monovalent multispecific composition contains 2 binding sites for three or more targets. In an additional embodiment, the multivalent and monovalent multispecific composition contains 2 binding sites for four or more targets. In another embodiment, the multivalent and monovalent multispecific composition contains 2 binding sites for five or more targets. According to some embodiments, at least 1, 2, 3, 4 or more of the targets are located on a cell surface. According to some embodiments, at least 1, 2, 3, 4 or more of the targets are soluble targets (e.g., chemokines, cytokines, and growth factors). In additional embodiments, the multivalent and monovalent multispecific composition binds 1, 2, 3, 4 or more of the targets described herein.

In additional embodiments, the targets bound by the multivalent and monovalent multispecific composition are associated with cancer. In a further embodiment the targets bound by the multivalent and monovalent multispecific composition are associated with 1, 2, 3, 4 or more different signaling pathways or modes of action associated with cancer.

In additional embodiments, the targets bound by the multivalent and monovalent multispecific composition are associated with a disease or disorder of the immune system. In a further embodiment the targets bound by the multivalent and monovalent multispecific composition are associated with 1, 2, 3, 4 or more different signaling pathways or modes of action associated with a disease or disorder of the immune system.

In additional embodiments, the targets bound by the multivalent and monovalent multispecific composition are associated with a disease or disorder of the skeletal system (e.g., osteoporosis), cardiovascular system, nervous system, or an infectious disease. In a further embodiment the targets bound by the multivalent and monovalent multispecific composition are associated with 1, 2, 3, 4, 5 or more different signaling pathways or modes of action associated with a disease or disorder of the skeletal system (e.g., osteoporosis), cardiovascular system, nervous system, or an infectious disease. In a further embodiment, the multivalent and monovalent multispecific composition binds at least 1, 2, 3, 4, 5 or more of the targets described herein.

In one embodiment, the multivalent and monovalent multispecific composition contains 2 binding sites for three or more targets. In an additional embodiment, the multivalent and monovalent multispecific composition contains 2 binding sites for four or more targets. In an additional embodiment, the multivalent and monovalent multispecific composition contains 2 binding sites for five or more targets.

In one embodiment, the multivalent and monovalent multispecific composition contains 2 binding sites for three or more targets. In an additional embodiment, the multivalent and monovalent multispecific composition contains 2 binding sites for four or more targets. In another embodiment, the multivalent and monovalent multispecific composition contains 2 binding sites for five or more targets. According to some embodiments, at least 1, 2, 3, 4, or more of the targets are associated with the cell membrane. According to some embodiments, at least 1, 2, 3, 4, or more of the targets are soluble targets (e.g., chemokines, cytokines, and growth factors). In additional embodiments, the multivalent and monovalent multispecific composition binds 1, 2, 3, 4, or more of the targets described herein.

In additional embodiments, the targets bound by the multivalent and monovalent multispecific composition are associated with cancer. In a further embodiment the targets bound by the multivalent and monovalent multispecific composition are associated with 1, 2, 3, 4, or more different signaling pathways or modes of action associated with cancer.

In additional embodiments, the targets bound by the multivalent and monovalent multispecific composition are associated with a disease or disorder of the immune system. In a further embodiment the targets bound by the—multivalent and monovalent multispecific composition are associated with 1, 2, 3, 4, or more different signaling pathways or modes of action associated with a disease or disorder of the immune system.

In additional embodiments, the multivalent and monovalent multispecific composition binds (1) a target on a cell or tissue of interest (e.g., a tumor associated antigen on a tumor cell, an immune cell, a diseased cell or an infectious agent) and (2) a target on an effector cell. According to one embodiment, the binding of one or more targets by the multivalent and monovalent multispecific composition directs an immune response to a cell, tissue, infectious agent, or other location of interest in a patient. In some embodiments the effector cell is a leukocyte, such as a T cell or natural killer cell. In other embodiments, the effector cell is an accessory cell, such as a myeloid cell or a dendritic cell.

In additional embodiments, the multivalent and monovalent multispecific composition binds (1) a target on a cell or tissue of interest (e.g., a tumor associated antigen on a tumor cell, an immune cell, a diseased cell or an infectious agent) and (2) a target on a leukocyte, such as a T-cell receptor molecule. According to one embodiment, the binding of one or more targets by the multivalent and monovalent multispecific composition directs an immune response to an infectious agent, cell, tissue, or other location of interest in a patient. For example, in some embodiments the multivalent and monovalent multispecific composition binds a target on the surface of a T cell. In particular embodiments, the composition binds a CD3 target selected from CD3 delta, CD3 epsilon, CD3 gamma, CD3 zeta, TCR alpha, TCR beta, and multimers of proteins in the CD3 (TCR) complex. In specific embodiments the multivalent and monovalent multispecific composition binds CD3. In other embodiments, the multivalent and monovalent multispecific composition binds CD2. In additional embodiments, the multivalent and monovalent multispecific composition binds a target expressed on a natural killer cell. Thus, in some embodiments, the multivalent and monovalent multispecific composition binds a target selected from: CD2, CD56, and CD161.

In additional embodiments, the multivalent and monovalent multispecific composition binds a target expressed on an accessory (e.g., myeloid) cell. In some embodiments, the multivalent and monovalent multispecific composition binds a target selected from: CD64 (i.e., Fc gamma RI), an MHC class 2 and its invariant chain, TLR1, TLR2, TLR4, TLR5, and TLR6.

In further embodiments, the multivalent and monovalent multispecific composition (e.g., an MRD containing antibody) has a single binding site (i.e., is monovalent) for a target. In some embodiments, the multivalent and monovalent multispecific composition has a single binding site for a target on a leukocyte, such as a T-cell (e.g., CD3), and multiple binding sites (i.e., is multivalent) for a target on a cell or tissue of interest (e.g., a tumor associated antigen on a tumor cell, such as a target disclosed herein). In further embodiments, the multispecific composition contains single binding sites for 2 different targets (i.e., monovalently binds more than one different target). In particular embodiments, the cell or tissue of interested is a cancer cell, immune cell, diseased cell, or an infectious agent.

In some embodiments, a multivalent and monovalent multispecific composition (e.g., an MRD-containing antibody) has a single binding site for CD3. In further embodiments, the multivalent and monovalent multispecific composition has a single binding site for CD3 and multiple binding sites for 1, 2, 3, 4, 5 or more different targets (e.g., a tumor antigen or other target disclosed herein). In additional embodiments, the multispecific composition has a single binding site for CD3 and a single binding site for a different target (i.e., monovalently binds CD3 and a different target). In other embodiments, a multivalent and monovalent multispecific composition has a single binding site for CD3 epsilon. In further embodiments, the multivalent and monovalent multispecific composition has a single binding site for CD3 epsilon and multiple binding sites for 1, 2, 3, 4, 5 or more different targets (e.g., a tumor antigen or other target disclosed herein). In further embodiments, the multispecific composition has a single binding site for CD3 epsilon and a single binding site for a different target (i.e., monovalently binds CD3 epsilon and a different target). In some embodiments, the multivalent and monovalent multispecific composition has multiple binding sites for a target on a cancer cell selected from breast cancer, colorectal cancer, endometrial cancer, kidney (renal cell) cancer, lung cancer, melanoma, Non-Hodgkin Lymphoma, leukemia, prostate cancer, bladder cancer, pancreatic cancer, and thyroid cancer.

In further embodiments, the invention is directed to treating a disease or disorder by administering a therapeutically effective amount of a multivalent and monovalent multispecific composition that has a single binding site for a target (i.e., that monovalently binds a target) to a patient in need thereof. In some embodiments, the administered multivalent and monovalent multispecific composition has a single binding site for a target on a leukocyte such as a T-cell (e.g., CD3). In further embodiments, the administered multivalent and monovalent multispecific composition has a single binding site for a target on a leukocyte such as a T-cell (e.g., CD3) and multiple binding sites for (i.e., is capable of multivalently binding) a target located on a cell or tissue of interest (e.g., a tumor antigen on a tumor cell). In further embodiments, the multispecific composition has a single binding site for a target on a leukocyte (e.g., CD3) and a single binding site for a different target. In some embodiments, the cell of interest is a tumor cell from a cancer selected from breast cancer, colorectal cancer, endometrial cancer, kidney (renal cell) cancer, lung cancer, melanoma, Non-Hodgkin Lymphoma, leukemia, prostate cancer, bladder cancer, pancreatic cancer, and thyroid cancer. In additional embodiments, the multivalent and monovalent multispecific composition has multiple binding sites for a target on a neurological tumor. In particular embodiments, the neurological tumor is a glioma (e.g., a glioblastoma, glioblastoma multiforme (GBM), and astrocytoma), ependymoma, oligodendroglioma, neurofibroma, sarcoma, medulloblastoma, primitive neuroectodermal tumor, pituitary adenoma, neuroblastoma or cancer of the meninges (e.g., meningioma, meningiosarcoma and gliomatosis).

In further embodiments, the invention is directed to treating a disease or disorder by administering to a patient in need thereof, a therapeutically effective amount of a multivalent and monovalent multispecific composition (e.g., an MRD-containing antibody) that has a single binding site for a target (i.e., that monovalently binds a target) and multiple binding sites for 1, 2, 3, 4, 5 or more different targets. In further embodiments, the multivalent and monovalent multispecific composition has single binding sites for 2 different targets. In some embodiments, the multivalent and monovalent multispecific composition has multiple binding sites for a target on a cancer cell selected from breast cancer, colorectal cancer, endometrial cancer, kidney (renal cell) cancer, lung cancer, melanoma, Non-Hodgkin Lymphoma, leukemia, prostate cancer, bladder cancer, pancreatic cancer, and thyroid cancer.

In additional embodiments, the invention is directed to treating a disease or disorder by administering to a patient in need thereof, a therapeutically effective amount of a multivalent and monovalent multispecific composition (e.g., an MRD-containing antibody) that has a single binding site for CD3 (e.g., CD3 epsilon) that monovalently binds CD3 and multiple binding sites for 1, 2, 3, 4, 5 or more different targets located on a cell or tissue of interest (e.g., a tumor antigen on a tumor cell). In some embodiments, the administered multivalent and monovalent multispecific composition has a single binding site for CD3 (e.g., CD3 epsilon) and a single binding site for a different target and also has multiple binding sites for a target located on a cell or tissue of interest (e.g., a tumor antigen on a tumor cell). In some embodiments, the multivalent and monovalent multispecific composition has multiple binding sites for a target on a cancer cell selected from breast cancer, colorectal cancer, endometrial cancer, kidney (renal cell) cancer, lung cancer, melanoma, Non-Hodgkin Lymphoma, leukemia, prostate cancer, bladder cancer, pancreatic cancer, and thyroid cancer.

In further embodiments, the multivalent and monovalent multispecific composition (e.g., an MRD-containing antibody) has a single binding site for (i.e., monovalently binds) a cell surface target that requires multimerization for signaling. In some embodiments, the multivalent and monovalent multispecific composition has a single binding site for a growth factor receptor. In other embodiments, the multivalent and monovalent multispecific composition has a single binding site for a TNF receptor superfamily member. In additional embodiments, the multispecific composition additionally has a single binding site for a different target (i.e., monovalently binds more than one different target).

In additional embodiments, the multivalent and monovalent multispecific composition (e.g., MRD-containing antibody) binds a target associated with an endogenous blood brain barrier (BBB) receptor mediated transport system and is capable of crossing to the brain (cerebrospinal fluid) side of the BBB. In some embodiments, the multivalent and monovalent multispecific composition has two or more binding sites for a target antigen associated with an endogenous BBB receptor mediated transport system. In additional embodiments, the multivalent and monovalent multispecific composition has a single binding site for a target associated with an endogenous BBB receptor mediated transport system (e.g., the insulin receptor, transferrin receptor, leptin receptor, lipoprotein receptor, and the IGF receptor mediated transport systems). In further embodiments, the multivalent and monovalent multispecific composition additionally binds 1, 2, 3, 4, 5, or more targets located on the brain side of the BBB. In particular embodiments, the MRD-containing antibody binds 1, 2, 3, 4, 5, or more targets associated with a neurological disease or disorder. In another embodiment, the multivalent and monovalent multispecific composition is administered to a patient to treat a brain cancer, metastatic cancer of the brain, or primary cancer of the brain. In a further embodiment, the multivalent and monovalent multispecific composition is administered to a patient to treat brain injury, stroke, spinal cord injury, or to manage pain.

In additional embodiments, targets bound by the multivalent and monovalent multispecific composition (e.g., MRD-containing antibody) are associated with a disease or disorder of the skeletal system (e.g., osteoporosis), cardiovascular system, nervous system, or an infectious disease. In a further embodiment a targets bound by the multivalent and monovalent multispecific composition are associated with 1, 2, 3, 4, 5 or more different signaling pathways or modes of action associated with one or more of the above diseases or disorders. In a further embodiment, the multivalent and monovalent multispecific composition binds 1, 2, 3, 4, 5 or more of the targets described herein.

In one embodiment, the multivalent and monovalent multispecific composition is a ZYBODY™ (referred to herein as an "MRD-containing antibody," or the like). In a further embodiment, the MRD-containing antibody contains binding sites for three or more targets. In an additional embodiment, the MRD-containing antibody contains 2 binding sites for four or more targets. In an additional embodiment, the MRD-containing antibody contains 2 binding sites for five or more targets.

In one embodiment, the multivalent and monovalent multispecific composition (e.g., MRD-containing antibody) contains 2 binding sites for three or more targets. In an additional embodiment, the multispecific composition (e.g., MRD-containing antibody) contains 2 binding sites for four or more targets. In another embodiment, the multispecific composition (e.g., MRD-containing antibody) contains 2 binding sites for five or more targets. According to some embodiments, at least 1, 2, 3, 4 or more of the targets are located on a cell surface. According to some embodiments, at least 1, 2, 3, 4 or more of the targets are soluble targets (e.g., chemokines, cytokines, and growth factors). In additional embodiments, the MRD-containing antibody binds at least 1, 2, 3, 4, 5 or more of the targets described herein.

In additional embodiments, the targets bound by the multivalent and monovalent multispecific composition (e.g., MRD-containing antibody) are associated with cancer. In a further embodiment the targets bound by MRD-containing antibody are associated with 1, 2, 3, 4 or more different signaling pathways or modes of action associated with cancer.

In additional embodiments, a target bound by the multivalent and monovalent multispecific composition (e.g., MRD-containing antibody) is associated with a disease or disorder of the immune system. In a further embodiment the targets bound by the MRD-containing antibody are associated with 1, 2, 3, 4, 5 or more different signaling pathways or modes of action associated with a disease or disorder of the immune system.

In additional embodiments, a target bound by the multivalent and monovalent multispecific composition (e.g., MRD-containing antibody) is associated with a disease or disorder of the skeletal system, cardiovascular system, nervous system, or an infectious disease. In a further embodiment a target bound by the MRD-containing antibody is associated with 1, 2, 3, 4 or more different signaling pathways or modes of action associated with one or more of the above diseases or disorders. In another embodiment, the MRD-containing antibody binds 1, 2, 3, 4 or more of the targets described herein.

The multivalent and multispecific compositions of the invention (e.g., MRD-containing antibodies) provide the ability to selectively target multiple targets (e.g., receptors and microenvironment associated targets) having for example, different, overlapping, or redundant mechanisms of action associated with the etiology or pathophysiology of a disease or disorder.

In additional embodiments, the invention encompasses a multivalent and monovalent multispecific composition (e.g., an MRD-containing antibody) that is covalently or otherwise associated with a cytotoxic agent. According to some embodiments, the cytoxic agent is covalently attached to an MRD-containing antibody by a linker. According to some embodiments, the cytotoxic agent is a chemotherapeutic agent, growth inhibitory agent, toxin (e.g., an enzymatically active toxin of bacterial, fungal, plant, or animal origin, or fragments thereof), radioactive isotope (i.e., a radioconjugate), or prodrug. The compositions of the invention are optionally linked to the cytotoxic agent by a linker. In particular embodiments, a linker attaching the multivalent and monovalent multispecific composition and the cytotoxic agent is cleavable by a protease. In particular embodiments, a linker attaching the multivalent and monovalent multispecific composition and the cytotoxic agent is cleavable under low pH or reducing conditions. Methods of using composition-cytoxic agent compositions of the invention (e.g., MRD-containing antibody drug conjugates) are also encompassed by the invention.

In additional embodiments, the multivalent and multispecific compositions is covalently or otherwise associated with a cytotoxic agent selected from, for example, a toxin, a chemotherapeutic agent, a drug moiety (e.g., a chemotherapeutic agent or prodrug), an antibiotic, a radioactive isotope, a chelating ligand (e.g., DOTA, DOTP, DOTMA, DTPA and TETA), and a nucleolytic enzyme. In particular embodiments, the cytotoxic agent is selected from auristatin and dolostantin, MMAE, MMAF, and a maytansinoid derivative (e.g., the DM1 (N(2')-deacetyl-N(2')-(3-mercapto-1-oxopropyl)-maytansine), DM3 (N(2')-deacetyl-N2-(4-mercapto-1-oxopentyl)-maytansine), and DM4 (N(2)-deacetyl-N2-(4-mercapto-4-methyl-1-oxopentyl)-maytansine).

In further embodiments, a multivalent and monovalent multispecific composition of the invention (e.g., an MRD-containing antibody) is administered in combination with a multitargeting therapeutic. In one embodiment, a multivalent and monovalent multispecific composition is administered in combination with a multitargeting protein kinase inhibitor. In another embodiment, a multivalent and monovalent multispecific composition is administered in combination with an NFKB inhibitor. In an additional embodiment, a multivalent and monovalent multispecific composition is administered in combination with an HDAC inhibitor. In a further embodiment, a multivalent and monovalent multispecific composition is administered in combination with an HSP70 or HSP90 inhibitor. In a further embodiment, a multivalent and monovalent multispecific composition is administered in combination with chemotherapy.

In some embodiments, a multivalent and monovalent multispecific composition of the invention (e.g., an MRD-containing antibody) is administered in combination with a monospecific therapeutic (e.g., a monoclonal antibody).

In some embodiments, a multivalent and monovalent multispecific composition of the invention is a full-length antibody comprising at least one modular recognition domain (MRD). In some embodiments, the full-length antibody comprises multiple MRDs. In additional embodiments, the full-length antibody comprises more than one type of MRD (i.e., multiple MRDs having the same or different specificities). Also embodied in the present invention are variants and derivatives of such antibody complexes.

The MRDs of the MRD containing antibodies can be operably attached to the antibodies at any location on the antibody (e.g., the amino terminus of the heavy chain or light chain or the carboxyl terminus of the heavy chain or light chain), can be linked at the same or different termini, and are optionally operably linked to one another or to the antibody by a linker.

The antibodies of the MRD containing antibodies can be any immunoglobulin molecule that binds to an antigen and can be of any type, class, or subclass. In some embodiments, the antibody is humanized or human. In other embodiments, the antibodies also include modifications that do not interfere with their ability to bind antigen. In particular embodiments, the multivalent and multispecific compositions (e.g., MRD-containing antibodies) include modifications that increase ADCC, decrease ADCC, increase CDC, or decrease CDC, that increase antibody half-life, or decrease antibody half-life compared to the antibody without the modification.

The antibodies of the multivalent and multispecific compositions (e.g., MRD-containing antibodies) of the invention can be any antibody that binds to a target of therapeutic or diagnostic value. In preferred embodiments, the antibody of the MRD-containing antibody binds to a validated target. In some embodiments, the antibodies corresponding to the MRD containing antibodies are in clinical trials for regulatory approval. In some embodiments, the antibodies corresponding to the MRD containing antibodies are marketed.

In one embodiment, the antibody binds to a cell surface antigen. In another embodiment, the antibody binds to an angiogenic factor. In a further embodiment, the antibody binds to an angiogenic receptor.

In some embodiments, the antibody of the MRD-containing antibody binds to a target selected from: EGFR, ErbB2, ErbB3, ErbB4, CD20, insulin-like growth factor-I receptor, VEGF, VEGF-R and prostate specific membrane antigen. In additional embodiments the antibody of the MRD-containing antibody binds to VEGF, VEGFR1, EGFR, ErbB2, IGF-IR, cMET, FGFR1, FGFR2, and CD20.

In one embodiment, the antibody of the MRD-containing antibody binds to EGFR. In another specific embodiment, the antibody is Erbitux®, nimotuzumab, or zalutumumab (e.g., Genmab). In another embodiment, the antibody binds to the same epitope as Erbitux® antibody or competitively inhibits binding of the Erbitux® antibody to EGFR. In a further specific embodiment, the antibody is the Erbitux® antibody. In one specific embodiment, the antibody binds to the same epitope as Erbitux®, nimotuzumab, zalutumumab (e.g., Genmab) antibody. In another specific embodiment, the antibody component, MRD component, and/or MRD-containing antibody competitively inhibits binding of Erbitux®, nimotuzumab, zalutumumab antibody to EGFR.

In one embodiment, an MRD-containing antibody binds EGFR and a target selected from: HGF, CD64, CDCP1, RON, cMET, ErbB2, ErbB3, IGF1R, PLGF, RGMa, PDGFRa, PDGFRb, VEGFR1, VEGFR2, TNFRSF10A (DR4), TNFRSF10B (DR5), IGF1,2, IGF2, CD3, CD4, NKG2D and tetanus toxoid. In some embodiments, the multivalent and monovalent multispecific composition (e.g., MRD-containing antibodies) binds at least 1, 2, 3, 4, 5 or more of these targets. In specific embodiments, the antibody component of the MRD-containing antibody binds EGFR. In further embodiments, the antibody component of the MRD-containing antibody is nimotuzumab, zalutumumab. In specific embodiments, the antibody component of the MRD-containing antibody is Erbitux®.

In a specific embodiment, the antibody of the MRD-containing antibody binds to ErbB2. In one embodiment, the antibody is HERCEPTIN® (trastuzumab) antibody or competitively inhibits HERCEPTIN® (trastuzumab) antibody binding to ErbB2.

In another specific embodiment, the antibody binds to VEGF. In another specific embodiment, the antibody binds to the same epitope as AVASTIN® (bevacizumab) antibody or competitively inhibits AVASTIN® antibody. In a further specific embodiment, the antibody is the AVASTIN® antibody.

In some embodiments, the antibody binds to a target that is associated with a disease or disorder of the immune system. In one embodiment, the antibody binds to TNF. In another specific embodiment, the antibody binds to the same epitope as HUMIRA® (adalimumab) antibody or competitively inhibits HUMIRA® antibody. In a further specific embodiment, the antibody is the HUMIRA® antibody. In one embodiment, the antibody binds to TNF. In another specific embodiment, the antibody binds to the same epitope as SIMPONI™ (golimumab) antibody or competitively inhibits SIMPONI™ antibody. In a further specific embodiment, the antibody is the SIMPONI™ antibody.

In some embodiments, the antibody component of the MRD containing antibody binds to a target that is associated with a disease or disorder of the metabolic, cardiovascular, musculoskeletal, neurological, or skeletal system. In other embodiments, the antibody component of the MRD containing antibody binds to a target that is associated with yeast, fungal, viral or bacterial infection or disease.

In one embodiment, the MRD is about 2 to 150 amino acids. In another embodiment, the MRD is about 2 to 60 amino acids. MRDs can be linked to an antibody or other MRDs directly or through a linker. The MRDs can be any target binding peptide. In some embodiments, the MRD target is a soluble factor. In other embodiments, the MRD target is a transmembrane protein such as a cell surface receptor. In another embodiment, the target of the MRD is a cellular antigen. In a specific embodiment, the target of the MRD is CD20.

In another embodiment, the target of the MRD is an integrin. In one aspect, the peptide sequence of the integrin targeting MRD is YCRGDCT (SEQ ID NO:3). In another aspect, the peptide sequence of the integrin targeting MRD is PCRGDCL (SEQ ID NO:4). In yet another aspect, the peptide sequence of the integrin targeting MRD is TCRGDCY (SEQ ID NO:5). In another aspect, the peptide sequence of the integrin targeting MRD is LCRGDCF (SEQ ID NO:6).

In an additional embodiment, the target of the MRD is an angiogenic cytokine. In one aspect, the peptide sequence of the angiogenic cytokine targeting (i.e., binding) MRD is MGAQTNFMPMDDLEQRLYEQFILQQGLE (SEQ ID NO:7).

In one embodiment, the target of the MRD is ErbB2. In another embodiment, the target to which the MRD binds is ErbB3. In an additional embodiment, the target to which the MRD binds is tumor-associated surface antigen or an epithelial cell adhesion molecule (Ep-CAM).

In one embodiment, the target to which the MRD binds is VEGF. In one aspect, the peptide sequence of the VEGF targeting MRD is VEPNCDIHVMWEWECFERL (SEQ ID NO:13).

In one embodiment, the target to which the MRD binds is an insulin-like growth factor-I receptor (IGF1R). An illustrative IGF1R targeting MRD includes, for example, a peptide sequence having the formula: NFYQCIDLLMAYPAEKSRGQWQECRTGG (SEQ ID NO:37);

In one embodiment, the target of the MRD is a tumor antigen. The "tumor antigen" as used herein may be understood as both those antigens (including mutations) exclusively expressed on tumor cells (i.e., tumor-specific antigens) and those antigens expressed on tumor cells and normal cells (e.g., antigens overexpressed on tumor cells).

In one embodiment, the target of the MRD is an epidermal growth factor receptor (EGFR). In another embodiment of the present invention, the target of the MRD is an angiogenic factor. In an additional embodiment, the target of the MRD is an angiogenic receptor.

In another embodiment, the MRD is a vascular homing peptide.

In one embodiment, the target of the MRD is a nerve growth factor.

In another embodiment, the antibody and/or MRD binds to EGFR, ErbB2, ErbB3, ErbB4, CD20, insulin-like growth factor-I receptor, or prostate specific membrane antigen.

The present invention also relates to an isolated polynucleotide comprising a nucleotide sequence encoding an MRD-containing antibody. In one aspect, a vector comprises a polynucleotide sequence encoding an MRD-containing antibody. In another aspect, the polynucleotide sequence encoding an MRD-containing antibody is operatively linked with a regulatory sequence that controls expression on the polynucleotide. In an additional aspect, a host cell comprises the polynucleotide sequence encoding an MRD-containing antibody.

Methods of making multivalent and multispecific compositions (e.g., MRD-containing antibodies) are also provided, as are the use of these MRD-antibody fusions in diagnostic and therapeutic applications. The present invention also relates to methods of designing and making multivalent and multispecific compositions (e.g., MRD-containing antibodies) having a full-length antibody comprising a MRD. In one aspect, the MRD is derived from a phage display library. In another aspect, the MRD is derived from natural ligands. In another aspect, the MRD is derived from yeast display or RNA display technology.

The present invention also relates to a method of treating or preventing a disease or disorder in a subject (patient) in need thereof, comprising administering an antibody comprising an MRD to the subject (patient). In one aspect, the disease is cancer. In another aspect, undesired angiogenesis in inhibited. In another aspect, angiogenesis is modulated. In yet another aspect, tumor growth is inhibited.

Certain embodiments provide for methods of treating or preventing a disease, disorder, or injury comprising administering to a patient in need thereof, a therapeutically effective amount of a multivalent and monovalent multispecific composition (e.g., an MRD-containing antibody) to a patient in need thereof. In some embodiments, the disease, disorder or injury is cancer. In other embodiments, the disease, disorder or injury is a disorder of the immune system. In one embodiment, the disorder of the immune system is inflammation. In another embodiment, the disorder of the immune system is an autoimmune disease. In an additional embodiment, the disorder of the immune system is selected from the group consisting of: rheumatoid arthritis, Crohn's disease, systemic lupus erythematous, inflammatory bowel disease, psoriasis, diabetes, ulcerative colitis, and multiple sclerosis. In one embodiment, the disease, disorder or injury is a metabolic disease. In another embodiment, the disease, disorder, or injury is an infectious disease. In specific embodiments, the infectious disease is human immunodeficiency virus (HIV) infection or AIDS, botulism, anthrax, or *Clostridium difficile*. In other embodiments, the disease, disorder, or injury is neurological. In a specific embodiment, the neurological disease, disorder or injury is pain. In a more specific embodiment, the pain is, acute pain or chronic pain.

In another embodiment, a method of treatment or prevention comprising administering an additional therapeutic agent along with an antibody comprising an MRD is provided. In other embodiments, the methods of treatment or prevention comprise administering an antibody comprising more than one type of MRD.

BRIEF DESCRIPTION OF THE DRAWINGS/FIGURES

FIGS. 17A and 17B depict the dose response curves of MRD-maltose binding protein (MBP) fusions assayed for direct binding to Ang2.

Figure 17A:
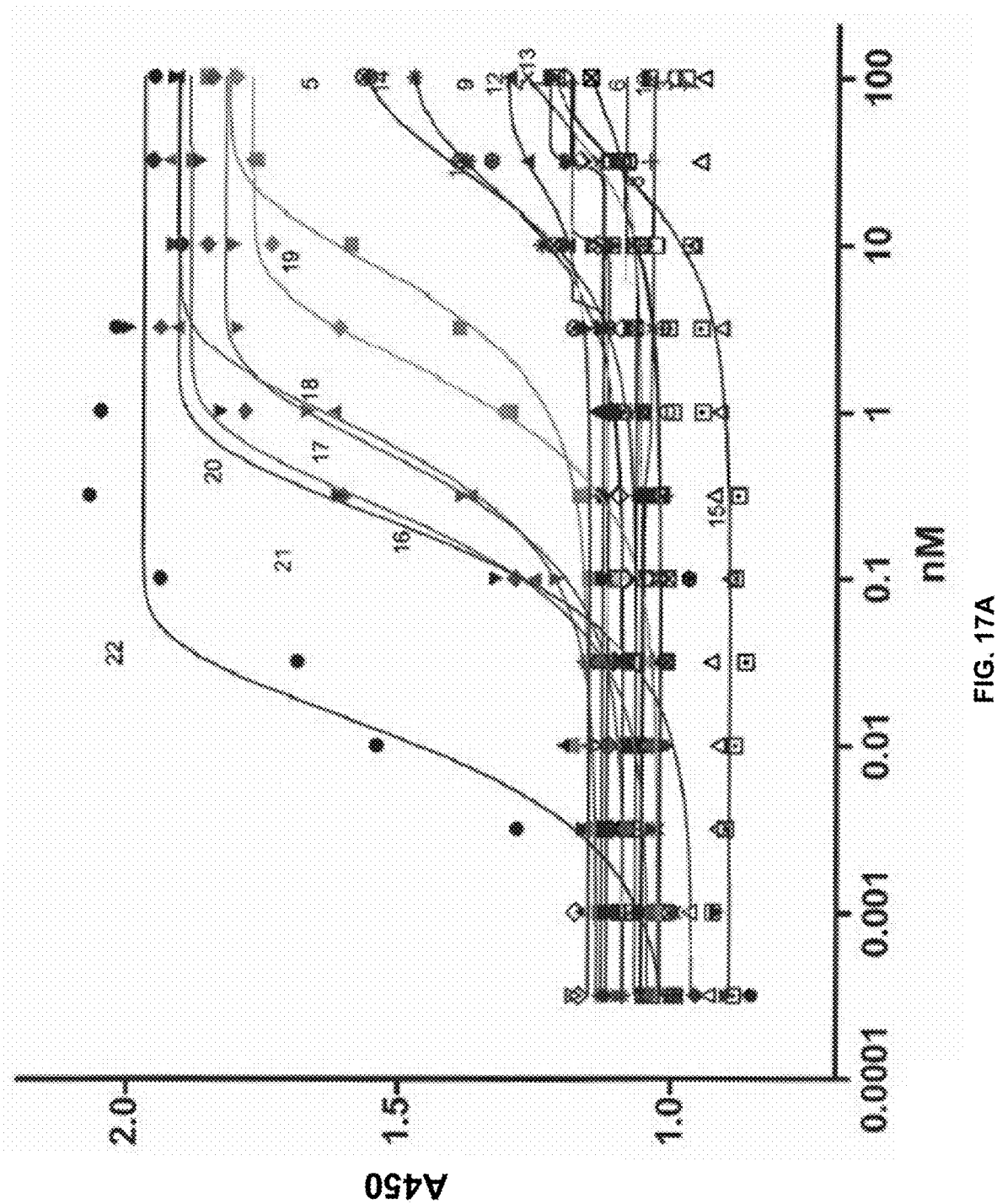

FIG. 17C indicates MRD-MBP fusion proteins tested, the amino acid sequence of the MRD, and the EC50 values (calculated using a 4 parameter fit). The MXD sequence motif in the MRD components of the MRD-MBP fusions is underlined and mutated residues are in bold and italics.

Figure 18A:
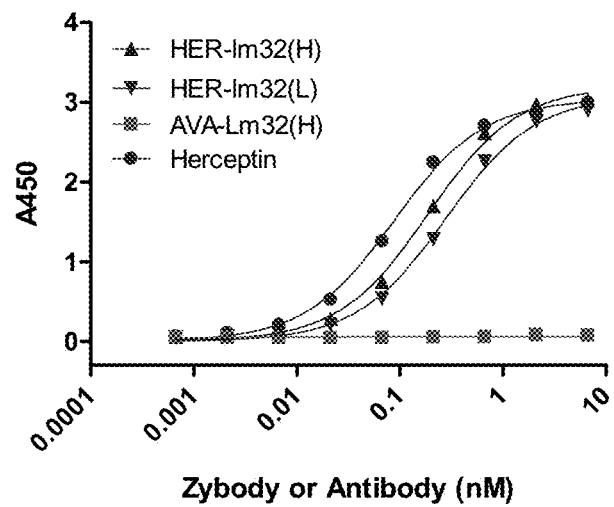

FIG. 18A depicts the results of an assay for direct binding of a HERCEPTIN® based zybody (i.e. an MRD containing HERCEPTIN® antibody sequences) antibody-MRDs and a HERCEPTIN® antibody to Her2 (ErbB2) Fc in the presence of biotinylated Ang2. Binding was detected with HRP-conjugated anti-human kappa chain mAb.

Figure 18B:
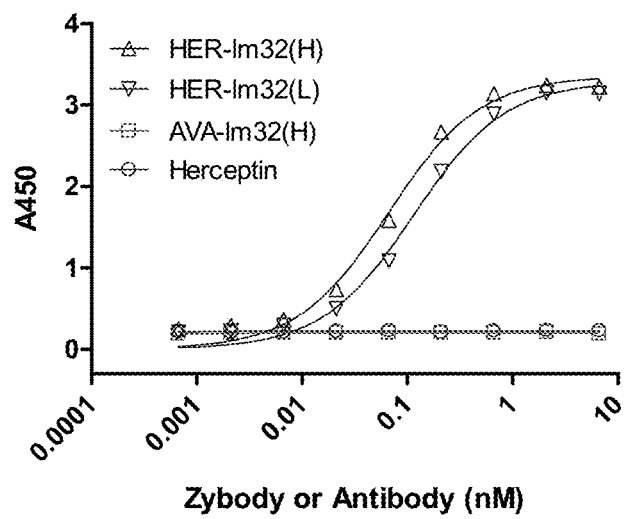

FIG. 18B depicts the results of an assay for direct binding of a HERCEPTIN® based zybody (i.e., an MRD containing HERCEPTIN® antibody sequences) and a HERCEPTIN® antibody to Her2 Fc in the presence of biotinylated Ang2. Binding was detected with horseradish peroxidase (HRP)-conjugated streptavidin.

Figure 19A:
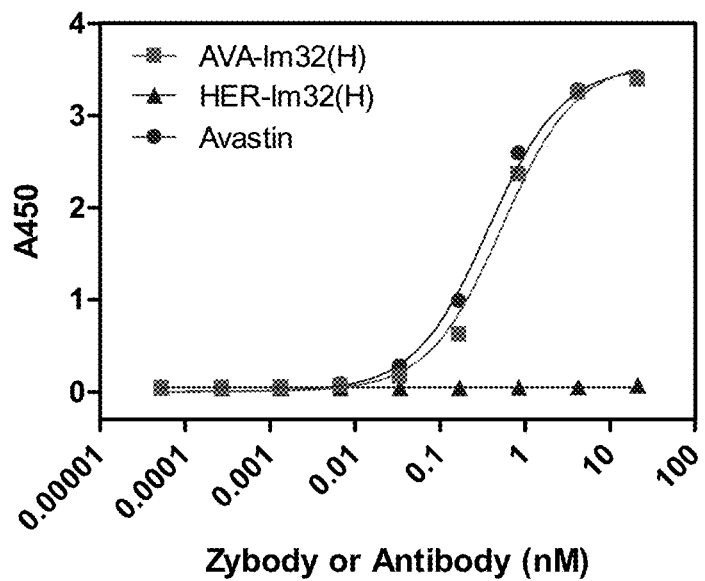

FIG. 19A depicts the results of an assay for direct binding of antibody-MRDs and an AVASTIN® antibody to VEGF in the presence of biotinylated Ang2. Binding was detected with HRP-conjugated anti-human kappa chain mAb.

Figure 19B:
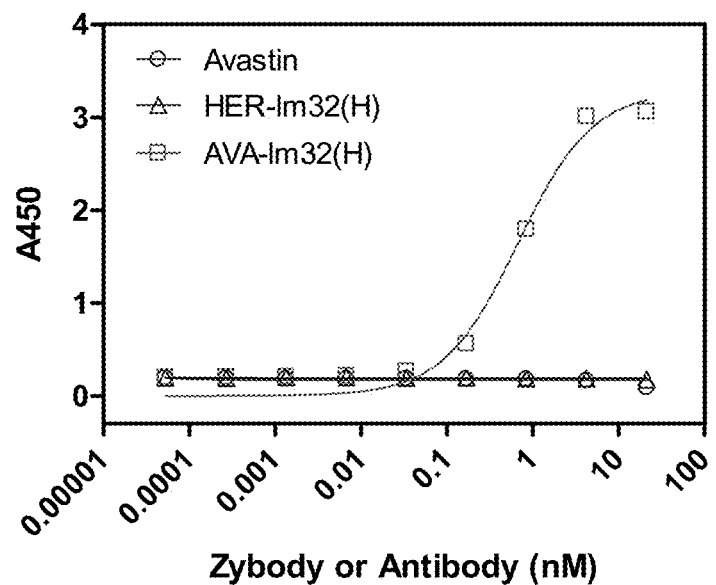

FIG. 19B depicts the results of an assay for direct binding of antibody-MRDs and an AVASTIN® antibody to VEGF in the presence of biotinylated Ang2. Binding was detected with HRP-conjugated streptavidin.

Figure 20A:
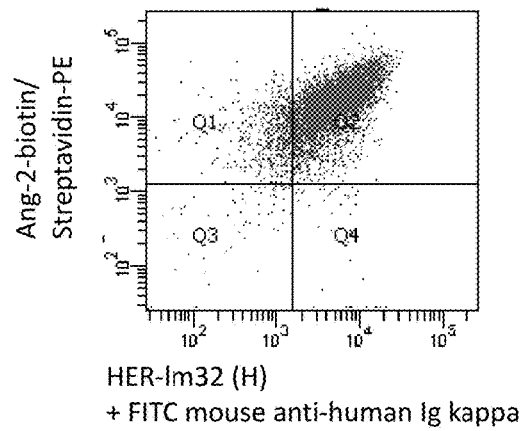
Figure 20B:
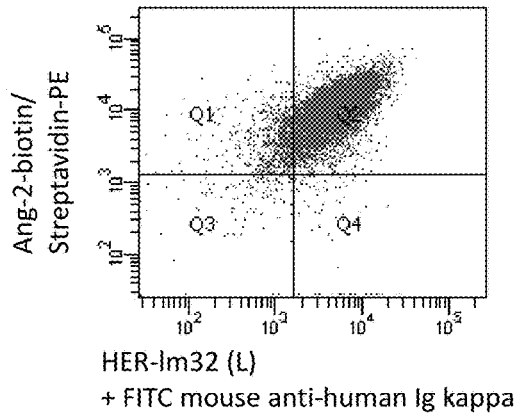
Figure 20C:
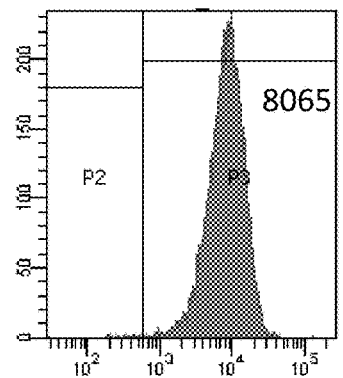
Figure 20D:
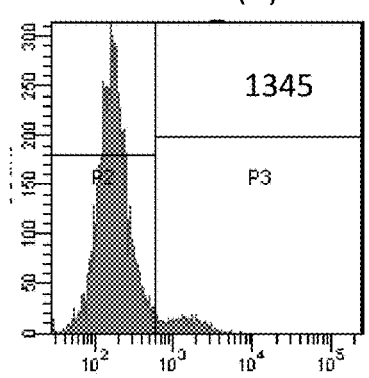
Figure 20E:
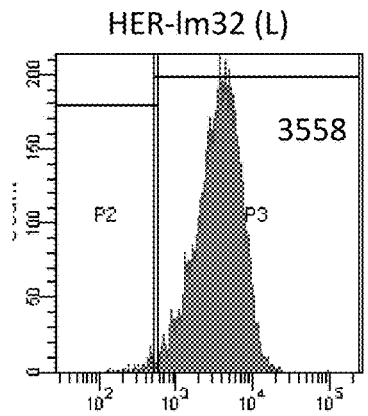
Figure 20F:
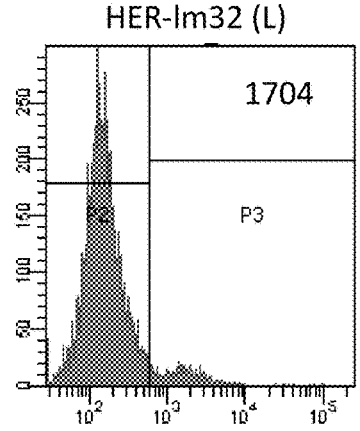

FIGS. 20A and 20B depict the results of a flow cytometry assay which demonstrates that antibody-MRDs simultaneously bind Her2 and Ang2 on BT-474 breast cancer cells.

FIGS. 20C-20F depict binding of antibody-MRDs to HER2 on BT-474 breast cancer cells.

Figure 21:
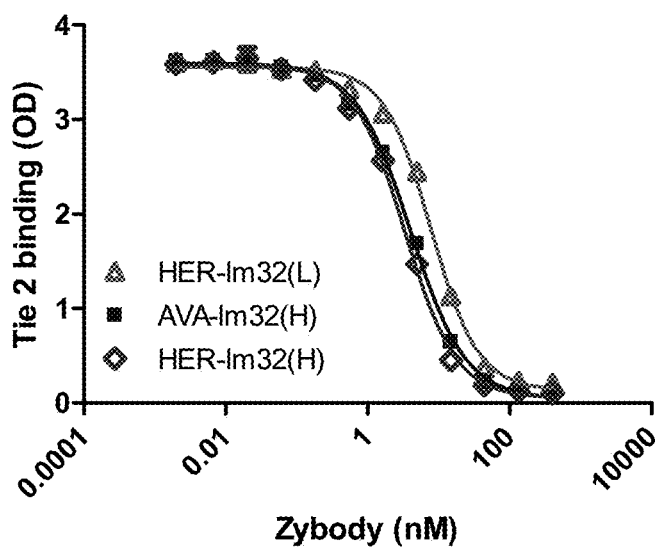

FIG. 21 depicts the results of an ELISA assay that demonstrates the inhibitory effect of antibody-MRDs on TIE-2 binding to plate immobilized Ang2.

Figure 22:
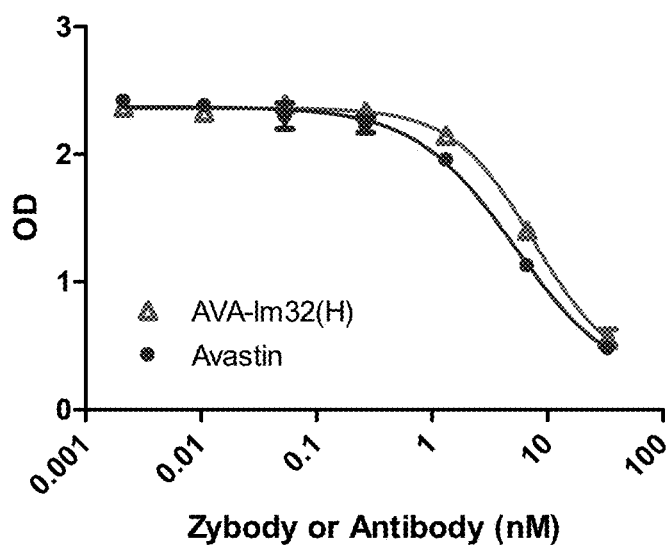

FIG. 22 depicts the results of a competitive binding assay that demonstrates the inhibition of binding of biotinylated antibody by antibody-MRD and unlabeled antibody.

Figure 23:
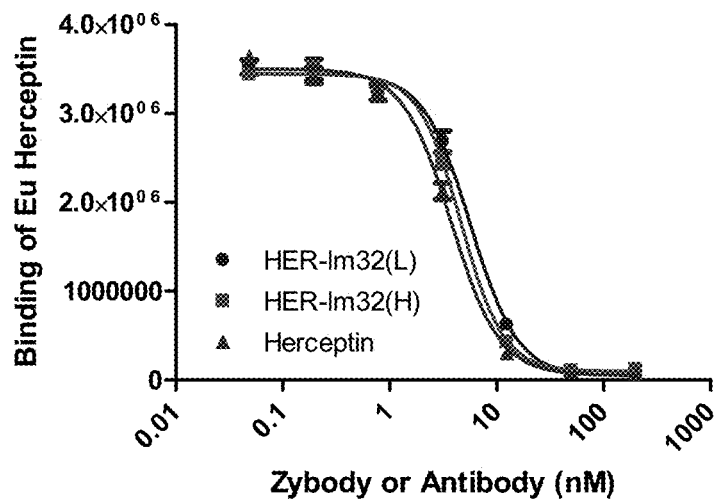

FIG. 23 depicts the results of a competitive binding assay that illustrates the inhibition of labeled antibody binding to BT-474 cells by antibody-MRDs and unlabeled antibody.

Figure 24A:
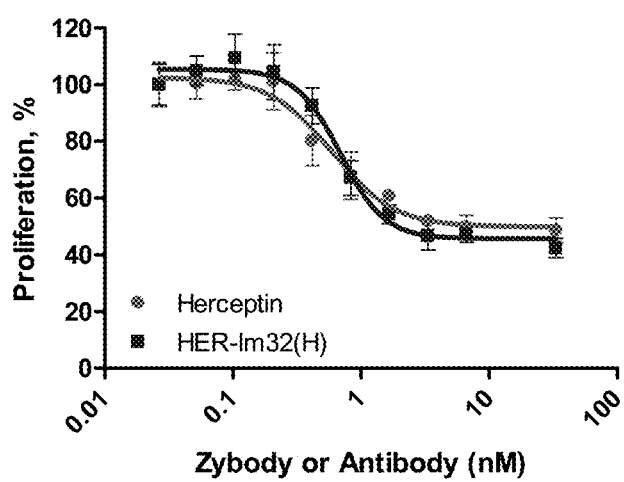

FIG. 24A depicts the fitted dose curves illustrating the inhibition of BT-474 cell proliferation by HERCEPTIN® with the lm32 MRD (SEQ ID NO:8) fused to the heavy chain and HERCEPTIN®.

Figure 24B:
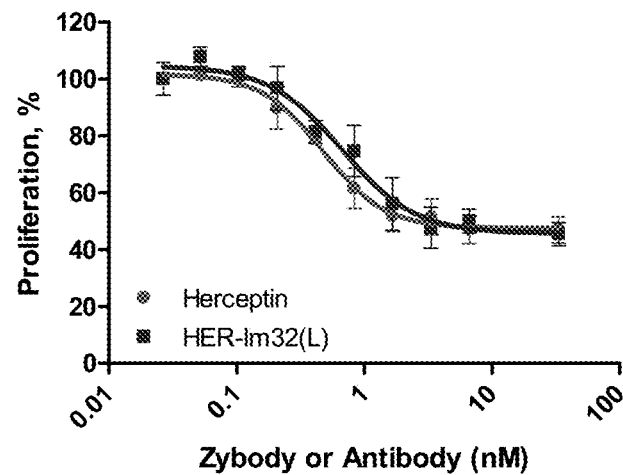

FIG. 24B depicts the fitted dose curves illustrating the inhibition of BT-474 cell proliferation by HERCEPTIN® with the lm32 MRD fused to the light chain and HERCEPTIN®.

Figure 24C:
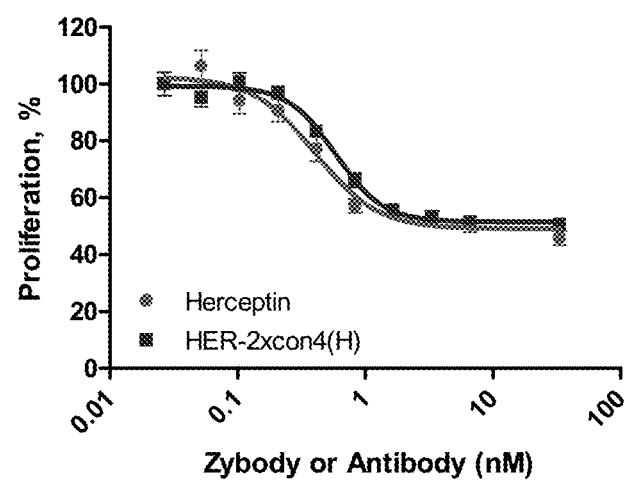

FIG. 24C depicts the fitted dose curves illustrating the inhibition of BT-474 cell proliferation by HERCEPTIN® with the 2xcon4 MRD fused to the heavy chain and HERCEPTIN®.

Figure 25A:
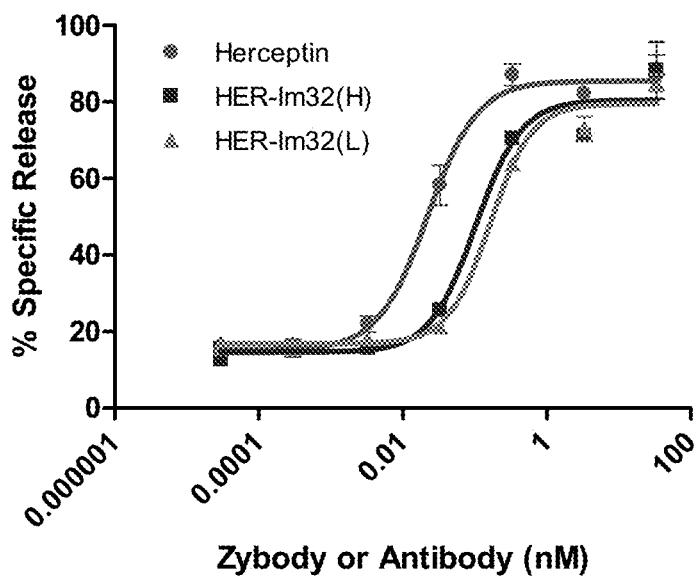

FIG. 25A depicts the results of a cytotoxicity assay illustrating ADCC-mediated killing of BT-474 cells by HERCEPTIN® with the lm32 MRD fused to the heavy chain, HERCEPTIN® with the lm32 MRD fused to the light chain, and HERCEPTIN®.

Figure 25B:
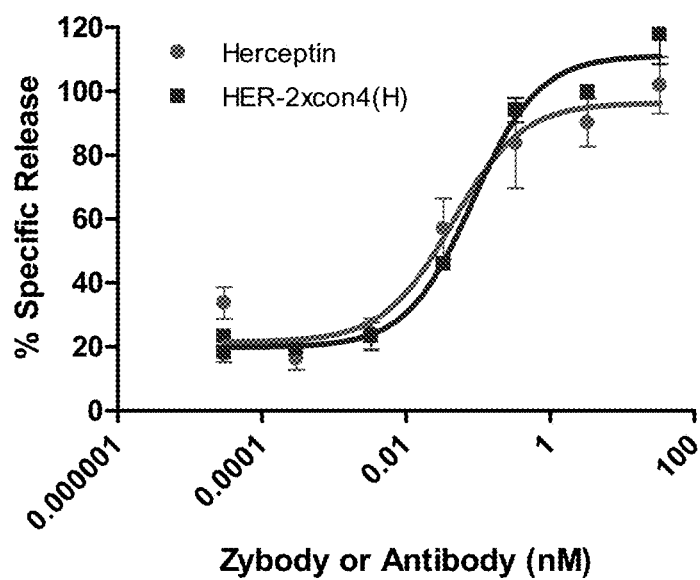

FIG. 25B depicts the results of a cytotoxicity assay illustrating ADCC-mediated killing of BT-474 cells by HERCEPTIN® with the 2xcon4 MRD fused to the heavy chain, and HERCEPTIN®.

Figure 26A:
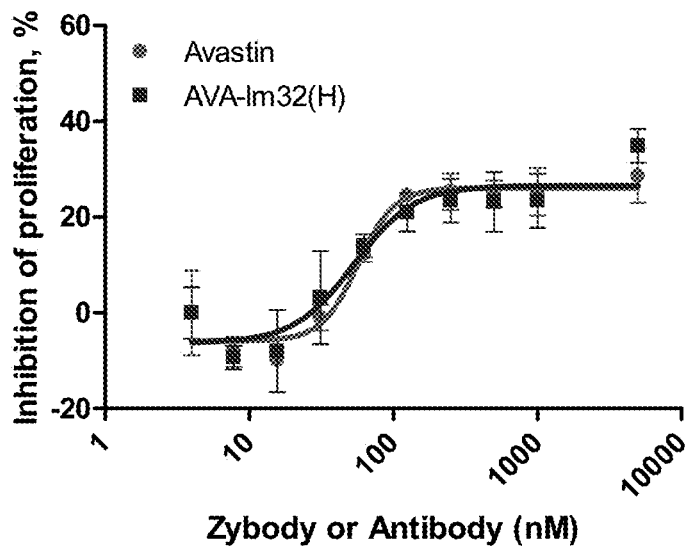

FIG. 26A depicts the inhibition of HUVEC proliferation by AVASTIN® with the lm32 MRD fused to the heavy chain and AVASTIN® using HUVECs obtained from GlycoTech (Gaithersburg, Md.).

Figure 26B:
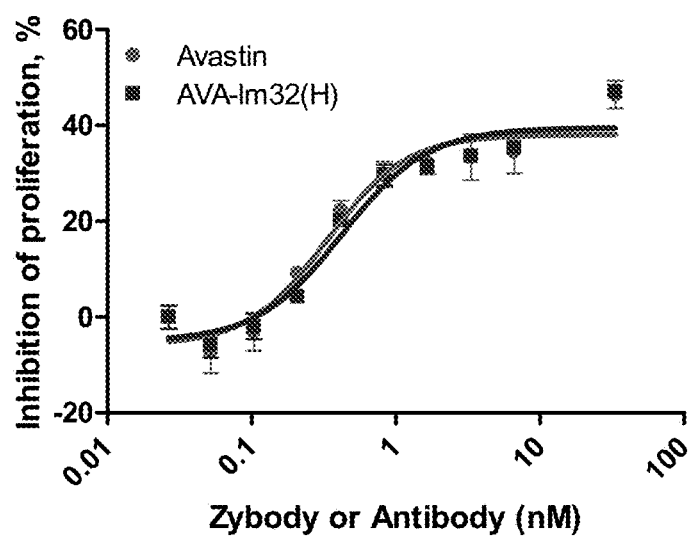

FIG. 26B depicts the inhibition of HUVEC proliferation by AVASTIN® with the lm32 MRD fused to the heavy chain and AVASTIN® using HUVECs obtained from Lonza.

Figure 27:
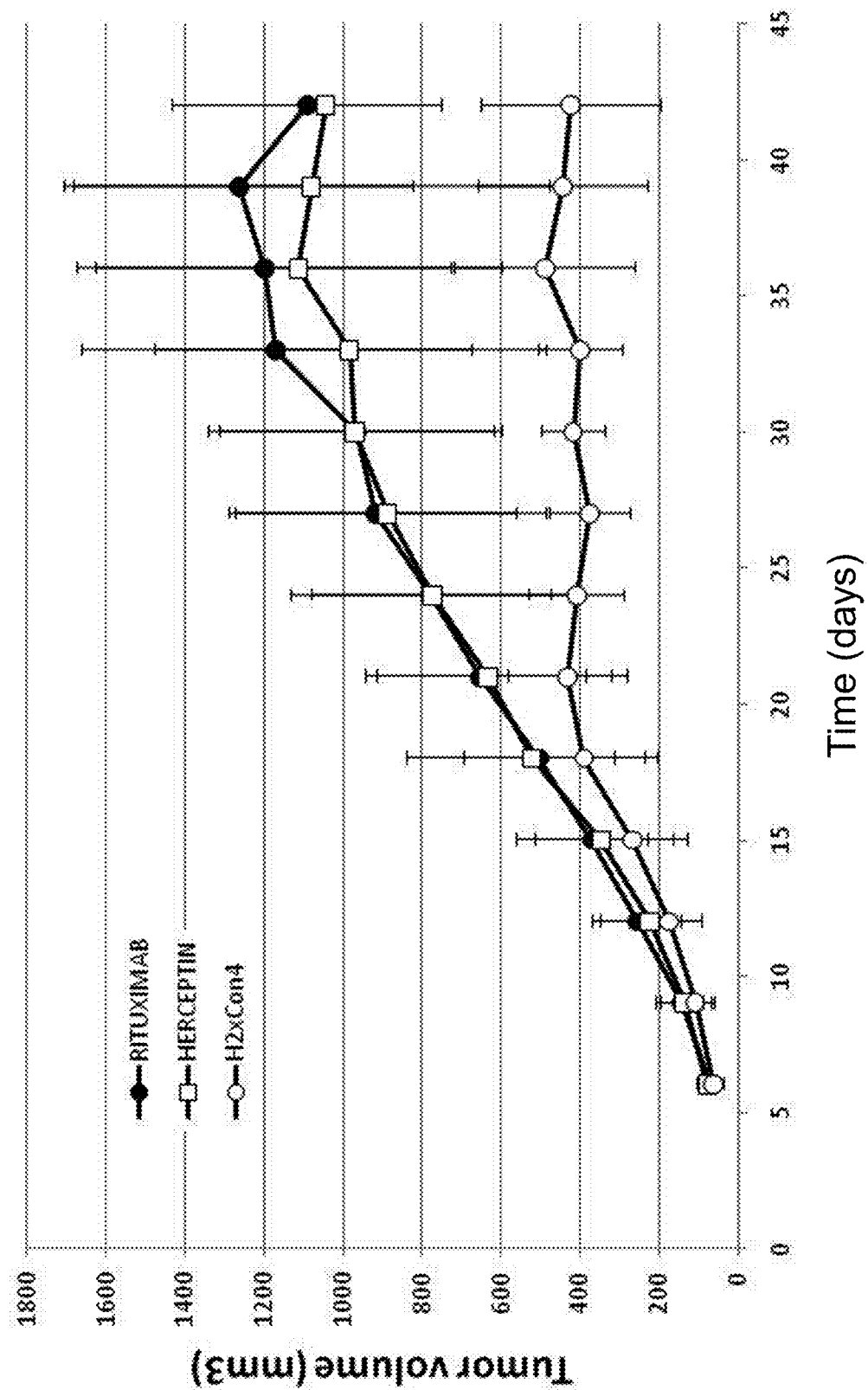

FIG. 27 depicts the effect of RITUXIMAB®, HERCEPTIN®, and an MRD-containing antibody on tumor volume in vivo.

Figures 28A, 28B:
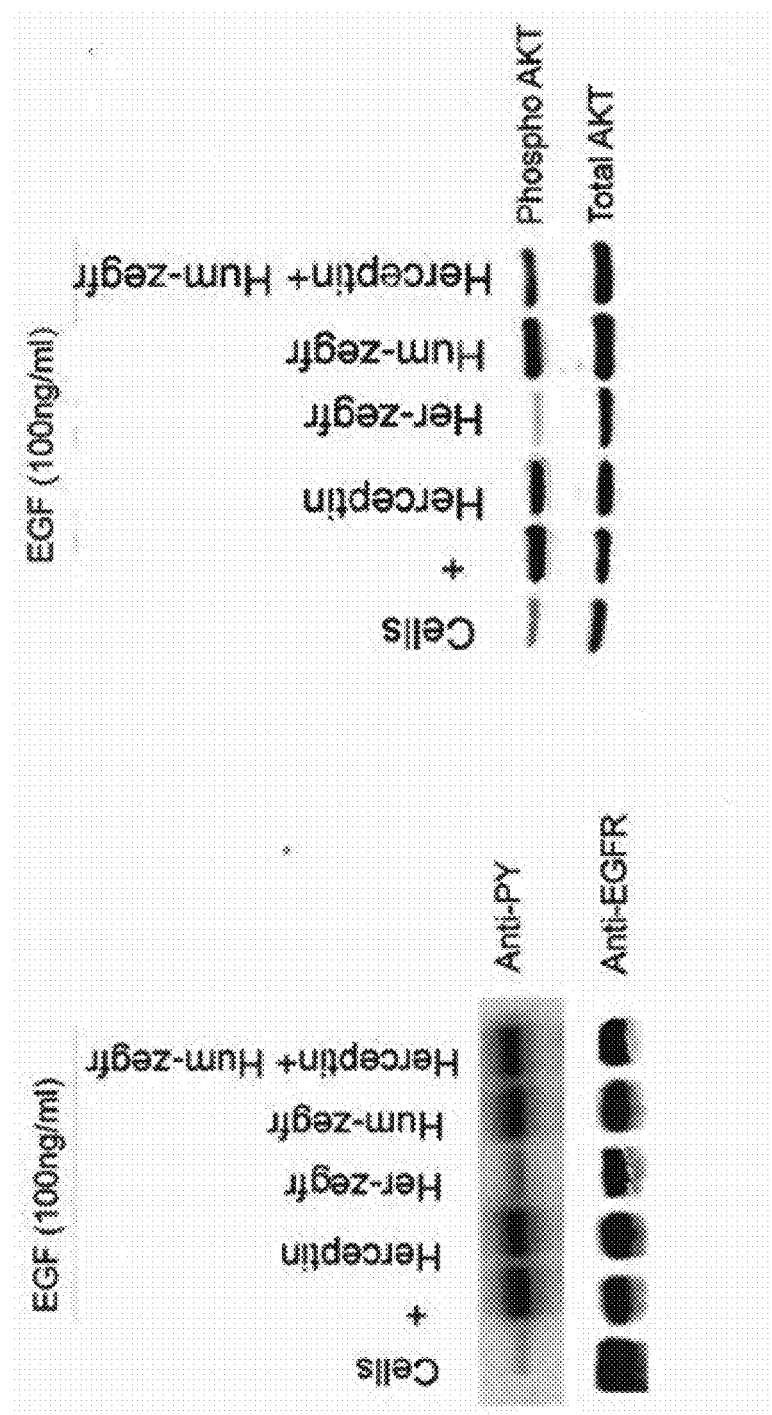

FIGS. 28A and 28B depict the increased effect of an antibody-containing MRD on receptor phosphorylation and AKT activation compared to the effect of an antibody in combination with the MRD.

Figure 29A:
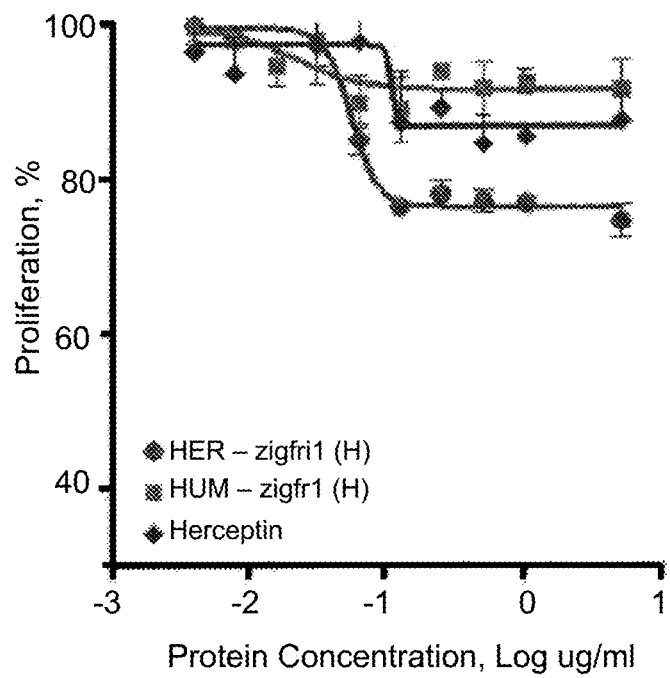

FIG. 29A depicts the increased effect of a bispecific MRD-containing antibody on cell proliferation compared to the effect of the antibody or the antibody in combination with the MRD.

Figure 29B:
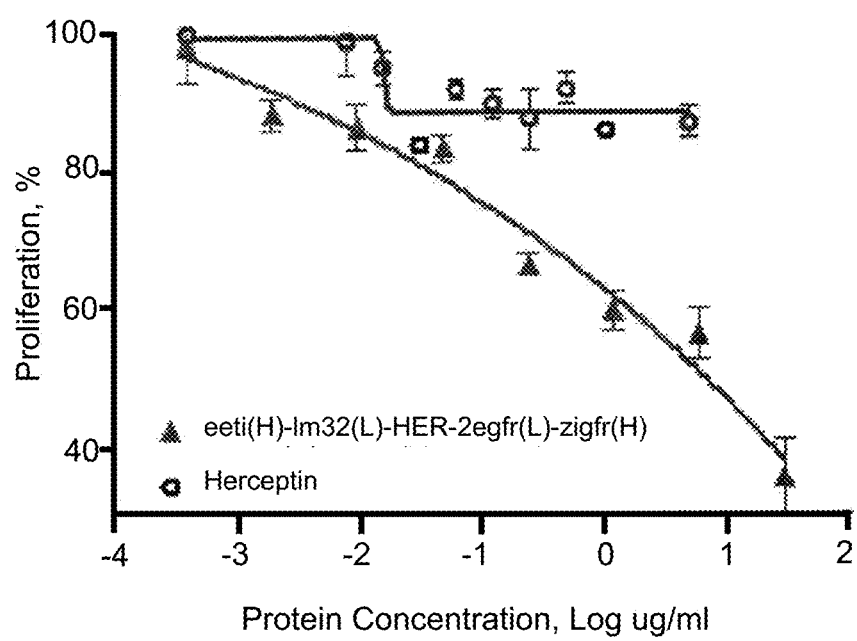

FIG. 29B depicts the increased effect of a pentaspecific MRD-containing antibody on cell proliferation compared to the effect of the antibody or the antibody in combination with the MRD.

Figure 30A:
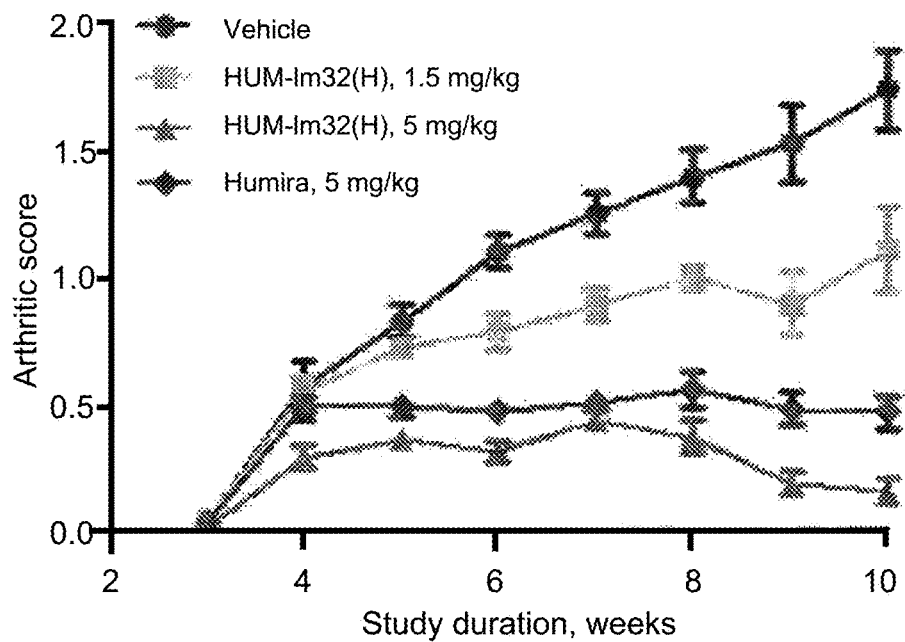
Figure 30B:
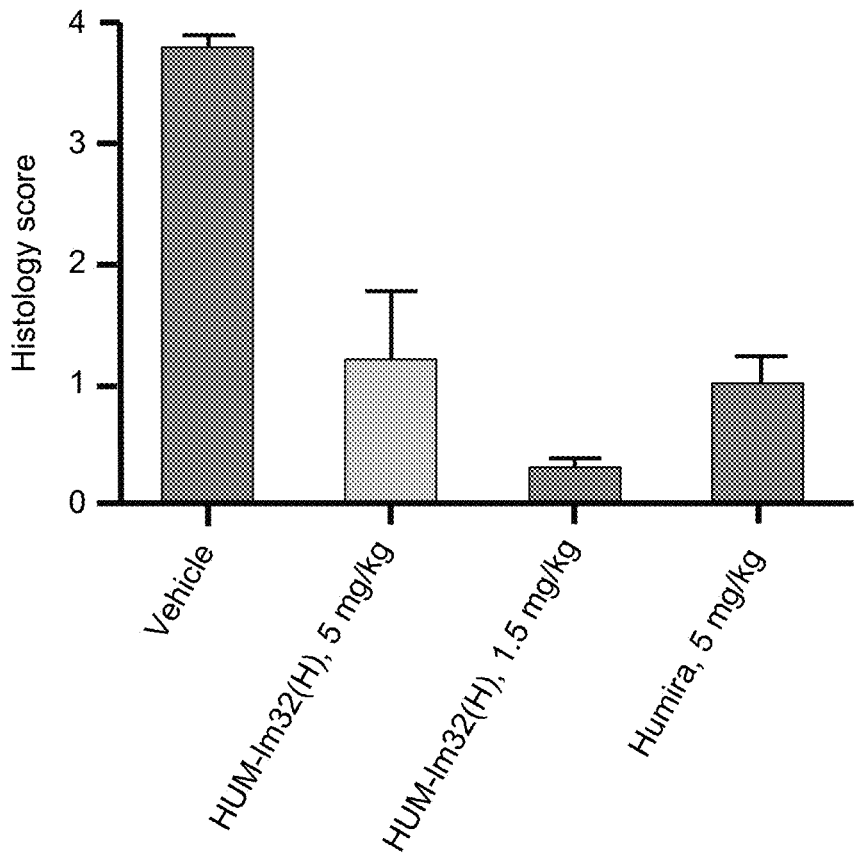

FIGS. 30A and 30B depict the increased efficacy of a HUMIRA antibody containing an Ang2-binding MRD in an arthritis model compared to HUMIRA.

Figure 31:
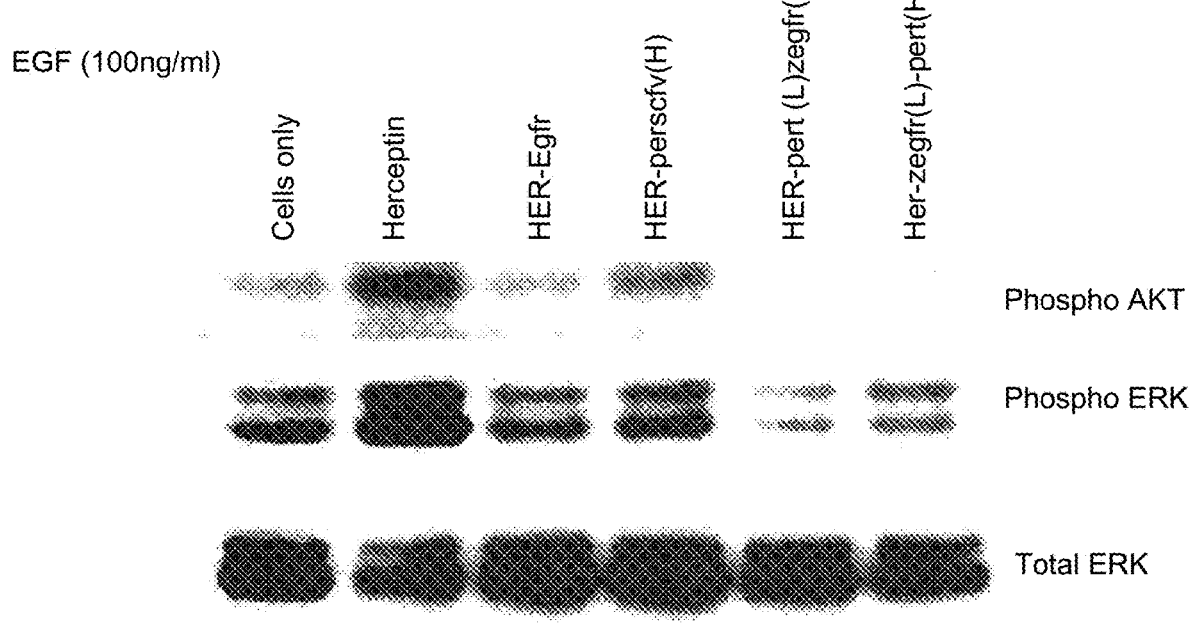

FIG. 31 shows inhibition of EGF-induced signaling in SK-BR3 cells by zybodies.

Figure 32:
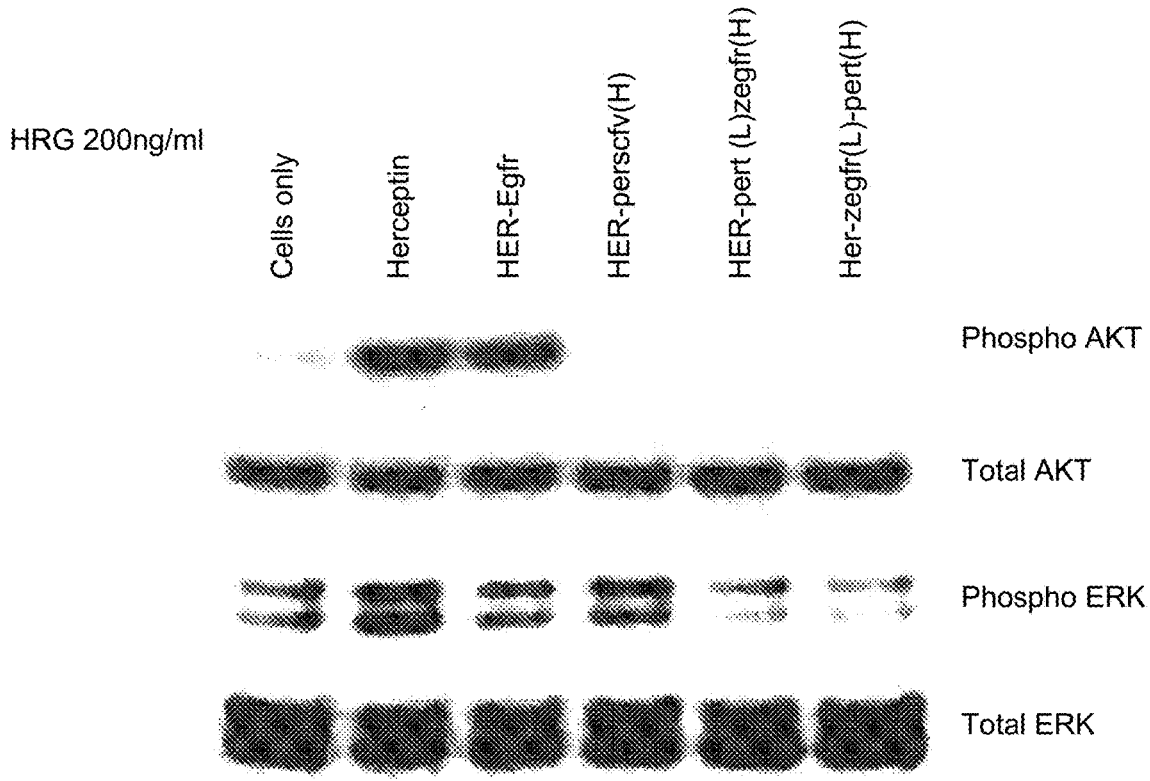

FIG. 32 shows inhibition of Heregulin-induced signaling in SK-BR3 zybodies.

Figures 33, 34A:
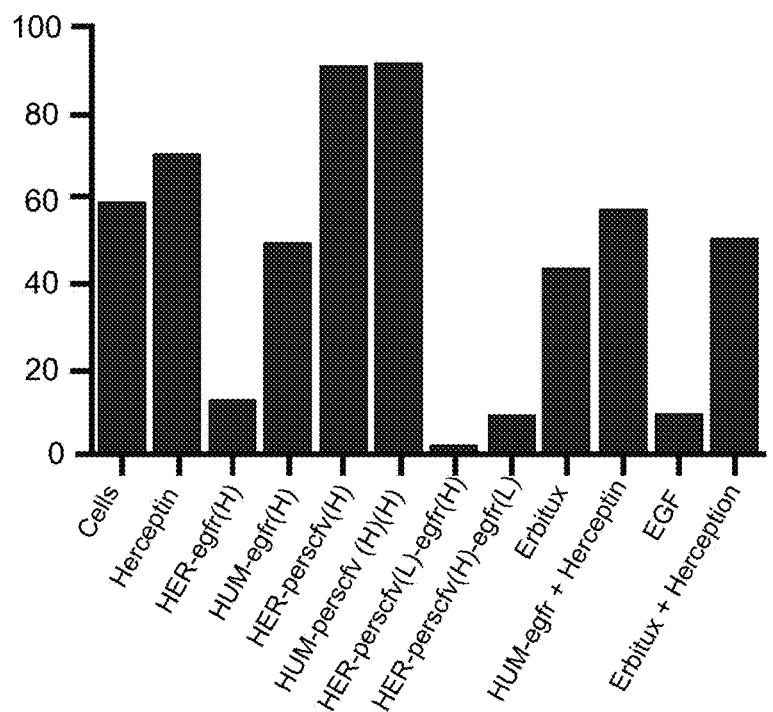
Figure 34B:
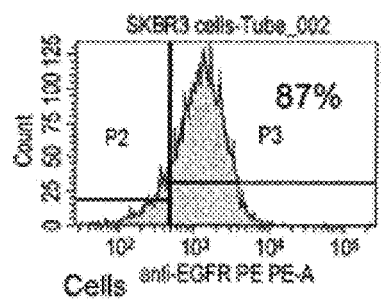
Figure 34C:
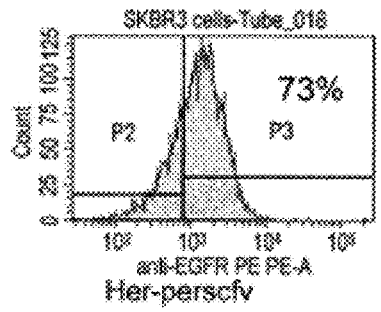
Figure 34D:
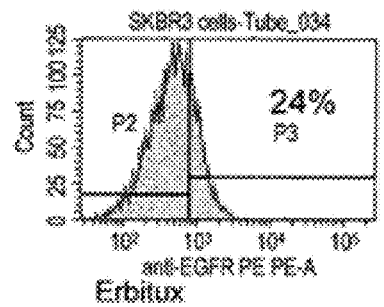
Figure 34E:
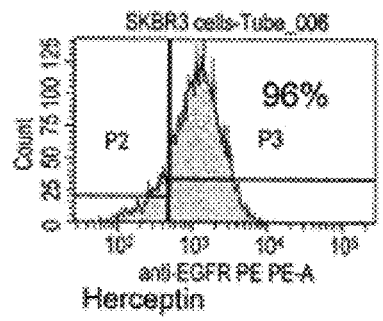
Figure 34F:
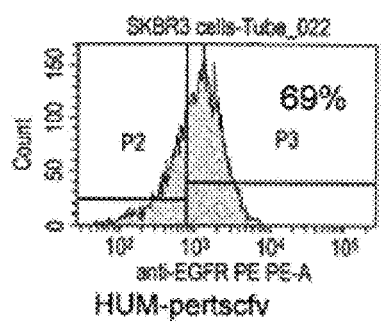
Figure 34G:
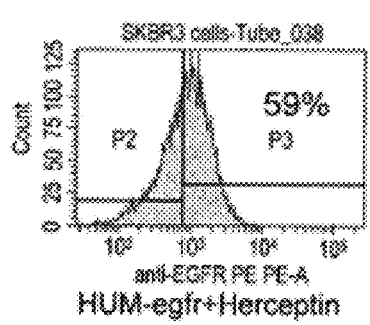
Figure 34H:
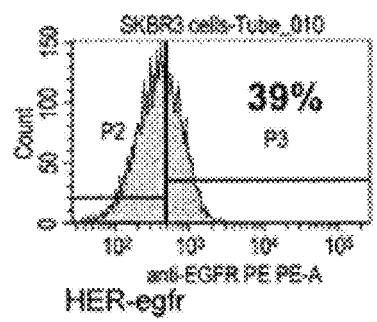
Figure 34I:
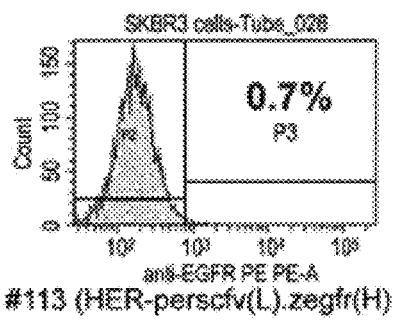
Figure 34J:
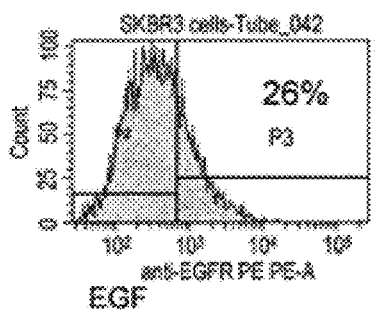
Figure 34K:
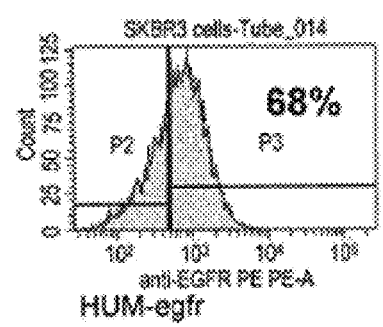
Figure 34L:
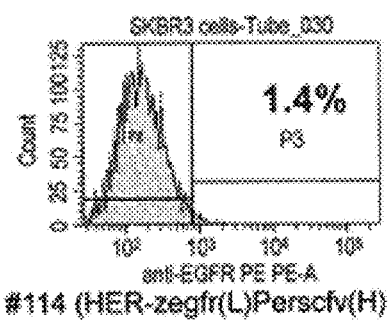
Figure 34M:
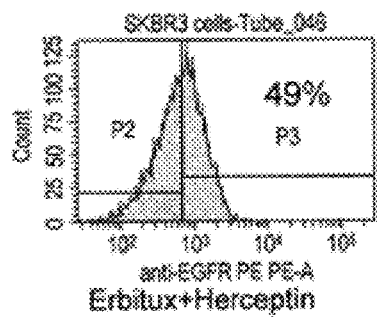

FIG. 33 shows inhibition of EGF and Heregulin-induced signaling in SK-BR3 cells by zybodies.

FIGS. 34A-34M show a bar-graph (A) and flow-cytometry results (B-M) depicting the down-regulation of EGFR expression on SK-BR3 cells by zybodies.

Figure 35:
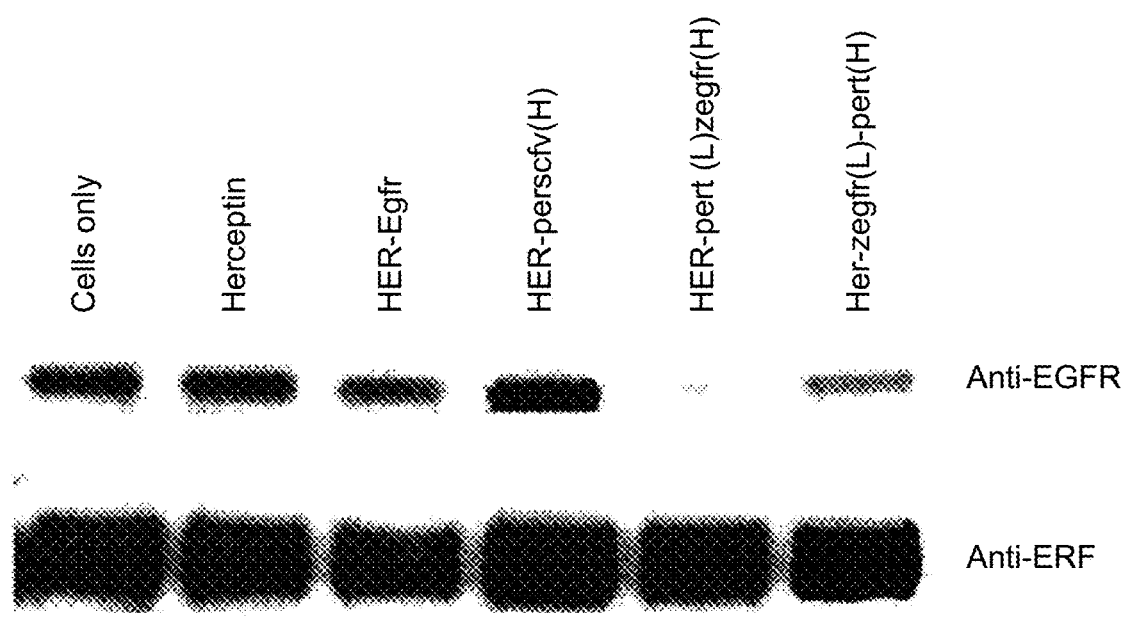

FIG. 35 shows down-regulation of EGFR in SKBR3 cells by zybodies.

DETAILED DESCRIPTION OF THE INVENTION

The following provides a description of antibodies containing at least one modular recognition domain (MRD). The linkage of one or more MRDs to an antibody results in a multi-specific molecule of the invention that retains structural and functional properties of traditional antibodies or Fc optimized antibodies and can readily be synthesized using conventional antibody expression systems and techniques. The antibody can be any suitable antigen-binding immunoglobulin, and the MRDs can be any suitable target-binding peptide. The MRDs can be operably linked to any location on the antibody, and the attachment can be direct or indirect (e.g., through a chemical or polypeptide linker). Compositions of antibodies comprising an MRD, methods of manufacturing antibodies comprising an MRD, and methods of using antibodies comprising MRDs are also described in the sections below.

The section headings used herein are for organizational purposes only and are not to be construed as in any way limiting the subject matter described.

Standard techniques may be used for recombinant DNA molecule, protein, and antibody production, as well as for tissue culture and cell transformation. Enzymatic reactions and purification techniques are typically performed according to the manufacturer's specifications or as commonly accomplished in the art using conventional procedures such as those set forth in Harlow et al., Antibodies: A Laboratory Manual, (Cold Spring Harbor Laboratory Press, 2nd ed. 1988) and Sambrook et al., (Molecular Cloning: A Laboratory Manual. Cold Spring Harbor Laboratory Press, Cold Spring Harbor, N.Y. (1989)) (both herein incorporated by reference), or as described herein. Unless specific definitions are provided, the nomenclature utilized in connection with, and the laboratory procedures and techniques of analytical chemistry, synthetic organic chemistry, and medicinal and pharmaceutical chemistry described herein, are those known and used in the art. Standard techniques may be used for chemical syntheses, chemical analyses, pharmaceutical preparation, formulation, delivery, and treatment of patients.

I. Definitions

The terms "multivalent and monovalent multispecific complexes", "multivalent and multispecific complexes", "MRD-containing antibodies," "antibody-MRD molecules," "MRD-antibody molecules," "antibodies comprising an MRD" and "Zybodies" are used interchangeably herein and do not encompass a peptibody. Each of these terms may also be used herein to refer to a "complex" of the invention. Multivalent and monovalent multispecific complexes can contain MRDs, antibodies, cytoxic agents, and binding motifs in addition to MRDs that bind to one or more targets. For example, a multivalent and monovalent multispecific complex (e.g., an MRD-containing antibody) can contain a portion of, or a derivative of, a binding sequence contained in antibody (e.g., a single binding domain, a ScFv, a CDR region) and/or can also include a cytotoxic agent (e.g., a therapeutic agent). Such molecules are also described in U.S. Provisional Application No. 61/481,063, which is herein incorporated by reference in its entirety. The terms "multivalent and monovalent multispecific complex(es)" and "multivalent and monovalent multispecific complexes" as used herein therefore refer to compositions that are able to bind 2 or more targets and that contain one binding site and/or multiple binding sites for different epitopes. Thus, this term is intended to include complexes containing multiple binding sites for each different epitope bound by the complex, or alternatively, complexes that contain at least one single binding site for a different epitope. The different epitopes can be on the same or different targets. Multivalent and monovalent multispecific complexes can be multivalent and multispecific and can therefore bind two or more targets and have two or more binding sites for each of the targets bound by the complex. Multivalent and monovalent multispecific complexes can also have one (or more) single binding sites for one (or more) target(s) and multiple binding sites for other targets and accordingly, these complexes are monovalent (with respect to the single binding site(s)), multivalent and multispecific. Moreover, multivalent and monovalent multispecific complexes can be monovalent and multispecific and thus, only contain single binding sites for two or more different targets.

The term "multivalent and monovalent multispecific complex-drug complex" or "MRD-containing antibody-cytotoxic agent" as used herein, refers to a multivalent and monovalent multispecific complex containing one or more cytotoxic agents.

The term "cytotoxic agent" as used herein, includes any agent that is detrimental to cells including for example, substance that inhibits or prevents the function of cells and/or causes destruction of cells. The term is intended to include a chemotherapeutic agent, a drug moiety (e.g., a cytokine or prodrug), an antibiotic, a radioactive isotope, a chelating ligand (e.g., DOTA, DOTP, DOTMA, DTPA and TETA), a nucleolytic enzyme, a toxins such as a small molecule toxin or enzymatically active toxin of bacterial, fungal, plant or animal origin, including fragments and/or variants of these toxins. In particular embodiments, the cytotoxic agent is a member selected from: auristatin, dolostantin, MMAE, MMAF, a maytansinoid derivative (e.g., the DM1 (N(2')-deacetyl-N(2')-(3-mercapto-1-oxopropyl)-maytansine), DM3 (N(2')-deacetyl-N2-(4-mercapto-1-oxopentyl)-maytansine) and DM4 (N(2')-deacetyl-N2-(4-mercapto-4-methyl-1-oxopentyl)-maytansine).

The term "antibody" is used herein to refer to immunoglobulin molecules that are able to bind antigens through an antigen binding domain (i.e., antibody combining site). The term "antibody" includes polyclonal, oligoclonal (mixtures of antibodies), and monoclonal antibodies, chimeric, single chain, and humanized antibodies. The term "antibody" also includes human antibodies. In some embodiments, an antibody comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains: CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. In other embodiments, the antibody is a homomeric heavy chain antibody (e.g., camelid antibodies) which lacks the first constant region domain (CH1) but retains an otherwise intact heavy chain and is able to bind antigens through an antigen binding domain. The variable regions of the heavy and light chains in the antibody-MRD fusions of the invention contain a functional binding domain that interacts with an antigen.

The term "monoclonal antibody" typically refers to a population of antibody molecules that contain only one species of antibody combining site capable of immunoreacting with a particular epitope. A monoclonal antibody thus typically displays a single binding affinity for any epitope with which it immunoreacts. As used herein, a "monoclonal antibody" may also contain an antibody molecule having a plurality of antibody combining sites (i.e., a plurality of variable domains), each immunospecific for a different epitope, e.g., a bispecific monoclonal antibody. Thus, as used herein, a "monoclonal antibody" refers to a homogeneous antibody population involved in the highly specific recognition and binding of one or two (in the case of a bispecific monoclonal antibody) antigenic determinants, or epitopes. This is in contrast to polyclonal antibodies that typically include different antibodies directed against different antigenic determinants. The term "monoclonal antibody" refers to such antibodies made in any number of manners including but not limited to by hybridoma, phage selection, recombinant expression, yeast, and transgenic animals.

A "dual-specific antibody" is used herein to refer to an immunoglobulin molecule that contains dual-variable-domain immunoglobulins, where the dual-variable-domain can be engineered from any two monoclonal antibodies.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity and/or affinity while the constant regions are homologous to the sequences in antibodies derived from another species (usually human) to avoid eliciting an immune response in that species.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementarity determining region (CDR) are replaced by residues from the CDR of a non-human species (e.g., mouse, rat, rabbit, hamster) that have the desired specificity and/or affinity (Jones et al., Nature, 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody from a non-human species that has the desired specificity and/or affinity. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise an immunoglobulin constant region or domain (Fc), typically that of a human immunoglobulin. Examples of methods used to generate humanized antibodies are described in U.S. Pat. Nos. 5,225,539, 4,816,567, Morrison, Science 229:1202 (1985); Oi et al., BioTechniques 4:214 (1986); Cabilly et al., Taniguchi et al., EP 171496; Morrison et al., EP 173494, WO86/01533; WO8702671; Boulianne et al., Nature 312:643 (1984); and Neuberger et al., Nature 314:268 (1985), each of which is herein incorporated by reference in its entirety.

As used herein, "human" antibodies include antibodies having the amino acid sequence of a human immunoglobulin or one or more human germlines and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al., A human antibody may still be considered "human" even if amino acid substitutions are made in the antibody. Examples of methods used to generate human antibodies are described in: Int. Appl. Publ. Nos. WO98/24893, WO92/01047, WO96/34096, and WO96/33735; European Pat. No. 0 598 877; U.S. Pat. Nos. 5,413,923, 5,625,126, 5,633,425, 5,569,825, 5,661,016, 5,545,806, 5,814,318, 5,885,793, 5,916,771, and 5,939,598; and Lonberg and Huszar, Int. Rev. Immunol. 13:65-93 (1995), which are herein incorporated by reference.

An "antibody combining site" is that structural portion of an antibody molecule comprised of heavy and light chain variable and hypervariable regions that specifically binds (immunoreacts with) an antigen. The term "immunoreact" in its various forms means specific binding between an antigenic determinant-containing molecule and a molecule containing an antibody combining site such as a whole antibody molecule or a portion thereof.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less intermolecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain (i.e., antibody combining site) formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol. 196:901-917 (1987), which are herein incorporated by reference). "Humanized antibody" or "chimeric antibody" includes antibodies in which CDR sequences derived from the germline of another mammalian species, such as a mouse, have been grafted onto human framework sequences.

The terms "T lymphocyte," "T cell," "T cells," and "T cell population," are used interchangeably herein to refer to a cell or cells which display on their surface one or more antigens characteristic of T cells, for example, CD3 and CD11b. The term includes progeny of a T cell or T cell population. A "T lymphocyte" or "T cell" includes a cell which expresses CD3 on its cell surface and a T cell antigen receptor (TCR) capable of recognizing antigen when displayed on the surface of autologous cells, or any antigen-presenting matrix, together with one or more MHC molecules or, one or more non-classical MHC molecules. The term "T cells" may refer to any T cells, including for example, lymphocytes that are phenotypically $CD3^+$ i.e., express CD3 on the cell surface.

As used herein, CD3, is used to refer individually or collectively to a molecule expressed as part of the T cell receptor and having a meaning as typically ascribed to it in the art. In humans, the term CD3 encompasses all known CD3 subunits, for example CD3 delta, CD3 epsilon, CD3 gamma, and CD3 zeta (TCR zeta), as well as CD3 alpha (TCR alpha), and CD3 beta (TCR beta) in individual or independently combined form.

The term "peptibody" refers to a peptide or polypeptide which comprises less than a complete, intact antibody. A peptibody can be an antibody Fc domain attached to at least one peptide. A peptibody does not include antibody variable regions, an antibody combining site, CH1 domains, or Ig light chain constant region domains.

The term "naturally occurring" when used in connection with biological materials such as a nucleic acid molecules, polypeptides, host cells, and the like refers to those which are found in nature and not modified by a human being.

The term "domain" as used herein refers to a part of a molecule or structure that shares common physical or chemical features, for example hydrophobic, polar, globular, helical domains or properties, e.g., a protein binding domain, a DNA binding domain or an ATP binding domain. Domains can be identified by their homology to conserved structural or functional motifs.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence to the antigen(s) to which the polypeptide or antibody binds. Methods of identifying nucleotide and amino acid conservative substitutions and non-conservative substitutions which do not eliminate polypeptide or antigen binding are well-known in the art (see, e.g., Brummell et al., Biochem. 32:1180-1187 (1993); Kobayashi et al., Protein Eng. 12(10):879-884 (1999); and Burks et al., Proc. Natl. Acad. Sci. USA 94:412-417 (1997)).

A "modular recognition domain" (MRD) or "target binding peptide" is a molecule, such as a protein, glycoprotein and the like, that can specifically (non-randomly) bind to a target molecule. The amino acid sequence of a MRD can typically tolerate some degree of variability and still retain a degree of capacity to bind the target molecule. Furthermore, changes in the sequence can result in changes in the binding specificity and in the binding constant between a preselected target molecule and the binding site. In one embodiment, the MRD is an agonist of the target it binds. An MRD agonist refers to a MRD that in some way increases or enhances the biological activity of the MRD's target protein or has biological activity comparable to a known agonist of the MRD's target protein. In another embodiment, the MRD is an antagonist of the target it binds. An MRD antagonist refers to an MRD that blocks or in some way interferes with the biological activity of the MRD's target protein or has biological activity comparable to a known antagonist or inhibitor of the MRD's target protein.

"Cell surface receptor" refers to molecules and complexes of molecules capable of receiving a signal and the transmission of such a signal across the plasma membrane of a cell. An example of a cell surface receptor of the present invention is an activated integrin receptor, for example, an activated αvβ3 integrin receptor on a metastatic cell. As used herein, "cell surface receptor" also includes a molecule expressed on a cell surface that is capable of being bound by an MRD containing antibody of the invention.

As used herein, a "target binding site" or "target site" is any known, or yet to be defined, amino acid sequence having the ability to selectively bind a preselected agent. Exemplary reference target sites are derived from the RGD-dependent integrin ligands, namely fibronectin, fibrinogen, vitronectin, von Willebrand factor and the like, from cellular receptors such as ErbB2, VEGF, vascular homing peptide or angiogenic cytokines, from protein hormones receptors such as insulin-like growth factor-I receptor, epidermal growth factor receptor and the like, and from tumor antigens.

The term "epitope" or "antigenic determinant" are used interchangeably herein and refer to that portion of any molecule capable of being recognized and specifically bound by a particular binding agent (e.g., an antibody or an MRD). When the recognized molecule is a polypeptide, epitopes can be formed from contiguous amino acids and noncontiguous amino acids and/or other chemically active surface groups of molecules (such as carbohydrates) juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

An antibody, MRD, antibody-containing MRD, or other molecule is said to "competitively inhibit" binding of a reference molecule to a given epitope if it binds to that epitope to the extent that it blocks, to some degree, binding of the reference molecule to the epitope. Competitive inhibition may be determined by any method known in the art, for example, competition ELISA assays. As used herein, an antibody, MRD, antibody-containing MRD, or other molecule may be said to competitively inhibit binding of the reference molecule to a given epitope, for example, by at least 90%, at least 80%, at least 70%, at least 60%, or at least 50%.

The term "protein" is defined as a biological polymer comprising units derived from amino acids linked via peptide bonds; a protein can be composed of two or more chains.

A "fusion polypeptide" is a polypeptide comprised of at least two polypeptides and optionally a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature. The two polypeptides may be operably attached directly by a peptide bond or may be linked indirectly through a linker described herein or otherwise known in the art.

The term "operably linked," as used herein, indicates that two molecules are attached so as to each retain functional activity. Two molecules are "operably linked" whether they are attached directly (e.g., a fusion protein) or indirectly (e.g., via a linker).

The term "linker" refers to a peptide located between the antibody and the MRD or between two MRDs. Linkers can have from about 1 to 20 amino acids, about 2 to 20 amino acids, or about 4 to 15 amino acids. One or more of these amino acids may be glycosylated, as is well understood by those in the art. In one embodiment, the 1 to 20 amino acids are selected from glycine, alanine, proline, asparagine, glutamine, and lysine. In another embodiment, a linker is made up of a majority of amino acids that are sterically unhindered, such as glycine and alanine. Thus, in some embodiments, the linker is selected from polyglycines (such as $(Gly)_5$, and $(Gly)_8$), poly(Gly-Ala), and polyalanines. The linker can also be a non-peptide linker such as an alkyl linker, or a PEG linker. For example, alkyl linkers such as —NH—$(CH_2)$s-C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker. In certain embodiments, the PEG linker has a molecular weight of about 100 to 5000 kDa, or about 100 to 500 kDa. The peptide linkers may be altered to form derivatives. In some embodiments, the linker is a non-peptide linker such as an alkyl linker, or a PEG linker. In further embodiments, the linker is a "cleavable linker" facilitating release of an MRD or cytotoxic agent within a cell or in the proximity of the cell.

"Target cell" refers to any cell in a subject (e.g., a human or animal) that can be targeted by a multispecific and multivalent composition (e.g., an antibody-containing MRD) or MRD of the invention. The target cell can be a cell expressing or overexpressing the target binding site, such as an activated integrin receptor.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells, or tissues infected with pathogens, cancerous cells, or, in cases of autoimmunity or pathological inflammation, normal human cells or tissues.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils). Some effector cells express specific Fc receptors and carry out specific immune functions. In certain embodiments, an effector cell is capable of inducing antibody-dependent cell-mediated cytotoxicity (ADCC), e.g., a neutrophil capable of inducing ADCC. For example, monocytes and macrophages, which express FcR, are involved in specific killing of target cells and presenting antigens to other components of the immune system, or binding to cells that present antigens. In other embodiments, an effector cell can phagocytose a target antigen or target cell. The expression of a particular FcR on an effector cell can be regulated by humoral factors such as cytokines. For example, expression of Fc alpha RI has been found to be up-regulated by G-CSF or GM-CSF. This enhanced expression increases the effector function of Fc alpha RI-bearing cells against targets. Exemplary functions of an effector cell include the phagocytosing or lysing of a target antigen or a target cell.

"Target cell" refers to any cell or pathogen whose elimination would be beneficial in a patient (e.g., a human or animal) and that can be targeted by a composition (e.g., antibody) of the invention.

"Patient," "subject," "animal" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles. In some embodiments, the patient is a human.

"Treating" or "treatment" includes the administration of the antibody comprising an MRD of the present invention to prevent or delay the onset of the symptoms, complications, or biochemical indicia of a disease, condition, or disorder, alleviating the symptoms or arresting or inhibiting further development of the disease, condition, or disorder. Treatment can be prophylactic (to prevent or delay the onset of the disease, or to prevent the manifestation of clinical or subclinical symptoms thereof) or therapeutic suppression or alleviation of symptoms after the manifestation of the disease, condition, or disorder. Treatment can be with the antibody-MRD composition alone, the MRD alone, or in combination of either with one or more additional therapeutic agents.

As used herein, the terms "pharmaceutically acceptable," or "physiologically tolerable" and grammatical variations thereof, as they refer to compositions, carriers, diluents and reagents, are used interchangeably and represent that the materials are capable of administration to or upon a human without the production of therapeutically prohibitive undesirable physiological effects such as nausea, dizziness, gastric upset and the like.

"Modulate," means adjustment or regulation of amplitude, frequency, degree, or activity. In another related aspect, such modulation may be positively modulated (e.g., an increase in frequency, degree, or activity) or negatively modulated (e.g., a decrease in frequency, degree, or activity).

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. A "cancerous tumor," or "malignant cell" is understood as a cell having specific structural properties, lacking differentiation and being capable of invasion and metastasis. Examples of cancers that may be treated using the antibody-MRD fusions of the invention include solid tumors and hematologic cancers. Additional, examples of cancers that may be treated using the antibody-MRD fusions of the invention include breast, lung, brain, bone, liver, kidney, colon, head and neck, ovarian, hematopoietic (e.g., leukemia), and prostate cancer. Further examples of cancer that may be treated using the multivalent and multispecific compositions (e.g., MRD-containing antibodies) include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers. Other types of cancer and tumors that may be treated using multivalent and multispecific compositions (e.g., MRD-containing antibodies) are described herein or otherwise known in the art.

An "effective amount" of an antibody, MRD, or MRD-containing antibody as disclosed herein is an amount sufficient to carry out a specifically stated purpose such as to bring about an observable change in the level of one or more biological activities related to the target to which the antibody, MRD, or MRD-containing antibody binds. In certain embodiments, the change increases the level of target activity. In other embodiments, the change decreases the level of target activity. An "effective amount" can be determined empirically and in a routine manner, in relation to the stated purpose.

The term "therapeutically effective amount" refers to an amount of an antibody, MRD, MRD-containing antibody, other multivalent and multispecific drug of the invention, or other drug effective to "treat" a disease or disorder in a patient or mammal. In the case of cancer, the therapeutically effective amount of the drug can reduce angiogenesis and neovascularization; reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth or tumor incidence; stimulate immune responses against cancer cells and/or relieve to some extent one or more of the symptoms associated with the cancer. See the definition herein of "treating". A "therapeutically effective amount" also may refer to an amount effective, at dosages and for periods of time necessary, to achieve a desired therapeutic result. A therapeutically effective amount of a composition of the invention may vary according to factors such as the disease state, age, sex, and weight of the individual, and the ability of the composition to elicit a desired response in the individual. A therapeutically effective amount is also one in which any toxic or detrimental effects of the therapeutic composition are outweighed by the therapeutically beneficial effects.

To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically, but not necessarily, since a prophylactic dose is used in subjects (patients) prior to or at an earlier stage of disease, the prophylactically effective amount will be less than the therapeutically effective amount.

Where embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the disclosed and/or claimed invention.

II. Modular Recognition Domains (MRDs)

The present invention describes an approach based on the adaptation of target binding peptides or modular recognition domains (MRDs) as fusions to catalytic or non-catalytic antibodies.

In certain embodiments, where the antibody component of the MRD-antibody fusion is a catalytic antibody, the MRD-antibody fusions provide for effective targeting to tumor cells or soluble molecules while leaving the prodrug activation capability of the catalytic antibody intact. MRDs can also extend the binding capacity of non-catalytic antibodies providing for an effective approach to extend the binding functionality of antibodies, particularly for therapeutic purposes.

One aspect of the present invention relates to development of a full-length antibody comprising at least one modular recognition domain (MRD). In another non-exclusive embodiment, the full-length antibody comprises more than one MRD, wherein the MRDs have the same or different specificities. In addition, a single MRD may be comprised of a tandem repeat of the same or different amino acid sequence that can allow for the binding of a single MRD to multiple targets and/or to a repeating epitope on a given target.

The interaction between a protein ligand and its target receptor site often takes place at a relatively large interface. However, only a few key residues at the interface contribute to most of the binding. The MRDs can mimic ligand binding. In certain embodiments, the MRD can mimic the biological activity of a ligand (an agonist MRD) or through competitive binding inhibit the bioactivity of the ligand (an antagonist MRD). MRDs in multivalent and multispecific compositions (e.g., MRD-containing antibodies) can also affect targets in other ways, e.g., by neutralizing, blocking, stabilizing, aggregating, or crosslinking the MRD target.

It is contemplated that MRDs of the present invention will generally contain a peptide sequence that binds to target sites of interests and have a length of about 2 to 150 amino acids, about 2 to 125 amino acids, about 2 to 100 amino acids, about 2 to 90 amino acids, about 2 to 80 amino acids, about 2 to 70 amino acids, about 2 to 60 amino acids, about 2 to 50 amino acids, about 2 to 40 amino acids, about 2 to 30 amino acids, or about 2 to 20 amino acids. It is also contemplated that MRDs have a length of about 10 to 150 amino acids, about 10 to 125 amino acids, about 10 to 100 amino acids, about 10 to 90 amino acids, about 10 to 80 amino acids, about 10 to 70 amino acids, about 10 to 60 amino acids, about 10 to 50 amino acids, about 10 to 40 amino acids, about 10 to 30 amino acids, or about 10 to 20 amino acids. It is further contemplated that MRDs have a length of about 20 to 150 amino acids, about 20 to 125 amino acids, about 20 to 100 amino acids, about 20 to 90 amino acids, about 20 to 80 amino acids, about 20 to 70 amino acids, about 20 to 60 amino acids, about 20 to 50 amino acids, about 20 to 40 amino acids, or about 20 to 30 amino acids. In certain embodiments, the MRDs have a length of about 2 to 60 amino acids. In other embodiments, the MRDs have a length of about 10 to 60 amino acids. In other embodiments, the MRDs have a length of about 10 to 50 amino acids. In additional embodiments, the MRDs have a length of about 10 to 40 amino acids. In additional embodiments, the MRDs have a length of about 10 to 30 amino acids.

In some embodiments, one or more of the MRD components of the multivalent and multispecific compositions (e.g., MRD-containing antibodies) have a dissociation constant or Kd of less than $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In one embodiment, one or more of the MRD components of the multivalent and multispecific compositions (e.g., MRD-containing antibodies) have a dissociation constant or Kd less than $5 \times 10^{-5}$ M. In another embodiment, one or more of the MRD components of the multivalent and multispecific compositions (e.g., MRD-containing antibodies) have a dissociation constant or Kd less than $5 \times 10^{-8}$ M. In another embodiment, one or more of the MRD components of the multivalent and multispecific compositions (e.g., MRD-containing antibodies) have a dissociation constant or Kd less than $5 \times 10^{-9}$ M. In another embodiment, one or more of the MRD components of the multivalent and multispecific compositions (e.g., MRD-containing antibodies) have a dissociation constant or Kd less than $5 \times 10^{-10}$ M. In another embodiment, one or more of the MRD components of the multivalent and multispecific compositions (e.g., MRD-containing antibodies) have a dissociation constant or Kd less than $5 \times 10^{-11}$ M. In another embodiment, one or more of the MRD components of the multivalent and multispecific compositions (e.g., MRD-containing antibodies) have a dissociation constant or Kd less than $5 \times 10^{-12}$ M.

In specific embodiments, one or more of the MRD components of the multivalent and multispecific compositions (e.g., MRD-containing antibodies) bind their targets with an off rate ($k_{off}$) of less than $5 \times 10^{-2}$ sec$^{-1}$, $10^{-2}$ sec$^{-1}$, $5 \times 10^{-3}$ sec$^{-1}$, or $10^{-3}$ sec$^{-1}$. More preferably, one or more of the MRD components of the multivalent and multispecific compositions (e.g., MRD-containing antibodies) bind their targets with an off rate ($k_{off}$) of less than $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$, or $10^{-7}$ sec$^{-1}$.

In other specific embodiments, one or more of the MRD components of the multivalent and multispecific compositions (e.g., MRD-containing antibodies) bind their targets with an on rate ($k_{on}$) of greater than $10^3$ M$^{-1}$sec$^{-1}$, $5 \times 10^3$ M$^{-1}$sec$^{-1}$, $10^4$ M$^{-1}$sec$^{-1}$, or $5 \times 10^4$ M$^{-1}$sec$^{-1}$. More preferably, one or more of the MRD components of the multivalent and multispecific compositions (e.g., MRD-containing antibodies) bind their targets with an on rate ($k_{on}$) of greater than $10^5$ M$^1$sec$^{-1}$, $5 \times 10^5$ M$^{-1}$sec$^{-1}$, $10^6$ M$^{-1}$sec$^{-1}$, or $5 \times 10^6$ M$^1$sec$^{-1}$, or $10^7$ M$^{-1}$ sec$^{-1}$.

In some embodiments, the MRDs are affibodies. Affibodies represent a class of affinity proteins based on a 58-amino acid residue protein domain derived from one of the IgG-binding domains of staphylococcal protein A. This three helix bundle domain has been used as a scaffold for the construction of combinatorial phagemid libraries, from which affibody variants that bind a desired target molecule, such as one or more of the targets disclosed herein, can routinely be selected using phage display technology (see, e.g., Nord et al., Nat. Biotechnol. 15:772-7 (1997), and Ronmark et al., A, Eur. J. Biochem. 2002; 269:2647-55). Further details of Affibodies and methods of production thereof are provided by reference to U.S. Pat. No. 5,831,012, which is herein incorporated by reference in its entirety.

In other embodiments, an MRD of the invention (e.g., an MRD on an MRD-containing antibody) contains one or more amino acid residues or sequences of amino acid residues (including derivatives, analogs, and mimetics thereof) that are preferentially targeted by chemistries or other processes that covalently or non-covalently link a molecular entity to the MRD, as compared to, the MRD without the preferentially targeted sequences or the antibody component of the MRD-containing antibody. For example, in some embodiments, the amino acid sequence of the MRD contains one or more residues having a reactive side chain (e.g., cysteine or lysine) that allows for selective or preferential linkage of the MRD to cytotoxic agents (e.g., drug and prodrug conjugates, toxins, and bioactive ligands) or imaging agents.

The use of these "linking" MRDs to arm an MRD-comprising antibody with a "payload" overcomes many of the issues associated with antibody destabilization and reduction in antibody activity that have frequently been observed using conventional methods for generating immunotoxins. The "payload" component of an MRD-comprising antibody complex of the invention can be any composition that confers a beneficial therapeutic, diagnostic, or prognostic effect, or that provide an advantage in manufacturing, purifying or formulating an MRD-containing antibody. In some embodiments, the payload is a chemotherapeutic drug, or a prodrug, such as, doxorubicin or a maytansinoid-like drug. In additional embodiments, the payload is another MRD, a toxin, a chemotherapeutic drug, a catalytic enzyme, a prodrug, a radioactive nuclide, a chelator (e.g., for the attachment of lanthanides) or another component of the multivalent and multispecific compositions of the invention as described herein.

In nonexclusive embodiments, the MRD does not contain an antigen binding domain, or another antibody domain such as a constant region, a variable region, a complementarity determining region (CDR), a framework region, an Fc domain, or a hinge region. In one non-exclusive embodiment, the MRD does not contain an antigen binding domain.

In another non-exclusive embodiment, the MRD does not contain three CDRs. In another non-exclusive embodiment, the MRD does not contain CDR1 and CDR2. In yet another non-exclusive embodiment, the MRD does not contain CDR1. In one nonexclusive embodiment, the MRD is not derived from a natural cellular ligand. In another nonexclusive embodiment, the MRD is not a radioisotope. In another nonexclusive embodiment, the MRD is not a protein expression marker such as glutathione S-transferase (GST), His-tag, Flag, hemagglutinin (HA), MYC or a fluorescent protein (e.g., GFP or RFP). In another nonexclusive embodiment, the MRD does not bind serum albumin. In an additional nonexclusive embodiment, the MRD is not a small molecule that is a cytotoxin. It yet another nonexclusive embodiment, the MRD does not have enzymatic activity. In another non-exclusive embodiment, the MRD has a therapeutic effect when administered alone and/or when fused to an Fc in a patient or animal model. In another non-exclusive embodiment, the MRD has a therapeutic effect when repeatedly administered alone and/or when fused to an Fc in a patient or animal model (e.g., 3 or more times over the course of at least six months).

In some embodiments, the MRD is conformationally constrained. In other embodiments, the MRD is not conformationally constrained. In some embodiments, the MRD contains one cysteine residue. The cysteine residue in the MRD can form an interchain bond (e.g., between cysteines within the same MRD, different peptide linked MRDs, and an MRD and a peptide linked immunoglobulin). In some embodiments, the MRD(s) participating in the interchain bond is/are associated with a single core target-binding domain. In other embodiments, the MRD(s) participating in the interchain bond is/are associated with multiple core target-binding domains. In an alternative embodiment, the cysteine residue in the MRD can form an interchain bond (e.g., between cysteines of non-peptide linked MRDs or an MRD and an immunoglobulin that are not linked by a peptide bind). In some embodiments, the MRD(s) associated with the interchain bond is/are associated with a single core target-binding domain (i.e., 2 MRDs located on different polypeptide chains form one or more interchain bonds and collectively form one target binding site). Thus, for example, the invention encompasses MRD-containing antibodies wherein MRDs located on the carboxyl terminus of the heavy chain interact (e.g., via disulfide bond) so as to form a single target binding site. In other embodiments, the MRD(s) associated with the interchain bond is/are associated with multiple core target-binding domains. Alternatively, as discussed herein, the MRD can contain one or more cysteine residues (or other residue having a reactive side chain (e.g., lysine)) that allows for selective or preferential linkage of the MRD to a cytotoxic agent.

In some embodiments, the MRD contains two cysteine residues outside the core target-binding domain. In some embodiments, the MRD contains two cysteine residues located within the core target-binding domain at each end of the target-binding domain. In some embodiments, a first cysteine is located near the terminus of the molecule (i.e. at the C-terminus of an MRD on the C-terminus of a linker or antibody chain or at the N-terminus of an MRD on the N-terminus of a linker or antibody chain). Thus, in some embodiments, a first cysteine is located within one amino acid, within two amino acids, within three amino acids, within four amino acids, within five amino acids, or within six amino acids of the terminus of the molecule. In some embodiments, a second cysteine is located near the MRD fusion location (i.e. at the N-terminus of an MRD on the C-terminus of a linker or antibody chain or at the C-terminus of an MRD on the N-terminus of a linker or antibody chain). Thus, in some embodiments, a second cysteine is located within one amino acid, within two amino acids, within three amino acids, within four amino acids, within five amino acids, within 10 amino acids, or within 15 amino acids from the MRD fusion.

In some embodiments, the MRD is capped with stable residues. In some embodiments, the MRD is disulfide capped. In some embodiments, the MRD does not contain cleavage sites.

In some embodiments, the MRD has been selected to not contain known potential human T-cell epitopes.

In some particular embodiments, the MRD has a particular hydrophobicity. For example, the hydrophobicity of MRDs can be compared on the basis of retention times determined using hydrophobic interaction chromatography or reverse phase liquid chromatography.

The MRD target can be any molecule that it is desirable for an MRD-containing antibody to interact with. For example, the MRD target can be a soluble factor or a transmembrane protein, such as a cell surface receptor. The MRD target can also be an extracellular component or an intracellular component. In certain non-exclusive embodiments, the MRD target is a factor that regulates cell proliferation, differentiation, or survival. In other nonexclusive embodiments, the MRD target is a cytokine. In another nonexclusive embodiment, the MRD target is a factor that regulates angiogenesis. In another nonexclusive embodiment, the MRD target is a factor that regulates cellular adhesion and/or cell-cell interaction. In certain non-exclusive embodiments, the MRD target is a cell signaling molecule. In another nonexclusive embodiment, the MRD target is a factor that regulates one or more immune responses, such as, autoimmunity, inflammation and immune responses against cancer cells. In another nonexclusive embodiment, the MRD target is a factor that regulates cellular adhesion and/or cell-cell interaction. In an additional nonexclusive embodiment, the MRD target is a cell signaling molecule. In another embodiment, an MRD can bind a target that is itself an MRD. The ability of MRDs to bind a target and block, increase, or interfere with the biological activity of the MRD target can be determined using or routinely modifying assays, bioassays, and/or animal models known in the art for evaluating such activity.

The MRDs are able to bind their respective target when the MRDs are attached to an antibody. In some embodiments, the MRD is able to bind its target when not attached to an antibody. In some embodiments, the MRD is a target agonist. In other embodiments, the MRD is a target antagonist. In certain embodiments, the MRD can be used to localize an MRD-containing antibody to an area where the MRD target is located.

The sequence of the MRD can be determined several ways. For example, MRD sequences can be derived from natural ligands or known sequences that bind to a specific target binding site. Additionally, phage display technologies have emerged as a powerful method in identifying peptides which bind to target receptors and ligands. In peptide phage display libraries, naturally occurring and non-naturally occurring (e.g., random peptide) sequences can be displayed by fusion with coat proteins of filamentous phage. The methods for elucidating binding sites on polypeptides using phage display vectors has been previously described, in particular in WO94/18221, which is herein incorporated by reference. The methods generally involve the use of a filamentous phage (phagemid) surface expression vector system for cloning and expressing polypeptides that bind to the pre-selected target site of interest.

The methods of the present invention for preparing MRDs include the use of phage display vectors for their particular advantage of providing a means to screen a very large population of expressed display proteins and thereby locate one or more specific clones that code for a desired target binding reactivity. The ability of the polypeptides encoded by the clones to bind a target and/or alter the biological activity of the target can be determined using or routinely modifying assays and other methodologies described herein or otherwise known in the art. For example, phage display technology can be used to identify and improve the binding properties of MRDs. See, e.g., Scott et al., Science 249:386 (1990); Devlin et al., Science 249:404 (1990); U.S. Pat. Nos. 5,223,409, 5,733,731, 5,498,530, 5,432,018, 5,338,665, 5,922,545; and Int. Appl. Publ. Nos. WO96/40987 and WO98/15833; which are herein incorporated by reference. In peptide phage display libraries, natural and/or non-naturally occurring peptide sequences can be displayed by fusion with coat proteins of filamentous phage. The displayed peptides can be affinity-eluted against a target of interest if desired. The retained phage may be enriched by successive rounds of affinity purification and repropagation. The best binding peptides may be sequenced to identify key residues within one or more structurally related families of peptides. See, e.g., Cwirla et al., Science 276:1696-9 (1997), in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman, Ann. Rev. Biophys. Biomol. Struct. 26:401-424 (1997).

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide such as an MRD may be designed. See, e.g., Takasaki et al., Nature Biotech. 15:1266-1270 (1997). These analytical methods may also be used to investigate the interaction between a target and an MRD selected by phage display, which can suggest further modification of the MRDs to increase binding affinity.

Other methods known in the art can be used to identify MRDs. For example, a peptide library can be fused to the carboxyl terminus of the lac repressor and expressed in *E. coli*. Another *E. coli*-based method allows display on the cell's outer membrane by fusion with a peptidoglycan-associated lipoprotein (PAL). These and related methods are collectively referred to as "*E. coli* display." In another method, translation of random RNA is halted prior to ribosome release, resulting in a library of polypeptides with their associated RNA still attached. This and related methods are collectively referred to as "ribosome display." Other known methods employ chemical linkage of peptides to RNA. See, for example, Roberts and Szostak, Proc. Natl. Acad. Sci. USA 94:12297-12303 (1997). This and related methods are collectively referred to as "RNA-peptide screening, RNA display and mRNA display." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. These and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells and Lowman, Curr. Opin. Biotechnol. 3:355-362 (1992). Furthermore, constrained libraries, linear libraries, and/or focused libraries (comprised of structurally related domains that share significant primary sequence homology) can be used to identify, characterize, and modify MRDs An improved MRD that specifically binds a desired target can also be prepared based on a known MRD sequence. For example, at least one, two, three, four, five, or more amino acid mutations (e.g., conservative or non-conservative substitutions), deletions or insertions can be introduced into a known MRD sequence and the resulting MRD can be screened for binding to the desired target and biological activity, such as the ability to antagonize target biological activity or to agonize target biological activity. In another embodiment, the sites selected for modification are affinity matured using phage display techniques known in the art. See, e.g., Lowman, Ann. Rev. Biophys. Biomol. Struct. 26:401-4 24 (1997).

Any technique for mutagenesis known in the art can be used to modify individual nucleotides in a DNA sequence, for purposes of making amino acid addition(s), substitution(s) or deletion(s) in the antibody sequence, or for creating/deleting restriction sites and sequences coding for desired amino acids (e.g., cysteine) to facilitate further manipulations. Such techniques include, but are not limited to, chemical mutagenesis, in vitro site-directed mutagenesis (Kunkel, Proc. Natl. Acad. Sci. USA 82:488 (1985); Hutchinson et al., J. Biol. Chem. 253:6551 (1978)), oligonucleotide-directed mutagenesis (Smith, Ann. Rev. Genet. 19:423-463 (1985); Hill et al., Methods Enzymol. 155:558-568 (1987)), PCR-based overlap extension (Ho et al., Gene 77:51-59 (1989)), PCR-based megaprimer mutagenesis (Sarkar et al., Biotechniques 8:404-407 (1990)), etc. Modifications can be confirmed by DNA sequencing.

Additional fusion proteins can be generated through the techniques of gene-shuffling, motif-shuffling, exon-shuffling, and/or codon-shuffling (collectively referred to as "DNA shuffling"). DNA shuffling can be employed to alter the activities of SYNAGIS® or fragments thereof (e.g., an antibody or a fragment thereof with higher affinities and lower dissociation rates). See, generally, U.S. Pat. Nos. 5,605,793, 5,811,238, 5,830,721, 5,834,252, and 5,837,458, and Patten et al., Curr. Opinion Biotechnol. 8:724-33 (1997); Harayama et al., Trends Biotechnol. 16(2):76-82 (1998); Hansson et al., J. Mol. Biol. 287:265-76 (1999); Lorenzo et al., Biotechniques 24(2):308-313 (1998); U.S. Appl. Publ. Nos. 20030118592 and 200330133939; and Int. Appl. Publ. No. WO02/056910; each of which is herein incorporated by reference in its entirety.

Additionally, MRDs can be identified based on their effects in assays that measure particular pathways or activities. For example, assays that measure signaling pathways (e.g., phosphorylation studies or multimerization), ion channel fluxes, intracellular cAMP levels, cellular activities such as migration, adherence, proliferation, or apoptosis, and viral entry, replication, budding, or integration can be used to identify, characterize, and improve MRDs.

Variants and derivatives of the MRDs that retain the ability to bind the target antigen are included within the scope of the present invention. Included within variants are insertional, deletional, and substitutional variants, as well as variants that include MRDs presented herein with additional amino acids at the N- and/or C-terminus, including from about 0 to 50, 0 to 40, 0 to 30, 0 to 20 amino acids and the like. It is understood that a particular MRD of the present invention may be modified to contain one, two, or all three types of variants. Insertional and substitutional variants may contain natural amino acids, unconventional amino acids, or both. In some embodiments, the MRD contains a sequence with no more than 1, 2, 3, 4, 5, 6, 7, 8, 9, 10, 15, or 20 amino acid differences when compared to an MRD sequence described herein. In some embodiments, the amino acid differences are substitutions. These substitutions can be conservative or non-conservative in nature and can include unconventional or non-natural amino acids. In other embodiments the MRD contains a sequence that competitively inhibits the ability of an MRD-containing sequence described herein to bind with a target molecule. The ability of an MRD to competitively inhibit another MRD-containing sequence can be determined using techniques known in the art, including ELISA and BIAcore analysis.

The ability of an MRD to bind its target can be assessed using any technique that assesses molecular interaction. For example, MRD-target interaction can be assayed as described in the Examples below or alternatively, using in vitro or in vivo binding assays such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC). Assays evaluating the ability of an MRD to functionally affect its target (e.g., assays to measure signaling, proliferation, migration etc.) can also be used to indirectly assess MRD-target interaction.

An improved MRD that has a particular half-life in vivo can also be prepared based on a known MRD sequence. For example, at least one, two, three, four, five, or more amino acid mutations (e.g., conservative or non-conservative substitutions), deletions or insertions can be introduced into a known MRD sequence and the resulting MRD can be screened for increased half-life. Thus, variants and derivatives of the MRDs that retain the ability to bind the target and have an increased half-life can be included in multivalent and multispecific compositions (e.g., MRD-containing antibodies). Thus, in some embodiments, an MRD in an MRD-containing antibody has a half-life of at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 110, at least about 120, at least about 130, at least about 140, or at least about 150 hours. In some embodiments, an MRD in an MRD-containing antibody has a half-life of at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 110, at least about 120, at least about 130, at least about 140, or at least about 150 hours.

Once the sequence of the MRD has been elucidated, the peptides may be prepared by any of the methods known in the art. For example, the MRD peptides can be chemically synthesized and operably attached to the antibody or can be synthesized using recombinant technology. For example, MRDs can be synthesized in solution or on a solid support using known techniques. Various automatic synthesizers are commercially available and can be used in accordance with known protocols. See, for example, Tam et al., J. Am. Chem.

Soc. 105:6442 (1983); Merrifield, Science 232:341-347 (1986); Barany and Merrifield, The Peptides, Gross and Meienhofer, eds, Academic Press, New York, 1-284; Barany et al., Int. J. Pep. Protein Res., 30:705-739 (1987); and U.S. Pat. No. 5,424,398, each of which is incorporated herein by reference in its entirety.

MRDs can be synthesized with covalently attached molecules that are not amino acids but aid in the purification, identification, and/or tracking of an MRD in vitro or in vivo. (e.g., biotin for reacting with avidin or avidin-labeled molecules).

The following MRD targets are described in more detail by way of example only.

In some embodiments described herein, the MRD targets an integrin. The role of integrins such as αvβ3 and αvβ5 as tumor-associated markers has been well documented. A recent study of 25 permanent human cell lines established from advanced ovarian cancer demonstrated that all lines were positive for αvβ5 expression and many were positive for αvβ3 expression. Studies have also shown that αvβ3 and αvβ5 is highly expressed on malignant human cervical tumor tissues. Integrins have also demonstrated therapeutic effects in animal models of Kaposi's sarcoma, melanoma, and breast cancer.

A number of integrin αvβ3 and αvβ5 antagonists are in clinical development. These include cyclic RGD peptides and synthetic small molecule RGD mimetics. Two antibody-based integrin antagonists are currently in clinical trials for the treatment of cancer. The first is VITAXIN® (MEDI-522, Abegrein), the humanized form of the murine anti-human αvβ3 antibody LM609. A dose-escalating phase I study in cancer patients demonstrated that VITAXIN® is safe for use in humans. Another antibody in clinical trials is CNT095, a fully human Ab that recognizes αv integrins. A Phase I study of CNT095 in patients with a variety of solid tumors has shown that it is well tolerated. Cliengitide (EMD 121974), a peptide antagonist of αvβ3 and αvβ5, has also proven safe in phase I trials. Furthermore, there have been numerous drug targeting and imaging studies based on the use of ligands for these receptors. These preclinical and clinical observations demonstrate the importance of targeting αvβ3 and αvβ5 and studies involving the use of antibodies in this strategy have consistently reported that targeting through these integrins is safe.

Clinical trials are also ongoing for antagonists targeting α5vβ1 for treating metastatic melanoma, renal cell carcinoma, and non-small cell lung cancer (M200 (volociximab) and malignant glioma (ATN-161).

Integrin-binding MRDs containing one or more RGD tripeptide sequence motifs represent an example of MRDs of the invention. Ligands having the RGD motif as a minimum recognition domain and from which MRDs of the invention can be derived are well known, a partial list of which includes, with the corresponding integrin target in parenthesis, fibronectin (α3β1, α5β1, αvβ1, α11bβ3, αvβ3, and α3β1) fibrinogen (αMβ2 and α11β1) von Willebrand factor (α11bβ3 and αvβ3), and vitronectin (α11bβ3, αvβ3 and αvβ5).

In one embodiment, the RGD containing targeting MRD is a member selected from the group consisting of: YCRGDCT (SEQ ID NO:3); PCRGDCL (SEQ ID NO:4); TCRGDCY (SEQ ID NO:5); and LCRGDCF (SEQ ID NO:6).

A MRD that mimics a non-RGD-dependent binding site on an integrin receptor and having the target binding specificity of a high affinity ligand that recognizes the selected integrin is also contemplated in the present invention. MRDs that bind to an integrin receptor and disrupt binding and/or signaling activity of the integrin are also contemplated.

In some embodiments, the MRD targets an angiogenic molecule. Angiogenesis is essential to many physiological and pathological processes. Ang2 has been shown to act as a proangiogenic molecule. Administration of Ang2-selective inhibitors is sufficient to suppress both tumor angiogenesis and corneal angiogenesis. Therefore, Ang2 inhibition alone or in combination with inhibition of other angiogenic factors, such as VEGF, can represent an effective antiangiogenic strategy for treating patients with solid tumors.

It is contemplated that MRDs useful in the present invention include those that bind to angiogenic receptors, angiogenic factors, and/or Ang2. In a specific embodiment, an MRD of the invention binds Ang2. In further embodiments, the TIE2 binding component comprises a fragment of ANG2 that binds TIE2. In particular embodiments, compositions of the invention bind TIE2 and comprise amino acids 283-449 of the human ANG2 disclosed in NCBI Ref. Seq. No. NP_001138.1.

In one embodiment, an MRD and/or –MRD-containing antibody binds Ang2 and contains a sequence selected from the group consisting of:

```
(ANGa)
                                    (SEQ ID NO: 9)
GAQTNFMPMDDLEQRLYEQFILQQGLE;

(ANGb)
                                    (SEQ ID NO: 11)
LWDDCYFFPNPPHCYNSP;

(ANGc)
                                    (SEQ ID NO: 12)
LWDDCYSYPNPPHCYNSP;

(ANGd)
                                    (SEQ ID NO: 15)
LWDDCYSFPNPPHCYNSP;

(ANGe)
                                    (SEQ ID NO: 16)
DCAVYPNPPWCYKMEFGK;

(ANGf)
                                    (SEQ ID NO: 17)
PHEECYFYPNPPHCYTMS;
and (ANGg)
                                    (SEQ ID NO: 18)
PHEECYSYPNPPHCYTMS.
```

In an additional embodiment, an MRD and/or –MRD-containing antibody binds Ang2 and contains a sequence selected from the group consisting of:

```
(ANGa)
                                    (SEQ ID NO: 9)
GAQTNFMPMDDLEQRLYEQFILQQGLE;

(ANGb)
                                    (SEQ ID NO: 11)
LWDDCYFFPNPPHCYNSP;

(ANGc)
                                    (SEQ ID NO: 12)
LWDDCYSYPNPPHCYNSP;

(ANGd)
                                    (SEQ ID NO: 15)
LWDDCYSFPNPPHCYNSP;
```

-continued (ANGe)
DCAVYPNPPWCYKMEFGK; (SEQ ID NO: 16)

(ANGf)
PHEECYFYPNPPHCYTMS; (SEQ ID NO: 17)
and (ANGg)
PHEECYSYPNPPHCYTMS. (SEQ ID NO: 18)

ANG-2 binding peptides disclosed in U.S. Pat. Nos. 7,309,483, 7,205,275, 7,138,370 7,063,965, 7,063,840, 7,045,302, 7,008,781, 6,825,008, 6,645,484, 6,627,415, 6,455,035, 6,441,137, 6,433,143, 6,265,564, 6,166,185, 5,879,672, 5,814,464, 5,681,714, 5,650,490, 5,643,755 and 5,521,073; and U.S. Appl. Publ. Nos. 2007/0225221, 2007/0093419, 2007/0093418, 2007/0072801, 2007/0025993, 2006/0122370, 2005/0186665, 2005/0175617, 2005/0106099, 2005/0100906, 2003/0236193, 2003/0229023, 2003/0166858, 2003/0166857, 2003/0162712, 2003/0109677, 2003/0092891, 2003/0040463, 2002/0173627 and 2002/0039992, and Intl. Appl. Publ. Nos. WO2006/005361, WO/2006/002854, WO2004/092215, WO/2004/076650, WO2003/057134, WO/2000/075323, WO2000/065085, WO/1998/018914 and WO1995/021866, the disclosures of each of which is herein incorporated by reference in its entirety.

In some embodiments, the MRD targets vascular endothelial growth factor (VEGF). In one embodiment, the antibody-MRD fusion comprises an MRD with the sequence ATWLPPP (SEQ ID NO:71), which inhibits VEGF-mediated angiogenesis. Binetruy-Tournaire et al., EMBO J. 19:1525-1533 (2000). In additional embodiments, an anti-VEGF antibody containing an MRD that targets VEGF is contemplated in the present invention. Anti-VEGF antibodies can be found for example in Presta et al., Cancer Research 57:4593-4599 (1997); and Fuh et al., J. Biol. Chem. 281:10 6625 (2006), each of which is herein incorporated by reference in its entirety.

Insulin-like growth factor-I receptor-specific MRDs can also be used in the present invention.

Vascular homing-specific MRDs are also contemplated for use in the present invention. A number of studies have characterized the efficacy of linking the vascular homing peptide to other proteins like IL12 or drugs to direct their delivery in live animals.

Numerous other target binding sites are contemplated as being the target of the antibody-MRD fusions of the present invention, including for example, FGFR1, FGFR2, EGFR, ErbB2, ErbB3, ErbB4, CD20, insulin-like growth factor-I receptor, and hepatocyte growth factor receptor. MRDs can be directed towards these target binding sites or the corresponding ligands.

In one embodiment, the MRD binds to IL6. In one embodiment, the MRD binds to IL6R.

In one embodiment, the MRD binds to HER2/3.

In another embodiment, the MRD binds ErbB2.

In some embodiments, the MRD binds to a human protein. In some embodiments, the MRD binds to both a human protein and its ortholog in mouse, rat, rabbit, or hamster.

III. Antibodies

The antibody in the multivalent and multispecific compositions (e.g., MRD-containing antibodies) described herein can be any suitable antigen-binding immunoglobulin. In certain embodiments, the MRD-containing antibody molecules described herein retain the structural and functional properties of traditional monoclonal antibodies. Thus, the antibodies retain their epitope binding properties, but advantageously also incorporate one or more additional target-binding specificities.

Antibodies that can be used in the multivalent and multispecific compositions (e.g., MRD-containing antibodies) include, but are not limited to, monoclonal, multispecific, human, humanized, primatized, and chimeric antibodies. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. In specific embodiments, the antibodies are IgG1. In other specific embodiments, the antibodies are IgG3.

Antibodies that can be used as part of the multivalent and multispecific compositions (e.g., MRD-containing antibodies) can be naturally derived or the result of recombinant engineering (e.g., phage display, xenomouse, and synthetic). The antibodies can include modifications, for example, to enhance half-life or to increase or decrease antibody dependent cellular cytotoxicity (ADCC) and/or complement dependent cytotoxicity (CDC) activity. Antibodies can be from or derived from any animal origin including birds and mammals or generated synthetically. In some embodiments, the antibodies are human, murine, donkey, rabbit, goat, guinea pig, camel, llama, horse, or chicken antibodies. In specific embodiments, the antibodies are human.

In certain embodiments, the heavy chain portions of one polypeptide chain of a multimer are identical to those on a second polypeptide chain of the multimer. In alternative embodiments, the heavy chain portion-containing monomers of the invention are not identical. For example, each monomer may comprise a different target binding site, forming, for example, a bispecific antibody.

Bispecific, bivalent antibodies, and methods of making them, are described, for instance in U.S. Pat. Nos. 5,731,168, 5,807,706, 5,821,333, and U.S. Appl. Publ. Nos. 2003/020734 and 2002/0155537; each of which is herein incorporated by reference in its entirety. Bispecific tetravalent antibodies, and methods of making them are described, for instance, in Int. Appl. Publ. Nos. WO02/096948 and WO00/44788, the disclosures of both of which are herein incorporated by reference in its entirety. See generally, Int. Appl. Publ. Nos. WO93/17715, WO92/08802, WO91/00360, and WO92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992).

The heavy chain portions of the antibody component of the MRD-antibody fusions for use in the methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge region derived, in part, from an IgG1 molecule and, in part, from an IgG4 molecule.

In some embodiments, the antigen binding domains of the antibody component of the multivalent and multispecific compositions (e.g., MRD-containing antibodies) bind to their target with a dissociation constant or Kd of less than $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In one embodiment, the antibody component of the multivalent and multispecific compositions (e.g., MRD-containing antibodies) have a dissociation constant or Kd of less than $5 \times 10^{-5}$ M. In another embodiment, antigen binding of the antibody component of the multivalent and multispecific compositions (e.g., MRD-containing antibodies) has a dissociation constant or Kd of less than $5 \times 10^{-8}$ M. In another embodiment, antigen binding of the antibody component of the multivalent and multispecific compositions (e.g., MRD-containing antibodies) has a dissociation constant or Kd of less than less than $5 \times 10^{-9}$ M. In another embodiment, the antibody component of the multivalent and multispecific compositions (e.g., MRD-containing antibodies) have a dissociation constant or Kd of less than $5 \times 10^{-10}$ M. In another embodiment, the antibody component of the multivalent and multispecific compositions (e.g., MRD-containing antibodies) have a dissociation constant or Kd of less than $5 \times 10^{-11}$ M. In another embodiment, the antibody component of the multivalent and multispecific compositions (e.g., MRD-containing antibodies) have a dissociation constant or Kd of less than $5 \times 10^{-12}$ M.

In specific embodiments, the antibody component of the MRD-containing antibody binds its target with an off rate ($k_{off}$) of less than $5 \times 10^{-2}$ sec$^{-1}$, $10^{-2}$ sec$^{-1}$, $5 \times 10^{-3}$ sec$^{-1}$, or $10^{-3}$ sec$^{-1}$. More preferably, the antibody component of the MRD-containing antibody binds its target with an off rate ($k_{off}$) of less than $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$, or $10^{-7}$ sec$^{-1}$.

In other specific embodiments, the antibody component of the MRD-containing antibody binds its target with an on rate ($k_{on}$) of greater than $10^3$ M$^{-1}$sec$^{-1}$, $5 \times 10^3$ M$^{-1}$sec$^{-1}$, $10^4$ M$^{-1}$sec$^{-1}$, or $5 \times 10^4$ M$^{-1}$sec$^{-1}$. More preferably, the antibody component of the MRD-containing antibody binds its target with an on rate ($k_{on}$) of greater than $10^5$ M$^{-1}$sec$^{-1}$, $5 \times 10^5$ M$^{-1}$sec$^{-1}$, $10^6$ M$^{-1}$sec$^{-1}$, or $5 \times 10^6$ M$^{-1}$sec$^{-1}$, or $10^7$ M$^{-1}$sec$^{-1}$.

Affinity maturation strategies and chain shuffling strategies (e.g., gene-shuffling, motif-shuffling, exon-shuffling, and/or codon-shuffling (collectively referred to as "DNA shuffling") are known in the art and can be employed to generate high affinity and/or to alter the activities (e.g., ADCC and CDC) of multivalent and multispecific compositions (e.g., multivalent and multispecific compositions (e.g., MRD-containing antibodies)). See, e.g., U.S. Pat. Nos. 5,605,793, 5,811,238, 5,830,721, 5,834,252 and 5,837,458; and Patten et al., Curr. Opinion Biotechnol. 8:724-733 (1997), Harayama, Trends Biotechnol. 16(2):76-82 (1998), Hansson et al., J. Mol. Biol. 287:265-276 (1999) and Lorenzo and Blasco, Biotechniques 24(2):308-313 (1998); each of which is herein incorporated by reference in its entirety. Advantageously, affinity maturation strategies and chain shuffling strategies can routinely be applied to generate multivalent and multispecific compositions (e.g., MRD-containing antibodies) can also include variants and derivatives that improve antibody function and/or desirable pharmacodynamic properties.

Accordingly, certain embodiments of the invention include an antibody-MRD fusion, in which at least a fraction of one or more of the constant region domains has been altered so as to provide desired biochemical characteristics such as reduced or increased effector functions, the ability to non-covalently dimerize, increased ability to localize at the site of a tumor, reduced serum half-life, or increased serum half-life when compared with an unaltered antibody of approximately the same immunoreactivity. The alterations of the constant region domains can be amino acid substitutions, insertions, or deletions.

"Antibody-dependent cell-mediated cytotoxicity" or "ADCC" refers to a form of cytotoxicity in which secreted Ig bound onto Fc receptors (FcRs) expressed on certain cytotoxic cells (e.g., Natural Killer (NK) cells, neutrophils, and macrophages) enables these cytotoxic effector cells to localize to an antigen-bearing target cell and subsequently kill the target cell with cytotoxins. Specific high-affinity IgG antibodies directed to the surface of target cells "arm" the cytotoxic cells and are required for such killing. Lysis of the target cell is extracellular, requires contact or close proximity between the cytotoxic cells and target cells, and does not involve complement.

As used herein, the term "enhances ADCC" (e.g., referring to cells) is intended to include any measurable increase in cell lysis when contacted with a variant MRD-containing antibody as compared to the cell killing of the same cell in contact with a MRD-containing antibody that has not been so modified in a way that alters ADCC in the presence of effector cells (for example, at a ratio of target cells:effector cells of 1:50), e.g., an increase in cell lysis by at least about 10%, 20%, 30%, 40%, 50%, 60%, 70%, 80%, 90%, 100%, 150%, 200%, 250%, 300%, or 325%.

In certain embodiments, the antibody component of the antibody-MRD fusion has been modified to increase antibody dependent cellular cytotoxicity (ADCC) (see, e.g., Bruhns et al., Blood 113:3716-3725 (2009); Shields et al., J. Biol. Chem. 276:6591-6604 (2001); Lazar et al., Proc. Natl. Acad. Sci. USA 103:4005-4010 (2006); Stavenhagen et al., Cancer Res., 67:8882-8890 (2007); Horton et al., Cancer Res. 68:8049-8057 (2008); Zalevsky et al., Blood 113:3735-3743 (2009); Bruckheimer et al., Neoplasia 11:509-517 (2009); Allan et al., WO2006/020114; Strohl, Curr. Op. Biotechnol. 20:685-691 (2009); and Watkins et al., WO2004/074455, each of which is herein incorporated by reference in its entirety). Examples of Fc sequence engineering modifications contained in the antibody component of the antibody-MRD fusions that increases ADCC include one or more modifications corresponding to: IgG1-S298A, E333A, K334A; IgG1-S239D, 1332E; IgG1-S239D, A330L, 1332E; IgG1-P2471, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L; wherein the numbering of the residues in the Fc region is that of the EU index as in Kabat.

In one embodiment, an Fc variant protein has enhanced ADCC activity relative to a comparable molecule. In a specific embodiment, an Fc variant protein has ADCC activity that is at least 2 fold, or at least 3 fold, or at least 5 fold or at least 10 fold or at least 50 fold or at least 100 fold greater than that of a comparable molecule. In another specific embodiment, an Fc variant protein has enhanced binding to the Fc receptor Fc gamma RIIIA and has enhanced ADCC activity relative to a comparable molecule. In other embodiments, the Fc variant protein has both enhanced ADCC activity and enhanced serum half-life relative to a comparable molecule.

The ability of any particular Fc variant protein to mediate lysis of the target cell by ADCC can be assayed using techniques known in the art. For example, to assess ADCC activity a multivalent and monovalent multispecific composition (e.g., an MRD-containing antibody) can be added to target cells in combination with immune effector cells, which can be activated by the antigen antibody complexes resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., J Immunol Methods 79:277-282 (1985); Bruggemann et al., J. Exp. Med. 166:1351-1361 (1987); Wilkinson et al., J. Immunol. Methods 258:183-191 (2001); Patel et al., J. Immunol. Methods 184:29-38 (1995). Alternatively, or additionally, ADCC activity of the multivalent and monovalent multispecific composition (e.g., an MRD-containing antibody) can be assessed in vivo, e.g., in an animal model such as that disclosed in Clynes et al., PNAS USA 95:652-656 (1998), and U.S. Pat. No. 7,662,925.

In certain embodiments, the antibody component of the antibody-MRD fusion has been modified to decrease ADCC (see, e.g., Idusogie et al., J. Immunol. 166:2571-2575 (2001); Sazinsky et al., Proc. Natl. Acad. Sci. USA 105:20167-20172 (2008); Davis et al., J. Rheumatol. 34:2204-2210 (2007); Bolt et al., Eur. J. Immunol. 23:403-411 (1993); Alegre et al., Transplantation 57:1537-1543 (1994); Xu et al., Cell Immunol. 200:16-26 (2000); Cole et al., Transplantation 68:563-571 (1999); Hutchins et al., Proc. Natl. Acad. Sci. USA 92:11980-11984 (1995); Reddy et al., J. Immunol. 164:1925-1933 (2000); Int. Appl. Publ. No. WO1997/11971, and WO2007/106585; U.S. Appl. Publ. 2007/0148167A1; McEarchern et al., Blood 109:1185-1192 (2007); Strohl, Curr. Op. Biotechnol. 20:685-691 (2009); and Kumagai et al., J. Clin. Pharmacol. 47:1489-1497 (2007), each of which is herein incorporated by reference in its entirety). Examples of Fc sequence engineering modifications contained in the antibody component of the antibody-MRD fusions that decreases ADCC include one or more modifications corresponding to: IgG1-K326W, E333S; IgG2-E333S; IgG1-N297A; IgG1-L234A, L235A; IgG2-V234A, G237A; IgG4-L235A, G237A, E318A; IgG4-S228P, L236E; IgG2-EU sequence 118-260; IgG4-EU sequence 261-447; IgG2-H268Q, V309L, A330S, A331S; IgG1-C220S, C226S, C229S, P238S; IgG1-C226S, C229S, E233P, L234V, L235A; and IgG1-L234F, L235E, P331S.

In certain embodiments, the antibody component of the antibody-MRD fusion has been modified to increase antibody-dependent cell phagocytosis (ADCP); (see, e.g., Shields et al., J. Biol. Chem. 276:6591-6604 (2001); Lazar et al., Proc. Natl. Acad. Sci. USA 103:4005-4010 (2006); Stavenhagen et al., Cancer Res., 67:8882-8890 (2007); Richards et al., Mol. Cancer Ther. 7:2517-2527 (2008); Horton et al., Cancer Res. 68:8049-8057 (2008), Zalevsky et al., Blood 113:3735-3743 (2009); Bruckheimer et al., Neoplasia 11:509-517 (2009); Allan et al., WO2006/020114; Strohl, Curr. Op. Biotechnol. 20:685-691 (2009); and Watkins et al., WO2004/074455, each of which is herein incorporated by reference in its entirety.). Examples of Fc sequence engineering modifications contained in the antibody component of the antibody-MRD fusions that increases ADCP include one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; IgG1-F243L, R292P, Y300L, V305I, P396L; IgG1-G236A, S239D, I332E.

In certain embodiments, the antibody component of the antibody-MRD fusion has been modified to decrease ADCP (see, e.g., Sazinsky et al., Proc. Natl. Acad. Sci. USA 105:20167-20172 (2008); Davis et al., J. Rheumatol. 34:2204-2210 (2007); Bolt et al., Eur. J. Immunol. 23:403-411 (1993); Alegre et al., Transplantation 57:1537-1543 (1994); Xu et al., Cell Immunol. 200:16-20 (2000); Cole et al., Transplantation 68:563-571 (1999); Hutchins et al., Proc. Natl. Acad. Sci. USA 92:11980-11984 (1995); Reddy et al., J. Immunol. 164:1925-1933 (2000); Intl. Appl. Publ. Nos. WO1997/11971 and WO2007/106585; U.S. Appl. Publ. 2007/0148167; McEarchern et al., Blood 109:1185-1192 (2007); Strohl, Curr. Op. Biotechnol. 20:685-691 (2009); and Kumagai et al., J. Clin. Pharmacol. 47:1489-1497 (2007), each of which is herein incorporated by reference in its entirety). Examples of Fc sequence engineering modifications contained in the antibody component of the antibody-MRD fusions that decreases ADCC include one or more modifications corresponding to: IgG1-N297A; IgG1-L234A, L235A; IgG2-V234A, G237A; IgG4-L235A, G237A, E318A; IgG4-S228P, L236E; IgG2 EU sequence 118-260; IgG4-EU sequence 261-447; IgG2-H268Q, V309L, A330S, A331S; IgG1-C220S, C226S, C229S, P238S; IgG1-C226S, C229S, E233P, L234V, L235A; and IgG1-L234F, L235E, P331S.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g., as described in Gazzano-Santoro et al., J. Immunol. Methods 202:163 (1996), can be performed. In one embodiment, an Fc variant protein has enhanced CDC activity relative to a comparable molecule. In a specific embodiment, an Fc variant protein has CDC activity that is at least 2 fold, or at least 3 fold, or at least 5 fold, or at least 10 fold, or at least 50 fold, or at least 100 fold greater than that of a comparable molecule. In other embodiments, the Fc variant protein has both enhanced CDC activity and enhanced serum half-life relative to a comparable molecule.

In certain embodiments, the antibody component of the antibody-MRD fusions have been modified to increase complement-dependent cytotoxicity (CDC) (see, e.g., (see, e.g., Idusogie et al., J. Immunol. 166:2571-2575 (2001); Strohl, Curr. Op. Biotechnol. 20:685-691 (2009); and Natsume et al., Cancer Res. 68:3863-3872 (2008), each of which is herein incorporated by reference in its entirety). Examples of Fc sequence engineering modifications contained in the antibody component of the antibody-MRD fusions that increases CDC include one or more modifications corresponding to: IgG1-K326A, E333A; and IgG1-K326W, E333S, IgG2-E333S.

In one embodiment, the present invention provides formulations, wherein the Fc region comprises a non-naturally occurring amino acid residue at one or more positions selected from the group consisting of 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, the Fc region can comprise a non-naturally occurring amino acid residue at additional and/or alternative positions known to one skilled in the art (see, e.g., U.S. Pat. Nos. 5,624,821, 6,277,375, and 6,737,056; and Int. Appl. Publ. Nos. WO01/58957, WO02/06919, WO04/016750, WO04/029207, WO04/035752 and WO05/040217).

In specific embodiments MRD-containing antibodies of the invention contain an Fc variant comprising at least one non naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241R. 243W, 243L 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 200H, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, the Fc region can comprise additional and/or alternative non-naturally occurring amino acid residues known to one skilled in the art (see, e.g., U.S. Pat. Nos. 5,624,821, 6,277,375, and 6,737,056; and Int. Appl. Publ. Nos. WO01/58957, WO02/06919, WO04/016750, WO04/029207, WO04/035752 and WO05/040217).

In certain embodiments, the multivalent and monovalent multispecific composition is an antibody-MRD fusions wherein the antibody component has been modified to increase inhibitory binding to Fc gamma RIIb receptor (see, e.g., Chu et al., Mol. Immunol. 45:3926-3933 (2008)). An example of Fc sequence engineering modifications contained in the antibody component of the antibody-MRD fusions that increases binding to inhibitory Fc gamma RIIb receptor is IgG1-S267E, L328F.

In certain embodiments, the antibody component of the antibody-MRD fusions have been modified to decrease CDC (see, e.g., Int. Appl. Publ. Nos. WO1997/11971 and WO2007/106585; U.S. Appl. Publ. No 2007/0148167A1; McEarchern et al., Blood 109:1185-1192 (2007); Hayden-Ledbetter et al., Clin. Cancer 15:2739-2746 (2009); Lazar et al., Proc. Natl. Acad. Sci. USA 103:4005-4010 (2006); Bruckheimer et al., Neoplasia 11:509-517 (2009); Strohl, Curr. Op. Biotechnol. 20:685-691 (2009); and Sazinsky et al., Proc. Natl. Acad. Sci. USA 105:20167-20172 (2008); each of which is herein incorporated by reference in its entirety). Examples of Fc sequence engineering modifications contained in the antibody component of the antibody-MRD fusions that decreases CDC include one or more modifications corresponding to: IgG1-S239D, A330L, 1332E; IgG2 EU sequence 118-260; IgG4-EU sequence 261-447; IgG2-H268Q, V309L, A330S, A331S; IgG1-C226S, C229S, E233P, L234V, L235A; IgG1-L234F, L235E, P331S; and IgG1-C226S, P230S.

The half-life on an IgG is mediated by its pH-dependent binding to the neonatal receptor FcRn. In certain embodiments the antibody component of the antibody-MRD fusion has been modified to enhance binding to FcRn (see, e.g., Petkova et al., Int. Immunol. 18:1759-1769 (2006); Dall'Acqua et al., J. Immunol. 169:5171-5180 (2002); Oganesyan et al., Mol. Immunol. 46:1750-1755 (2009); Dall'Acqua et al., J. Biol. Chem. 281:23514-23524 (2006), Hinton et al., J. Immunol. 176:346-356 (2006); Datta-Mannan et al., Drug Metab. Dispos. 35:86-94 (2007); Datta-Mannan et al., J. Biol. Chem. 282:1709-1717 (2007); Int. Appl. Publ. No. WO2006/130834; Strohl, Curr. Op. Biotechnol. 20:685-691 (2009); and Yeung et al., J. Immunol. 182:7663-7671 (2009); each of which is herein incorporated by reference in its entirety).

In additional embodiments, the antibody of the antibody-MRD fusion has been modified to selectively bind FcRn at pH6.0, but not pH 7.4. Examples of Fc sequence engineering modifications contained in the antibody component of the antibody-MRD fusions that increases half-life include one or more modifications corresponding to: IgG1-M252Y, S254T, T256E; IgG1-T250Q, M428L; IgG1-H433K, N434Y; IgG1-N434A; and IgG1-T307A, E380A, N434A.

In other embodiments the antibody component of the antibody-MRD fusion has been modified to decrease binding to FcRn (see, e.g., Petkova et al., Int. Immunol. 18:1759-1769 (2006); Datta-Mannan et al., Drug Metab. Dispos. 35:86-94 (2007); Datta-Mannan et al., J. Biol. Chem. 282: 1709-1717 (2007); Strohl, Curr. Op. Biotechnol. 20:685-691 (2009); and Vaccaro et al., Nat. Biotechnol. 23:1283-1288 (2005), each of which is herein incorporated by reference in its entirety). Examples of Fc sequence engineering modifications contained in the antibody component of the antibody-MRD fusions that decrease half-life include one or more modifications corresponding to: IgG1-M252Y, S254T, T256E; H433K, N434F, 436H; IgG1-I253A; and IgG1-P257I, N434H or D376V, N434H.

In some embodiments, the antibody-MRD fusions have been glyocoengineered or the Fc portion of the MRD-containing antibody has been mutated to increase effector function using techniques known in the art. For example, the inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well know immunological techniques without undue experimentation.

Methods for generating antibodies containing non-naturally occurring Fc regions are known in the art. For example, amino acid substitutions and/or deletions can be generated by mutagenesis methods, including, but not limited to, site-directed mutagenesis (Kunkel, Proc. Natl. Acad. Sci. USA 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). Site-directed mutagenesis can be performed by the overlap-extension PCR method (Higuchi, in "PCR Technology: Principles and Applications for DNA Amplification", Stockton Press, New York, pp. 61-70 (1989)). Alternatively, the technique of overlap-extension PCR (Higuchi, ibid.) can be used to introduce any desired mutation(s) into a target sequence (the starting DNA). Other methods useful for the generation of antibodies containing non-naturally occurring Fc regions are known in the art (see, e.g., U.S. Pat. Nos. 5,624,821, 5,885,573, 5,677,425, 6,165,745, 6,277,375, 5,869,046, 6,121,022, 5,624,821, 5,648,260, 6,528,624, 6,194,551, 6,737,056, 6,821,505 and 6,277,375; U.S. Appl. Publ. No. 2004/0002587 and Int Appl. Publ. Nos. WO94/29351, WO99/58572, WO00/42072, WO02/060919, WO04/029207, WO04/099249 and WO04/063351).

Multivalent and multispecific compositions (e.g., MRD-containing antibodies) used according to the methods of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, or derivatization by known protecting/blocking groups. Any of numerous chemical modifications may be carried out by known techniques, including, but not limited to acetylation, formylation, etc. Additionally, the derivative may contain one or more non-classical amino acids.

According to some embodiments the antibody component of compositions of the invention is engineered to contain one or more free cysteine amino acids having a thiol reactivity within a desirable range (e.g., 0.6 to 1.0), wherein the cysteine engineered antibody is prepared by a process comprising replacing one or more amino acid residues of a parent antibody by cysteine. In some embodiments one or more free cysteine amino acid residues are located in a light chain. In additional embodiments one or more free cysteine amino acid residues are located in a heavy chain. In additional embodiments one or more free cysteine amino acid residues are located in a both the heavy and light chain. In some embodiments, the cysteine engineered MRD-containing antibody contains a free cysteine amino acid having a thiol reactivity value in the range of 0.6 to 1.0, and a sequence modification in the light chain or the heavy chain that is disclosed in U.S. Pat. No. 7,855,275. In other embodiments, the cysteine engineered antibody contains a free cysteine amino acid having a thiol reactivity value in the range of 0.6 to 1.0, and a sequence modification in the light chain or the heavy chain that is not disclosed in U.S. Pat. No. 7,855,275, the contents of which are herein incorporated by reference in its entirety.

In additional embodiments, the MRD-containing antibody is engineered to contain one or more free selenocysteine amino acids or another non-natural amino acid capable of forming disulfide bonds. Antibodies containing the same and methods for making such antibodies are known in the art. See, e.g., Hofer et al., Proc. Natl. Acad. Sci. 105(34): 12451-12456 (2008); and Hofer et al., Biochem. 48(50): 12047-12057 (2009), each of which is herein incorporated by reference in its entirety. In some embodiments one or more free selenocysteine amino acid residues are located in a light chain. In additional embodiments one or more free selenocysteine amino acid residues are located in a heavy chain. In additional embodiments one or more free selenocysteine amino acid residues are located in a both the heavy and light chain.

In certain embodiments, the multivalent and multispecific compositions (e.g., MRD-containing antibodies) have been modified so as to not elicit a deleterious immune response in the animal to be treated, e.g., in a human. In one embodiment, the antibody is modified to reduce immunogenicity using art-recognized techniques. For example, antibody components of the multivalent and multispecific compositions (e.g., MRD-containing antibodies) can be humanized, primatized, deimmunized, or chimerized. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into human frameworks and constant regions with or without retention of critical framework residues; or (c) transplanting the entire non-human variable domains, but "cloaking" them with human-like sections by replacement of surface residues. Such methods are disclosed in Morrison et al., Proc. Natl. Acad. Sci. 81:6851-6855 (1984); Morrison et al., Adv. Immunol. 44:65-92 (1988); Verhoeyen et al., Science 239:1534-1536 (1988); Padlan, Molec. Immun. 28:489-498 (1991); Padlan, Molec. Immun. 31:169-217 (1994), and U.S. Pat. Nos. 5,585,089, 5,693,761, 5,693,762, and 6,190,370, each of which is herein incorporated by reference in its entirety.

De-immunization can also be used to decrease the immunogenicity of an MRD-containing antibody. As used herein, the term "de-immunization" includes alteration of an MRD-containing antibody to modify T cell epitopes (see, e.g., Int. Appl. Pub. WO9852976A1, and WO0034317A2, each if which is herein incorporated by reference in its entirety). For example, VH and VL sequences from the starting antibody are analyzed and a human T cell epitope "map" is generated from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of antibodies for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Many different antibody components of the multivalent and multispecific compositions (e.g., MRD-containing antibodies) can be used in the methods described herein. It is contemplated that catalytic and non-catalytic antibodies can be used in the present invention. For example, Antibody 38C2 is an antibody-secreting hybridoma and has been previously described in Int. Appl. Pub. WO97/21803. 38C2 contains an antibody combining site that catalyzes the aldol addition reaction between an aliphatic donor and an aldehyde acceptor. In a syngeneic mouse model of neuroblastoma, systemic administration of an etoposide prodrug and intra-tumor injection of Ab 38C2 inhibited tumor growth.

The antibody target of the MRD-containing antibody (i.e., the target of the antigenic binding domain) can be any molecule that it is desirable for a MRD-antibody fusion to interact with. For example, the antibody target can be a soluble factor or the antibody target can be a transmembrane protein, such as a cell surface receptor. The antibody target can also be an extracellular component or an intracellular component. In certain embodiments, the antibody target is a factor that regulates cell proliferation, differentiation, or survival. In other embodiments, the antibody target is a cytokine. In another nonexclusive embodiment, the antibody target is a factor that regulates angiogenesis. In another nonexclusive embodiment, the antibody target is a factor that regulates one or more immune responses, such as, autoimmunity, inflammation and immune responses against cancer cells. In another nonexclusive embodiment, the antibody target is a factor that regulates cellular adhesion and/or cell-cell interaction. In certain nonexclusive embodiments, the antibody target is a cell signaling molecule. The ability of an antibody to bind to a target and to block, increase, or interfere with the biological activity of the antibody target can be determined using or routinely modifying assays, bioassays, and/or animal models known in the art for evaluating such activity.

In some embodiments the antibody target of the MRD-containing antibody is a disease-related antigen. The antigen can be an antigen characteristic of a particular cancer, and/or of a particular cell type (e.g., a hyperproliferative cell), and/or of a particular pathogen (e.g., a bacterial cell (e.g., tuberculosis, smallpox, anthrax), a virus (e.g., HIV), a parasite (e.g., malaria, leichmaniasis), a fungal infection, a mold, a mycoplasm, a prion antigen, or an antigen associated with a disorder of the immune system.

In some embodiments, the antibody target of the MRD-containing antibody is a target that has been validated in an animal model or clinical setting.

In other embodiments, the antibody target of the MRD-containing antibody is a cancer antigen.

In one embodiment, the antibody target of the MRD-containing antibody is: PDGFRA, PDGFRB, PDGF-A, PDGF-B, PDGF-CC, PDGF-C, PDGF-D, VEGFR1, VEGFR2, VEGFR3, VEGFC, VEGFD, neuropilin 2 (NRP2), betacellulin, PLGF, RET (rearranged during transfection), TIE1, TIE2 (TEK), CA125, CD3, CD4, CD7, CD10, CD13, CD25, CD32, CD32b, CD44, CD49e (integrin alpha 5), CD55, CD64, CD90 (THY1), CD133 (prominin 1), CD147, CD166, CD200, ALDH1, ESA, SHH, DHH, IHH, patched1 (PTCH1), smoothened (SMO), WNT1, WNT2B, WNT3A, WNT4, WNT4A, WNT5A, WNT5B, WNT7B, WNT8A, WNT10A, WNT10B, WNT16B, LRP5, LRP6, FZD1, FZD2, FZD4, FZD5, FZD6, FZD7, FZD8, Notch, Notch1, Notch3, Notch4, DLL4, Jagged, Jagged1, Jagged2, Jagged3, TNFSF1 (TNFb, LTa), TNFRSF1A (TNFR1, p55, p60), TNFRSF1B (TNFR2), TNFSF6 (Fas Ligand), TNFRSF6 (Fas, CD95), TNFRSF6B (DcR3), TNFSF7 (CD27 Ligand, CD70), TNFRSF7 (CD27), TNFSF8 (CD30 Ligand), TNFRSF8 (CD30), TNFSF11 (RANKL), TNFRSF11A (RANK), TNFSF12 (TWEAK), TNFRSF12 (TWEAKR), TNFSF13 (APRIL), TNFSF13B (BLYS), TNFRSF13B (TACT), TNFRSF13C (BAFFR), TNFSF15 (TL1A), TNFRSF17 (BCMA), TNFRSF19L (RELT), TNFRSF19 (TROY), TNFRSF21 (DR6), TNFRSF25 (DR3), ANG1 (ANGPT1), ANG3 (ANGPTL1), ANG4 (ANGPT4), IL1 alpha, IL1 beta, IL1R1, IL1R2, IL2, IL2R, IL5, IL5R, IL6, IL6R, IL8, IL8R, IL10, IL10R, IL12, IL12R, IL13, IL13R, IL15, IL15R, IL18, IL18R, IL19, IL19R, IL21R, IL23, IL23R, mif, XAG1, XAG3, REGIV, FGF1, FGF2, FGF3, FGF4, FGFR1, FGFR2, FGFR3, ALK, ALK1, ALK7, ALCAM, Artemin, Axl, TGFb, TGFb2, TGFb3, TGFBR1, IGFIIR, BMP2, BMP5, BMP6, BMPRI, GDF3, GDF8, GDF9, N-cadherin, E-cadherin, VE-cadherin, NCAM, L1CAM (CD171), ganglioside GM2, ganglioside GD2, calcitonin, PSGR, DCC, DCP1, CXCR2, CXCR7, CCR3, CCR5, CCR7, CCR10, CXCL1, CXCL5, CXCL6, CXCL8, CXCL12, CCL3, CCL4, CCL5, CCL11, Claudin1, Claudin2, Claudin3, Claudin4, TMEFF2, neuregulin, MCSF, CSF, CSFR (fms), GCSF, GCSFR, BCAM, HPV, hCG, SR1F, PSA, FOLR2 (folate receptor beta), BRCA1, BRCA2, HLA-DR, ABCC3, ABCB5, HM1.24, LFA1, LYNX, S100A8, S100A9, SCF, Von Willebrand factor, Lewis Y6 receptor, Lewis Y, CA G250 (CA9), integrin avb3 (CNTO95), integrin avb5, activin B1 alpha, leukotriene B4 receptor (LTB4R), neurotensin NT receptor (NTR), 5T4 oncofetal antigen, Tenascin C, MMP, MMP2, MMP7, MMP9, MMP12, MMP14, MMP26, cathepsin G, cathepsin H, cathepsin L, SULF1, SULF2, MET, UPA, MHC1, MN (CA9), TAG-72, TM4SF1, Heparanase (HPSE), syndecan (SDC1), Ephrin B2, Ephrin B4, or relaxin2. MRD that binds to one of the above targets is encompassed by the invention. Multivalent and multispecific compositions (e.g., MRD-containing antibodies) having 1, 2, 3, 4, 5, 6, or more MRDs that bind to 1, 2, 3, 4, 5, 6, or more of the above targets are also encompassed by the invention. The above antibody and MRD targets and those otherwise described herein are intended to be illustrative and not limiting.

In another embodiment, the antibody target of the MRD-containing antibody is CD19, CD22, CD30, CD33, CD38, CD44v6, TNFSF5 (CD40 Ligand), TNFRSF5 (CD40), CD52, CD54 (ICAM), CD74, CD80, CD200, EPCAM (EGP2), neuropilin 1 (NRP1), TEM1, mesothelin, TGFbeta 1, TGFBRII, phosphatidlyserine, folate receptor alpha (FOLR1), TNFRSF10A (TRAIL R1 DR4), TNFRSF10B (TRAIL R2 DR5), CXCR4, CCR4, CCL2, HGF, CRYPTO, VLA5, TNFSF9 (41BB Ligand), TNFRSF9 (41BB), CTLA4, HLA-DR, IL6, TNFSF4 (OX40 Ligand), TNFRSF4 (OX40), MUC1, MUC18, mucin CanAg, ganglioside GD3, EGFL7, PDGFRa, IL21, IGF1, IGF2, CD117 (cKit), PSMA, SLAMF7, carcinoembryonic antigen (CEA), FAP, integrin avb3, or integrin α5β3. An MRD that binds to one of the above targets are encompassed by the invention. Multivalent and multispecific compositions (e.g., MRD-containing antibodies) having 1, 2, 3, 4, 5, 6, or more MRDs that bind to 1, 2, 3, 4, 5, 6, or more of the above targets are also encompassed by the invention.

In particular embodiments, the antibody of the MRD-containing antibody competes for target binding with an antibody selected from: siplizumab CD2 (e.g., MEDI-507, MedImmune), blinatumomab CD19 CD3 (e.g., MT103, Micromet/MedImmune); XMAB®5574 CD19 (Xencor), SGN-19A CD19 (Seattle Genetics), ASG-5ME (Agenesys and Seattle Genetics), MEDI-551 CD19 (MedImmune), epratuzumab CD22 (e.g., hLL2, Immunomedics/UCB), inotuzumab ozogamicin CD22 (Pfizer), iratumumab CD30 (e.g., SGN-30 (Seattle Genetics) and MDX-060 (Medarex)), XMAB®2513 CD30 (Xencor), brentuximab vedotin CD30 (e.g., SGN-35, Seattle Genetics), gemtuzumab ozogamicin CD33 (e.g., MYLOTARG®, Pfizer), lintuzumab CD33 (e.g., antibody of Seattle Genetics), MOR202, CD38 (MorphoSys), daratumumab CD38 (e.g., Genmab antibody), CP870893 CD40 (Pfizer), dacetuzumab CD40 (e.g., SGN40, Seattle Genetics), ANTOVA® CD40 (Biogen Idec), lucatumumab CD40 (e.g., HCD122, Novartis) XMAB®5485 CD40 (Xencor), teneliximub, ruplizumab CD40L (e.g., ANTOVA®) bivatuzumab mertansine CD44v6, alemtuzumab CD52 (e.g., CAMPATH®/MABCAMPATH®, Genzyme/Bayer), BI505 ICAM1 (Bioinvent), milatuzumab CD74 (e.g., antibody of Immunomedics), galiximab CD80 (Biogen Idec), BMS663513 4-1BB (Bristol-Myers Squibb), Alexion CD200 antibody (Alexion), edrecolomab EPCAM (e.g., MAb17-1A, PANOREX® (GlaxoSmithKline), AT003 EPCAM (Affitech)), adecatumumab EPCAM (e.g., MT201, Micromet), oportuzumab monatox EPCAM, Genentech anti-NRP1 antibody, MORABOO4 TEM1 (Morphotek), MORAB009 mesothelin (Morphotek), lerdelimumab TGFb1 (e.g., CAT-152, Cambridge Antibody Technology), metelimumab TGFb1 (e.g., CAT-192, Cambridge Antibody Technology), ImClone anti-TGFBRII antibody, bavituximab phosphatidylserine (e.g., antibody of Peregrine (Peregrine Pharmaceuticals)), AT004 phosphatidylserine (Affitech), AT005 phosphatidylserine (Affitech), MORAB03 folate receptor alpha (Morphotek), farletuzumab folate receptor alpha cancer (e.g., MORAB003, Morphotek), CS1008 DR4 (Sankyo), mapatumumab DR4 (e.g., HGS-ETR1, Human Genome Sciences), LBY135 DR5 (Novartis), AMG66 DR5 (Amgen), Apomab DR5 (Genentech), PRO95780 (Genentech), lexatumumab DR5 (e.g., HGS-ETR2, Human Genome Sciences), conatumumab DR5 (e.g., AMG655, Amgen), tigatuzumab DR5 (e.g., CS-1008), AT009 CXCR4 (Affitech), AT008 CCR4 (Affitech), CNTO-888 CCL2 (Centocor), AMG102 HGF (Amgen), CRYPTO antibody (Biogen Idec), M200 antibody VLA5 (Biogen Idec), ipilimumab CTLA4 (e.g., MDX-010, Bristol-Myers Squibb/Medarex), belatacept CTLA4 ECD (e.g., CP-675,206, Pfizer), IMMU114 HLA-DR (Immunomedics), apolizumab HLA-DR, toclizumab IL6R (e.g., ACTEMR®A/ROAC-TREMRA®, Hoffman-La Roche), OX86 OX40, pemtumomab PEM/MUC1 (Theragyn), ABX-MA1 MUC-18 (Abgenix), clivatuzumab MUC-18 (e.g., hPAM4, Immunomedics), cantuzumab mertansine mucin CanAg, ecromeximab (Ludwig Institute), Genentech anti-EGFL7 antibody, AMG820 CSFR (Amgen), olaratumab PDGFRa (e.g., antibody of Imclone (Imclone)), IL21 antibody Zymogenetics (Zymogenetics), MEDI-573 IGF1/IGF2 (MedImmune), AMG191 cKit (Amgen), etaracizumab (e.g., MEDI-522, MedImune), and MLN591 PSMA (Millennium Pharmaceuticals), elotuzumab SLAMF7 (e.g., HuLuc63, BMS), labetuzumab CEA (CEA-CIDE®, Immunomedics), sibrotuzumab FAP, CNTO95 integrin avb3 (Centocor), VITAXIN® integrin avb3 (MedImmune), and voloximab α5β1 (antibody targets are italicized). MRDs that compete for target binding with one of the above antibodies are encompassed by the invention. Multivalent and multispecific compositions (e.g., MRD-containing antibodies) having 1, 2, 3, 4, 5, 6, or more MRDs that compete for target binding with 1, 2, 3, 4, 5, 6, or more of the above antibodies are also encompassed by the invention.

In additional embodiments, the antibody of the MRD-containing antibody competes for target binding with an antibody selected from: MDX-1342 CD19 (BMS), SGN-CD19A CD19 (Seattle Genetics), an anti-CD20 antibody described in U.S. Pat. No. 5,500,362, ofatumumab CD20 (e.g., ARZERRA®, GENMAB), veltuzumab CD20 (hA20, Takeda and Nycomed), PRO70769 CD20 (Genentech; see e.g., Intl. Appl. No. PCT/US2003/040426), AMG780 Tie2/Ang1 (Amgen), REGN910 ANG2 (Regeneron), and anti-CD22 antibody described in U.S. Pat. No. 5,789,554 (Immunomedics), lumiliximab CD23 (e.g., IDEC152, Biogen), IDEC-152 CD23 (Biogen), MDX-1401 CD30 (BMS), HeFi-1 CD30 (NCI), daratumumab CD38, an anti CD-40 antibody described in Intl. Appl. Publ. No. WO2007124299 (Novartis), IDEC-131 CD40L (Biogen), MDX-1411 CD70 (BMS), SGN-75 CD70 ADC (Seattle Genetics), HuMax-CD74™ CD74 ADC (Genmab), IDEC-114 CD80 (Biogen), TRC105 CD105/endoglin (Tracon), ABX-CBL CD147 (Amgen), RG1HuMax-TF™ Tissue Factor (TF)(Genmab), HuMax-Her2™ ErbB2 (Genmab), Trastuzumab-DM1 ErbB2-DM1 (Genentech), AMG888 HER3 (Amgen and Daiichi Sankyo), HuMV833 VEGF (Tsukuba Research Lab, see, e.g., Intl. Appl. Publ. No. WO/2000/034337), IMC-18F1 VEGFR1 (Imclone), IMC-1C11 VEGFR (Imclone), DC101 VEGFR2 (Imclone), KSB-102 EGFR (KS Biomedix), mAb-806 EGFR (Ludwig Institute for Cancer Research), MR1-1 EGFRvIII toxin (IVAX, National Cancer Institute), HuMax-EGFR EGFR (Genmab, see, e.g., U.S. application Ser. No. 10/172,317), IMC-11F8 EGFR (Imclone), CDX-110 EGFRvIII (AVANT Immunotherapeutics), zalumumab EGFR (Genmab), 425, EMD55900 and EMD62000 EGFR (Merck KGaA, see, e.g., U.S. Pat. No. 5,558,864), ICR62 EGFR (Institute of Cancer Research, see, e.g., Intl. Appl. Publ. No. WO95/20045), SC100 EGFR (Scancell and ISU Chemical), MOR201 FGFR-3 (Morphosys), ARGX-111 c-Met (arGEN-X), HuMax-cMet™ cMet (Genmab), GC-1008 TGFb1 (Genzyme), MDX-070 PMSA (BMS), huJ591 PSMA (Cornell Research Foundation), muJ591 PSMA (Cornell Research Foundation), GC1008 TGFb (Genzyme), NG-1 Ep-CAM (Xoma), MOR101 ICAM-1 (CD54) (Morphosys), MOR102 ICAM-1 (CD54) (Morphosys), ABX-MA1 MUC18 (Abgenix), HumaLYM (Intracel), HumaRAD-HN (Intracel), HumaRAD-OV (Intracel), ARGX-110 and ARGX-111 (arGEN-X), HuMax-Lymphoma (Genmab and Amgen), Milatuzumab CD74 (e.g., IMMU-115, IMMU-110; Immunomedics), HuMax-Cancer Heparanase I (Genmab), Hu3 S193 Lewis (y) (Wyeth, Ludwig Institute of Cancer Research), RAV12 N-linked carbohydrate epitope (Raven), nimotuzumab (TheraCIM, hR3; YM Biosciences, see, e.g., U.S. Pat. Nos. 5,891,996 and 6,506,883), BEC2 GD3 (Imclone), $^{90}$Ytacatuzumab tetraxetan alpha fetoprotein (e.g., FP-CIDE®, Immunomedics), KRN330 (Kirin), huA33 A33 (Ludwig Institute for Cancer Research), mAb 216 B cell glycosylated epitope (NCI), REGN421 DLL4 (Regeneron), ASG-5ME SLC44A4 ADC (AGS-5), ASG-22ME Nectin-4 ADC, CDX-1307 (MDX-1307), hCGb (Celldex), parathyroid hormone-related protein (PTH-rP)(UCB), MT293 cleaved collagen (TRC093/D93, Tracon), KW-2871 GD3 (Kyowa), KIR (1-7F9) KIR (Novo), A27.15 transferrin receptor (Salk Institute, see, e.g., Intl. Appl. Publ. No. WO2005/111082) and E2.3 transferrin receptor (Salk Institute). MRDs that compete for target binding with one of the above antibodies are encompassed by the invention. Multivalent and multispecific compositions (e.g., MRD-containing antibodies) having 1, 2, 3, 4, 5, 6, or more MRDs that compete for target binding with 1, 2, 3, 4, 5, 6, or more of the above antibodies are also encompassed by the invention. In additional embodiments, one of the above-described antibodies is the antibody of the MRD-containing antibody.

In particular embodiments, the antibody of the MRD-containing antibody is an antibody selected from: siplizumab CD2 (e.g., MEDI-507, MedImmune), blinatumomab CD19 CD3 (e.g., MT103, Micromet/MedImmune); XMAB®5574 CD19, (Xencor), SGN-19A CD19 (Seattle Genetics), ASG-5ME (Agenesys and Seattle Genetics), MEDI-551 CD19 (MedImmune), epratuzumab CD22 (e.g., hLL2, Immunomedics/UCB), inotuzumab ozogamicin CD22, iratumumab CD30 (e.g., SGN-30 (Seattle Genetics) and MDX-060 (Medarex)), XMAB®2513 CD30 (Xencor), brentuximab vedotin CD30 (e.g., SGN-35, Seattle Genetics), gemtuzumab ozogamicin CD33 (e.g., MYLOTARG®, Pfizer), lintuzumab CD33 (e.g., antibody of Seattle Genetics), MOR202 CD38 (MorphoSys), daratumumab CD38 Genmab antibody), CP870893 CD40 (Pfizer), dacetuzumab CD40 (e.g., SGN40, Seattle Genetics), ANTOVA® CD40 (Biogen Idec), lucatumumab CD40 (e.g., HCD122, Novartis) XMAB®5485 CD40 (Xencor), teneliximab, ruplizumab CD40L (e.g., ANTOVA®), bivatuzumab mertansine CD44v6, alemtuzumab CD52 (e.g., CAMPATH®/MAB-CAMPATH®, Genzyme/Bayer), BI505 ICAM1 (Bioinvent), milatuzumab CD74 (e.g., antibody of Immunomedics), galiximab CD80 (Biogen Idec), BMS663513

4-1BB (Bristol-Myers Squibb), Alexion CD200 antibody (Alexion), edrecolomab EPCAM (e.g., MAb17-1A, PANOREX® (GlaxoSmithKline), AT003 EPCAM (Affitech)), adecatumumab EPCAM (e.g., MT201, Micromet), oportuzumab monatox EPCAM, Genentech anti-NRP1 antibody, MORAB004 TEM1 (Morphotek), MORAB009 mesothelin (Morphotek), lerdelimumab TGFb1 (e.g., CAT-152, Cambridge Antibody Technology), metelimumab TGFb1 (e.g., CAT-192, Cambridge Antibody Technology), ImClone anti-TGFBRII antibody, bavituximab phosphatidylserine (e.g., antibody of Peregrine (Peregrine Pharmaceuticals)), AT004 phosphatidylserine (Affitech), AT005 phosphatidylserine (Affitech), MORAB03 folate receptor alpha (Morphotek), farletuzumab folate receptor alpha cancer (e.g., MORAB003, Morphotek), CS1008 DR4 (Sankyo), mapatumumab DR4 (e.g., HGS-ETR1, Human Genome Sciences), LBY135 DR5 (Novartis), AMG66 DR5 (Amgen), Apomab DR5 (Genentech), PRO95780 (Genentech), lexatumumab DR5 (e.g., HGS-ETR2, Human Genome Sciences), conatumumab DR5 (e.g., AMG655, Amgen), tigatuzumab (e.g., CS-1008), AT009 CXCR4 (Affitech), AT008 CCR4 (Affitech), CNTO-888 CCL2 (Centocor), AMG102 HGF (Amgen), CRYPTO antibody (Biogen Idec), M200 antibody VLA5 (Biogen Idec), ipilimumab CTLA4 (e.g., MDX-010, Bristol-Myers Squibb/Medarex), belatacept CTLA4 ECD (e.g., CP-675,206, Pfizer), IMMU114 HLA-DR (Immunomedics), apolizumab HLA-DR, toclizumab IL6R (e.g., ACTEMR®A/ROACTREMRA®, Hoffman-La Roche) OX86 OX40, pemtumomab PEM/MUC1 (Theragyn), ABX-MA1 MUC-18 (Abgenix), cantuzumab mertansine mucin CanAg, ecromeximab (Ludwig Institute), Genentech anti-EGFL7 antibody, AMG820 CSFR (Amgen), olaratumab PDGFRa (e.g., antibody of Imclone (Imclone)), IL21 antibody Zymogenetics (Zymogenetics), MEDI-573 IGF1/IGF2 (MedImmune), AMG191 cKit (Amgen), etaracizumab (e.g., MEDI-522, MedImmuune), MLN591 PSMA (Millennium Pharmaceuticals), elotuzumab SLAMF7 (e.g., HuLuc63, PDL), labetuzumab CEA (CEA-CIDE®, Immunomedics), sibrotuzumab FAP, CNTO95 integrin avb3 (Centocor), VITAXIN® integrin avb3 (MedImmune), and voloximab α5β1 (e.g., M200, PDL and Biogen Idec).

In an additional embodiment, the antibody target of the MRD-containing antibody is ALK1. In one embodiment, the antibody is PF-3,446,962 (Pfizer). In another embodiment, the antibody binds to the same epitope as PF-3,446,962. In a further embodiment, the antibody competitively inhibits binding of PF-3,446,962 to ALK1. Multivalent and multispecific compositions (e.g., MRD-containing antibodies) having 1, 2, 3, 4, 5, 6, or more MRDs that compete for ALK1 binding with PF-3,446,962 are also encompassed by the invention.

In an additional embodiment, the antibody target of the MRD-containing antibody is CD22. In one embodiment, the antibody is inotuzumab (e.g., inotuzumab ozogamicin CMC-544, PF-5,208,773; Pfizer). In one embodiment, the antibody binds to the same epitope as inotuzumab. In another embodiment, the antibody competitively inhibits binding of inotuzumab to CD22. Multivalent and multispecific compositions (e.g., MRD-containing antibodies) having 1, 2, 3, 4, 5, 6, or more MRDs that compete for CD22 binding with inotuzumab are also encompassed by the invention.

In an additional embodiment, the antibody target of the MRD-containing antibody is CRYPTO. In one embodiment, the antibody is the Biogen CRYPTO antibody that has advanced to phase I clinical trials (Biogen Idec). In another embodiment, the antibody binds to the same epitope as the Biogen CRYPTO antibody. In a further embodiment, the antibody competitively inhibits binding of the Biogen CRYPTO antibody to CRYPTO. Multivalent and multispecific compositions (e.g., MRD-containing antibodies) having 1, 2, 3, 4, 5, 6, or more MRDs that compete for CRYPTO binding with the Biogen CRYPTO antibody are also encompassed by the invention.

In an additional embodiment, the antibody target of the MRD-containing antibody is TNFSF5 (CD40 LIGAND). In one embodiment, the antibody is the Biogen CD40L antibody that has advanced to phase I clinical trials (Biogen Idec). In another embodiment, the antibody binds to the same epitope as the Biogen CD40L antibody. In a further embodiment, the antibody competitively inhibits binding of the Biogen CD40L antibody to CD40L. Multivalent and multispecific compositions (e.g., MRD-containing antibodies) having 1, 2, 3, 4, 5, 6, or more MRDs that compete for CD40L binding with the Biogen CD40L antibody are also encompassed by the invention.

In an additional embodiment, the antibody target of the MRD-containing antibody is CD80. In one embodiment, the antibody is galiximab (Biogen Idec). In another embodiment, the antibody binds to the same epitope as galiximab. In a further embodiment, the antibody competitively inhibits binding of galiximab to CD80. Multivalent and multispecific compositions (e.g., MRD-containing antibodies) having 1, 2, 3, 4, 5, 6, or more MRDs that compete for CD80 binding with galiximab are also encompassed by the invention.

In additional embodiments, an MRD-containing antibody binds CD80 and a target selected from: CD2, CD3, CD4, CD19, CD20, CD22, CD23, CD30, CD33, TNFRSF5 (CD40), CD52, CD74, TNFRSF10A (DR4), TNFRSF10B (DR5), VEGFR1, VEGFR2 and VEGF. In additional embodiments, an MRD-containing antibody binds CD80 and a target selected from: CD3, CD4 and NKG2D. Multivalent and multispecific compositions (e.g., MRD-containing antibodies) that bind CD80 and also at least bind 2, 3, 4, 5 or more of these targets are also encompassed by the invention. In specific embodiments, the antibody component of the MRD-containing antibody binds CD80. In further embodiments, the antibody component of the MRD-containing antibody is galiximab.

In an additional embodiment, the antibody target of the MRD-containing antibody is MCSF. In one embodiment, the antibody is PD-360,324 (Pfizer). In another embodiment, the antibody binds to the same epitope as PD-360,324. In a further embodiment, the antibody competitively inhibits binding of PD-360,324 to MCSF. Multivalent and multispecific compositions (e.g., MRD-containing antibodies) having 1, 2, 3, 4, 5, 6, or more MRDs that compete for MCSF binding with PD-360,324 are also encompassed by the invention.

In an additional embodiment, the antibody target of the MRD-containing antibody is CD44. In one embodiment, the antibody is PF-3,475,952 (Pfizer). In another embodiment, the antibody binds to the same epitope as PF-3,475,952. In a further embodiment, the antibody competitively inhibits binding of PF-3,475,952 to CD44. Multivalent and multispecific compositions (e.g., MRD-containing antibodies) having 1, 2, 3, 4, 5, 6, or more MRDs that compete for CD44 binding with PF-3,475,952 are also encompassed by the invention.

In an additional embodiment, the antibody target of the MRD-containing antibody is p-cadherin (CDH3). In one embodiment, the antibody is PF-3,732,010 (Pfizer). In another embodiment, the antibody binds to the same epitope as PF-3,732,010. In a further embodiment, the antibody competitively inhibits binding of PF-3,732,010 to p-cadherin. Multivalent and multispecific compositions (e.g., MRD-containing antibodies) having 1, 2, 3, 4, 5, 6, or more MRDs that compete for p-cadherin binding with PF-3,732,010 are also encompassed by the invention.

In another embodiment, the antibody target of the MRD-containing antibody is ANG2 (ANGPT2). In one embodiment, the antibody is MEDI3617 (MedImmune). In one embodiment, the antibody binds to the same epitope as MEDI3617. In another embodiment, the antibody competitively inhibits binding of MEDI3617 to ANG2. Multivalent and multispecific compositions (e.g., MRD-containing antibodies) having 1, 2, 3, 4, 5, 6, or more MRDs that compete for ANG2 binding with MEDI3617 are also encompassed by the invention.

In other embodiments, the antibody component of the MRD-containing antibody is an ANG-2 binding antibody disclosed in U.S. Pat. Nos. 7,063,965, 7,063,840, 6,645,484, 6,627,415, 6,455,035, 6,433,143, 6,376,653, 6,166,185, 5,879,672, 5,814,464, 5,650,490, 5,643,755, 5,521,073; U.S. Appl. Publ. Nos. 2011/0158978 (e.g., H4L4), 2006/0246071, 2006/0057138, 2006/0024297, 2006/0018909, 2005/0100906, 2003/0166858, 2003/0166857, 2003/0124129, 2003/0109677, 2003/0040463 and 2002/0173627; or Intl. Appl. Publ. Nos. WO2006/020706, WO2006/045049, WO2006/068953, or WO2003/030833 (the disclosure of each of which is herein incorporated by reference in its entirety). Multivalent and multispecific compositions (e.g., MRD-containing antibodies) having 1, 2, 3, 4, 5, 6, or more MRDs that compete for ANG2 binding with these antibodies are also encompassed by the invention.

In another embodiment, an MRD-containing antibody binds ANG2 and additionally binds a target selected from: VEGF (i.e., VEGFA), VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TNF, FGFR3, EFNa1, EFNa2, ANG1, ANG2, IL1, IL1beta, IL6, IL8, IL18, HGF, PDGFA, PLGF, PDGFB, CXCL12, KIT, GCSF, CXCR4, PTPRC, TIE2, VEGFR1, VEGFR2, VEGFR3, Notch 1, DLL4, EGFL7, α2β1 integrin, α4β1 integrin, α5β1 integrin, αvβ3 integrin, TGFb, MMP2, MMP7, MMP9, MMP12, PLAU, VCAM1, PDGFRA, and PDGFRB. Multivalent and multispecific compositions (e.g., MRD-containing antibodies) that bind ANG2 and at least 1, 2, 3, 4, 5 or more of these targets are also encompassed by the invention. In further embodiments, the antibody component of the MRD-containing antibody is MEDI3617, AMG780 or REGN910. In further embodiments, the antibody component of the MRD-containing antibody is H4L4.

In particular embodiments, the MRD-containing antibody binds ANG2 and TNF. In additional embodiments, the MRD-containing antibody binds ANG2 and IL6. In other embodiments, the MRD-containing antibody binds ANG2 and IL1. In further embodiments, the administered MRD-containing antibody binds ANG2, IL6 and TNF. In further embodiments, the administered MRD-containing antibody binds ANG2, IL1 and TNF. In further embodiments, the MRD-containing antibody binds ANG2, IL1, IL6 and TNF.

In particular embodiments, the MRD-containing antibody binds ANG2 and TNF and the antibody component of the MRD-containing antibody is adalimumab. In another embodiment, the MRD-containing antibody competes with adalimumab for binding to TNF.

In additional embodiments, the antibody component of the MRD-containing antibody binds ANG2. In further embodiments, the antibody component of the MRD-containing antibody is an ANG2 binding antibody selected from SAITAng-2-1, SAITAng-2-2, SAITAng-2-3, SAITAng-2-4 or another antibody disclosed in Intl. Appl. Publ. No. WO2009/142460. Multivalent and multispecific compositions (e.g., MRD-containing antibodies) having an antibody and/or 1, 2, 3, 4, 5, 6, or more MRDs that compete for ANG2 binding with one or more of these antibodies are also encompassed by the invention.

In additional embodiments, the antibody component of the MRD-containing antibody binds TIE2. In further embodiments, the antibody component of the MRD-containing antibody is a TIE2 binding antibody disclosed in U.S. Pat. Nos. 6,365,154 and 6,376,653; U.S. Appl. Publ. Nos. 2007/0025993, 2006/0057138 and 2006/0024297; or Intl. Appl. Publ. Nos. WO2006/020706, WO2000/018437 and WO2000/018804 (the disclosure of each of which is herein incorporated by reference in its entirety). Multivalent and multispecific compositions (e.g., MRD-containing antibodies) having an antibody and/or 1, 2, 3, 4, 5, 6, or more MRDs that compete for TIE binding with one or more these antibodies are also encompassed by the invention.

In certain embodiments, the antibody target of the MRD-containing antibody is EGFR (ErbB1), ErbB2, ErbB3, ErbB4, CD20, insulin-like growth factor-I receptor, prostate specific membrane antigen, an integrin, or cMet.

In one embodiment, the antibody in the MRD-containing antibody specifically binds EGFR (ErbB1). In a specific embodiment, the antibody is ERBITUX® (IMC-C225). In one embodiment, the antibody binds to the same epitope as ERBITUX®. In another embodiment, the antibody competitively inhibits binding of ERBITUX® to EGFR. In another embodiment, the antibody in the MRD-containing antibody inhibits EGFR dimerization. In another specific embodiment, the antibody is matuzumab (e.g., EMD 72000, Merck Serono) or panitumumab (e.g., VECTIBIX®, Amgen). In another embodiment, the antibody binds to the same epitope as matuzumab or panitumumab. In another embodiment, the antibody competitively inhibits binding of matuzumab or panitumumab to EGFR. In another embodiment, the antibody is ABX-EGF (Immunex) or MEDX-214 (Medarex). In another embodiment, the antibody binds to the same epitope as ABX-EGF or MEDX-214. In another embodiment, the antibody competitively inhibits binding of ABX-EGF or MEDX-214 to EGFR. In another specific embodiment, the antibody is zalutumumab (Genmab) or nimotuzumab (Biocon). In an additional embodiment, the antibody binds to the same epitope as zalutumumab (Genmab) or nimotuzumab (Biocon). In another embodiment, the antibody competitively inhibits binding of zalutumumab (Genmab) or nimotuzumab (Biocon) to EGFR.

In one embodiment, an MRD-containing antibody binds EGFR (ErbB1) and a target selected from: HGF, CD64, CDCP1, RON, cMET, ErbB2, ErbB3, IGF1R, PLGF, RGMa, PDGFRa, PDGFRb, VEGFR1, VEGFR2, TNFRSF10A (DR4), TNFRSF10B (DR5), IGF1,2, IGF2, CD3, CD4, NKG2D and tetanus toxoid. In some embodiments, the multivalent and monovalent multispecific composition (e.g., MRD-containing antibodies) binds at least 1, 2, 3, 4, 5 or more of these targets. In specific embodiments, the antibody component of the MRD-containing antibody binds EGFR. In further embodiments, the antibody component of the MRD-containing antibody is matuzumab, panitumumab, MEDX-214, or ABX-EGF. In further embodiments, the antibody component of the MRD-containing antibody is nimotuzumab (Biocon) or zalutumumab. In specific embodiments, the antibody component of the MRD-containing antibody is Erbitux®.

In specific embodiments, the MRD containing antibody binds ErbB1 and additionally binds ErbB3. In some embodiments, the antibody component of the MRD-containing antibody binds ErbB1 and an MRD of the MRD-containing antibody binds ErbB3. In a particular embodiment, the antibody component of the MRD-containing antibody is cetuximab. In additional embodiments, the antibody component of the MRD-containing antibody competes for ErbB1-binding with cetuximab. In another embodiment, the antibody in the MRD-containing antibody is an ErbB1-binding antibody selected from: nimotuzumab (Biocon), matuzumab (Merck KGaA), panitumumab (Amgen), zalutumumab (Genmab), MEDX-214, and ABX-EGF. In additional embodiments, the antibody component, MRD component and/or MRD-containing antibody competes for ErbB1-binding with an antibody selected from: nimotuzumab, matuzumab, panitumumab, and zalutumumab. In other embodiments, the antibody component of the MRD-containing antibody binds ErbB3 and an MRD of the MRD-containing antibody binds ErbB1 In additional embodiments, the antibody component of the MRD-containing antibody is an ErbB3-binding antibody selected from MM121 (Merrimack), 8B8 (Genentech), AV203 (Aveo), and AMG888 (Amgen). In additional embodiments, the antibody component, MRD component and/or MRD-containing antibody competes for ErbB3 binding with an antibody selected from MM121, 8B8, AV203, and AMG888.

In one embodiment the MRD-containing antibody specifically binds ErbB2 (Her2). In a specific embodiment, the antibody is trastuzumab (e.g., HERCEPTIN®, Genentech/Roche). In one embodiment, the antibody binds to the same epitope as trastuzumab. In another embodiment, the antibody competitively inhibits binding of trastuzumab to ErbB2. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, 3, 4, 5, 6, or more of the above antibodies are also encompassed by the invention Thus, the invention encompasses MRD-containing antibodies comprising at least 1, 2, 3, 4, 5, 6, or more MRDs that compete for target binding with at least 1, 2, 3, 4, 5, 6 of the above antibodies.

In other embodiments, the antibody in the MRD-containing antibody specifically binds to ErbB2. In one embodiment, the antibody in the MRD-containing antibody is an antibody that specifically binds to the same epitope as the anti-ErbB2 antibody trastuzumab (e.g., HERCEPTIN®, Genentech). In another embodiment, the antibody in the MRD-containing antibody is an antibody that competitively inhibits ErbB2-binding by the anti-ErbB2 antibody trastuzumab. In yet another embodiment, the antibody in the MRD-containing antibody is the anti-ErbB2 antibody trastuzumab. In another embodiment, the antibody in the MRD-containing antibody inhibits HER2 dimerization. In another embodiment, the antibody in the MRD-containing antibody inhibits HER2 heterodimerization with HER3 (ErbB3). In a specific embodiment, the antibody is pertuzumab (e.g., OMNITARG® and phrMab2C4, Genentech). In another embodiment, the antibody specifically binds to the same epitope as pertuzumab. In another embodiment, the antibody in the MRD-containing antibody is an antibody that competitively inhibits binding of ErbB2 by pertuzumab. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2 or more of the above antibodies are also encompassed by the invention. Accordingly, in one embodiment the antibody in the MRD-containing antibody is trastuzumab and 1, 2, 3, 4, 5, 6, or more MRDs in the MRD-containing antibody competitively inhibit binding of ErbB2 by pertuzumab.

In another embodiment, the antibody in the MRD-containing antibody is an ErbB2-binding antibody selected from the group: MDX-210 (Medarex), tgDCC-E1A (Targeted Genetics), MGAH22 (MacroGenics), and pertuzumab (OMNITARG™, 2C4; Genentech). An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, 3, or 4 of the above antibodies are also encompassed by the invention. Thus, the invention encompasses MRD-containing antibodies comprising at least 1, 2, 3, 4, 5, 6, or more MRDs that compete for target binding with at least 1, 2, 3 or 4 of the above antibodies.

In specific embodiments, the MRD containing antibody binds ErbB2 and additionally binds ErbB3. In some embodiments, the antibody component of the MRD-containing antibody binds ErbB2 and an MRD of the MRD-containing antibody binds ErbB3. In a particular embodiment, the antibody component of the MRD-containing antibody is trastuzumab. In additional embodiments, the antibody component, MRD component and/or MRD-containing antibody competes for ErbB2-binding with trastuzumab. In another embodiment, the antibody in the MRD-containing antibody is an ErbB2-binding antibody selected from: MDX-210 (Medarex), tgDCC-E1A (Targeted Genetics), MGAH22 (MacroGenics), and pertuzumab (OMNITARG™). In additional embodiments, the antibody component, MRD component and/or MRD-containing antibody competes for ErbB2-binding with an antibody selected from: MDX-210, tgDCC-E1A, MGAH22, and pertuzumab. In other embodiments, the antibody component of the MRD-containing antibody binds ErbB3 and an MRD of the MRD-containing antibody binds ErbB2.

In some embodiments, the antibody in the MRD-containing antibody comprises the CDRs of the anti-ErbB2 antibody trastuzumab. The CDR, VH, and VL sequences of trastuzumab are provided in Table 1.

TABLE 1

| CDR | Sequence |
| --- | --- |
| VL-CDR1 | RASQDVNTAVAW (SEQ ID NO: 59) |
| VL-CDR2 | SASFLYS (SEQ ID NO: 60) |
| VL-CDR3 | QQHYTTPPT (SEQ ID NO: 61) |
| VH-CDR1 | GRNIKDTYIH (SEQ ID NO: 62) |
| VH-CDR2 | RIYPTNGYTRYADSVKG (SEQ ID NO: 63) |
| VH-CDR3 | WGGDGFYAMDY (SEQ ID NO: 64) |
| VL | DIQMTQSPSSLSASVGDRVTITCRASQDVNTAV AWYQQKPGKAPKLLIYSASFLYSGVPSRFSGSR SGTDFTLTISSLQPEDFATYYCQQHYTTPPTFG QGTKVEIKRT (SEQ ID NO: 65) |
| VH | EVQLVESGGGLVQPGGSLRLSCAASGFNIKDTY IHWVRQAPGKGLEWVARIYPTNGYTRYADSVKG RFTISADTSKNTAYLQMNSLRAEDTAVYYCSRW GGDGFYAMDYWGQGTLVTVSS (SEQ ID NO: 66) |

In one embodiment the MRD-containing antibody specifically binds ErbB3 (Her3). In a specific embodiment, the antibody is MM121 (Merrimack Pharmaceuticals) or AMG888 (Amgen). In one embodiment, the antibody binds to the same epitope as MM121 or AMG888. In another embodiment, the antibody competitively inhibits binding of MM121 or AMG888 to ErbB3. In another specific embodiment, the antibody is AV-203 (AVEO). In one embodiment, the antibody binds to the same epitope as AV-203. In another embodiment, the antibody competitively inhibits binding of AV-203. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1 or both of the above antibodies are also encompassed by the invention In one embodiment the MRD-containing antibody specifically binds VEGF (VEGFA). In a specific embodiment, the antibody is bevacizumab (e.g., AVASTIN®, Genentech/Roche). In one embodiment, the antibody binds to the same epitope as bevacizumab. In another embodiment, the antibody competitively inhibits binding of bevacizumab to VEGFA. In another embodiment the MRD-containing antibody is AT001 (Affitech). In one embodiment, the antibody binds to the same epitope as AT001. In another embodiment, the antibody competitively inhibits binding of AT001 to VEGFA. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1 or both of the above antibodies are also encompassed by the invention.

In some embodiments, the antibody in the MRD-containing antibody comprises the CDRs of the anti-VEGF antibody bevacizumab. The CDR, VH, and VL sequences of bevacizumab are provided in Table 2.

TABLE 2

| CDR | Sequence |
|---|---|
| VL-CDR1 | SASQDISNYLN (SEQ ID NO: 72) |
| VL-CDR2 | FTSSLHS (SEQ ID NO: 73) |
| VL-CDR3 | QQYSTVPWT (SEQ ID NO: 74) |
| VH-CDR1 | GYTFTNYGMN (SEQ ID NO: 75) |
| VH-CDR2 | WINTYTGEPTYAADFKR (SEQ ID NO: 76) |
| VH-CDR3 | YPHYYGSSHWYFDV (SEQ ID NO: 77) |
| VL | DIQMTQSPSSLSASVGDRVTITCSASQDISNYL NWYQQKPGKAPKVLIYFTSSLHSGVPSRFSGSG SGTDFTLTISSLQPEDFATYYCQQYSTVPWTFG QGTKVEIKR (SEQ ID NO: 78) |
| VH | EVQLVESGGGLVQPGGSLRLSCAASGYTFTNYG MNWVRQAPGKGLEWVGWINTYTGEPTYAADFKR RFTFSLDTSKSTAYLQMNSLRAEDTAVYYCAKY PHYYGSSHWYFDVWGQGTLVTVSS (SEQ ID NO: 79) |

In other specific embodiments, the antibody in the MRD-containing antibody specifically binds VEGF. In a specific embodiment, the antibody is bevacizumab (e.g., AVASTIN®, Genentech). In one embodiment, the antibody binds to the same epitope as bevacizumab. In another embodiment, the antibody competitively inhibits binding of bevacizumab to VEGF. In another specific embodiment, the antibody is r84 (Peregrine) or 2C3 (Peregrine). In another embodiment, the antibody binds to the same epitope as r84 or 2C3. In another embodiment, the antibody competitively inhibits VEGF binding by r84 or 2C3. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, or 3 of the above antibodies are also encompassed by the invention.

In one embodiment, an MRD-containing antibody binds VEGF and additionally binds an angiogenic target selected from: VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TNFSF2 (TNFa), FGFR3, EFNa1, EFNa2, ANG1, ANG2, IL6, IL8, IL18, HGF, TIE2, PDGFA, PLGF, PDGFB, CXCL12, KIT, GCSF, CXCR4, PTPRC, TIE2, VEGFR1, VEGFR2, VEGFR3, Notch 1, DLL4, EGFL7, α2β1 integrin, α4β1 integrin, α5β1 integrin, αvβ3 integrin, TGFb, MMP2, MMP7, MMP9, MMP12, PLAU, VCAM1, PDGFRA, and PDGFRB. Multivalent and multispecific compositions (e.g., MRD-containing antibodies) that bind VEGF and at least 1, 2, 3, 4, 5 or more of these targets are also encompassed by the invention. In specific embodiments, the antibody component of the MRD-containing antibody binds VEGF. In further embodiments, the antibody component of the MRD-containing antibody is r85, 2C3 or AT001. In a specific embodiment, the antibody component of the MRD-containing antibody is bevacizumab.

In one embodiment, an MRD-containing antibody binds VEGF and additionally binds a target selected from: IL1 beta, phosphatidylserine, TNFSF11 (RANKL), TNFSF12 (TWEAK), IGF1,2, IGF2, IGF1, DKK1, SDF2, CXC3CL1 (fractalkine), sclerostin and tetanus toxoid and HGF. In another embodiment, an MRD-containing antibody binds VEGF and additionally binds a target selected from: ErbB3, EGFR, cMet, VEGF, RON (MST1R), DLL4, CDCP1 CD318), NRP1, ROBO4, CD13, CTLA4 (CD152), ICOS (CD278), CD20, CD22, CD30, CD33, CD80 and IL6R. Multivalent and multispecific compositions (e.g., MRD-containing antibodies) that bind VEGF and at least 1, 2, 3, 4, 5 or more of these targets are also encompassed by the invention. In specific embodiments, the antibody component of the MRD-containing antibody binds VEGF. In further embodiments, the antibody component of the MRD-containing antibody is r85, 2C3 or AT001. In a specific embodiment, the antibody component of the MRD-containing antibody is bevacizumab.

In another embodiment, the MRD-containing antibody specifically binds VEGFR1. In one embodiment, the antibody competitively inhibits binding of Aflibercept (Regeneron) to VEGFR1. In another embodiment, the antibody in the MRD-containing antibody inhibits VEGFR1 dimerization. An MRD that competes for target binding with Aflibercept is also encompassed by the invention. Multivalent and multispecific compositions (e.g., MRD-containing antibodies) having 1, 2, 3, 4, 5, 6, or more MRDs that compete for target binding with Aflibercept are also encompassed by the invention.

In another embodiment, the MRD-containing antibody specifically binds VEGFR2. In a specific embodiment, the antibody is ramucirumab (e.g., IMC1121B and IMC1C11, ImClone). In another embodiment, the antibody in the MRD-containing antibody inhibits VEGFR2 dimerization. In one embodiment, the antibody binds to the same epitope as ramucirumab. In another embodiment, the antibody competitively inhibits binding of ramucirumab to VEGFR2. In another embodiment, the antibody competitively inhibits binding of Aflibercept to VEGFR2. An MRD that competes for target binding with ramucirumab is also encompassed by the invention. Multivalent and multispecific compositions (e.g., MRD-containing antibodies) having 1, 2, 3, 4, 5, 6, or more MRDs that compete for target binding with ramucirumab or Aflibercept are also encompassed by the invention.

In other embodiments, the antibody in the MRD-containing antibody specifically binds to an FGF receptor (e.g., FGFR1, FGFR2, FGFR3, or FGFR4). In one embodiment, the antibody in the MRD-containing antibody is an antibody that specifically binds to FGFR1 (e.g., FGFR1-IIIC). In a specific embodiment, the antibody is IMC-A1 (Imclone). In one embodiment, the antibody binds to the same epitope as IMC-A1. In another embodiment, the antibody competitively inhibits binding of IMC-A1 to FGFR1. In an additional embodiment, the antibody competitively inhibits binding of FP-1039 (Five Prime) to an FGF ligand of FGFR1. In another embodiment, the antibody in the MRD-containing antibody is an antibody that specifically binds to FGFR2 (e.g., FGFR2-IIIB and FGFR2-IIIC). In a further embodiment, the antibody in the MRD-containing antibody is an antibody that specifically binds to FGFR3. In a specific embodiment, the antibody is IMC-A1 (Imclone). In one embodiment, the antibody binds to the same epitope as PRO-001 (ProChon Biotech), R3Mab (Genentech), or 1A6 (Genentech). In another embodiment, the antibody competitively inhibits binding of PRO-001 (ProChon Biotech), R3Mab (Genentech), or 1A6 (Genentech). An MRD that competes for target binding with one of the above antibodies or ligand traps is also encompassed by the invention. Multivalent and multispecific compositions (e.g., MRD-containing antibodies) having 1, 2, 3, 4, 5, 6, or more MRDs that compete for target binding with 1 or more of the above antibodies or ligand traps are also encompassed by the invention.

In one embodiment, the antibody in the MRD-containing antibody specifically binds CD20. In a specific embodiment the antibody is rituximab (e.g., RITUXAN®/MAB-THERA®, Genentech/Roche/Biogen Idec). In one embodiment, the antibody binds to the same epitope as rituximab. In another embodiment, the antibody competitively inhibits binding of rituximab to CD20. In an additional embodiment, the antibody is GA101 (Biogen Idec/Roche/Glycart). In one embodiment, the antibody binds to the same epitope as GA101. In another embodiment, the antibody competitively inhibits binding of GA101 to CD20. In an additional embodiment, the antibody is PF-5,230,895 (SBI-087; Pfizer). In one embodiment, the antibody binds to the same epitope as PF-5,230,895. In another embodiment, the antibody competitively inhibits binding of PF-5,230,895 to CD20. In another specific embodiment, the antibody is ocrelizumab (e.g., 2H7; Genentech/Roche/Biogen Idec). In one embodiment, the antibody binds to the same epitope as ocrelizumab. In another embodiment, the antibody competitively inhibits binding of ocrelizumab to CD20. In another specific embodiment, the MRD-containing antibody is selected from: obinutuzumab (e.g., GA101; Biogen Idec/Roche/Glycart), ofatumumab (e.g., ARZERRA® and HuMax-CD20 Genmab), veltuzumab (e.g., IMMU-160, Immunomedics), AME-133 (Applied Molecular Evolution), SGN35 (Millennium), TG-20 (GTC Biotherapeutics), afutuzumab (Hoffman-La Roche) and PRO131921 (Genentech). In another embodiment, the antibody binds to the same epitope as an antibody selected from: obinutuzumab, ofatumumab, veltuzumab, AME-133, SGN35, TG-20 and PRO131921. In another embodiment, the antibody competitively inhibits CD20 binding by an antibody selected from: obinutuzumab, ofatumumab, veltuzumab, AME-133, SGN35, TG-20, afutuzumab, and PRO131921. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, 3, 4, 5, 6, or more of the above antibodies are also encompassed by the invention. Thus, the invention encompasses MRD-containing antibodies comprising at least 1, 2, 3, 4, 5, 6, or more MRDs that compete for target binding with at least 1, 2, 3, 4, 5, 6 of the above antibodies.

In additional embodiments, an MRD-containing antibody binds CD20 and a target selected from: CD19, CD22, CD30, TNFRSF5 (CD40), CD52, CD74, CD80, CD138, VEGFR1, VEGFR2, EGFR, TNFRSF10A (DR4), TNFRSF10B (DR5), TNF, NGF, VEGF, IGF1,2, IGF2, IGF1 and RANKL. In additional embodiments, an MRD-containing antibody binds CD20 and a target selected from: CD3, CD4 and NKG2D. Multivalent and multispecific compositions (e.g., MRD-containing antibodies) that bind CD20 and also bind 2, 3, 4, 5 or more of these targets are also encompassed by the invention. In specific embodiments, the antibody component of the MRD-containing antibody binds CD20. In further embodiments, the antibody component of the MRD-containing antibody is an antibody selected from: rituximab, GA101, PF-5,230,895, ocrelizumab obinutuzumab, ofatumumab, veltuzumab, AME-133, SGN35, TG-20, afutuzumab and PRO131921.

In one embodiment the MRD-containing antibody specifically binds IGF1R. In a specific embodiment, the antibody is selected from: cixutumumab (e.g., IMC-A12, Imclone), figitumumab (e.g., CP-751,871, Pfizer), AMG479 (Amgen), BIIB022 (Biogen Idec), SCH 717454 (Schering-Plough), and R1507 (Hoffman La-Roche). In one embodiment, the antibody binds to the same epitope as an antibody selected from: cixutumumab, figitumumab, AMG479, BIIB022, SCH 717454, and R1507. In another embodiment, the antibody competitively inhibits IGF1R binding by an antibody selected from: cixutumumab, figitumumab, AMG479, BIIB022, SCH 717454, and R1507. In a specific embodiment, the antibody is figitumumab. In another specific embodiment, the antibody binds to the same epitope as figitumumab. In a further specific embodiment, the antibody competitively inhibits IGF1R binding by figitumumab. In an additional specific embodiment, the antibody is BIIB022. In another specific embodiment, the antibody binds to the same epitope as BIIB022. In a further specific embodiment, the antibody competitively inhibits IGF1R binding by BIIB022. In another embodiment, the antibody in the MRD-containing antibody inhibits IGF1R dimerization. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for IGF1R binding with 1, 2, 3, 4, 5, 6, or more of the above antibodies are also encompassed by the invention. Thus, the invention encompasses MRD-containing antibodies comprising at least 1, 2, 3, 4, 5, 6, or more MRDs that compete for IGF1R binding with at least 1, 2, 3, 4, 5, 6 of the above antibodies.

In additional embodiments, an MRD-containing antibody binds IGF1R and a target selected from: EGFR, ErbB2, ErbB3, PDGFRa, PDGFRb, cMet, TNFRSF10A (DR4), TNFRSF10B (DR5), CD20, NKG2D, VEGF, PGE2, IGF1, IGF2 and IGF1,2. In additional embodiments, an MRD-containing antibody binds IGF1R and a target selected from: CD3, CD4 and NKG2D. Multivalent and multispecific compositions (e.g., MRD-containing antibodies) that bind IGF1R and bind at 1, 2, 3, 4, 5 or more of these targets are also encompassed by the invention. In specific embodiments, the antibody component of the MRD-containing antibody binds IGF1R. In further embodiments, the antibody component of the MRD-containing antibody is selected from: cixutumumab, figitumumab, AMG479, BIIB022, SCH 717454, and R1507.

In additional embodiments, the multivalent and monovalent multispecific composition (e.g., MRD-containing antibody) binds a target (e.g., ligand, receptor, or accessory protein) associated with an endogenous blood brain barrier (BBB) receptor mediated transport system (e.g., the insulin receptor, transferrin receptor, leptin receptor, lipoprotein receptor, and the IGF receptor mediated transport systems) and is capable of crossing to the brain side of the BBB. In some embodiments, the multivalent and monovalent multispecific composition (e.g., MRD-containing antibody) has 2, 3, 4, 5, or more binding sites (i.e., is capable of multivalently binding) a target antigen (e.g., ligand, receptor, or accessory protein) associated with an endogenous BBB receptor mediated transport system (e.g., the insulin receptor, transferrin receptor, leptin receptor, lipoprotein receptor, and the IGF receptor mediated transport systems). In additional embodiments, the multivalent and monovalent multispecific composition (e.g., MRD-containing antibody) has a single binding site for a target associated with an endogenous BBB receptor mediated transport system. In further embodiments, the multivalent and monovalent multispecific composition has 2, 3, 4, 5, or more single binding sites for a target associated with an endogenous BBB receptor mediated transport system. In further embodiments, the MRD-containing antibody binds 1, 2, 3, 4, 5, or more targets located on the brain (cerebrospinal fluid) side of the BBB. In further embodiments, the MRD-containing antibody additionally binds 1, 2, 3, 4, 5, or more targets located on the brain (cerebrospinal fluid) side of the BBB. In particular embodiments, the MRD-containing antibody binds 1, 2, 3, 4, 5, or more targets associated with a neurological disease or disorder. In particular embodiments, the neurological disease or disorder is selected from brain cancer, a neurodegenerative disease, schizophrenia, epilepsy, Alzheimer's disease, Parkinson's disease, Huntington's disease, ALS, multiple sclerosis, Neuromyelitis optica and Neuro-AIDS (e.g., HIV-associated dementia). Accordingly, the invention encompasses methods of treating a patient by administering a therapeutically effective amount of a multivalent and monovalent multispecific composition to treat a neurological disease or disorder selected from brain cancer, a neurodegenerative disease, schizophrenia, epilepsy, Alzheimer's disease, Parkinson's disease, Huntington's disease, ALS, multiple sclerosis, Neuromyelitis optica and Neuro-AIDS (e.g., HIV-associated dementia). In another embodiment, the multivalent and monovalent multispecific composition is administered to a patient to treat a brain cancer, metastatic cancer of the brain, or primary cancer of the brain. In additional embodiments, the multivalent and monovalent multispecific composition is administered to a patient to treat a neurological tumor such as, a glioma (e.g., a glioblastoma, glioblastoma multiforme (GBM), and astrocytoma), ependymoma, oligodendroglioma, neurofibroma, sarcoma, medulloblastoma, primitive neuroectodermal tumor, pituitary adenoma, neuroblastoma or cancer of the meninges (e.g., meningioma, meningiosarcoma and gliomatosis). In particular embodiments the invention encompasses methods of treating a patient by administering a therapeutically effective amount of a multivalent and monovalent multispecific composition to treat a neurodegenerative disease.

In some embodiments, the multivalent and monovalent multispecific composition (e.g., MRD-containing antibody) binds an endogenous BBB receptor mediated transport system selected from the insulin receptor, transferrin receptor, leptin receptor, lipoprotein receptor, and the IGF receptor mediated transport systems.

In some embodiments, the multivalent and multispecific composition (e.g., MRD-containing antibody) binds transferrin receptor. In additional embodiments, the MRD-containing antibody binds a target selected from: low-density lipoprotein receptor 1 (LRP-1), a LRP-1 ligand or a functional fragment or variant thereof that binds LRP-1, Low-density lipoprotein receptor 2 (LRP-2), a LRP-2 ligand or a functional fragment or variant thereof that binds LRP-1, a transferrin protein or a functional fragment or variant thereof, insulin receptor, TMEM30A, leptin receptor, IGF receptor, an IGFR ligand or a functional fragment or variant thereof, diphtheria receptor, a diphtheria receptor ligand or a functional fragment or variant thereof, choline transporter, a complex that binds choline receptor, an amino acid transporter (e.g., LAT1/CD98, SLC3A2, and SLC7A5), an amino acid transporter ligand or a functional fragment or variant thereof, RAGE, a RAGE ligand or a functional fragment or variant thereof, SLC2A1 and a SLC2A1 ligand or a functional fragment or variant thereof.

In additional embodiments, the multivalent and multispecific composition (e.g., MRD-containing antibody) binds RAGE. In further embodiments, the multivalent and multispecific composition (e.g., MRD-containing antibody) binds RAGE and a target selected from: Abeta, endothelin1, TNF, IL6, MCSF, an AGE, a S100 member, HMGB1, LPS and TLR2. Multivalent and multispecific compositions that bind RAGE and also bind 2, 3, 4, 5 or more of these targets are also encompassed by the invention. In specific embodiments, the antibody component of the MRD-containing antibody binds RAGE.

In additional embodiments, the multivalent and multispecific composition (e.g., MRD-containing antibody) binds a target antigen associated with an endogenous blood brain barrier (BBB) receptor mediated transport system and also binds a target antigen selected from alpha-synuclein, RGM A, NOGO A, NgR, OMGp MAG, CSPG, neurite inhibiting semaphorins (e.g., Semaphorin 3A and Semaphorin 4) an ephrin, A-beta, AGE (S100 A, amphoterin), NGF, soluble A-B, aggrecan, midkine, neurocan, versican, phosphacan, Te38, and PGE2, IL1, IL1R, IL6, IL6R, IL12, IL18, IL23, TNFSF12 (TWEAK), TNFRSF5 (CD40), TNFSF5 (CD40 LIGAND), CD45RB, CD52, CD200, VEGF, VLA4, TNF alpha, Interferon gamma, GMCSF, FGF, C5, CXCL13, CCR2, CB2, MIP 1a and MCP-1. In a further embodiment, the MRD-containing antibody has a single binding site for a target associated with an endogenous blood brain barrier (BBB) receptor mediated transport system and further binds a target selected from alpha-synuclein, RGM A, NOGO A, NgR, OMGp MAG, CSPG, neurite inhibiting semaphorins (e.g., Semaphorin 3A and Semaphorin 4) an ephrin, A-beta, AGE (S100 A, amphoterin), NGF, soluble A-B, aggrecan, midkine, neurocan, versican, phosphacan, Te38, PGE2, IL1, IL1R, IL6, IL6R, IL12, IL18, IL23, TNFSF12 (TWEAK), TNFRSF5 (CD40), TNFSF5 (CD40 LIGAND), CD45RB, CD52, CD200, VEGF, VLA4, TNF alpha, Interferon gamma, GMCSF, FGF, C5, CXCL13, CCR2, CB2, MIP 1a and MCP-1.

In additional embodiments, the MRD-containing antibody is administered to a patient to treat a neurological disease or disorder selected from brain cancer, a neurodegenerative disease, schizophrenia, epilepsy, Alzheimer's disease, Parkinson's disease, Huntington's disease, ALS, multiple sclerosis, Neuromyelitis optica and Neuro-AIDS (e.g., HIV-associated dementia). In one embodiment, the multivalent and monovalent multispecific composition contains 2 binding sites for 2 or more of the above targets. In a further embodiment, the multivalent and monovalent multispecific composition contains 2 binding sites for 3 or more targets. In additional embodiments, the targets bound by the multivalent and monovalent multispecific composition are associated with cancer. In a further embodiment the targets bound by the multivalent and monovalent multispecific composition are associated with 1, 2, 3, 4, 5 or more different signaling pathways or modes of action associated with cancer.

In one embodiment, the antibody in the MRD-containing antibody specifically binds integrin. In a specific embodiment, the antibody is selected from: MEDI-522 avb3 (VITAXIN®, MedImmune), CNTO 95 a5b3 (Centocor), JC7U αvβ3, and volociximab a5b1 (e.g., M200, PDL and Biogen Idec). In another embodiment, the antibody binds to the same epitope as an antibody selected from: MEDI-522, CNTO 95, JC7U αvβ3, and volociximab. In another embodiment, the antibody competitively inhibits integrin binding by an antibody selected from: MEDI-522, CNTO 95, JC7U, and M200. In a specific embodiment, the antibody is natalizumab (e.g., TSABRI®, Biogen Idec). In one embodiment, the antibody binds to the same epitope as natalizumab. In another embodiment, the antibody competitively inhibits integrin binding by natalizumab. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, 3, 4, 5, 6, or more of the above antibodies are also encompassed by the invention.

In one embodiment, the antibody in the MRD-containing antibody specifically binds cMet. In a specific embodiment, the antibody is selected from: MetMab (OA-5D5, Genentech), AMG-102 (Amgen) and DN30. In another embodiment, the antibody binds to the same epitope as an antibody selected from: MetMab), AMG-102 and DN30. In another embodiment, the antibody competitively inhibits cMET binding by an antibody selected from: MetMab (OA-5D5), AMG-102 and DN30. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, or 3 of the above antibodies are also encompassed by the invention.

In one embodiment, the antibody in the MRD-containing antibody specifically binds cMet and the antibody is selected from: 11E1, CE-355621, LA480 and LMH87. In another embodiment, the antibody binds to the same epitope as an antibody selected from: MetMab), AMG-102 and DN30. In another embodiment, the antibody competitively inhibits cMET binding by an antibody selected from: 11E1, CE-355621, LA480 and LMH87. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, 3 or 4 of the above antibodies are also encompassed by the invention.

In additional embodiments, an MRD-containing antibody binds cMET and a target selected from: ErbB2, ErbB3, EGFR, IGF1R, NRP1, RON, PDGFRa, PDGFRb, VEGF, VEGFR1, VEGFR2, TGF beta, TGF beta R2, CD82, CD152, NGF, BMP2, BMP4, BMP5, BMP9, BMP10, BMPR-IA, ALK1, a3b1 integrin and HGF. Multivalent and multispecific compositions (e.g., MRD-containing antibodies) that bind cMET and also bind at least 1, 2, 3, 4, 5 or more of these targets are also encompassed by the invention. In specific embodiments, the antibody component of the MRD-containing antibody binds cMET. In further embodiments, the antibody component of the MRD-containing antibody is an antibody selected from: MetMab, AMG-102 and DN30. In other embodiments, the antibody component of the MRD-containing antibody is an antibody selected from: 11E1, CE-355621, LA480 and LMH87.

In additional embodiments, an MRD-containing antibody binds MST1R (RON). In a specific embodiment, an MRD-containing antibody binds RON and a target selected from: EGFR, ErbB2, ErbB3, VEGFR1, VEGFR2, cMET, CXCR4, VEGF, MST, MTSP1, CDCP1, EPHB2, NGF, CXCL12 and HGF (SF). Multivalent and multispecific compositions (e.g., MRD-containing antibodies) that bind MST1R and also bind at least 1, 2, 3, 4, 5 or more of these targets are also encompassed by the invention. In specific embodiments, the antibody component of the MRD-containing antibody binds MST1R.

In one embodiment, the antibody in the MRD-containing antibody specifically binds HGF (SF). In a specific embodiment, the antibody is AMG-102 (Amgen) or SCH 900105 (AV-229, AVEO). In another embodiment, the antibody binds to the same epitope as AMG-102 (Amgen) or SCH 900105 (AV-229, AVEO). In another embodiment, the antibody competitively inhibits HGF binding by AMG-102 (Amgen) or SCH 900105 (AV-229, AVEO). An MRD that competes for target binding with AMG-102 (Amgen) or SCH 900105 (AV-229, AVEO) is also encompassed by the invention. Multivalent and multispecific compositions (e.g., MRD-containing antibodies) having 1, 2, 3, 4, 5, 6, or more MRDs that compete for target binding with 1, 2, or 3 of the above antibodies are also encompassed by the invention.

In a specific embodiment, an MRD-containing antibody binds HGF and a target selected from: ErbB2, ErbB3, EGFR, IGF1R, NRP1, RON, PDGFRa, PDGFRb, VEGF, VEGFR1, VEGFR2, TGF beta, TGF beta R2, CD82, CD152, NGF, BMP2, BMP4, BMP5, BMP9, BMP10, BMPR-IA, ALK1, a3b1 integrin, cMET, MST1R (RON), CXCR4, MST, MTSP1, CDCP1, EPHB2, NGF, CXCL12 NRP1 and phosphatidylserine. Multivalent and multispecific compositions (e.g., MRD-containing antibodies) that bind HGF and also bind at least 1, 2, 3, 4, 5 or more of these targets are also encompassed by the invention. In specific embodiments, the antibody component of the MRD-containing antibody binds HGF. In further embodiments, the antibody component of the MRD-containing antibody is AMG-102 or SCH 900105.

In an additional embodiment, the antibody in the MRD-containing antibody specifically binds a5b1 integrin (VLA5). In a specific embodiment, the antibody is volociximab (e.g., M200 Biogen Idec). In another embodiment, the antibody binds to the same epitope as volociximab. In a further embodiment, the antibody competitively inhibits a5b1 integrin binding by volociximab. An MRD that competes for a5b1 integrin binding with volociximab is also encompassed by the invention. Multivalent and multispecific compositions (e.g., MRD-containing antibodies) having 1, 2, 3, 4, 5, 6, or more MRDs that compete for a5b1 integrin binding with volociximab are also encompassed by the invention.

In another embodiment, the antibody target of the MRD-containing antibody is an antigen associated with an autoimmune disorder, inflammatory or other disorder of the immune system or is associated with regulating an immune response.

In another embodiment the MRD-containing antibody improves the performance of antigen presenting cells (e.g., dendritic cells). In one embodiment the antibody target of the MRD-containing antibody is a member selecting from: CD19, CD20, CD21, CD22, CD23, CD27, CD28, CD30, CD30L, TNFSF14 (LIGHT, HVEM Ligand), CD70, ICOS, ICOSL (B7-H2), CTLA4, PD-1, PDL1 (B7-H1), B7-H4, B7-H3, PDL2 (B7-DC), BTLA, CD46, CD80 (B7-1), CD86 (B7-2), HLA-DR, CD74, PD1, TNFRSF4 (OX40), TNFRSF9 (41BB), TNFSF4 (OX40 Ligand), TNFSF9 (41BB Ligand), TNFRSF1A (TNFR1, p55, p60), TNFRSF1B (TNFR2), TNFRSF13B (TACI), TNFRSF13C (BAFFR), TNFRSF17 (BCMA), TNFRSF18 (GITR), MHC-1, TNFRSF5 (CD40), TLR4, TNFRSF14 (HVEM), FcgammaRIIB, and IL4R.

In one embodiment the antibody target of the MRD-containing antibody is an immunoinhibitory target selected from: IL1, IL1 beta, IL1Ra, L-5, IL6, IL6R, CD26L, CD28, CD80, FcRn, and Fc Gamma RIIB. An MRD that binds to one of the above targets is encompassed by the invention. Multivalent and multispecific compositions (e.g., MRD-containing antibodies) having 1, 2, 3, 4, 5, 6, or more MRDs that bind to 1, 2, 3, 4, 5, 6, or more of the above targets are also encompassed by the invention.

In one embodiment, an MRD-containing antibody binds prostaglandin E2 (PGE2). In a specific embodiment, an MRD-containing antibody binds IL6R and a target selected from: EGFR, IGF1R, IL6R, TNF, NGF, IL1 beta, IL6, IL17A, VEGF, IL15, IL18, S1P and Abeta. Multivalent and multispecific compositions (e.g., MRD-containing antibodies) that bind PGE2 and also bind at least 1, 2, 3, 4, 5 or more of these targets are also encompassed by the invention. In specific embodiments, the antibody component of the MRD-containing antibody binds PGE2.

In another embodiment the antibody target of the MRD-containing antibody is an immunostimulatory target (e.g., an agonist of a target associated immune cell activation (such as TNFRSF9 (41BB) or TNFRSF5 (CD40)) or an antagonist of an inhibitory immune checkpoint (such as CTLA-4)). In one embodiment the antibody target of the MRD-containing antibody is an immunostimulatory target selected from: CD25, CD28, CTLA-4, PD1, PDL1, B7-H1, B7-H4, IL10, TGFbeta, TNFSF4 (OX40 Ligand), TNFRSF4 (OX40), TNFSF5 (CD40 Ligand), TNFRSF5 (CD40), TNFSF9 (41BB Ligand), TNFRSF9 (41BB), TNFSF14 (LIGHT, HVEM Ligand), TNFRSF14 (HVEM), TNFSF15 (TL1A), TNFRSF25 (DR3), TNFSF18 (GITR Ligand) and TNFRSF18 (GITR). An MRD that binds to one of the above targets is encompassed by the invention. Multivalent and multispecific compositions (e.g., MRD-containing antibodies) having 1, 2, 3, 4, 5, 6, or more MRDs that bind to 1, 2, 3, 4, 5, 6, or more of the above targets are also encompassed by the invention. In specific embodiments, the MRD-containing antibody binds 2, 3 or all 4 targets selected from CTLA-4, TNFRSF18 (GITR), 4-1BB, and TNFRSF5 (CD40). In one embodiment, the MRD-containing antibody binds CTLA-4 and TNFRSF9 (41BB). In another embodiment, the MRD-containing antibody binds CTLA-4 and TNFRSF18 (GITR). In another embodiment, the MRD-containing antibody binds CTLA-4 and TNFRSF5 (CD40). In another embodiment, the MRD-containing antibody binds TNFRSF5 (CD40) and TNFRSF9 (41BB). In another embodiment, the MRD-containing antibody binds TNFRSF4 (OX40) and TNFRSF9 (41BB). In another embodiment, the MRD-containing antibody binds PD1 and B7-H1. In an additional embodiment the MRD-containing antibody enhances an immune response, such as the immune system's anti-tumor response or an immune response to a vaccine.

In another embodiment the antibody target of the MRD-containing antibody is a cytokine selected from: IL1 alpha, IL1 beta, IL18, TNFSF2 (TNFa), LTalpha, LT beta, TNFSF11 (RANKL), TNFSF13B (BLYS), TNFSF13 (APRIL), IL6, IL7, IL10, IL12, IL15, IL17A, IL23, OncoStatinM, TGFbeta, BMP2-15, PDGF (e.g., PDGF-A, PDGF-B, PDGF-CC, PDGF-C, PDGF-D), an FGF family member (e.g., FGF1, FGF2, FGF4, FGF7, FGF8b and FGF19), VEGF (e.g., VEGFA and VEGFB), MIF, and a type I interferon. An MRD that binds to one of the above targets is encompassed by the invention. Multivalent and multispecific compositions (e.g., MRD-containing antibodies) having 1, 2, 3, 4, 5, 6, or more MRDs that bind to 1, 2, 3, 4, 5, 6, or more of the above targets are also encompassed by the invention. Thus, the invention encompasses MRD-containing antibodies comprising at least 1, 2, 3, 4, 5, 6, or more MRDs that bind to at least 1, 2, 3, 4, 5, 6 of the above targets.

In another embodiment the antibody target of the MRD-containing antibody is a cytokine selected from: TNF, CD25, CD28, CTLA-4, PD1, PDL1, B7-H1, B7-H4, IL10, TGF-beta, TNFSF4 (OX40 Ligand), TNFRSF4 (OX40), TNFSF5 (CD40 Ligand), TNFRSF5 (CD40), TNFSF9 (41BB Ligand), TNFRSF9 (41BB), TNFSF14 (LIGHT, HVEM Ligand), TNFRSF14 (HVEM), TNFSF15 (TL1A), TNFRSF25 (DR3), TNFSF18 (GITR Ligand), and TNFRSF18 (GITR). An MRD that binds to one of the above targets is encompassed by the invention. Multivalent and multispecific compositions (e.g., MRD-containing antibodies) having 1, 2, 3, 4, 5, 6, or more MRDs that bind to 1, 2, 3, 4, 5, 6, or more of the above targets are also encompassed by the invention. Thus, the invention encompasses MRD-containing antibodies comprising at least 1, 2, 3, 4, 5, 6, or more MRDs that bind to at least 1, 2, 3, 4, 5, 6 of the above targets.

In one embodiment the antibody target of the MRD-containing antibody is IL1Ra, IL1Rb, IL2, IL3, IL4, IL7, IL10, IL11, IL15, IL16, IL17, IL17A, IL17F, IL18, IL19, IL25, IL32, IL33, interferon beta, SCF, BCA1/CXCL13, CXCL1, CXCL2, CXCL6, CXCL13, CXCL16, C3AR, C5AR, CXCR1, CXCR2, CCR1, CCR3, CCR7, CCR8, CCR9, CCR10, ChemR23, CCL3, CCL5, CCL11, CCL13, CCL17, CCL18, CCL19, CCL20, CCL21, CCL22, CCL24, CCL25, CCL26, CCL27, MPL, GP130, TLR2, TLR3, TLR4, TLR5, TLR7, TLR8, TLR9, TREM1, TREM2, FcRn, FcGamma RIIB, oncostatin M, lymphotoxin alpha (LTa), integrin beta 7 subunit, CD49a (integrin alpha 1), integrin a5b3, MIF, ESM1, WIF1, cathepsin B, cathepsin D, cathepsin K, cathepsin S, TNFSF2 (TNFa), TNFSF3 (LTb), TNFRSF3 (LTBR), TNFSF6 (Fas Ligand), TNFRSF6 (Fas, CD95), TNFRSF6B (DcR3), TNFSF8 (CD30 Ligand), TNFRSF8 (CD30), TNFSF9 (41BB Ligand), TNFRSF9 (41BB), TNFSF11 (RANKL), TNFRSF11A (RANK), TNFSF14 (LIGHT, HVEM Ligand), TNFRSF14 (HVEM), TNFRSF16 (NGFR), TNFSF18 (GITR Ligand), TNFRSF18 (GITR), TNFRSF19L (RELT), TNFRSF19 (TROY), TNFRSF21 (DR6), CD14, CD23 CD25, CD28, CD36, CD36L, CD39, CD52, CD91, CD153, CD164, CD200, CD200R, BTLA, CD80 (B7-1), CD86 (B7-2), B7h, ICOS, ICOSL (B7-H2), MHC, CD, B7-H3, B7-H4, B7x, SLAM, KIM-1, SLAMF2, SLAMF3, SLAMF4, SLAMF5, SLAMF6, or SLAMF7. An MRD that binds to one of the above targets is encompassed by the invention. Multivalent and multispecific compositions (e.g., MRD-containing antibodies) having 1, 2, 3, 4, 5, 6, or more MRDs that bind to 1, 2, 3, 4, 5, 6, or more of the above targets are also encompassed by the invention. Thus, the invention encompasses MRD-containing antibodies comprising at least 1, 2, 3, 4, 5, 6, or more MRDs that bind to at least 1, 2, 3, 4, 5, 6 of the above targets. The above antibody and MRD targets and those otherwise described herein are intended to be illustrative and not limiting.

In another embodiment, the antibody target of the MRD-containing antibody is TNFSF1A (TNF/TNF-alpha), TNFRSF1A (TNFR1, p55, p60), TNFRSF1B (TNFR2), TNFSF7 (CD27 Ligand, CD70), TNFRSF7 (CD27), TNFSF13B (BLYS), TNFSF13 (APRIL), TNFRSF13B (TACI), TNFRSF13C (BAFFR), TNFRSF17 (BCMA), TNFSF15 (TL1A), TNFRSF25 (DR3), TNFSF12 (TWEAK), TNFRSF12 (TWEAKR), TNFSF4 (OX40 Ligand), TNFRSF4 (OX40), TNFSF5 (CD40 Ligand), TNFRSF5 (CD40), IL1, IL1 beta, IL1R, IL2R, IL4-Ra, IL5, IL5R, IL6, IL6R, IL9, IL12, IL13, IL14, IL15, IL15R, IL17f, IL17R, IL17Rb, IL17RC, IL20, IL21, IL22RA, IL23, IL23R, IL31, TSLP, TSLPR, interferon alpha, interferon gamma, B7Rp-1, cKit, GMCSF, GMCSFR, CTLA-4, CD2, CD3, CD4, CD11a, CD18, CD20, CD22, CD26L, CD30, TNFRSF5 (CD40), CD80, CD86, CXCR3, CXCR4, CCR2, CCR4, CCR5, CCR8, CCL2, CXCL10, PLGF, PD1, B7-DC (PDL2), B7-H1 (PDL1), alpha4 integrin, A4B7 integrin, C5, RhD, IgE, or Rh. An MRD that binds to one of the above targets is encompassed by the invention. Multivalent and multispecific compositions (e.g., MRD-containing antibodies) having 1, 2, 3, 4, 5, 6, or more MRDs that bind to 1, 2, 3, 4, 5, 6, or more of the above targets are also encompassed by the invention. Thus, the invention encompasses MRD-containing antibodies comprising at least 1, 2, 3, 4, 5, 6, or more MRDs that bind to at least 1, 2, 3, 4, 5, 6 of the above targets.

In particular embodiments, the antibody target of the MRD-containing antibody competes for target binding with: SGN-70 CD70 (Seattle Genetics), SGN-75 CD70 (Seattle Genetics), Belimumab BLYS (e.g., BENLYSTA®, Human Genome Sciences/GlaxoSmithKline), Atacicept BLYS/APRIL (Merck/Serono), TWEAK (e.g., Biogen mAb), TL1A antibodies of CoGenesys/Teva (e.g., hum11D8, hum25B9, and hum1B4 (U.S. Appl. Publ. No. 2009/0280116), OX40 mAb, humAb OX40L (Genentech), rilonacept IL1 trap (e.g., ARCALYST®, Regeneron), catumaxomab IL1beta (e.g., REMOVAB®, Fresenius Biotech GmbH), Xoma052 IL1beta (Lilly), canakinumab IL1beta (e.g., ILARIS® (Novartis) and ACZ885 (Novartis)), AMG108 IL1R (Amgen), daclizumab IL2Ra (e.g., ZENAPAX®, Hoffman-La Roche), basiliximab IL2Ra (e.g., SIMULECT®, Novartis), AMGN-317 IL4a (Amgen), pascolizumab IL4 (PDL), mepolizumab IL5 (e.g., BOSATRIA®, GlaxoSmithKline), reslizumab IL5 (e.g., SCH55700, Ception Therapeutics), benralizumab IL5R (e.g., MEDI-563 MedImmune), BIW-8405, IL5R (BioWa), etanercept TNFR2-fc (e.g., ENBREL®, Amgen), siltuximab IL6 (e.g., CNT0328, Centocor), CNT0136 IL6 (Centocor), CDP-6038 IL6 (UCB), AMGN-220 IL6 (Amgen), REGN-88 IL6R (Regeneron), tocilizumab IL6R (e.g., ACTEMRA™/ROACTEMRA™, Chugai/Roche), MEDI-528 IL9 (MedImmune), briakinumab IL12/13 (e.g., ABT-874, Abbott), ustekinumab IL12, IL23 (e.g., STELARA® and CNTO 1275, Centocor), TNX-650 IL13 (Tanox), lebrikizumab IL13 (Genentech), tralokinumab IL13 (e.g., CAT354, e.g., Cambridge Antibody Technology), AMG714 IL15 (Amgen), CRB-15 IL15R (Hoffman La-Roche), AMG827 IL17R (Amgen), IL17RC antibody of Zymogenetics/Merck Serono, IL20 antibody of Zymogenetics, IL20 antibody of Novo Nordisk, IL21 antibody of Novo Nordisk (e.g., NCT01038674), IL21 antibody Zymogenetics (Zymogenetics), IL22RA antibody of Zymogenetics, IL31 antibody of Zymogenetics, AMG157 TSLP (Amgen), MEDI-545 interferon alpha (MedImmune), MEDI-546 interferon alpha receptor (MedImmune), AMG811 interferon gamma (Amgen), INNO202 interferon gamma (Innogenetics/Advanced Biotherapy), HuZAF interferon-gamma (PDL), AMG557 B7RP1 (Amgen), AMG191 cKit (Amgen), MOR103 GMCSF (MorphoSys) mavrilimumab GMCSFR (e.g., CAM-3001, MedImmune), tremelimumab CTLA4 (e.g., CP-675,206, Pfizer), iplimumab CTLA4 (e.g., MDX-010, BMS/Medarex), alefacept CD2 (e.g., AMEVIVE®, Astellas), siplizumab CD2 (e.g., MEDI-507, MedImmune), otelixizumab CD3 (e.g., TRX4, Tolerx/GlaxoSmithKline), teplizumab CD3 (e.g., MGA031, MacroGenics/Eli Lilly), visilizumab CD3 (e.g., NUVION®, PDL), muromonab-CD3 CD3 (Ortho), ibalizumab (e.g., TMB-355 and TNX-355, TaiMed Biologics), zanolimumab CD4 (e.g., HUMAX-CD4®, Genmab), cedelizumab CD4 (Euroasian Chemicals), keliximab CD4, priliximab CD4 (e.g., cMT412, Centocor), BT-061 CD4 (BioTest AG), efalizumab CD11a (e.g., RAPTIVA®/XANELIM™, Genentech/Roche/Merck-Serono), MLN01 CD18 (Millennium Pharmaceuticals), epratuzumab CD22 (e.g., Amgen antibody) and hLL2; (Immunomedics/UCB)), aselizumab CD26L, iratumumab CD30 (e.g., SGN30 (Seattle Genetics) and MDX-060 (Medarex), SGN40 CD40 (Seattle Genetics), ANTOVA® CD40 ligand (Biogen Idec), abatacept CD80 CD86 (e.g., ORENCIA®, Bristol-Myers Squibb), CT-011 PD1 (Cure Tech), GITR (e.g., TRX518, (Tolerx), AT010 CXCR3 (Affitech), MLN1202 CCR2 (Millennium Pharmaceuticals), AMG-761 CCR4 (Amgen), HGS004 CCR5 (Human Genome Sciences), PRO 140 (Progenics), MDX-1338 CXCR4 (Medarex), CNTO-888 CCL2 (Centocor), ABN912 CCL2 (Novartis), MDX-1100 CXCL10 (Medarex), TB-403 PLGF (BioInvent), natalizumab integrin Alpha4 subunit (e.g., TYSABRI®, Biogen Idec/Elan), vedolizumab integrin A4B7 (e.g., MLN2, Millennium Pharmaceuticals/Takeda), eculizumab C5 Compliment (e.g., SOLIRIS®, Alexion), pexelizumab C5 Compliment (Alexion), omalizumab IgE (e.g., XOLAIR®, Genentech/Roche/Novartis), talizumab (e.g., TNX-901, Tanox), toralizumab (IDEC 131, IDEC), bertilimumab eotaxin (e.g., iCo-008, iCos Therapeutics Inc.), ozrolimupab RhD (e.g., Sym001, Symphogen A/S), atorolimumab or morolimumab (Rh factor). An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, 3, 4, 5, 6, or more of the above antibodies are also encompassed by the invention. Thus, the invention encompasses MRD-containing antibodies comprising at least 1, 2, 3, 4, 5, 6, or more MRDs that compete for target binding with at least 1, 2, 3, 4, 5 or 6 of the above antibodies.

In particular embodiments, the antibody of the MRD-containing antibody is: SGN-70 CD70 (Seattle Genetics), SGN-75 CD70 (Seattle Genetics), Belimumab BLYS (e.g., BENLYSTA®, Human Genome Sciences/GlaxoSmithKline), BIIB023 TWEAK (Biogen Idec), TL1A antibodies of CoGenesys/Teva (e.g., 11D8, 25B9, and 1B4 (U.S. Appl. Publ. No. 2009/0280116), OX40 mAb, humAb OX40L (Genentech), catumaxomab IL1beta (e.g., REMOVAB®, Fresenius Biotech GmbH), canakinumab IL1beta (e.g., ILARIS® (Novartis) and ACZ885 (Novartis)), AMG108 IL1R (Amgen), daclizumab IL2Ra (e.g., ZENAPAX®, Hoffman-La Roche), basiliximab IL2Ra (e.g., SIMULECT®, Novartis), AMGN-317 IL4a (Amgen), pascolizumab IL4 (PDL), mepolizumab IL5 (e.g., BOSATRIA®, GlaxoSmithKline), reslizumab IL5 (e.g., SCH55700, Ception Therapeutics), benralizumab IL5R (e.g., MEDI-563, MedImmune), BIW-8405, IL5R (BioWa), siltuximab IL6 (e.g., CNT0328, Centocor), CNTO-136 IL6 (Centocor), CDP-6038 IL6 (UCB), AMGN-220 IL6 (Amgen), REGN-88 IL6R (Regeneron), tocilizumab IL6R (e.g., ACTEMRA™/ROACTEMRA™, Chugai/Roche), MEDI-528 IL9 (MedImmune), briakinumab IL12/13 (e.g., ABT-874, Abbott), ustekinumab IL12, IL23 (e.g., CNTO 1275, Centocor), lebrikizumab IL13 (Genentech), TNX-650 IL13 (Tanox), CAT354 IL13 (Cambridge Antibody Technology), AMG714 IL15 (Amgen), CRB-15 IL15R (Hoffman LaRoche), AN: G827 IL17R (Amgen), IL17RC antibody of Zymogenetics/Merck Serono, IL20 antibody of Zymogenetics, IL20 antibody of Novo Nordisk, IL21 antibody of Novo Nordisk, IL21 antibody Zymogenetics (Zymogenetics), IL22RA antibody of Zymogenetics, IL31 antibody of Zymogenetics, AMG157 TSLP (Amgen), MEDI-545 interferon alpha (MedImmune), MEDI-546 interferon alpha receptor (MedImmune), AMG811 interferon gamma (Amgen), INNO202 interferon gamma (Innogenetics/Advanced Biotherapy), HuZAF interferon-gamma (PDL), AMG557 B7RP1 (Amgen), AMG191 cKit (Amgen), MOR103 GMCSF (MorphoSys), CAM-3001 GMCSFR (MedImmune), tremelimumab CTLA4 (e.g., CP-675,206, Pfizer), iplimumab CTLA4 (e.g., MDX-010, BMS/Medarex), siplizumab CD2 (e.g., MEDI-507, MedImmune), otelixizumab CD3 (e.g., TRX4, Tolerx/GlaxoSmithKline), muromonab-CD3 CD3 (Ortho), teplizumab CD3 (e.g., MGA031, MacroGenics/Eli Lilly), visilizumab CD3 (e.g., NUVION®, PDL), zanolimumab CD4 (e.g., HUMAX-CD4®, Genmab), cedelizumab CD4 (Euroasian Chemicals), keliximab CD4, priliximab CD4 (e.g., cMT412, Centocor), BT-061 CD4 (BioTest AG), ibalizumab (e.g., TMB-355 and TNX-355, TaiMed Biologics), efalizumab CD11a (e.g., RAPTIVA®/XANELIM™, Genentech/Roche/Merck-Serono), MLN01 CD18 (Millennium Pharmaceuticals), epratuzumab CD22 (e.g., Amgen antibody) and hLL2 (Immunomedics/UCB)), aselizumab CD26L iratumumab CD30 (e.g., SGN30 (Seattle Genetics) and MDX-060 (Medarex), SGN40 CD40 (Seattle Genetics), ANTOVA® CD40 ligand (Biogen Idec), CT-011 PD1 (Cure Tech), AT010 CXCR3 (Affitech), MLN3897 CCR1 (Millennium Pharmaceuticals), MLN1202 CCR2 (Millennium Pharmaceuticals), AMG-761 CCR4 (Amgen), HGS004 CCR5 (Human Genome Sciences), PRO 140 (Progenics), MDX-1338 CXCR4 (Medarex), CNTO-888 CCL2 (Centocor), ABN912 CCL2 (Novartis), MDX-1100 CXCL10 (Medarex), TB-403 PLGF (BioInvent), natalizumab integrin Alpha4 subunit (e.g., TYSABRI®, Biogen Idec/Elan), vedolizumab integrin A4B7 (e.g., MLN02, Millennium Pharmaceuticals/Takeda), eculizumab C5 Compliment (e.g., SOURIS®, Alexion pharmaceuticals), omalizumab IgE (e.g., XOLAIR®, Genentech/Roche/Novartis), talizumab (e.g., TNX-901, Tanox), toralizumab (DEC 131, IDEC), bertilimumab eotaxin (e.g., iCo-008, iCo Therapeutics Inc.), ozrolimupab RhD (e.g., Sym001, Symphogen A/S), atorolimumab or morolimumab (Rh factor).

In additional embodiments, the antibody target of the MRD-containing antibody competes for target binding with an antibody selected from: oxelumab (e.g., RG4930; Genmab), AMG139 (Amgen), AMG181 (Amgen), CNTO 148 TNF (Medarex), an anti-TNF antibody described in U.S. Pat. No. 6,258,562 (BASF), Humicade® TNF (Celltech), HuM291CD3 fc receptor (PDL), Mik-beta-1 IL-2Rb (CD122) (Hoffman LaRoche), REGN668 IL-4R (Regeneron), sarilumab IL-6R (e.g., REGN88, Regeneron), HuMax-Inflam IL-8 (e.g., HuMax-Inflam™/MDX-018; Genmab and Medarex), anti-IL-12 and/or anti-IL-12p40 antibody disclosed in U.S. Pat. No. 6,914,128 (Abbott), HuMax-IL15 IL15 (Medarex and Genmab), ABX-IL8 IL8 (Abgenix), an anti-IL-18 antibody disclosed in US Appl. Pub. No. 2005/0147610 (Abbott), hCBE-11 LTBR (Biogen), HuMax-TAC IL-2Ra (CD22) (Genmab, see, e.g., Intl. Appl. Publ. No. WO2004045512, MLN01 Beta2 integrin (Xoma), D3H44 ATF (Genentech), MT203 GMCSF (Micromet and Takeda), IFX1/CaCP29 (InflaRx GmbH), CAT-213 Eotaxin 1 (Cambridge Antibody Technologies), MDX-018 IL-8 (e.g., HuMax-Inflam™; Medarex), REGN846 IL-4R (Regeneron, see, e.g., US Appl. Pub. No. 20100291107), REGN728 (Regeneron), RGN846 (Regeneron), T2-18C3 IL1A (MABp1;)(Biotech), RA-18C3 IL1A (XBiotech) and CV-18C3 IL1A (XBiotech). An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, 3, 4, 5, 6, or more of the above antibodies are also encompassed by the invention. Thus, the invention encompasses MRD-containing antibodies comprising at least 1, 2, 3, 4, 5, 6, or more MRDs that compete for target binding with at least 1, 2, 3, 4, 5, or 6 of the above antibodies.

In additional embodiments, one of the above-described antibodies is the antibody of the MRD-containing antibody.

In an additional embodiment, the antibody in the MRD-containing antibody specifically binds CTLA4. In a specific embodiment, the antibody is tremelimumab (e.g., CP-675, 206, Pfizer). In another embodiment, the antibody binds to the same epitope as tremelimumab. In a further embodiment, the antibody competitively inhibits binding of tremelimumab to CTLA4. In an additional specific embodiment, the antibody is ipilimumab (e.g., MDX-010, Bristol-Myers Squibb/Medarex). In one embodiment, the antibody binds to the same epitope as ipilimumab. In a further embodiment, the antibody competitively inhibits binding of ipilimumab to CTLA4. Multivalent and multispecific compositions (e.g., MRD-containing antibodies) having 1, 2, 3, 4, 5, 6, or more MRDs that compete for CTLA4 binding with tremelimumab or ipilimumab are also encompassed by the invention.

In an additional embodiment, the antibody in the MRD-containing antibody specifically binds TNFSF12 (TWEAK). In a specific embodiment, the antibody is the TWEAK antibody of Biogen that has advanced to Phase I clinical trials. In another embodiment, the antibody binds to the same epitope as the Biogen TWEAK antibody. In a further embodiment, the antibody competitively inhibits binding of the Biogen TWEAK antibody to TWEAK. Multivalent and multispecific compositions (e.g., MRD-containing antibodies) having 1, 2, 3, 4, 5, 6, or more MRDs that compete for TWEAK binding with the Biogen TWEAK antibody are also encompassed by the invention.

In an additional embodiment, the antibody in the MRD-containing antibody specifically binds IL2Ra (CD25). In a specific embodiment, the antibody is daclizumab (e.g., ZENAPAX®). In another embodiment, the antibody binds to the same epitope as daclizumab. In a further embodiment, the antibody competitively inhibits binding of daclizumab to IL2Ra (CD25). Multivalent and multispecific compositions (e.g., MRD-containing antibodies) having 1, 2, 3, 4, 5, 6, or more MRDs that compete for IL2Ra (CD25) binding with daclizumab are also encompassed by the invention.

In an additional embodiment, the antibody in the MRD-containing antibody specifically binds CD40 (TNFRSF5). In a specific embodiment, the antibody is CP-870893 CD40 (Pfizer). In another embodiment, the antibody binds to the same epitope as CP-870893. In a further embodiment, the antibody competitively inhibits binding of CP-870893 to CD40. Multivalent and multispecific compositions (e.g., MRD-containing antibodies) having 1, 2, 3, 4, 5, 6, or more MRDs that compete for CD40 binding with CP-870893 are also encompassed by the invention.

In an additional embodiment, the antibody in the MRD-containing antibody specifically binds Alpha4 integrin. In a specific embodiment, the antibody is natalizumab (e.g., TYSABRI®; Biogen Idec/Elan). In one embodiment, the antibody binds to the same epitope as natalizumab. In a further embodiment, the antibody competitively inhibits binding of natalizumab to Alpha4 integrin. Multivalent and multispecific compositions (e.g., MRD-containing antibodies) having 1, 2, 3, 4, 5, 6, or more MRDs that compete for Alpha4 integrin binding with natalizumab are also encompassed by the invention.

In an additional embodiment, the antibody in the MRD-containing antibody specifically binds IL22. In a specific embodiment, the antibody is PF-5,212,367 (ILV-094) (Pfizer). In another embodiment, the antibody binds to the same epitope as PF-5,212,367. In a further embodiment, the antibody competitively inhibits binding of PF-5,212,367 to IL22. Multivalent and multispecific compositions (e.g., MRD-containing antibodies) having 1, 2, 3, 4, 5, 6, or more MRDs that compete for IL22 binding with PF-5,212,367 are also encompassed by the invention.

In an additional embodiment, the antibody in the MRD-containing antibody specifically binds MAdCAM. In a specific embodiment, the antibody is PF-547,659 (Pfizer). In another embodiment, the antibody binds to the same epitope as PF-547,659. In a further embodiment, the antibody competitively inhibits binding of PF-547,659 to MAdCAM. Multivalent and multispecific compositions (e.g., MRD-containing antibodies) having 1, 2, 3, 4, 5, 6, or more MRDs that compete for MAdCAM binding with PF-547,659 are also encompassed by the invention.

In one embodiment, the antibody in the MRD-containing antibody specifically binds TNF. In a specific embodiment, the antibody is adalimumab (e.g., HUMIRA®/TRUDEXA®, Abbott). In one embodiment, the antibody binds to the same epitope as adalimumab. In another embodiment, the antibody competitively inhibits binding of adalimumab to TNF. In another specific embodiment, the antibody is ATN-103 (Pfizer). In one embodiment, the antibody binds to the same epitope as ATN-103. In another embodiment, the antibody competitively inhibits binding of ATN-103 to TNF. In another specific embodiment, the antibody is infliximab. In one embodiment, the antibody binds to the same epitope as infliximab. In another embodiment, the antibody competitively inhibits binding of infliximab to TNF. In another specific embodiment, the antibody is selected from: certolizumab (e.g., CIMZIA®, UCB), golimumab (e.g., SIM-PONI™, Centocor), and AME-527 (Applied Molecular Evolution). In one embodiment, the antibody binds to the same epitope as certolizumab, golimumab, or AME-527. In another embodiment, the antibody competitively inhibits binding of certolizumab, golimumab, or AME-527, to TNF. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, 3, 4, or 5, of the above antibodies are also encompassed by the invention.

In some embodiments, the antibody in the MRD-containing antibody comprises the CDRs of the anti-TNF antibody adalimumab. The CDR, VH, and VL sequences of adalimumab are provided in Table 3.

TABLE 3

| CDR | Sequence |
| --- | --- |
| VL-CDR1 | RASQGIRNYLA (SEQ ID NO: 80) |
| VL-CDR2 | AASTLQS (SEQ ID NO: 81) |
| VL-CDR3 | QRYNRAPYT (SEQ ID NO: 82) |
| VH-CDR1 | DYAMH (SEQ ID NO: 83) |
| VH-CDR2 | AITWNSGHIDYADSVEG (SEQ ID NO: 84) |
| VH-CDR3 | VSYLSTASSLDY (SEQ ID NO: 85) |
| VL | DIQMTQSPSSLSASVGDRVTITCRASQGIRNYL AWYQQKPGKAPKLLIYAASTLQSGVPSRFSGSG SGTDFTLTISSLQPEDVATYYCQRYNRAPYTFG QGTKVEIKR (SEQ ID NO: 86) |
| VH | EVQLVESGGGLVQPGRSLRLSCAASGFTFDDYA MHWVRQAPGKGLEWVSAITWNSGHIDYADSVEG RFTISRDNAKNSLYLQMNSLRAEDTAVYYCAKV SYLSTASSLDYWGQGTLVTVSS (SEQ ID NO: 87) |

In one embodiment, an MRD-containing antibody binds TNF (i.e., TNF alpha) and additionally binds a target selected from: Te38, IL12, IL12p40, IL13, IL15, IL17, IL18, IL1beta, IL23, MIF, PGE2, PGE4, VEGF, TNFSF11 (RANKL), TNFSF13B (BLYS), GP130, CD22 and CTLA-4. In another embodiment, an MRD-containing antibody binds TNF alpha, IL6, and TNFSF13B (BLYS). In another embodiment, an MRD-containing antibody binds TNF alpha and TNFSF12 (TWEAK). In additional embodiments, the MRD-containing antibody binds TNF and TNFSF15 (TL1A). In another embodiment, an MRD-containing antibody binds TNF and additionally binds a target selected from NGF, SOST (sclerostin), LPA, IL17A, DKK, alpha Vbeta3, IL23p19, IL2, IL2RA (CD25), IL6, IL6R, IL12p40, IL6, IL10, IL21, IL22 and CD20 binds TNF. Multivalent and multispecific compositions (e.g., MRD-containing antibodies) that bind TNF alpha and at least 1, 2, 3, 4, 5 or more of these targets are also encompassed by the invention. In specific embodiments, the antibody component of the MRD-containing antibody binds TNF alpha. In further embodiments, the antibody component of the MRD-containing antibody is adalimumab, infliximab certolizumab golimumab, CNTO 148, AME-527 or ATN-103.

In other embodiments, the target of the antibody of the MRD-containing antibody is IL6. In some embodiments, the antibody of the MRD-containing antibody is siltuximab (CNT0328, Centocor), CNTO-136 (Centocor), CDP-6038 (UCB), or AMGN-220 (Amgen). In other embodiments, the antibody of the MRD-containing antibody competes with siltuximab (CNT0328, Centocor), CNTO-136 (Centocor), CDP-6038 (UCB), or AMGN-220 (Amgen) for binding to IL6. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2, or more of the above antibodies are also encompassed by the invention.

In one embodiment, an MRD-containing antibody binds IL6. In a specific embodiment, an MRD-containing antibody binds IL6 and a target selected from: IL1, IL1beta, IL1Ra, IL5, CD8, TNFRSF5 (CD40), PDL1, IL6R, IL17A, TNF, VEGF, TNFSF11 (RANKL) and PGE2. Multivalent and multispecific compositions (e.g., MRD-containing antibodies) that bind IL6 and also bind at least 1, 2, 3, 4, 5 or more of these targets are also encompassed by the invention. In specific embodiments, the antibody component of the MRD-containing antibody binds IL6. In further embodiments, the antibody component of the MRD-containing antibody is siltuximab, CNTO136, CDP-6038 or AMGN-220.

In other embodiments, the target of the antibody of the MRD-containing antibody is IL6R. In some embodiments, the antibody of the MRD-containing antibody is REGN-88 (Regeneron) or tocilizumab (ACTEMRA™/RO-ACTEMRA™, Chugai/Roche). In other embodiments, the antibody of the MRD-containing antibody competes with siltuximab, REGN-88 (Regeneron) or tocilizumab (ACTEMRA™/ROACTEMRA™, Chugai/Roche) for binding to IL6R. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1 or both of the above antibodies are also encompassed by the invention.

In one embodiment, an MRD-containing antibody binds IL6R. In a specific embodiment, an MRD-containing antibody binds IL6R and a target selected from: CD8, TNFRSF5 (CD40), PDL1, IL6, IL17A, TNF, VEGF, TNF (RANKL) and PGE2. Multivalent and multispecific compositions (e.g., MRD-containing antibodies) that bind IL6R and also bind at least 1, 2, 3, 4, 5 or more of these targets are also encompassed by the invention. In specific embodiments, the antibody component of the MRD-containing antibody binds IL6R. In further embodiments, the antibody component of the MRD-containing antibody is REGN-88 or tocilizumab.

In some embodiments, an MRD-containing antibody binds TNFSF15 (TL1A). In further embodiments, the MRD-containing antibody binds TL1A and a target selected from: TNF, IFN alpha, IFN gamma, IL1, IL1beta, IL6, IL8, IL12, IL15, IL17, IL18, IL23 and IL32. Multivalent and multispecific compositions (e.g., MRD-containing antibodies) that bind TL1A and also bind at least 1, 2, 3, 4, 5 or more of these targets are also encompassed by the invention. These compositions have applications in treating diseases and disorders including inflammatory bowel disease and autoimmune diseases such as rheumatoid arthritis. In specific embodiments, the antibody component of the MRD-containing antibody binds TL1a.

In some embodiments, an MRD-containing antibody binds interferon alpha. In further embodiments, the MRD-containing antibody binds interferon alpha and TNFSF13B (BLYS). In further embodiments, the MRD-containing antibody binds interferon alpha, TNFSF13B (BLYS), and a neutrophil extracellular trap (NET). These compositions have applications in treating diseases and disorders including autoimmune diseases such as rheumatoid arthritis and systemic lupus erythematous. In specific embodiments, the antibody component of the MRD-containing antibody binds interferon alpha.

The multivalent and multispecific compositions of the invention also have applications in treating neurologic diseases or disorders including neurodegenerative diseases, pain and neural injury or trauma. In particular embodiments, the target of the antibody of the MRD-containing antibody is: amyloid beta (Abeta), beta amyloid, complement factor D, PLP, ROBO4, ROBO, GDNF, NGF, LINGO, or myostatin. In specific embodiments, the antibody in the MRD-containing antibody is gantenerumab (e.g., R1450, Hoffman La-Roche), bapineuzumab beta amyloid 9 (Elan and Pfizer), solanezumab beta amyloid 9 (Eli Lilly), tanezumab NGF (e.g., RN624, Pfizer), BIIB033 LINGO (Biogen Idec), PF-3,446,879 myostatin (Pfizer), or stamulumab myostatin (Wyeth). In another embodiment, the antibody specifically binds to the same epitope as gantenerumab, bapineuzumab, solarezumab, tanezumab, the Biogen LINGO antibody, or stamulumab. In another embodiment, the antibody in the MRD-containing antibody is an antibody that competitively inhibits target binding by gantenerumab, bapineuzumab, solarezumab, tanezumab, BIIB033, or stamulumab. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2 or more of the above antibodies are also encompassed by the invention.

In an additional embodiment, the target of the antibody of the MRD-containing antibody is beta amyloid. In a specific embodiment, the antibody in the MRD-containing antibody is RN1219 (PF-4,360,365; Pfizer). In another embodiment, the antibody specifically binds to the same epitope as RN1219. In a further embodiment, the antibody in the MRD-containing antibody is an antibody that competitively inhibits beta amyloid binding by RN1219. An MRD that competes for beta amyloid binding with RN1219 is also encompassed by the invention. Multivalent and multispecific compositions (e.g., MRD-containing antibodies) having 1, 2, 3, 4, 5, 6, or more MRDs that compete for beta amyloid binding with RN1219 are also encompassed by the invention.

In an additional embodiment, the target of the antibody of the MRD-containing antibody is NGF. In a specific embodiment, the antibody in the MRD-containing antibody is tanezumab (e.g., RN624, Pfizer). In another embodiment, the antibody specifically binds to the same epitope as tanezumab. In a further embodiment, the antibody in the MRD-containing antibody is an antibody that competitively inhibits NGF binding by tanezumab. An MRD that competes for NGF binding with tanezumab is also encompassed by the invention. Multivalent and multispecific compositions (e.g., MRD-containing antibodies) having 1, 2, 3, 4, 5, 6, or more MRDs that compete for NGF binding with tanezumab are also encompassed by the invention.

In a specific embodiment, an MRD-containing antibody binds NGF and a target selected from: MTX, NKG2D, RON, IL6R, ErbB3, TNFRSF21 (DR6), CD3, IGFR, DLL4, P1GF, CD20, EGFR, HER2, CD19, CD22, TNFRSF5 (CD40), CD80, cMET, NRP1, TNF, LINGO, HGF, IGF1, IGF1,2, IGF2, NGF, Te38, NogoA, RGM A, MAG, OMGp, NgR, TNFSF12 (TWEAK), PGE2, IL1 beta, Semaphorin 3A and Semaphorin 4. Multivalent and multispecific compositions (e.g., MRD-containing antibodies) that bind NGF and also bind at least 1, 2, 3, 4, 5 or more of these targets are also encompassed by the invention. In specific embodiments, the antibody component of the MRD-containing antibody binds NGF. In further embodiments, the antibody component of the MRD-containing antibody is tanezumab. In additional embodiments, the antibody component of the MRD-containing antibody competes for NGF binding with tanezumab. In further embodiments, the antibody component of the MRD-containing antibody is MEDI-578. In additional embodiments, the antibody component of the MRD-containing antibody competes for NGF binding with MEDI-578.

In an additional embodiment, the target of the antibody of the MRD-containing antibody is LINGO (e.g., LINGO1). In a specific embodiment, the antibody in the MRD-containing antibody is BIIB033 (Biogen Idec). In another embodiment, the antibody specifically binds to the same epitope as BIIB033. In a further embodiment, the antibody in the MRD-containing antibody is an antibody that competitively inhibits LINGO binding by BIIB033. An MRD that competes for LINGO binding with BIIB033 is also encompassed by the invention. Multivalent and multispecific compositions (e.g., MRD-containing antibodies) having 1, 2, 3, 4, 5, 6, or more MRDs that compete for LINGO binding with BIIB033 are also encompassed by the invention.

In a specific embodiment, an MRD-containing antibody binds LINGO and a target selected from: MTX, NKG2D, RON, IL6R, ErbB3, TNFRSF21 (DR6), CD3, IGFR, DLL4, P1GF, CD20, EGFR, HER2, CD19, CD22, TNFRSF5 (CD40), CD80, cMET, NRP1, TNF, TNF (TWEAK), HGF, IGF1, IGF1,2, IGF2, NGF, Te38, NogoA, RGM A, MAG, OMGp, NgR, NGF, PGE2, IL1 beta, Semaphorin 3A and Semaphorin 4. Multivalent and multispecific compositions (e.g., MRD-containing antibodies) that bind LINGO and also bind at least 1, 2, 3, 4, 5 or more of these targets are also encompassed by the invention. In specific embodiments, the antibody component of the MRD-containing antibody binds LINGO. In further embodiments, the antibody component of the MRD-containing antibody is BIIB033.

In a specific embodiment, the target of an antibody of an MRD-containing antibody is TNFSF12 (TWEAK). In another embodiment, the antibody in the MRD-containing antibody binds TNFSF12 (TWEAK) and a target selected from: MTX, NKG2D, RON, IL6R, ErbB3, TNFRSF21 (DR6), CD3, IGFR, DLL4, P1GF, CD20, EGFR, HER2, CD19, CD22, TNFRSF5 (CD40), CD80, cMET, NRP1, TNF, LINGO, HGF, IGF1, IGF1,2, IGF2, NGF, Te38, NogoA, RGM A, MAG, OMGp, NgR, NGF, PGE2, IL1 beta, Semaphorin 3A and Semaphorin 4. Multivalent and multispecific compositions (e.g., MRD-containing antibodies) that bind TNFSF12 (TWEAK) and also bind at least 1, 2, 3, 4, 5 or more of these targets are also encompassed by the invention. In specific embodiments, the antibody component of the MRD-containing antibody binds TNFSF12 (TWEAK). In further embodiments, the antibody component of the MRD-containing antibody is BIIB023.

In another embodiment, the target of the antibody of the MRD-containing antibody is: oxidized LDL, gpIIB, gpIIIa, PCSK9, Factor VIII, integrin a2bB3, AOC3, or mesothelin. In specific embodiments, the antibody in the MRD-containing antibody is BI-204 oxidized LDL (BioInvent), abciximab gpIIB, gpIIIa (e.g., REOPRO, Eli Lilly), AMG-145 PCSK9 (Amgen), TB-402 Factor VIII (BioInvent), vapaliximab, or tadocizumab integrin a2bB3 (Yamonochi Pharma). In another embodiment, the antibody specifically binds to the same epitope as BI-204, abciximab, AMG-145, TB-402, or tadocizumab. In another embodiment, the antibody in the MRD-containing antibody is an antibody that competitively inhibits binding of BI-204, abciximab, AMG-145, TB-402, vapaliximab, or tadocizumab. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2 or more of the above antibodies are also encompassed by the invention.

In other embodiments, the antibody of the MRD-containing antibody is associated with bone growth and/or metabolism. In certain embodiments the antibody target of the MRD-containing antibody is TNFSF11 (RANKL). In other embodiments the antibody target of the MRD-containing antibody is: DKK1, osteopontin, cathepsin K, TNFRSF19L (RELT), TNFRSF19 (TROY), or sclerostin (CDP-7851 UCB Celltech). In another embodiment antibody target of the MRD-containing antibody is TNFSF11 (RANKL). In a specific embodiment, the antibody in the MRD-containing antibody is denosumab (e.g., AMG-162, Amgen). In another embodiment, the antibody specifically binds to the same epitope as denosumab. In another embodiment, the antibody in the MRD-containing antibody is an antibody that competitively inhibits binding of TNFSF11 (RANKL) by denosumab. In another specific embodiment, the antibody is AMG617 or AMG785 (e.g., CDP7851, Amgen). In another embodiment, the antibody specifically binds to the same epitope as AMG617 or AMG785. In another embodiment, the antibody in the MRD-containing antibody is an antibody that competitively inhibits binding of sclerostin by AMG617 or AMG785. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2 or more of the above antibodies are also encompassed by the invention.

In one embodiment, an MRD-containing antibody binds TNFSF11 (RANKL). In a specific embodiment, an MRD-containing antibody binds TNFSF11 and a target selected from: sclerostin (SOST), endothelin-1, DKK1, IL1, IL6, IL7, IL8, IL11, IL17A, MCSF, IGF1, IGF2, IGF1,2 IGF1R, TNF, FGF1, FGF2, FGF4, FGF7, FGF8a, FGF8b, FGF18, FGF19, FGFR1 (e.g., FGFR1-IIIC), FGFR2 (e.g., FGFR2-IIIa, FGFR2-IIIb, and FGFR2-IIIc), FGFR3, TGF beta, TGF beta R2, BMP2, BMP4, BMP5, BMP9, BMP10, BMPR-IA, PDGF, PDGFRa, PDGFRb PTH, PTH related protein (PTHrP), and PGE2. Multivalent and multispecific compositions (e.g., MRD-containing antibodies) that bind TNFSF11 and also bind at least 1, 2, 3, 4, 5 or more of these targets are also encompassed by the invention. In specific embodiments, the antibody component of the MRD-containing antibody binds TNFSF11. In further embodiments, the antibody component of the MRD-containing antibody is denosumab, AMG617 or AMG785.

In additional embodiments, the antibody target of the MRD-containing antibody is a bacterial antigen, a viral antigen, a mycoplasm antigen, a prion antigen, or a parasite antigen (e.g., one infecting a mammal).

In other embodiments, the target of the antibody of the MRD-containing antibody is a viral antigen. In one embodiment, the target of the antibody of the MRD-containing antibody is anthrax, hepatitis b, rabies, Nipah virus, west nile virus, a mengititis virus, or CMV. In other embodiments, the antibody of the MRD-containing antibody competes with antigen binding with ABTHRAX® (Human Genome Sciences), exbivirumab, foravirumab, libivirumab, rafivirumab, regavirumab, sevirumab (e.g., MSL-109, Protovir), tuvirumab, raxibacumab, Nipah virus M102.4, or MGAWN1® (MacroGenics) for target binding. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2 or more of the above antibodies are also encompassed by the invention. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2 or more of the above antibodies are also encompassed by the invention.

In other embodiments, the target of the antibody of the MRD-containing antibody is RSV. In other embodiments, the antibody of the MRD-containing antibody is motavizumab (e.g., NUMAX®, MEDI-577; MedImmune) or palivizumab RSV fusion f protein (e.g., SYNAGIS®, MedImmune). In other embodiments, the antibody of the MRD-containing antibody competes with motavizumab or palivizumab RSV fusion f protein, for target binding. In other embodiments, the antibody of the MRD-containing antibody is felvizumab. In other embodiments, the antibody of the MRD-containing antibody competes with felvizumab for target binding. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2 or more of the above antibodies are also encompassed by the invention.

In other embodiments, the target of the antibody of the MRD-containing antibody is a bacterial or fungal antigen. In other embodiments, the antibody of the MRD-containing antibody competes for antigen binding with nebacumab, edobacomab (e.g., E5), tefibazumab (Inhibitex), panobacumab (e.g., KBPA101, Kenta), pagibaximab (e.g., BSYX-A110, Biosynexus), urtoxazumab, or efungumab (e.g., MYCOGRAB®, Novartis). In other embodiments, the antibody of the MRD-containing antibody is nebacumab, edobacomab, tefibazumab (Inhibitex), panobacumab, pagibaximab, urtoxazumab, or efungumab. An MRD that competes for target binding with one of the above antibodies is also encompassed by the invention. Multivalent and multispecific compositions (e.g., MRD-containing antibodies) having 1, 2, 3, 4, 5, 6, or more MRDs that compete for target binding with 1, 2 or more of the above antibodies are also encompassed by the invention.

In another specific embodiment, the antibody in the MRD-containing antibody is the catalytic antibody 38C2. In another embodiment, the antibody binds to the same epitope as 38C2. In another embodiment, the antibody competitively inhibits 38C2.

Other antibodies of interest include A33 binding antibodies. Human A33 antigen is a transmembrane glycoprotein of the Ig superfamily. The function of the human A33 antigen in normal and malignant colon tissue is not yet known. However, several properties of the A33 antigen suggest that it is a promising target for immunotherapy of colon cancer. These properties include (i) the highly restricted expression pattern of the A33 antigen, (ii) the expression of large amounts of the A33 antigen on colon cancer cells, (iii) the absence of secreted or shed A33 antigen, (iv) the fact that upon binding of antibody A33 to the A33 antigen, antibody A33 is internalized and sequestered in vesicles, and (v) the targeting of antibody A33 to A33 antigen expressing colon cancer in preliminary clinical studies. Fusion of a MRD directed toward A33 to a catalytic or non-catalytic antibody would increase the therapeutic efficacy of A33 targeting antibodies.

In some embodiments, the antibody in the MRD-containing antibody binds to a human target protein. In some embodiments, the MRD binds to both a human protein and its ortholog in mouse, rat, rabbit, or hamster.

The antibodies in the multivalent and multispecific compositions (e.g., MRD-containing antibodies) are able to bind their respective targets when the MRDs are attached to the antibody. In certain embodiments, the antibody binds its target independently. In some embodiments, the antibody is a target agonist. In other embodiments, the antibody is a target antagonist. In certain embodiments, the antibody can be used to localize an MRD-containing antibody to an area where the antibody target is located.

It is contemplated that the antibodies used in the present invention may be prepared by any method known in the art. For example, antibody molecules and multivalent and multispecific compositions (e.g., MRD-containing antibodies) can be "recombinantly produced," i.e., produced using recombinant DNA technology.

Monoclonal antibodies that can be used as the antibody component of the multivalent and multispecific compositions (e.g., MRD-containing antibodies) can be prepared using hybridoma methods, such as those described by Kohler and Milstein, Nature 256:495 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (MA); enzyme-linked immunosorbent assay (ELISA)) can then be propagated either in vitro, for example, using known methods (see, e.g., Goding, Monoclonal Antibodies: Principles and Practice, Academic Press, 1986) or in vivo, for example, as ascites tumors in an animal. The monoclonal antibodies can then be purified from the culture medium or ascites fluid as described for polyclonal antibodies above.

Alternatively monoclonal antibodies can also be made using recombinant DNA methods, for example, as described in U.S. Pat. No. 4,816,567. For example, in one approach polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. In other approaches, recombinant monoclonal antibodies or antibody fragments having the desired immunoreactivity can be isolated from phage display libraries expressing CDRs of the desired species using techniques known in the art (McCafferty et al., Nature 348:552-554 (1990); Clackson et al., Nature 352:624-628 (1991); and Marks et al., J. Mol. Biol. 222:581-597 (1991)).

The polynucleotide(s) encoding a monoclonal antibody can further be modified in a number of different ways, using recombinant DNA technology to generate alternative antibodies. For example, polynucleotide sequences that encode one or more MRDs and optionally linkers, can be operably fused, for example, to the 5' or 3' end of sequence encoding monoclonal antibody sequences. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. Techniques for site-directed and high-density mutagenesis of the variable region are known in the art and can be used to optimize specificity, affinity, etc. of a monoclonal antibody.

In certain embodiments, the antibody of the MRD-containing antibody is a human antibody. For example, human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., J. Immunol. 147 (1):86-95 (1991); and U.S. Pat. Nos. 5,750,373 and 6,787,637). In one embodiment, the human antibody can be derived from the "minilocus" approach" in which an exogenous Ig locus is mimicked through inclusion of individual genes from the Ig locus (see e.g., U.S. Pat. No. 5,545,807). Methods of preparing a human antibody from a phage library, and optionally optimizing binding affinity are known in the art and described, for example, in Vaughan et al., Nat. Biotech. 14:309-314 (1996); Sheets et al., Proc. Nat'l. Acad. Sci. 95:6157-6162 (1998); Hoogenboom et al., Nat. Biotechnology 23:1105-1116 (2005); Hoogenboom et al., J. Mol. Biol. 227:381 (1991); Persic et al., Gene 187:9-18 (1997); Jostock et al., J. Immunol. Methods 289:65-80 (2004); Marks et al., J. Mol. Biol., 222:581 (1991)); et al., Proc. Natl. Acad. Sci. USA, 88:7978-7982 (1991); et al., Proc. Natl. Acad. Sci. USA 91:3809-3813 (1994); Yang et al., J. Mol. Biol. 254:392-403 (1995); and Barbas et al., Proc. Natl. Acad. Sci. USA 89:4457-4461 (1992). Techniques for the generation and use of antibody phage libraries are also described in: U.S. Pat. Nos. 5,545,807, 5,969,108, 6,172,197, 5,885,793, 6,521,404, 6,544,731, 6,555,313, 6,582,915, 6,593,081, 6,300,064, 6,653,068, 6,706,484, and 7,264,963; and Rothe et al., J. Mol. Bio. 130:448-54 (2007) (each of which is herein incorporated by reference in its entirety). Affinity maturation strategies and chain shuffling strategies (Marks et al., Bio/Technology 10:779-783 (1992) (which is herein incorporated by reference in its entirety) are known in the art and can be employed to generate high affinity human antibodies.

Antibodies can also be made in mice that are transgenic for human immunoglobulin genes or fragments of these genes and that are capable, upon immunization, of producing a broad repertoire of human antibodies in the absence of endogenous immunoglobulin production. This approach is described in: Lonberg, Nat. Biotechnol 23:1117-1125 (2005), Green et al., Nature Genet. 7:13-21 (1994), and Lonberg et al., Nature 368:856-859 (1994); U.S. Pat. Nos. 5,545,807, 5,545,806, 5,569,825, 5,625,126, 5,633,425, 5,661,016, 6,596,541, 7,105,348, and 7,368,334 (each of which is herein incorporated by reference in its entirety).

IV. Linkers

Multivalent and multispecific compositions (e.g., MRD-containing antibodies) of the invention can contain a single linker, multiple linkers, or no linker. Thus, a MRD may be operably attached (linked) to the antibody directly, or operably attached through an optional linker peptide. Similarly, a MRD may be operably attached to one or more MRD(s) directly, or operably attached to one or more MRD(s) through one or more optional linker peptide(s). Linkers can be of any size or composition so long as they are able to operably attach an MRD and an antibody such that the MRD enables the MRD containing antibody to bind the MRD target.

In some embodiments, linkers have about 1 to 20 amino acids, about 1 to 15 amino acids, about 1 to 10 amino acids, about 1 to 5 amino acids, about 2 to 20 amino acids, about 2 to 15 amino acids, about 2 to 10 amino acids, or about 2 to 5 amino acids. The linker can also have about 4 to 15 amino acids. In certain embodiments, the linker peptide contains a short linker peptide with the sequence GGGS (SEQ ID NO:1), a medium linker peptide with the sequence SSGGGGSGGGGGGSS (SEQ ID NO:2), or a long linker peptide with the sequence SSGGGG SGGGGGGSSRSS (SEQ ID NO:19). In another embodiment, the MRD is inserted into the fourth loop in the light chain constant region. For example, the MRD can be inserted between the underlined letters in the following amino acid sequence:

(SEQ ID NO: 102)
RTVAAPSVFIFPPSDEQLKSGTASVVCLLNNFYPREAKVQWKVDK<u>LG</u>TN
SQESVTEQDSKDSTYSLSSTLTLSKADYEKHKVYACEVTHQGLSLPVTK
SFNRGEC.

The linker can also be a non-peptide linker such as an alkyl linker, or a PEG linker. For example, alkyl linkers such as —NH—(CH$_2$)s-C(O)—, wherein s=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. An exemplary non-peptide linker is a PEG linker. In certain embodiments, the PEG linker has a molecular weight of about 100 to 5000 kDa, or about 100 to 500 kDa.

In some embodiments, the linker is a "cleavable linker" facilitating release of an MRD or cytotoxic agent in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-131 (1992); U.S. Pat. No. 5,208,020; U.S. Appl. Pub. No. 20090110753) can be used wherein it is desirable that the covalent attachment between an MRD or a cytoxic agent and the multivalent and monovalent multispecific composition (e.g., MRD-containing antibody) is intracellularly cleaved when the composition is internalized into the cell. The terms "intracellularly cleaved" and "intracellular cleavage" refer to a metabolic process or reaction inside a cell on an antibody-drug conjugate (ADC) whereby the covalent attachment, i.e., linked via a linker between the MRD and cytotoxic agent, MRD and antibody, antibody and cytotoxic agent, or between two MRDs is broken, resulting in the free MRD and/or cytotoxic agent dissociated from the antibody inside the cell. The cleaved moieties of the zybody-ADC are thus intracellular metabolites.

Linker optimization can be evaluated using the techniques described in Examples 1-18 and techniques otherwise known in the art. Linkers preferably should not disrupt the ability of an MRD and/or an antibody to bind target molecules.

V. Antibodies Containing MRDs

Using the methods described herein, multi-specificity and greater multi-valency can be achieved through the fusion of MRDs to antibodies.

The MRDs of the multivalent and multispecific compositions (e.g., MRD-containing antibodies) prepared according to the present invention, may be operably linked to an antibody through the peptide's N-terminus or C-terminus. The MRD may be operably linked to the antibody at the C-terminal end of the heavy chain of the antibody, the N-terminal end of the heavy chain of the antibody, the C-terminal end of the light chain of the antibody, or the N-terminal end of the light chain of the antibody. Optimization of the MRD composition, MRD-antibody attachment location and linker composition can be performed using the binding assays described in Examples 1-18 and bioassays and other assays known in the art for the appropriate target related biological activity.

In one embodiment, an MRD-containing antibody is an MRD-containing antibody described in U.S. Application No. 61/489,249, filed May 24, 2011, which is herein incorporated by reference in its entirety.

In one embodiment, multivalent and multispecific compositions (e.g., MRD-containing antibodies) contain an MRD operably linked to either the antibody heavy chain, the antibody light chain, or both the heavy and the light chain. In one embodiment, an MRD-containing antibody contains at least one MRD linked to one of the antibody chain terminals. In another embodiment, an MRD-containing antibody of the invention contains at least one MRD operably linked to two of the antibody chain terminals. In another embodiment, an MRD-containing antibody contains at least one MRD operably linked to three of the antibody chain terminals. In another embodiment, an MRD-containing antibody contains at least one MRD operably attached to each of the four antibody chain terminals (i.e., the N and C terminals of the light chain and the N and C terminals of the heavy chain).

In certain specific embodiments, the MRD-containing antibody has at least one MRD operably attached to the N-terminus of the light chain. In another specific embodiment, the MRD-containing antibody has at least one MRD operably attached to the N-terminus of the heavy chain. In another specific embodiment, the MRD-containing antibody has at least one MRD operably attached to the C-terminus of the light chain. In another specific embodiment, the MRD-containing antibody has at least one MRD operably attached to the C-terminus of the heavy chain.

An MRD-containing antibody can be "multispecific" (e.g., bispecific, trispecific tetraspecific, pentaspecific or of greater multispecificity), meaning that it recognizes and binds to two or more different epitopes present on one or more different antigens (e.g., proteins). Thus, whether an MRD-containing antibody is "monospecific" or "multispecific," (e.g., bispecific, trispecific, and tetraspecific) refers to the number of different epitopes that the MRD-containing antibody binds. Multispecific antibodies may be specific for different epitopes of a target polypeptide (e.g., as described herein) or may be specific for a target polypeptide as well as for a heterologous epitope, such as a heterologous polypeptide target or solid support material. The present invention contemplates the preparation of mono-, bi-, tri-, tetra-, and penta-specific antibodies as well as antibodies of greater multispecificity. In one embodiment, the MRD-containing antibody binds two different epitopes. In an additional embodiment the MRD-containing antibody binds two different epitopes simultaneously. In another embodiment, the MRD-containing antibody binds three different epitopes. In an additional embodiment the MRD-containing antibody binds three different epitopes simultaneously. In another embodiment, the MRD-containing antibody binds four different epitopes. In an additional embodiment the MRD-containing antibody binds four different epitopes simultaneously. In another embodiment, the MRD-containing antibody binds five different epitopes (see, e.g., FIG. 2D). In an additional embodiment the MRD-containing antibody binds five different epitopes simultaneously.

In other embodiments two MRDs of the MRD-containing antibody bind the same antigen. In other embodiments three, four, five, six, seven, eight, nine or ten MRDs of the MRD-containing antibody bind the same antigen. In other embodiments at least two MRDs of the MRD-containing antibody bind the same antigen. In other embodiments at least three, four, five, six, seven, eight, nine or ten MRDs of the MRD-containing antibody bind the same antigen. In other embodiments two MRDs of the MRD-containing antibody bind the same epitope. In other embodiments three, four, five, six, seven, eight, nine or ten MRDs of the MRD-containing antibody bind the same epitope. In other embodiments at least two MRDs of the MRD-containing antibody bind the same epitope. In other embodiments at least three, four, five, six, seven, eight, nine or ten MRDs of the MRD-containing antibody bind the same epitope.

In other embodiments, the antibody and one MRD of the MRD-containing antibody bind the same antigen. In other embodiments the antibody and two, three, four, five, six, seven, eight, nine or ten MRDs of the MRD-containing antibody bind the same antigen. In other embodiments, the antibody and at least one MRD of the MRD-containing antibody bind the same antigen. In other embodiments the antibody and at least two, three, four, five, six, seven, eight, nine or ten MRDs of the MRD-containing antibody bind the same antigen. In other embodiments, the antibody and one MRD of the MRD-containing antibody bind the same epitope. In other embodiments the antibody and two, three, four, five, six, seven, eight, nine or ten MRDs of the MRD-containing antibody bind the same epitope. In other embodiments, the antibody and at least one MRD of the MRD-containing antibody bind the same epitope. In other embodiments the antibody and at least two, three, four, five, six, seven, eight, nine or ten MRDs of the MRD-containing antibody bind the same epitope.

The present invention also provides for two or more MRDs which are linked to any terminal end of the antibody. Thus, in one non-exclusive embodiment, two, three, four, or more MRDs are operably linked to the N-terminal of the heavy chain. In another non-exclusive embodiment, two, three, four, or more MRDs are operably linked to the N-terminal of the light chain. In another non-exclusive embodiment, two, three, four, or more MRDs are operably linked to the C-terminal of the heavy chain. In another non-exclusive embodiment, two, three, four, or more MRDs are operably linked to the C-terminal of the light chain. It is envisioned that these MRDs can be the same or different. In addition, any combination of MRD number and linkages can be used. For example, two MRDs can be operably linked to the N-terminal of the heavy chain of an antibody which contains one MRD linked to the C-terminal of the light chain. Similarly, three MRDs can be operably linked to the C-terminal of the light chain and two MRDs can be operably linked to the N-terminal of the light chain.

Multivalent and multispecific compositions (e.g., MRD-containing antibodies) can contain one, two, three, four, five, six, seven, eight, nine, ten or more than ten MRDs.

Figure 1:
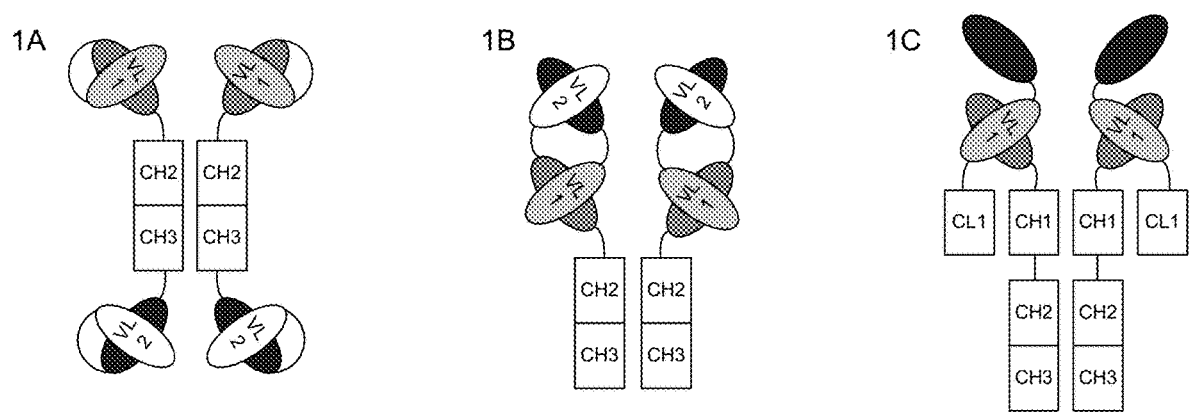
FIGS. 1A-1C show the schematic representation of different designs of multi-specific and multivalent molecules. MRDs are depicted as triangles, circles, diamonds, and squares.
Figure 2:
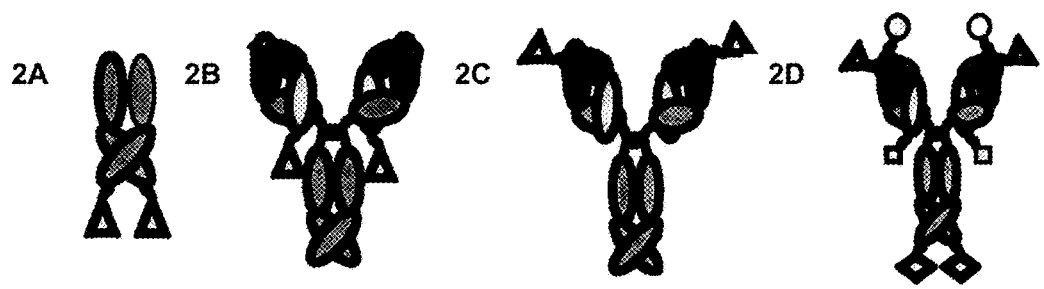
FIG. 2A shows a typical peptibody as a C-terminal fusion with the heavy chain of Fc.
FIG. 2B shows an MRD containing antibody with a C-terminal MRD fusion with the light chain of the antibody.
FIG. 2C shows an MRD containing antibody with an N-terminal MRD fusion with the light chain of the antibody.
FIG. 2D shows an MRD containing antibody with unique MRD peptides fused to each terminus of the antibody.

In one embodiment, the multivalent and monovalent multispecific composition (e.g., MRD-containing antibody) contains one MRD (see, e.g., FIGS. 2B and 2C). In another embodiment, the multivalent and monovalent multispecific composition (e.g., MRD-containing antibody) contains two MRDs. In another embodiment, the multivalent and monovalent multispecific composition (e.g., MRD-containing antibody) contains three MRDs. In another embodiment, the multivalent and monovalent multispecific composition (e.g., MRD-containing antibody) contains four MRDs (see, e.g., FIGS. 2B and 2C). In another embodiment, the multivalent and monovalent multispecific composition (e.g., MRD-containing antibody) contains five MRDs. In another embodiment, the multivalent and monovalent multispecific composition (e.g., MRD-containing antibody) contains six MRDs. In an additional embodiment, the multivalent and monovalent multispecific composition (e.g., MRD-containing antibody) contains between two and ten MRDs.

In one embodiment, the multivalent and monovalent multispecific composition (e.g., MRD-containing antibody) contains at least one MRD. In another embodiment, the multivalent and monovalent multispecific composition (e.g., MRD-containing antibody) contains at least two MRDs. In another embodiment, the multivalent and monovalent multispecific composition (e.g., MRD-containing antibody) contains at least three MRDs. In another embodiment, the multivalent and monovalent multispecific composition (e.g., MRD-containing antibody) contains at least four MRDs. In another embodiment, the multivalent and monovalent multispecific composition (e.g., MRD-containing antibody) contains at least five MRDs. In another embodiment, the multivalent and monovalent multispecific composition (e.g., MRD-containing antibody) contains at least six MRDs.

In another embodiment, the multivalent and monovalent multispecific composition (e.g., MRD-containing antibody) contains two different MRDs. In another embodiment, the multivalent and monovalent multispecific composition (e.g., MRD-containing antibody) contains three different MRDs. In another embodiment, the multivalent and monovalent multispecific composition (e.g., MRD-containing antibody) contains four different MRDs. In another embodiment, the multivalent and monovalent multispecific composition (e.g., MRD-containing antibody) contains five different MRDs. In another embodiment, the multivalent and monovalent multispecific composition (e.g., MRD-containing antibody) contains six different MRDs. In an additional embodiment, the multivalent and monovalent multispecific composition (e.g., MRD-containing antibody) contains between two and ten different MRDs.

In another embodiment, the multivalent and monovalent multispecific composition (e.g., MRD-containing antibody) contains at least two different MRDs. In another embodiment, the multivalent and monovalent multispecific composition (e.g., MRD-containing antibody) contains at least three different MRDs. In another embodiment, the multivalent and monovalent multispecific composition (e.g., MRD-containing antibody) contains at least four different MRDs. In another embodiment, the multivalent and monovalent multispecific composition (e.g., MRD-containing antibody) contains at least five different MRDs. In another embodiment, the multivalent and monovalent multispecific composition (e.g., MRD-containing antibody) contains at least six different MRDs.

Thus, the multivalent and multispecific compositions (e.g., MRD-containing antibodies) can be MRD monomeric (i.e., containing one MRD at the terminus of a peptide chain optionally connected by a linker) or MRD multimeric (i.e., containing more than one MRD in tandem optionally connected by a linker). The multimeric multivalent and multispecific compositions (e.g., MRD-containing antibodies) can be homo-multimeric (i.e., containing more than one of the same MRD in tandem optionally connected by linker(s) (e.g., homodimers, homotrimers, homotetramers etc.)) or hetero-multimeric (i.e., containing two or more MRDs in which there are at least two different MRDs optionally connected by linker(s) where all or some of the MRDs linked to a particular terminus are different (e.g., heterodimer, heterotrimer, heterotetramer etc.)). In one embodiment, the multivalent and monovalent multispecific composition (e.g., MRD-containing antibody) contains two different monomeric MRDs located at different immunoglobulin termini. In another embodiment, the multivalent and monovalent multispecific composition (e.g., MRD-containing antibody) contains three different monomeric MRDs located at different immunoglobulin termini. In another embodiment, the multivalent and monovalent multispecific composition (e.g., MRD-containing antibody) contains four different monomeric MRDs located at different immunoglobulin termini. In another embodiment, the multivalent and monovalent multispecific composition (e.g., MRD-containing antibody) contains five different monomeric MRDs located at different immunoglobulin termini. In another embodiment, the multivalent and monovalent multispecific composition (e.g., MRD-containing antibody) contains six different monomeric MRDs located at different immunoglobulin termini.

In an alternative embodiment, the multivalent and monovalent multispecific composition (e.g., MRD-containing antibody) contains at least one dimeric and one monomeric MRD located at different immunoglobulin termini. In another alternative embodiment, the multivalent and monovalent multispecific composition (e.g., MRD-containing antibody) contains at least one homodimeric and one monomeric MRD located at different immunoglobulin termini. In another alternative embodiment, the multivalent and monovalent multispecific composition (e.g., MRD-containing antibody) contains at least one heterodimeric and one monomeric MRD located at different immunoglobulin termini.

In an alternative embodiment, the multivalent and monovalent multispecific composition (e.g., MRD-containing antibody) contains at least one multimeric and one monomeric MRD located at different immunoglobulin termini. In another alternative embodiment, the multivalent and monovalent multispecific composition (e.g., MRD-containing antibody) contains at least one homomultimeric and one monomeric MRD located at different immunoglobulin termini. In another alternative embodiment, the multivalent and monovalent multispecific composition (e.g., MRD-containing antibody) contains at least one heteromultimeric and one monomeric MRD located at different immunoglobulin termini.

In an alternative embodiment, the multivalent and monovalent multispecific composition (e.g., MRD-containing antibody) contains MRDs operably linked to at least two different immunoglobulin termini. In a specific embodiment, the MRDs fused to at least one of the immunoglobulins are a multimer. In one embodiment, the MRDs fused to a least one of the immunoglobulins are a homomultimeric (i.e., more than one of the same MRD operably linked in tandem, optionally linked via a linker). In another embodiment, the MRDs fused to at least one of the immunoglobulins are a heteromultimeric (i.e., two or more different MRDs operably linked in tandem, optionally linked via a linker). In an additional embodiment, the MRDs fused to at least one of the immunoglobulins are a dimer. In another embodiment, the MRDs fused to a least one of the immunoglobulins are a homodimer. In another embodiment, the MRDs fused to at least one of the immunoglobulins are a heterodimer.

The multiple MRDs can target the same target binding site, or two or more different target binding sites. Where the MRDs bind to different target binding sites, the binding sites may be on the same or different target molecules.

Similarly, the antibody and the MRD in a multivalent and monovalent multispecific composition (e.g., MRD-containing antibody) may bind to the same target molecule or to different target molecules.

In some embodiments, at least one MRD and the antibody in the multivalent and monovalent multispecific composition (e.g., MRD-containing antibody) can bind to their targets simultaneously. In one embodiment, each MRD in the multivalent and monovalent multispecific composition (e.g., MRD-containing antibody) and the antibody can bind to its target simultaneously. Therefore, in some embodiments, the multivalent and monovalent multispecific composition (e.g., MRD-containing antibody) binds two, three, four, five, six, seven, eight, nine, ten or more targets simultaneously.

The ability of a multivalent and monovalent multispecific composition (e.g., MRD-containing antibody) to bind to multiple targets simultaneously can be assayed using methods known in the art, including, for example, those methods described in the examples below.

Multivalent and Multispecific Compositions Having Monovalent Specificity

In additional embodiments, the multivalent and multispecific compositions (e.g., MRD-containing antibodies) of the invention have a single binding site for (i.e., monovalently bind) a target.

In some embodiments, the antigen binding domains of an antibody component of a multivalent and monovalent multispecific composition of the invention binds to different target epitopes (i.e., the antibody is bispecific). The term "bispecific antibody" is intended to include any antibody, which has two different binding specificities, i.e. the antibody binds two different epitopes, which may be located on the same target antigen or, more commonly, on different target antigens. Methods for making bispecific antibodies are known in the art. (See, for example, Millstein et al., Nature, 305:537-539 (1983); Traunecker et al., EMBO J. 10:3655-3659 (1991); Suresh et al., Methods in Enzymology 121:210 (1986); Kostelny et al., J. Immunol. 148(5): 1547-1553 (1992); Hollinger et al., Proc. Natl. Acad. Sci. USA 90:6444-6448 (1993); Gruber et al., J. Immunol. 152:5368 (1994); Tutt et al., J. Immunol. 147:60-69 (1991); U.S. Pat. Nos. 4,474,893, 4,676,980, 4,714,681, 4,925,648, 5,573,920, 5,601,819, 5,731,168, 5,807,706, and 5,821,333; Intl. Appl. Publ. Nos. WO94/04690, WO91/00360, WO92/05793, WO92/08802, WO92/200373, WO93/17715, WO00/44788, and WO02/096948; EP 1870459A1 and EP 03089, the contents of each of which is herein incorporated by reference in its entirety).

One method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the invention have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass (e.g., IgG1 or IgG3) or different subclasses (e.g., IgG1 and IgG3, or IgG3 and IgG4)

In one embodiment, a bispecific antibody component of a multispecific and multivalent composition (e.g., MRD-containing antibody) comprises a T366W mutation in the "knobs chain" and T366S, L368A, Y407V mutations in the "hole chain," and optionally an additional interchain disulfide bridge between the CH3 domains by, e.g., introducing a Y349C mutation into the "knobs chain" and a E356C mutation or a S354C mutation into the "hole chain;" R409D, K370E mutations in the "knobs chain" and D399K, E357K mutations in the "hole chain;" R409D, K370E mutations in the "knobs chain" and D399K, E357K mutations in the "hole chain;" a T366W mutation in the "knobs chain" and T366S, L368A, Y407V mutations in the "hole chain;" R409D, K370E mutations in the "knobs chain" and D399K, E357K mutations in the "hole chain;" Y349C, T366W mutations in one of the chains and E356C, T366S, L368A, Y407V mutations in the counterpart chain; Y349C, T366W mutations in one chain and S354C, T366S, L368A, Y407V mutations in the counterpart chain; Y349C, T366W mutations in one chain and S354C, T366S, L368A, Y407V mutations in the counterpart chain; and Y349C, T366W mutations in one chain and S354C, T366S, L368A, Y407V mutations in the counterpart chain (numbering according to the EU index of Kabat).

In some embodiments, a bispecific antibody component of a composition of the invention (e.g., MRD-containing antibody) is an IgG4 antibody or a modified IgG4 antibody, or contains an IgG4 heavy chain or a modified IgG4 heavy chain. IgG4 antibodies are dynamic molecules that undergo Fab arm exchange by swapping an IgG4 heavy chain and attached light chain for a heavy-light chain pair from another IgG4 molecule, thus resulting in bispecific antibodies. Accordingly, Fab arm exchange by swapping of MRD-containing-IgG4 antibodies whether caused in vivo or in vitro under physiologic conditions will lead to bispecific antibody compositions. In particular embodiments, an IgG4 heavy chain of a composition of the invention contains an S228P substitution. This substitution has been shown to significantly inhibit Fab arm exchange in the resulting mutant IgG4 antibodies, and to thereby reduce the likelihood of Fab-arm-exchange between a recombinant antibodies and endogenous IgG4. (See, e.g., Labrijn et al., Nat. Biotechnol. 27(8):767-71 (2009)). In additional embodiments, an IgG4 heavy chain of a composition of the invention contains a substitution of the Arg at position 409 (e.g., with Lys, Ala, Thr, Met or Leu), the Phe at position 405 (e.g., with Lys, Ala, Thr, Met or Leu) or the Lys at position 370. In other embodiments, the CH3 region of an IgG4 heavy chain of a composition of the invention has been replaced with the CHH3 region of IgG1, IgG2 or IgG3. In additional embodiments, interactions between one or more MRDs located at the C-termini of distinct heavy chains (e.g., IgG4 or IgG4 and IgG3) favor and/or stabilize heterodimers between the heavy chains, or otherwise reduces Fab arm exchange by the heterodimer.

Exemplary bispecific antibody components of multivalent and multispecific compositions of the invention include, IgG4 and IgG1, IgG4 and IgG2, IgG4 and IgG2, IgG4 and IgG3, IgG1 and IgG3 chain heterodimers. Such heterodimeric heavy chain antibodies, can routinely be engineered by, for example, modifying selected amino acids forming the interface of the CH3 domains in human IgG4 and the IgG1 or IgG3 so as to favor heterodimeric heavy chain formation. In additional embodiments, interactions between one or more MRDs located at the C-termini of heteromeric heavy chains favors or stabilizes heteromultimeric formation or structure, respectively.

IgG4 antibodies are known to have decreased ADCC activity and half-life compared to other immunoglobulins subclasses such as, IgG1 and IgG3. Accordingly, IgG4 subclass-based formats provide an attractive format for developing therapeutics that bind to and block cell receptors, but do not deplete the target cell. Alternatively, in those embodiments for which increased effector activity is desired, an IgG4 heavy chain of a composition of the invention can be modified as described herein or otherwise known in the art, so as to increase effector function (e.g., modification of the residues at positions 327, 330 and 331; numbering according to EU index of Kabat). Similarly, where increased half-life is desired, an IgG4 heavy chain of a composition of the invention can be engineered as described herein, or otherwise known in the art to more selectively bind the FcRn at pH 6.0, but not pH 7.4, by for example, incorporating mutations located at the interface between the CH2 and CH3 domains, such as substitutions at T250Q/M428L as well as M252Y/S254T/T256E and H433K/N434F (numbering according to the EU index of Kabat).

As exemplified above, it is envisioned that in some embodiments, the multivalent and multispecific compositions (e.g., MRD-containing antibodies) of the invention have a single binding site for (i.e., monovalently bind) a target. In some embodiments, the single binding site (i.e., monovalent binding site) is an antibody antigen binding domain. In other embodiments, the single binding site is an MRD. Thus, the multivalent and multispecific compositions of the invention encompass (and can be routinely engineered to include) MRD-containing antibodies that that contain 1, 2, 3, 4 or more single binding sites for a target. The single binding site(s) may be provided by one or more MRDs located at any one or more of the 4 immunoglobulin heavy chain termini or 4 immunoglobulin light chain termini. Moreover, single binding site may be provided by one of the antigen binding domains of the antibody (wherein an MRD of the MRD-containing antibody binds the same target epitope of the other antigen binding domain of the antibody. Moreover, in a specific embodiment, the compositions of the invention encompass (and can be routinely engineered to include) MRD-containing antibodies that contain 1, 2, 3, 4 or more single binding sites for a target and do not bivalenty bind another target In further embodiments, the multivalent and monovalent multispecific composition (e.g., MRD-containing antibodies) has a single binding site for (i.e., monovalently binds) a cell surface target that forms multimers (e.g., homomers or heteromers). In some embodiments, the single binding site binds a cell surface target that requires multimerization for signaling. In some embodiments, the multivalent and monovalent multispecific composition (e.g., an MRD-containing antibody) has a single binding site that binds a cell surface target and inhibits binding of another molecule (such as a ligand) to the cell surface target. In other embodiments, binding of the single binding site inhibits multimerization of the target (e.g., homomeric and heteromeric multimerization). In additional embodiments, the composition has single binding sites for different targets (i.e., monovalently binds more than one different target). In some embodiments, the multiple single binding sites of the composition bind targets on the same cell. In additional embodiments, the multiple single binding sites of the composition bind targets on different cells. Numerous receptors are known in the art that require multimerization for affecting their normal function. Such receptors are envisioned to be targets of single binding sites in the multivalent and multispecific compositions (e.g., MRD-containing antibodies) of the invention. In some embodiments, the composition has a single binding site for a receptor tyrosine kinase. In some embodiments, the composition has a single binding site for a growth factor receptor. In additional embodiments the composition has a single binding site for a G protein coupled receptor. In additional embodiments the composition has a single binding site for a chemokine receptor. In other embodiments, the composition has a single binding site for a TNF receptor superfamily member. In particular embodiments, the composition has a single binding site for a receptor selected from: RAGE, c-Met, ErbB2, VEGFR1, VEGFR2, VEGFR3, FGFR1 (e.g., FGFR1-IIIC), FGFR2 (e.g., FGFR2-IIIa, FGFR2-IIIb, and FGFR2-IIIc), FGFR3, PDGFRA, PDGFRB, netrin, CD28, TNFRSF1A (TNFR1, p55, p60), TNFRSF1B (TNFR2), TNFSF6 (Fas Ligand), TNFRSF6 (Fas, CD95), TNFRSF21 or TNFRSF25, TNFRSF7 (CD27), TNFSF8 (CD30 Ligand), TNFRSF8 (CD30), TNFSF11 (RANKL), TNFRSF11A (RANK), TNFRSF21 (DR6), TNFRSF25 (DR3), and LRP6.

In additional embodiments, the multivalent and monovalent multispecific composition (e.g., an MRD-containing antibody) has a single binding site for (i.e., monovalently binds) a cell surface target that forms a multimer and multiple sites (i.e., multivalently binds) for two or more different targets. In other embodiments, the multivalent and monovalent multispecific composition has a single binding site for a cell surface target and multiple binding sites for 1, 2, 3, 4, 5 or more different targets. In further embodiments, at least 1, 2, 3, 4, 5 or more of the targets bound by the multivalent and monovalent multispecific composition are located on a cell surface. In other embodiments, at least 1, 2, 3, 4, 5 or more of the targets bound by the multivalent and monovalent multispecific composition are soluble targets (e.g., chemokines, cytokines, and growth factors). In additional embodiments, the composition binds 1, 2, 3, 4, 5 or more of the targets described herein. In further embodiments, the targets bound by the composition are tumor antigens (including tumor antigens and tumor associated antigens). In additional embodiments, a target bound by the composition is associated with a disease or disorder of the immune system. In further embodiments, a targets bound by the composition is associated with a disease or disorder of the skeletal system (e.g., osteoporosis), cardiovascular system, nervous system, or an infectious disease.

In some embodiments, an MRD-containing antibody has a single binding site for TNFRSF21 (DR6). In further embodiments, the MRD-containing antibody has a single binding site for DR6 and binds a target selected from: AGE (S100A, amphoterin), IL1, IL6, IL18, IL12, IL23, TNFSF12 (TWEAK), TNF alpha, VEGF, TNFRSF5 (CD40), TNFSF5 (CD40 LIGAND), interferon gamma, GMCSF, an FGF, CXCL13, MCP 1, CCR2, NogoA, RGM A, OMgp MAG, a CPSG, LINGO, alpha-synuclein, a semaphorin (e.g., Semaphorin 3A, Semaphorin 4), an ephrin, VLA4, CD45, RB, C5, CD52 and CD200. Multivalent and multispecific compositions (e.g., MRD-containing antibodies) that bind DR6 and also bind at least 1, 2, 3, 4, 5 or more of these targets are also encompassed by the invention. These compositions have applications in treating diseases and disorders including neurological diseases and disorders such as multiple sclerosis and other neurodegenerative diseases. In specific embodiments, the antibody component of the MRD-containing antibody binds DR6.

In some embodiments, an MRD-containing antibody has a single binding site for TNFRSF25 (DR3). In further embodiments, the MRD-containing antibody has a single binding site for DR3 and binds a target selected from: TNF, IFN alpha, IFN gamma, IL1, IL1beta, IL6, IL8, IL12, IL15, IL17, IL18, IL23 and IL32. Multivalent and multispecific compositions (e.g., MRD-containing antibodies) that bind DR3 and also bind at least 1, 2, 3, 4, 5 or more of these targets are also encompassed by the invention. These compositions have applications in treating diseases and disorders including inflammatory bowel disease and autoimmune diseases such as rheumatoid arthritis. In specific embodiments, the antibody component of the MRD-containing antibody binds DR3.

In further embodiments, the multivalent and monovalent multispecific composition (e.g., MRD-containing antibodies) has multiple binding site for (i.e., multivalently binds) a cell surface target that forms multimers (e.g., homomers or heteromers). In some embodiments, the multiple binding sites bind a cell surface target that requires multimerization for signaling. In some embodiments, the multivalent and monovalent multispecific composition (e.g., an MRD-containing antibody) has multiple binding sites for a cell surface target. In further embodiments, binding of the multiple binding sites result in multimerization of the target (e.g., homomeric and heteromeric multimerization). In additional embodiments, the composition has multiple binding sites for different targets (i.e., multivalently binds more than one different target). In some embodiments, the multiple single binding sites of the composition bind targets on the same cell. In additional embodiments, the multiple single binding sites of the composition bind targets on different cells. Numerous receptors are known in the art that require multimerization for affecting their normal function. Such receptors are envisioned to be targets of the multivalent and multispecific compositions (e.g., MRD-containing antibodies). In some embodiments, the composition has multiple binding sites for a receptor tyrosine kinase. In some embodiments, the composition has a multiple binding site for a growth factor receptor. In additional embodiments the composition has multiple binding sites for a G protein coupled receptor. In additional embodiments the composition has multiple binding sites for a chemokine receptor. In other embodiments, the composition has multiple binding sites for a TNF receptor superfamily member.

In some embodiments, an MRD-containing antibody binds TNFRSF10A (DR4). In further embodiments, the MRD-containing antibody binds DR4 and a target selected from: ErbB2, EGFR, IGF1R, TNFRSF10b (DR5), CD19, CD20, CD22, CD30, CD33, TNFRSF5 (CD40), TNFRSF9 (41BB), IL6, and IGF1,2. Multivalent and multispecific compositions (e.g., MRD-containing antibodies) that bind DR4 and also bind at least 2, 3, 4, 5 or more of these targets are also encompassed by the invention. These compositions have applications in treating diseases and disorders including cancers such as breast cancer, colorectal cancer, head and neck cancer, B-cell lymphomas, hairy cell leukemia, B-cell chronic lymphocytic leukemia and melanoma. In specific embodiments, the antibody component of the MRD-containing antibody binds DR4. In further embodiments, the antibody component of the MRD-containing antibody is CS1008 or mapatumumab.

In some embodiments, an MRD-containing antibody binds TNFRSF10B (DR5). In some embodiments, an MRD-containing antibody binds DR5 and a target selected from: ErbB2, EGFR, IGF1R, TNFRSF10A (DR4), CD19, CD20, CD22, CD30, CD33, TNFRSF5 (CD40), TNFRSF9 (41BB), IL6, and IGF1,2. Multivalent and multispecific compositions (e.g., MRD-containing antibodies) that bind DR5 and also bind at least 2, 3, 4, 5 or more of these targets are also encompassed by the invention. These compositions have applications in treating diseases and disorders including cancers such as breast cancer, colorectal cancer, head and neck cancer, B-cell lymphomas, hairy cell leukemia, B-cell chronic lymphocytic leukemia, and melanoma. In specific embodiments, the antibody component of the MRD-containing antibody binds DR5. In further embodiments, the antibody component of the MRD-containing antibody is LBY135, AMG66, Apomab, PRO95780, lexatumumab, conatumumab or tigatuzumab.

Compositions that Redirect Effector Cell Function

The invention also encompasses multivalent and multispecific compositions such as, multivalent and multispecific compositions (e.g., MRD-containing antibodies) that are capable of juxtaposing host effector cells with cells that are desired to be eliminated (e.g., immune cells, cancer cells, diseased cells, infectious agents, and cells infected with infectious agents). The multivalent and multispecific functionalities of the compositions of the invention are particularly well suited for redirecting host immune responses and provide numerous advantages over alternative multispecific composition platforms under development. In one embodiment, the multivalent and monovalent multispecific composition (e.g., an MRD-containing antibody) binds (1) a target on a cell, tissue, or infectious agent of interest (e.g., an immune cell or a tumor antigen on a tumor cell) and (2) a target on an effector cell so as to direct an immune response to the cell, tissue, or infectious agent of interest. The target(s) to which the multivalent and monovalent multispecific composition binds can be monomeric or multimeric. Moreover, the mulitmeric target to which a multivalent and monovalent multispecific composition binds can be homomultimeric or heteromultimeric. In additional embodiments, the multivalent and monovalent multispecific composition binds at least 2, 3, 4, or 5 targets on the cell, tissue, or infectious agent of interest. In additional embodiments, one or more targets bound by the multivalent and monovalent multispecific composition is a tumor antigen (e.g., tumor antigens and tumor/cancer associated antigens). The multivalent and multispecific compositions also have applications in treating diseases and disorders including, but not limited to, diseases of the immune system, skeletal system, cardiovascular system, and nervous system, as well as infectious disease. Thus, in some embodiments, 1, 2, 3, 4, 5 or more targets bound by the multivalent and monovalent multispecific composition is associated with a disease or disorder of the immune system (for example, a disease or disorder of the immune system disclosed herein, such as inflammation or an autoimmune disease (e.g., rheumatoid arthritis)). In additional embodiments, 1, 2, 3, 4, 5 or more targets bound by the multivalent and monovalent multispecific composition is associated with a disease or disorder of the skeletal system (e.g., osteoporosis or another disease or disorder of the skeletal system as disclosed herein). In additional embodiments, 1, 2, 3, 4, 5 or more targets bound by the multivalent and monovalent multispecific composition is associated with a disease or disorder of the cardiovascular system (e.g., a disease or disorder of the cardiovascular system disclosed herein). In additional embodiments, 1, 2, 3, 4, 5 or more targets bound by the multivalent and monovalent multispecific composition is associated with a disease or disorder of the nervous system (e.g., a disease or disorder of the nervous system disclosed herein). In additional embodiments, 1, 2, 3, 4, 5 or more targets bound by the multivalent and monovalent multispecific composition is associated with an infectious agent or disease (e.g., an infectious disease or agent disclosed herein).

Effector cells that can be bound by a multivalent and monovalent multispecific composition (e.g., an MRD-containing antibody) of the invention include, but are not limited to, T cells, monocytes/macrophages, and natural killer cells.

In one embodiment, the target on a cell to which a multivalent and monovalent multispecific composition (e.g., an MRD-containing antibody) directs an immune response is a tumor antigen. The multivalent and multispecific compositions of the invention (e.g., MRD-containing antibodies) are envisioned to be capable of binding virtually any type of tumor and any type of tumor antigen. Exemplary types of tumors that can be targeted include, but are not limited to, one or more cancers selected from the group: colorectal cancer, esophageal, gastric, head and neck cancer, thyroid cancer, multiple myeloma, renal cancer, pancreatic cancer, lung cancer, biliary cancer, glioma, melanoma, liver cancer, prostate cancer, and urinary bladder cancer breast cancer, ovarian cancer, cervical cancer, and endometrial cancer. Exemplary types of tumors that may be targeted include hematological cancers. Hematological cancers that may be targeted include, but are not limited to, one or more cancers selected from the group Hodgkin's lymphoma, medullary non-Hodgkin's lymphoma, acute lymphoblastic leukemia, lymphocytic leukemia, and chronic myelogenous leukemia, acute myelogenous leukemia.

Exemplary tumor antigens include ErbB1, ErbB2, ErbB3, VEGFR1, VEGFR2, EGFRvIII, CD16, CD19, CD20, oncostatin M, PSA, PSMA, integrin avb6, ADAMS, CD22, CD23, CD25, CD28, CD36, CD45, CD46, CD56, CD79a/CD79b, CD103, JAM-3, gp100, ALCAM, PIPA, A33, carboxypeptidease M, E-cadherin, CA125, CDK4, CEA, CTLA-4, RAAG10, transferrin receptor, p-15, GD2, MUM-1, MAGE-1, MAGE-3, KSA, MOC31, MIC-1, EphA2, GAGE-1, GAGE-2, MART, KID31, CD44v3, CD44v6, and ROR1. Additional exemplary tumor antigens are described herein and/or known in the art.

In one embodiment, the target on a cell to which a multivalent and monovalent multispecific composition (e.g., an MRD-containing antibody) directs an immune response is an immune cell or an inflammatory cell.

In some embodiments, the invention encompasses a multivalent and monovalent multispecific composition that binds a tumor antigen that is not expressed on tumor cells themselves, but rather on the surrounding reactive and tumor supporting, non-malignant cells comprising the tumor stroma (i.e., tumor associated antigens). The tumor stroma comprises endothelial cells forming new blood vessels and stromal fibroblasts surrounding the tumor vasculature. In one embodiment, a multivalent and monovalent multispecific composition binds a tumor associated antigen on an endothelial cell. In an additional embodiment, a multivalent and monovalent multispecific composition binds a tumor antigen and also binds a tumor associated antigen on a fibroblast cell. In a further embodiment, a multivalent and monovalent multispecific composition binds a tumor antigen and also binds fibroblast activation protein (FAP).

Infectious agents to which a multivalent and monovalent multispecific composition (e.g., an MRD-containing antibody) can direct an immune response include, but are not limited to, prokaryotic and eukaryotic cells, viruses (including bacteriophage), foreign objects (e.g., toxins), and infectious organisms such as funghi, and parasites (e.g., mammalian parasites), as described herein and infectious agents associated with infectious diseases described herein. The term infectious agents is also intended to encompass other prokaryotic and eukaryotic cells, viruses (including bacteriophage), foreign objects (e.g., toxins), and infectious organisms such as funghi, and parasites otherwise known in the art.

In further embodiments, the multivalent and monovalent multispecific composition (e.g., an MRD-containing antibody) binds (1) a target on a cell, tissue, or infectious agent of interest (e.g., a tumor antigen on a tumor cell) and (2) has a single binding site for a target on an effector cell so as to direct an immune response to the cell, tissue, or infectious agent of interest. In some embodiments the single binding site is an MRD. In other embodiments, the single binding site is an antibody antigen binding domain. In further embodiments, binding of the multivalent and monovalent multispecific composition does not elicit a signal when the composition binds a target on an effector cell. In additional embodiments, the multivalent and monovalent multispecific composition binds at least 2, 3, 4, or 5 targets on the cell, tissue, or infectious agent of interest. According to some embodiments, at least 1, 2, 3, 4, 5 or more of the targets of the multivalent and monovalent multispecific composition are located on a cell surface. In additional embodiments, 1, 2, 3, 4, 5 or more targets bound by the multivalent and monovalent multispecific composition is a tumor antigen (e.g., tumor antigens and tumor/cancer associated antigens). In additional embodiments, one or more targets bound by the multivalent and monovalent multispecific composition are associated with a disease or disorder of the immune system. In additional embodiments, one or more targets bound by the multivalent and monovalent multispecific composition are associated with a disease or disorder of the skeletal system (e.g., osteoporosis), cardiovascular system, nervous system, or an infectious disease.

In additional embodiments, the multivalent and monovalent multispecific composition (e.g., an MRD-containing antibody) binds (1) a target on a cell, tissue, or infectious agent of interest (e.g., a tumor antigen on a tumor cell) and (2) a target on a leukocyte so as to direct an immune response to the cell, tissue, or infectious agent of interest. In additional embodiments, the multivalent and monovalent multispecific composition binds at least 2, 3, 4, or 5 targets on the cell, tissue, or infectious agent of interest. According to some embodiments, at least 1, 2, 3, 4, 5 or more of the targets of the multivalent and monovalent multispecific composition are located on a cell surface. In additional embodiments the multivalent and monovalent multispecific composition binds 1, 2, 3, 4, 5 or more targets described herein. In additional embodiments, 1, 2, 3, 4, 5 or more targets bound by the multivalent and monovalent multispecific composition are a tumor antigen (e.g., tumor antigens and tumor/cancer associated antigens). In additional embodiments, one or more targets bound by the multivalent and monovalent multispecific composition are associated with a disease or disorder of the immune system. In additional embodiments, one or more targets bound by the multivalent and monovalent multispecific composition are associated with a disease or disorder of the skeletal system (e.g., osteoporosis), cardiovascular system, nervous system, or an infectious disease.

The invention also encompasses multivalent and multispecific compositions that bind a target expressed on a leukocyte. In some embodiments, the multivalent and monovalent multispecific composition (e.g., an MRD-containing antibody) binds (1) a target on a cell, tissue, or infectious agent of interest (e.g., a tumor antigen on a tumor cell) and (2) has a single binding site for a target on a leukocyte so as to direct an immune response to the cell, tissue, or infectious agent of interest. In additional embodiments, the multivalent and monovalent multispecific composition binds at least 2, 3, 4, or 5 targets on the cell, tissue, or infectious agent of interest. According to some embodiments, at least 1, 2, 3, 4, 5 or more of the targets of the multivalent and monovalent multispecific composition are located on a cell surface. In additional embodiments, 1, 2, 3, 4, 5 or more antigens and tumor/cancer associated antigens). In additional embodiments, 1, 2, 3, 4, 5 or more targets bound by the multivalent and monovalent multispecific composition are associated with a disease or disorder of the immune system. In additional embodiments, 1, 2, 3, 4, 5 or more targets bound by the multivalent and monovalent multispecific composition are associated with a disease or disorder of the skeletal system (e.g., osteoporosis), cardiovascular system, nervous system, or an infectious disease.

In one embodiment, the multivalent and monovalent multispecific composition binds a target expressed on a T cell. In some embodiments, the multivalent and monovalent multispecific composition (e.g., an MRD-containing antibody) binds (1) a target on a cell, tissue, or infectious agent of interest (e.g., a tumor antigen on a tumor cell) and (2) a target on a T cell so as to juxtapose myeloid cells with the cell, tissue, or infectious agent of interest. In some embodiments, the multivalent and monovalent multispecific composition has multiple binding sites for (i.e., multivalently binds) a target on a T cell. In other embodiments, the multivalent and monovalent multispecific composition has a single binding site for (i.e., monovalently binds) a target on a T cell. In some embodiments the single binding site is an MRD. In other embodiments, the single binding site is an antibody antigen binding domain. In further embodiments, binding of the multivalent and monovalent multispecific composition does not elicit a signal when the composition binds a target on a T cell. In other embodiments, the binding of the multivalent and monovalent multispecific composition does not result in lysis of the T cell expressing the target. In some embodiments, the multivalent and monovalent multispecific composition binds a target selected from: CD2, CD3, CD4, CD8, CD161, a chemokine receptor, CD95, and CCR5. In additional embodiments, the multivalent and monovalent multispecific composition binds at least 2, 3, 4, or 5 targets on the cell, tissue, or infectious agent of interest. According to some embodiments, at least 1, 2, 3, 4, 5 or more of the targets of the multivalent and monovalent multispecific composition are located on a cell surface. In additional embodiments, 1, 2, 3, 4, 5 or more targets bound by the multivalent and monovalent multispecific composition is a tumor antigen (e.g., tumor antigens and tumor/cancer associated antigens). In additional embodiments, 1, 2, 3, 4, 5 or more targets bound by the multivalent and monovalent multispecific composition are associated with a disease or disorder of the immune system. In additional embodiments, 1, 2, 3, 4, 5 or more targets bound by the multivalent and monovalent multispecific composition are associated with a disease or disorder of the skeletal system (e.g., osteoporosis), cardiovascular system, nervous system, or an infectious disease.

In further embodiments, the multivalent and monovalent multispecific composition contains a fusion protein containing one or more peptides that bind to a protein on the surface of a cell, such as a T cell. In additional embodiments, the multivalent and monovalent multispecific composition bind target membrane proximal protein sequences on a cell and inhibit the cross-linking (e.g., multimerization) of the target protein or its associated proteins. In a particular embodiment, the multivalent and monovalent multispecific composition binds to a T cell and inhibits the cross-linking of the cell protein or its associated proteins. For example, in one embodiment, the multivalent and multispecific antibody comprises the amino terminal 27 amino acids of mature CD3 epsilon. In another embodiment, the multivalent and monovalent multispecific composition comprises a fusion protein containing one or more proteins corresponding to the G Domain of a CD3 protein (e.g., CD3 epsilon, CD3 gamma, CD3 alpha (TCRA) or CD3 beta (TCRB). Thus, in some embodiments, the fusion protein comprises a polypeptide having an amino acid sequence selected from:

```
                                        (SEQ ID NO: 21)
        GYYVCYPRGSKPEDANFYLYLRARVC, (SEQ ID NO: 22)
        YLYLRAR, (SEQ ID NO: 23)
        YRCNGTDIYKDKESTVQVHYRMC,
        and (SEQ ID NO: 24)
        DKESTVQVH.
```

In additional embodiments, the composition comprises a fusion protein containing one or more proteins corresponding to a portion of the extracellular domain of a CD3 protein (e.g., CD3 epsilon, CD3 gamma, CD3 alpha (TCRA) or CD3 beta (TCRB)) that is able to bind CD3, or a CD3 multimer. Thus, in some embodiments, the fusion protein comprises a portion of a CD3 protein that is able to bind CD3 or a CD3 multimer wherein the portion comprises a CD3 binding fragment of a polypeptide having an amino acid sequence selected from: KIPIEELEDRVFVNCNCN-TSITWVEG TVGTLLSDITRLDLGKRILDPRGI-YRCNGTDIY KDKESTVQVHYRMCQSCVELD (human CD3 delta mature ECD, SEQ ID NO:25), QSIKGNHLVK-VYDYQEDGSVLLTCDAEAK NITWFKDGKMIGFLT-EDKKKWNLGSNAKDPRGMYQCKGSQNKSQ-PLQVYYRMCQNC IELN (human CD3 gamma mature ECD, Ig-like domain highlighted; SEQ ID NO:26), GNEEMGGITQTPYKVSISGTTVILTCPQYPGSEIL-WQHNDKNIGGDEDDKNIGS DEDHL SLKEFSELEQS-GYYVCYPRGSKPEDANFYLYLRARVCENCMEM-DVM (human CD3 epsilon mature ECD, Ig-like domain highlighted, SEQ ID NO:27), and QSFGLLDPK (human CD3 zeta mature ECD, SEQ ID NO:28), In alternative embodiments, the fusion protein comprises a chemokine fragment that binds a target on the cell surface. In some embodiments, the chemokine fragment is a portion of a chemokine selected from: CCL20 (LARC/Ckβ4), CCL25 (TECK/Ckβ15), CXCL12 (SDF-1), CXCL13 (BCA-1), CXCL16 (SRPSOX), and CX3CL1 (Fractalkine). In some embodiments, the chemokine fragment is a portion of a chemokine selected from: CCL5 (RANTES), CCL8 (MCP- 2), CXCL9 (MIG/CRG-10), CXCL10 (IP-10/CRG-2) and CXCL11 (TAC/IP-9). In some embodiments, the chemokine fragment is a portion of a chemokine selected from CCL3 (MIP-1a) and CCL4 (MIP-1B).

In specific embodiments, the multivalent and monovalent multispecific composition (e.g., an MRD-containing antibody) binds CD3. In particular embodiments, the composition binds a CD3 target selected from CD3 delta, CD3 epsilon, CD3 gamma, CD3 zeta, TCR alpha, TCR beta, the TCR complex, or a heteromeric or homomultimeric combination thereof. In a further embodiment, the composition binds CD3 epsilon. In additional embodiments, the multivalent and monovalent multispecific composition binds CD3 and multiple binding sites for 1, 2, 3, 4, 5 or more different targets (e.g., a tumor antigen as disclosed herein or otherwise known in the art). In additional embodiments, the multivalent and monovalent multispecific composition has a single binding site for (i.e., monovalently binds) CD3. In further embodiments, the multivalent and monovalent multispecific composition has a single MRD that binds CD3 and multiple binding sites for 1, 2, 3, 4, 5 or more different targets (e.g., a tumor antigen as disclosed herein or otherwise known in the art). In further embodiments, the multivalent and monovalent multispecific composition has a single antibody antigen binding domain that binds CD3 and multiple binding sites for 1, 2, 3, 4, 5 or more different targets (e.g., a tumor antigen as disclosed herein or otherwise known in the art). In particular embodiments, the CD3 binding compositions of the invention are not single chain antibodies.

In some embodiments, the multivalent and monovalent multispecific composition (e.g., an MRD-containing antibody) binds human CD3 and a CD3 ortholog from another organism. In additional embodiments, the multivalent and monovalent multispecific composition binds human CD3 and a CD3 ortholog from another primate. In further embodiments, the multivalent and monovalent multispecific composition binds human CD3 and a CD3 ortholog from cynomolgus Monkey or rhesus Monkey. In other embodiments, the multivalent and monovalent multispecific composition binds human CD3 and a CD3 ortholog from a primate selected from *Saguinus Oedipus* and *Callithrix jacchus*). In an additional embodiment, the multivalent and monovalent multispecific composition binds human CD3 and a CD3 ortholog from cynomolgus monkey, and a CD3 ortholog from mouse or rat. In particular embodiments, the human CD3 epsilon binding compositions of the invention are not single chain antibodies. In additional particular embodiments, the CD3 binding compositions of the invention are not single chain antibodies.

According to one embodiment, the multivalent and monovalent multispecific composition (e.g., an MRD-containing antibody) binds human CD3 epsilon. In a particular embodiment, the, multivalent and monovalent multispecific composition binds human CD3 epsilon protein having the sequence of amino acids 23-207 set forth in NCBI Ref. Seq. No. NP_000724. In another embodiment, the multivalent and monovalent multispecific composition binds a polypeptide having the amino acid sequence of QDGNEEMGGITQTPYKVSISGTT VILT (SEQ ID NO:29). In an additional embodiment, the multivalent and monovalent multispecific composition binds a polypeptide having the amino acid sequence of QDGNEEMGGI (SEQ ID NO:30). In a further embodiment, the multivalent and monovalent multispecific composition binds a polypeptide having the amino acid sequence of QDGNEEMGG (SEQ ID NO:31).

In particular embodiments, the human CD3 epsilon binding compositions of the invention are not single chain antibodies.

In some embodiments, a multivalent and monovalent multispecific composition (e.g., an MRD-containing antibody) has a single binding site for CD3 epsilon (i.e., monovalently binds CD3 epsilon) and multiple binding sites for 1, 2, 3, 4, 5 or more different targets (e.g., a B cell or other target disclosed herein). In further embodiments, the multivalent and monovalent multispecific composition (e.g., an MRD-containing antibody) competes for binding to CD3 with an antibody selected from: OKT-3, otelixizumab, teplizumab, visilizumab, muromonab, X35-3, VIT3, BMA030 (BW264/56), CLB-T3/3, CRIS7, YTH12.5, F111409, CLB-T3.4.2, TR-66, WT31, WT32, SPv-T3b, 11D8, XIII-141, XIII46, XIII-87, 12F6, T3/RW2-8C8, T3/RW24B6, OKT3D, M-T301, SMC2 and F101.01. In additional embodiments, an MRD of an MRD-containing antibody competes for binding to CD3 with an antibody selected from: OKT-3, otelixizumab, teplizumab, visilizumab, muromonab X35-3, VIT3, BMA030 (BW264/56), CLB-T3/3, CRIS7, YTH12.5, F111409, CLB-T3.4.2, TR-66, WT31, WT32, SPv-T3b, 11D8, XIII-141, XIII43, XIII-87, 12F6, T3/RW2-8C8, T3/RW24B6, OKT3D, M-T301, SMC2 and F101.01. In further embodiments, the multivalent and monovalent multispecific composition (e.g., MRD-containing antibody) competes for binding to CD3 with a CD3 binding composition disclosed in Int. Appl. Pub Nos. WO2004/106380 and WO99/54440; Tunnacliffe et al., Int. Immunol. 1:546-550 (1989); Kjer-Nielsen, PNAS 101:7675-7680 (2004); or Salmeron et al., J. Immunol. 147: 3047-3052 (1991).

In additional embodiments, the multivalent and monovalent multispecific composition (e.g., an MRD-containing antibody) binds human CD3 epsilon and a CD3 epsilon ortholog from another organism. In some embodiments, the multivalent and monovalent multispecific composition (e.g., an MRD-containing antibody) binds human CD3 epsilon and a CD3 epsilon ortholog from another primate. In additional embodiments, the multivalent and monovalent multispecific composition binds human CD3 epsilon and a CD3 epsilon ortholog from cynomolgus monkey or rhesus monkey. In additional embodiments, the multivalent and monovalent multispecific composition binds human CD3 epsilon and a CD3 epsilon ortholog from a primate selected from *Saguinus Oedipus* and *Callithrix jacchus*. In an additional embodiment, the multivalent and monovalent multispecific composition binds human CD3 epsilon and a CD3 epsilon ortholog from cynomolgus monkey, and a CD3 epsilon ortholog from mouse or rat. In particular embodiments, an MRD of the multivalent and monovalent multispecific composition binds CD3 epsilon.

In another embodiment the multivalent and monovalent multispecific composition (e.g., an MRD-containing antibody) binds human CD3 delta. In a particular embodiment, the, multivalent and monovalent multispecific composition binds human CD3 delta having the sequence of amino acids 22-171 set forth in NCBI Ref. Seq. No. NP_000723. In particular embodiments, an MRD of the multivalent and monovalent multispecific composition binds CD3 delta. In other embodiments, an antibody antigen binding domain of the multivalent and monovalent multispecific composition binds CD3 delta. In particular embodiments, the human CD3 epsilon binding compositions of the invention are not single chain antibodies.

In an additional embodiment, the multivalent and monovalent multispecific composition (e.g., an MRD-containing antibody) binds human CD3 gamma protein having the sequence of amino acids 23-182 set forth in NCBI Ref. Seq. No. NP_000064. In particular embodiments, an MRD of the multivalent and monovalent multispecific composition binds gamma. In particular embodiments, an MRD of the multivalent and monovalent multispecific composition binds CD3 gamma. In other embodiments, an antibody antigen binding domain of the multivalent and monovalent multispecific composition binds CD3 gamma. In particular embodiments, the human CD3 gamma binding compositions of the invention are not single chain antibodies.

In an additional embodiment, the multivalent and monovalent multispecific composition (e.g., an MRD-containing antibody) binds human CD3 zeta protein having the sequence of amino acids 22-164 set forth in NCBI Ref. Seq. No. NP_932170. In particular embodiments, an MRD of the multivalent and monovalent multispecific composition binds CD3 zeta. In other embodiments, an antibody antigen binding domain of the multivalent and monovalent multispecific composition binds CD3 zeta. In particular embodiments, the human CD3 zeta binding compositions of the invention are not single chain antibodies.

The invention also encompasses multivalent and multispecific compositions that bind a target expressed on a natural killer cell. In some embodiments, the multivalent and monovalent multispecific composition (e.g., an MRD-containing antibody) binds (1) a target on a cell, tissue, or infectious agent of interest (e.g., a tumor antigen on a tumor cell) and (2) a target on a natural killer cell. In some embodiments, the multivalent and monovalent multispecific composition has multiple binding sites for (i.e., multivalently binds) a target on a natural killer cell. In other embodiments, the multivalent and monovalent multispecific composition has a single binding site for (i.e., monovalently binds) a target on a natural killer cell. In some embodiments the single binding site is an MRD. In other embodiments, the single binding site is an antibody antigen binding domain. In further embodiments, binding of the multivalent and monovalent multispecific composition does not elicit a signal when the composition binds a target on a natural killer cell. In some embodiments, the multivalent and monovalent multispecific composition binds a target selected from: KLRD1, KLRK1, KLRB1, 2B4 (CD244), KIR2D4, KIR2D5, and KIR3DL1. In other embodiments, the multivalent and monovalent multispecific composition binds a target selected from: CD56, CD2, and CD161. In additional embodiments, the multivalent and monovalent multispecific composition binds at least 2, 3, 4, or 5 targets on the cell, tissue, or infectious agent of interest. According to some embodiments, at least 1, 2, 3, 4, 5 or more of the targets of the multivalent and monovalent multispecific composition are located on a cell surface. In additional embodiments, 1, 2, 3, 4, 5 or more targets bound by the multivalent and monovalent multispecific composition are a tumor antigen (e.g., tumor antigens and tumor/cancer associated antigens). In additional embodiments, 1, 2, 3, 4, 5 or more targets bound by the multivalent and monovalent multispecific composition are associated with a disease or disorder of the immune system. In additional embodiments, 1, 2, 3, 4, 5 or more targets bound by the multivalent and monovalent multispecific composition are associated with a disease or disorder of the skeletal system (e.g., osteoporosis), cardiovascular system, nervous system, or an infectious disease.

In specific embodiments, the multivalent and monovalent multispecific composition binds CD2. According to one embodiment, the multivalent and monovalent multispecific composition (e.g., an MRD-containing antibody) binds human CD2. In a particular embodiment, the multivalent and monovalent multispecific composition binds human CD2 protein having the sequence of amino acids 25-209 set forth in NCBI Ref. Seq. No. NP_001758. In some embodiments, the multivalent and monovalent multispecific composition has multiple binding sites for CD2. In some embodiments the single binding site is an MRD. In other embodiments, the single binding site is an antibody antigen binding domain. In other embodiments, the multivalent and monovalent multispecific composition has a single binding site for CD2. In further embodiments, binding of the multivalent and monovalent multispecific composition to CD2 does not elicit a signal by the cell on which CD2 is expressed. In additional embodiments, the multivalent and monovalent multispecific composition binds CD2 and 1, 2, 3, 4, 5 or more different targets (e.g., a tumor antigen as disclosed herein or otherwise known in the art). In particular embodiments, the CD2 binding compositions of the invention are not single chain antibodies.

In some embodiments, the multivalent and monovalent multispecific composition (e.g., an MRD-containing antibody) binds human CD2 and a CD2 ortholog from another organism. In additional embodiments, the multivalent and monovalent multispecific composition binds human CD2 and a CD2 ortholog from another primate. In further embodiments, the multivalent and monovalent multispecific composition binds human CD2 and a CD2 ortholog from cynomolgus monkey or rhesus monkey.

In some embodiments, the multivalent and monovalent multispecific composition (e.g., an MRD-containing antibody) binds a target on a myeloid cell. In some embodiments, the multivalent and monovalent multispecific composition (e.g., an MRD-containing antibody) binds (1) a target on a cell, tissue, or infectious agent of interest (e.g., a tumor antigen on a tumor cell) and (2) a target on an immune accessory cell (e.g., myeloid cell) so as to juxtapose myeloid cells with the cell, tissue, or infectious agent of interest. In some embodiments, the multivalent and monovalent multispecific composition has multiple binding sites for (i.e., multivalently binds) a target on a myeloid cell. In other embodiments, the multivalent and monovalent multispecific composition has a single binding site for (i.e., monovalently binds) a target on an accessory cell (e.g., myeloid cell). In some embodiments the single binding site is an MRD. In other embodiments, the single binding site is an antibody antigen binding domain. In further embodiments, binding of the multivalent and monovalent multispecific composition does not elicit a signal when the composition binds a target on a myeloid cell. In some embodiments, the multivalent and monovalent multispecific composition binds an Fc gamma receptor selected from CD16 (i.e., Fc gamma RIII), CD64 (i.e., Fc gamma RI), and CD32 (i.e., Fc gamma RII). In particular embodiments, the multivalent and monovalent multispecific composition binds CD64 (i.e., Fc gamma RI). In some embodiments, the multivalent and monovalent multispecific composition binds a target selected from, MHC class 2 and its invariant chain, TLR1, TLR2, TLR4, TLR5 and TLR6. In additional embodiments, the multivalent and monovalent multispecific composition binds at least 2, 3, 4, or 5 targets on the cell, tissue, or infectious agent of interest. According to some embodiments, at least 1, 2, 3, 4, 5 or more of the targets of the multivalent and monovalent multispecific composition are located on a cell surface. In additional embodiments, 1, 2, 3, 4, 5 or more targets bound by the multivalent and monovalent multispecific composition are a tumor antigen (e.g., tumor antigens and tumor/cancer associated antigens). In additional embodiments, 1, 2, 3, 4, 5 or more targets bound by the multivalent and monovalent multispecific composition are associated with a disease or disorder of the immune system. In additional embodiments, 1, 2, 3, 4, 5 or more targets bound by the multivalent and monovalent multispecific composition are associated with a disease or disorder of the skeletal system (e.g., osteoporosis), cardiovascular system, nervous system, or an infectious disease.

In some embodiments, the multivalent and monovalent multispecific composition (e.g., an MRD-containing antibody) binds a target of interest on a cancer cell. In additional embodiments, the multivalent and monovalent multispecific composition binds a target of interest on an immune cell. In further embodiments, the multivalent and monovalent multispecific composition binds a target of interest on a diseased cell. In other embodiments, the multivalent and monovalent multispecific composition (e.g., an MRD-containing antibody) binds a target of interest on an infectious agent (e.g., a bacterial cell or a virus).

In further embodiments, the invention encompasses a method of treating a disease or disorder by administering to a patient in need thereof, a therapeutically effective amount of a multivalent and monovalent multispecific composition of the invention. Particular embodiments are directed to a method of treating a disease or disorder by administering to a patient in need thereof, a therapeutically effective amount a multivalent and monovalent multispecific composition (e.g., an MRD-containing antibody) that has a single binding site for a target (i.e., that monovalently binds a target). In some embodiments, the administered multivalent and monovalent multispecific composition has a single binding site for a target on a leukocyte, such as a T-cell (e.g., CD3). In additional embodiments, the administered multivalent and monovalent multispecific composition has a single binding site for a target on a leukocyte, such as a T-cell (e.g., CD3) and multiple binding sites for (i.e., is capable of multivalently binding) a target located on a cell or tissue of interest (e.g., a tumor antigen on a tumor cell).

In further embodiments, the invention is directed to treating a disease or disorder by administering to a patient a therapeutically effective amount of a multivalent and monovalent multispecific composition (e.g., an MRD-containing antibody) that has a single binding site for a target (i.e., that monovalently binds a target) and multiple binding sites for 1, 2, 3, 4, 5 or more different targets.

In additional embodiments, the invention is directed to treating a disease or disorder by administering to a patient in need thereof, a therapeutically effective amount of a multivalent and monovalent multispecific composition (e.g., an MRD-containing antibody) that has a single binding site for CD3 (e.g., CD3 epsilon) that monovalently binds CD3 and multiple binding sites for 1, 2, 3, 4, 5 or more different targets.

According to some embodiments, the tumor cell is from a cancer selected from breast cancer, colorectal cancer, endometrial cancer, kidney (renal cell) cancer, lung cancer, melanoma, Non-Hodgkin Lymphoma, leukemia, prostate cancer, bladder cancer, pancreatic cancer, and thyroid cancer.

In some embodiments, the MRD(s) and the antibody in the MRD-containing antibody are antagonists of their respective targets. In other embodiments, the MRD(s) and the antibody in the MRD-containing antibody are agonists of their respective target. In yet other embodiments, at least one of the MRDs in the MRD-containing antibody is an antagonist of its target molecule and the antibody is an agonist of its target molecule. In yet another embodiment, at least one of the MRDs in the MRD-containing antibody is an agonist of its target molecule, and the antibody is an antagonist of its target molecule.

In some embodiments, both the MRD(s) and the antibody in the MRD-containing antibody bind to soluble factors. In some embodiments, both the MRD(s) and the antibody in the MRD-containing antibody bind to cell surface molecules. In some embodiments, at least one MRD in the MRD-containing antibody binds to a cell surface molecule and the antibody in the MRD-containing antibody binds to a soluble factor. In some embodiments, at least one MRD in the MRD-containing antibody binds to a soluble factor and the antibody in the MRD-containing antibody binds to a cell surface molecule.

An improved multivalent and monovalent multispecific composition (e.g., MRD-containing antibody) that specifically binds a desired target or targets can also be prepared based on a previously known MRD or multivalent and monovalent multispecific composition (e.g., MRD-containing antibody). For example, 1, 2, 3, 4, 5, 6, 7, 8, 9, 10, 10-20, 20-30, 30-50, 50-100, 100-150 or more than 150 amino acid substitutions, deletions or insertions can be introduced into an MRD or multivalent and monovalent multispecific composition (e.g., MRD-containing antibody) sequence and the resulting MRD or multivalent and monovalent multispecific composition (e.g., MRD-containing antibody) can be screened for binding to the desired target or targets, for antagonizing target activity, or for agonizing target activity as described in the examples or using techniques known in the art.

Additional peptide sequences may be added, for example, to enhance the in vivo stability of the MRD or affinity of the MRD for its target.

In certain embodiments, the binding of a multivalent and monovalent multispecific composition (e.g., MRD-containing antibody) to its target (e.g., a cell) is enhanced compared to the binding of the MRD alone, the antibody alone, and/or a combination of the MRD and antibody. In some embodiments, the binding is at least about 2-fold, at least about 5-fold, at least about 10-fold, at least about 20-fold, at least about 50-fold, at least about 75-fold, at least about 100-fold, at least about 500-fold, or at least about 1000-fold improved.

In addition, in some embodiments, the binding of a multivalent and monovalent multispecific composition (e.g., MRD-containing antibody) to a target (e.g., a cell or a molecule containing multiple epitopes) expressing both the MRD target and the antibody target is enhanced compared to the binding of the multivalent and monovalent multispecific composition (e.g., MRD-containing antibody) to a target (e.g., a cell or a molecule containing multiple epitopes) expressing only the MRD target or only the antibody target. In some embodiments, the binding is at least about 2-fold, at least about 5-fold, at least about 10-fold, at least about 20-fold, at least about 50-fold, at least about 75-fold, at least about 100-fold, at least about 500-fold, or at least about 1000-fold improved. This increased avidity can enable multivalent and multispecific compositions (e.g., MRD-containing antibodies) to bind to targets that have previously been difficult to target, e.g., G-protein coupled receptors and carbohydrate molecules.

In addition, in some embodiments, the binding of a multivalent and monovalent multispecific composition (e.g., MRD-containing antibody) to an MRD target is enhanced in a region (e.g., of the body) where the antibody target is localized compared to a region where the antibody target is not expressed or is expressed at a lower level. In some embodiments, the binding of a multivalent and monovalent multispecific composition (e.g., MRD-containing antibody) to an antibody target is enhanced in a region (e.g., of the body) where the MRD target is localized compared to a region where the MRD target is not expressed or is expressed at a lower level. In some embodiments, the binding is at least about 2-fold, at least about 5-fold, at least about 10-fold, at least about 20-fold, at least about 50-fold, at least about 75-fold, at least about 100-fold, at least about 500-fold, or at least about 1000-fold improved.

In preferred embodiments, the multivalent and monovalent multispecific composition (e.g., MRD-containing antibody) retains particular activities of the parent antibody. Thus, in certain embodiments, the multivalent and monovalent multispecific composition (e.g., MRD-containing antibody) is capable of inducing complement dependent cytotoxicity. In certain embodiments, the multivalent and monovalent multispecific composition (e.g., MRD-containing antibody) is capable of inducing antibody dependent cell mediated cytotoxicity (ADCC). In additional embodiments, the multivalent and monovalent multispecific composition (e.g., MRD-containing antibody) is capable of inducing apoptosis. In additional embodiments, the multivalent and monovalent multispecific composition (e.g., MRD-containing antibody) is capable of reducing tumor volume. In additional embodiments, the multivalent and multispecific compositions (e.g., MRD-containing antibodies) are capable of inhibiting tumor growth.

In some embodiments, the multivalent and monovalent multispecific composition (e.g., MRD-containing antibody) shows improved activity or pharmacodynamic properties compared to the corresponding antibody without the attached MRD. Thus, in certain embodiments, the multivalent and monovalent multispecific composition (e.g., MRD-containing antibody) has greater avidity than the corresponding antibody without the attached MRD. In other embodiments, the multivalent and monovalent multispecific composition (e.g., MRD-containing antibody) results in increased receptor aggregation compared to the corresponding antibody without the attached MRD. In another embodiment, the multivalent and monovalent multispecific composition (e.g., MRD-containing antibody) antagonizes target activity to a greater extent than the corresponding antibody without the attached MRD. In another embodiment, the multivalent and monovalent multispecific composition (e.g., MRD-containing antibody) agonizes target activity to a greater extent than the corresponding antibody without the attached MRD. In another embodiment, the multivalent and monovalent multispecific composition (e.g., MRD-containing antibody) has an improved pharmacodymamic profile than the corresponding antibody without the attached MRD.

In another embodiment, the MRD-containing antibody has a greater therapeutic efficacy than the corresponding antibody without the attached MRD.

In other embodiments, the multivalent and multispecific compositions (e.g., MRD-containing antibodies) have one or more of the following effects: inhibit proliferation of tumor cells, reduce the tumorigenicity of a tumor, inhibit tumor growth, increase patient survival, trigger cell death of tumor cells, differentiate tumorigenic cells to a non-tumorigenic state, or prevent metastasis of tumor cells.

In certain embodiments, the multivalent and monovalent multispecific composition (e.g., MRD-containing antibody) is at least as stable as the corresponding antibody without the attached MRD. In certain embodiments, the multivalent and monovalent multispecific composition (e.g., MRD-containing antibody) is more stable than the corresponding antibody without the attached MRD. MRD-antibody stability can be measured using methods known to those in the art, including, for example, ELISA techniques. In some embodiments, the multivalent and monovalent multi specific composition (e.g., MRD-containing antibody) is stable in whole blood at 37° C. for at least about 10 hours, at least about 15 hours, at least about 20 hours, at least about 24 hours, at least about 25 hours, at least about 30 hours, at least about 35 hours, at least about 40 hours, at least about 45 hours, at least about 48 hours, at least about 50 hours, at least about 55 hours, at least about 60 hours, at least about 65 hours, at least about 70 hours, at least about 72 hours, at least about 75 hours, at least about 80 hours, at least about 85 hours, at least about 90 hours, at least about 95 hours, or at least about 100 hours.

In certain embodiments, the multivalent and monovalent multispecific composition (e.g., MRD-containing antibody) has at least the same affinity for Fc receptors as the corresponding parent antibody. In other nonexclusive embodiments, the multivalent and monovalent multispecific composition (e.g., MRD-containing antibody) has at least the same affinity for complement receptors as the corresponding parent antibody. In other nonexclusive embodiments, the multivalent and monovalent multispecific composition (e.g., MRD-containing antibody) has at least the same half-life as the corresponding parent antibody. In other embodiments, the multivalent and monovalent multispecific composition (e.g., MRD-containing antibody) can be expressed at levels commensurate with the corresponding parent antibody.

In additional embodiments, the multivalent and monovalent multispecific composition (e.g., MRD-containing antibody) has an increased affinity for Fc receptors compared to the corresponding parent antibody. In other nonexclusive embodiments, the multivalent and monovalent multispecific composition (e.g., MRD-containing antibody) has an increased affinity for complement receptors compared to the corresponding parent antibody. In other nonexclusive embodiments, the multivalent and monovalent multispecific composition (e.g., MRD-containing antibody) has an increased half-life compared to the corresponding parent antibody. In other embodiments, the multivalent and monovalent multispecific composition (e.g., MRD-containing antibody) can be expressed at increased levels compared to that of the corresponding parent antibody.

Immunoconjugates (MRD-Containing Antibody Drug Conjugates)

The use of antibody-drug conjugates for the local delivery of cytotoxic agents, allows targeted delivery of the drug to tumors, and intracellular accumulation therein, where systemic administration of these unconjugated drug agents may result in unacceptable levels of toxicity to normal cells as well as the tumor cells sought to be eliminated (Baldwin et al., Lancet pages 603-05 (1986); Thorpe, "Antibody Carriers Of Cytotoxic Agents In Cancer Therapy: A Review," in Monoclonal Antibodies '84: Biological And Clinical Applications, A. Pinchera et al., (ed.s), pp. 475-506) (1985)).

In additional embodiments, the invention encompasses a multivalent and monovalent multispecific composition (e.g., an MRD-containing antibody) that is covalently or otherwise associated with a cytotoxic agent (payload) (i.e., as multivalent and monovalent multispecific-cytoxic agent complexes (e.g., MRD-containing antibody-cytoxic agent complexes). According to some embodiments, the cytoxic agent is covalently attached to a multivalent and monovalent multispecific composition (e.g., MRD-containing antibody) by a linker. According to some embodiments, the linker attaching the multivalent and monovalent multispecific composition and the cytotoxic agent is cleavable by a protease. In additional embodiments, the cytotoxic agent is a chemotherapeutic agent, growth inhibitory agent, toxin (e.g., an enzymatically active toxin of bacterial, fungal, plant, or animal origin, or fragments thereof), a radioactive isotope (i.e., a radioconjugate) or a prodrug. Methods of using immunoconjugates (MRD-containing Antibody drug conjugates) are also encompassed by the invention.

Cytotoxic agents that may be covalently or otherwise associated with multivalent and multispecific compositions (e.g., an MRD-containing antibody) include, but are not limited to any agent that is detrimental to (e.g., kills) cells. Cytotoxins useful in the compositions and methods of the invention include, inter alia, alkylating agents, intercalating agents, antiproliferative agents, anti-mititotic agents, tubulin binding agents, *vinca* alkaloids, enediynes, trichothecenes, podophyllotoxins or podophyllotoxin derivatives, the pteridine family of drugs, taxanes, anthracyclines (e.g., daunorubicin (formerly daunomycin) and doxorubicin), antibiotics (e.g., dactinomycin (formerly actinomycin, dolastatins (e.g., dolastatin 10, dolastatin 11, and dolastatin 15)), topoisomerase inhibitors, and platinum complex chemotherapeutic agents (e.g., cis-platinum).

In some embodiments, compositions of the invention include a cytoxic agent that is a tubulin depolymerizing agent. Thus, in some embodiments, compositions of the invention include an auristatin or an auristatin derivative or analog. In one embodiment, compositions of the invention contain monomethyl auristatin E (MMAE). In another embodiment, compositions of the invention contain monomethyl auristatin F (MMAF). In additional embodiments, an immunoconjugate composition of the invention contains dolastatin or a dolastatin peptidic analog or derivative, e.g., an auristatin (see, e.g., U.S. Pat. Nos. 5,635,483, 5,780,588, and 5,663,149).

In additional embodiments, compositions of the invention include a maytansinoid molecule. Maytansinoids are mitotic inhibitors which act by inhibiting tubulin polymerization. Methods of making maytansinoids and their therapeutic use are disclosed, for example, in U.S. Pat. Nos. 5,208, 020; 5,416,064, 6,441,163 and European Pat. EP 0 425 235 B1; each of which is herein incorporated by reference in its entirety.

Thus, in some embodiments, the cytotoxin is a maytansinoid or a maytansinoid derivative or analog. Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines. Maytansine compounds suitable for use as maytansinoid drug moieties are well known in the art, and can be isolated from natural sources according to known methods, produced using genetic engineering techniques (see Yu et al PNAS 99:7968-7973 (2002)), or maytansinol and maytansinol analogues can be prepared synthetically according to known methods.

In particular embodiments compositions of the invention include the maytansinoid DM1 (N(2')-deacetyl-N(2')-(3-mercapto-1-oxopropyl)-maytansine). In other particular embodiments compositions of the invention include the maytansinoid DM2. In additional embodiments, compositions of the invention include the maytansinoid DM3 (N(2')-deacetyl-N2-(4-mercapto-1-oxopentyl)-maytansine) or DM4 (N(2')-deacetyl-N2-(4-mercapto-4-methyl-1-oxopentyl)-maytansine).

In some embodiments, compositions of the invention include a cytoxic agent that is an alkylating agent. In particular embodiments, the cytotoxic agent is selected from mechlorethamine, thiotepa, thioepa chlorambucil, melphalan, carmustine SNU), BCNU lomustine (CCNU), cyclothosphamide, busulfan, dibromomannitol, and streptozoicin.

In other embodiments, compositions of the invention include a cytoxic agent that is an antimetabolite. In particular embodiments, the cytotoxic agent is selected from methotrexate, dichloromethotrexate, 6-mercaptopurine, 6-thioguanine, cytarabine, 5-fluorouracil and 5-fluorouracil decarbazine.

In additional embodiments, the multivalent and mulitspecific composition-drug conjugate (e.g., MRD-containing antibody-drug conjugate) is capable of producing double-stranded DNA breaks. In further embodiments, the MRD-containing antibody-drug conjugate contains a member of the calicheamicin family of antibiotics capable of producing double-stranded DNA breaks at sub-picomolar concentrations. In further embodiments, a multivalent and mulitspecific composition-drug conjugate (e.g., MRD-containing antibody-drug conjugate) contains calicheamycin. For the preparation of conjugates of the calicheamicin family, see e.g., U.S. Pat. Nos. 5,712,374, 5,714,586, 5,739,116, 5,767, 285, 5,770,701, 5,770,710, 5,773,001, and 5,877,296 (all to American Cyanamid Company). Structural analogues of calicheamicin which can be contained in the multivalent and mulitspecific composition-drug conjugate (e.g., MRD-containing antibody-drug conjugate) of the invention include, but are not limited to, gamma$_1^1$, alpha$_2^1$, alpha$_3^1$, N-acetylamma$_1^1$, PSAG and theta$_1^1$ (Hinman et al., Cancer Research 53:3336-3342 (1993), and Lode et al., Cancer Research 58:2925-2928 (1998).

In other embodiments, multivalent and mulitspecific composition-drug conjugate (e.g., MRD-containing antibody-drug conjugate) compositions of the invention include a cytoxic agent selected from adriamicin, doxorubicin, mitomycin C, busulfan, cytoxin, chlorambucil, etoposide, etoposide phosphate, CC-1065, duocarmycin, KW-2189, CC1065, taxotere (docetaxel), methopterin, aminopterin, topotecan, camptothecin, porfiromycin, bleomycin, teniposide, esperamicins, mithramycin, anthramycin (AMC), fludarabine, tamoxifen, taxotere (docetaxel), cytosine arabinoside (Ara-C), adenosine arabinoside, cisplatin, carboplatin, cis-dichlorodiamine platinum (II) (DDP) cisplatin, chloroquine, cyclosporin A, docetaxel, paclitaxel, taxol, vinorelbine, vindesine, cytochalasin B, gramicidin D, ethidium bromide, emetine, mitomycin, ifosfamide, cyclophosphamide, tenoposide, carminomycin, porfiromycin, dihydroxy anthracin dione, mitoxantrone, mithramycin, dactinomycin, actinomycin D, puromycin 1-dehydrotestosterone, adriamycin, glucocorticoids, procaine, tetracaine, lidocaine, propranolol, epithiolone, QFA, combretastatin, combretastatin A4 phosphate, vinblastine, vincristine, colchicine, geldanamycin, doxorubicinchlorambucil, Auristatin F phenylene diamine (AFP)), monomethylauristatin, the family of agents known collectively LL-E33288 complex described in U.S. Pat. Nos. 5,053,394, 5,770,710, as well as esperamicins (U.S. Pat. No. 5,877,296) or a derivative or analog thereof and derivatives and analog thereof.

Additional suitable toxins and chemotherapeutic agents are described in Remington's Pharmaceutical Sciences, 19th Ed. (Mack Publishing Co. 1995), and in Goodman and Gilman's The Pharmacological Basis of Therapeutics, 7th Ed. (MacMillan Publishing Co. 1985). Moreover, for further discussion of types of cytotoxins, linkers and other methods that can be use or routinely adapted to conjugate therapeutic agents to the MRD-comprising antibody complex, see e.g., Intl. Appl. Publ. WO2007/059404; Saito et al., Adv. Drug Deliv. Rev. 55:199-215 (2003); Trail et al., Cancer Immunol Immunother. 52:328-337 (2003); Payne, Cancer Cell 3:207-212 (2003); Allen, Nat. Rev. Cancer 2:750-763(2002); Pastan et al., Curr. Opin. Investig. Drugs 3:1089-1091 (2002); and Senter et al., Adv. Drug Deliv. Rev. 53:247-264 (2001), each of which is hereby incorporated by reference in its entirety.

Cytotoxin chemotherapeutic agents that can be used in the immunoconjugates of the invention (e.g., multivalent and mulitspecific composition-drug conjugates such as MRD-containing antibody-drug conjugates) include poisonous lectins and plant or other toxins (e.g., ricin, abrin, modeccin, botulina, and diphtheria toxins). It is envisioned that multiple copies of a toxin or combinations of various toxins can optionally be coupled to a multispecific and multivalent composition of the invention (e.g., an MRD-containing antibody) thereby providing additional cytotoxicity. Enzymatically active toxins and fragments thereof that can be used in compositions of the invention include, but are not limited to diphtheria A chain, nonbinding active fragments of diphtheria toxin, exotoxin A chain (from *Pseudomonas aeruginosa*), *Pseudomonas* exotoxin, *Pseudomonas* endotoxin, ricin A chain, abrin A chain, modeccin A chain, alpha-sarcin, *Aleurites fordii* proteins, ribonuclease, DNase I, Staphylococcal enterotoxin-A, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, for example, Pastan et al., Cell 47:641 (1986), Goldenberg et al., Cancer Journal for Clinicians 44:43 (1994) and Intl Appl. Publ. Nos. WO93/21232 and WO93/21232, each of which is herein incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., J. Am. Chem. Soc. 111:5463-5465 (1989); Pettit et al., Anti-Cancer Drug Design 13:243-277 (1998); Pettit et al., Synthesis 719-725 (1996); Pettit et al., J. Chem. Soc. Perkin Trans. 15:859-863 (1996); and Doronina et al., Nat. Biotechnol 21(7):778-784 (2003).

According to some embodiments, the compositions of the invention comprise a highly radioactive atom. A variety of radioactive isotopes are available for the production of radioconjugated multivalent and multispecific compositions (e.g., MRD-containing antibodies). Examples include $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu. When the conjugate is used for detection, it may comprise a radioactive atom for scintiographic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels can be incorporated in the conjugate using techniques known in the art. For example, the peptide can be biosynthesized or can be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODO-GEN method (Fraker et al Biochem. Biophys. Res. Commun. 80: 49-57 (1978)) can be used to incorporate iodine-123. "Monoclonal Antibodies in Immunoscintigraphy" (Chatal, CRC Press 1989) describes in detail other methods that can be routinely applied to label the compositions of the invention.

A linker can be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-131 (1992); U.S. Pat. No. 5,208,020, U.S. Pat. Appl. Publ. No. 20110293513) can be used. Thus, the invention encompasses multivalent and multispecific compositions containing one or more linkers that can contain any of a variety of groups as part of its chain that will cleave in vivo, e.g., in a cell, at a rate which is enhanced relative to that of constructs that lack such groups. Also provided are conjugates of the linker arms with therapeutic and diagnostic agents. The linkers are useful to form prodrug analogs of therapeutic agents and to reversibly link a therapeutic or diagnostic agent (e.g., a cytotoxin or MRD) to a targeting agent, a detectable label, or a solid support. The linkers can be stable in plasma so as not to release an MRD or cytotoxic agent. In the case of cytotoxins the linkers can be stable in plasma and labile once internalized so as to release the cytotoxin in an active form.

MRDs and/or cytotoxic agents are optionally attached to one another or to the multivalent and monovalent multispecific composition (e.g., MRD-containing antibody) of the invention with a linker as described herein or otherwise known in the art. Conjugates of the MRD-containing antibody with an MRD or a cytotoxic agent can be made using a variety of bifunctional protein coupling agents known in the art, including, but not limited to, coupling agents containing a group selected from: 6-maleimidocaproyl (MC), maleimidocaproyl-polyethylene glycol ("MC(PEG)6-OH" (amenable to attachment to antibody cysteines)), maleimidopropanoyl (MP), MPBH, valine-citrulline (val-cit (exemplary dipeptide in a protease cleavable linker)), methyl-valine-citrulline ("Me-Val-CitN," a linker in which a peptide bond has been modified to prevent its cleavage by cathepsin B) alanine-phenylalanine (ala-phe), p-aminobenzyloxycarbonyl (PAB (an example of a "self immolative" linker component)), valine-citrullin-p-aminobenzyloxycaronyl ("vc-PAB"), N-Succinimidyl 4-(2-pyridylthio) pentanoate (SPP), N-succinimidyl 4-(N-maleimidomethyl) cyclohexane-1 carboxylate (SMCC), LC-SMCC, N-Succinimidyl (4-iodo-acetyl) aminobenzoate (SIAB), IT (iminothiolane), SPDP (N-succinimidyl-3-(2-pyridyldithio) propionate), 6-maleimidocaproyl-valine-citrulline-p-aminobenzyloxy-carbonyl (MC-vc-PAB), ethyleneoxy-$CH_2CH_2O$— as one or more repeating units ("EO" or "PEO"), BMPS, EMCS, GMBS, HBVS, MBS, SBAP, SIA, SMPB, SMPH, sulfo-EMCS, sulfo-GMBS, sulfo-KMUS, sulfo-MBS, sulfo-SMCC, sulfo-SIAB, sulfo-SMPB, SVSB (succinimidyl-(4-vinylsulfone) benzoate), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Additional linker components are known in the art and some are described herein.

In some embodiments, the multivalent and monovalent multispecific composition is covalently attached to a cytotoxic agent via a linker at 1-5, 5-10, 1-10, or 1-20 sites on the multivalent and multispecific composition. According to additional embodiments, the multivalent and monovalent multispecific composition is covalently attached to a cytotoxic agent via a linker at more than 2, 5 or 10 sites on the multivalent and multispecific composition.

In additional embodiments, the multivalent and monovalent multispecific composition (e.g., MRD containing antibody) complex is associated with a prodrug. Prodrug synthesis, chemical linkage to antibodies, and pharmacodynamic properties are known in the art and can routinely be applied to make and use multivalent and multivalent compositions of the invention that contain prodrugs, such as, MRD-containing antibody-prodrug compositions. See, e.g., Intl. Publ. No. WO96/05863 and in U.S. Pat. No. 5,962,216, each of which is herein incorporated by reference in its entirety.

Alternatively, a fusion protein comprising an antibody and a cytotoxic agent can be made, e.g., by recombinant techniques or peptide synthesis. A recombinant DNA molecule can comprise regions encoding the antibody and cytotoxic portions of the conjugate either adjacent to one another or separated by a region encoding a linker peptide which does not destroy the desired properties of the conjugate.

The multivalent and monovalent multispecific composition (e.g., MRD-containing antibody) composition of the invention also can be conjugated to a radioactive isotope to generate cytotoxic radiopharmaceuticals, also referred to as radioimmunoconjugates. Examples of radioactive isotopes that can be conjugated to multivalent and monovalent multispecific compositions (e.g., MRD containing antibodies) for use diagnostically or therapeutically include, but are not limited to, iodine$^{131}$, indium$^{111}$, yttrium$^{90}$, and lutetium$^{177}$. Methods for preparing radioimmunconjugates are established in the art. Examples of radioimmunoconjugates are commercially available, including Zevalin™. (IDEC Pharmaceuticals) and Bexxar™ (Corixa Pharmaceuticals), and similar methods can be used to prepare radioimmunoconjugates using the MRD-containing antibodies of the invention.

Methods for the conjugation of linker-drug moieties to cell-targeted proteins such as antibodies are known in the art and include those described for example, in U.S. Pat. Nos. 5,208,020 and 6,441,163; Intl. Appl. Publ. Nos. WO2005037992, WO2005081711, and WO2006/034488, each of which is herein incorporated by reference in its entirety. See, also e.g., Arnon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985); Hellstrom et al., "Antibodies For Drug Delivery", in Controlled Drug Delivery (2nd Ed.), Robinson et al., (eds.), pp. 623-53 (Marcel Dekker, Inc. 1987); Saito et al., Adv. Drug Deliv. Rev. 55:199-215 (2003); Trail et al., Cancer Immunol. Immunother. 52:328-337 (2003); Payne, Cancer Cell 3:207-212 (2003); Allen et al., Nat. Rev. Cancer 2:750-763 (2002); Pastan et al., Curr. Opin. Investig. Drugs 3:1089-1091 (2002); and Senter et al., Adv. Drug Deliv. Rev. 53:247-264 (2001), the contents of each of which is herein incorporated by reference in its entirety.

In some embodiments, a multivalent and monovalent multispecific composition of the invention comprising a cytotoxic agent (e.g., an MRD-containing antibody-cytotoxic agent conjugate) and may generally be referred to herein as an immunoconjugate. In some embodiments, an immunoconjugate of the invention binds a cell surface target that is internalized into the cell. In further embodiments, the binding of an immunoconjugate of the invention (e.g., an MRD-containing antibody-cytotoxic agent conjugate) to a cell surface target results in the internalization of the immunoconjugate into the cell in vitro. In further embodiments, the binding of immunoconjugate to a cell surface target results in the internalization of the composition into the cell in vivo. Methods for treating a patient described herein can comprise: administering to the patient a therapeutically effective amount of an immunoconjugate (e.g., a multivalent and monovalent multispecific composition of the invention comprising a cytotoxic agent, such as an MRD-containing antibody-cytotoxic agent conjugate) that comprises a cytotoxic agent and binds a target that is internalized into a cell. In some embodiments, the immunoconjugate comprises a cytotoxic agent disclosed herein. In additional embodiments, the immunoconjugate comprises a cytotoxic agent selected from an alkylating agent, antiproliferative agent, tubulin binding agent, vinca alkaloid, enediyne, podophyllotoxin, podophyllotoxin derivative, a member of the pteridine family of drugs, taxane, a dolastatin, topoiosomerase inhibitor, or a platinum complex chemotherapeutic agent. In further embodiments, the cytoxic agent is a maytansinoid or a maytansinoid derivative or analog. In specific embodiments the cytoxic agent is the maytansinoid DM1, DM2, or DM3. In additional embodiments, the cytotoxic agent is auristatin or an auristatin derivative or analog. In specific embodiments the cytoxic agent is MMAE or MMAF. The cytotoxic agents are optionally attached to the other components of the immunoconjugate by a linker. In some embodiments the cytotoxic agent is attached to the other components of the immunoconjugate by an enzyme cleavable linker. In additional embodiments, the cytotoxic agent is attached to the other components of the immunoconjugate by an acid-labile linker.

In further embodiments, the cytoxic agent of an immunoconjugate of the invention has a free drug potency of less than $10^{-7}$M, $10^{-8}$M, or $10^{-9}$M. In additional embodiments, the cytoxin has a free drug potency of $10^{-8}$ to $10^{-11}$ M.

In some embodiments, a target bound by the immunoconjugate is selected from CD19, CD22, CD30, CD33, CD56, CD70, CD79a, CD80, CD83, CD95, CD126, CD133, CD138, PSMA, EphA2, ErbB2 (CD340), SLC44A4, MN (carbonic anhydrase IX), GPNMB (glycoprotein non-metastatic melanoma protein), Cripto, and αV integrin. In additional embodiments, a target bound by the immunoconjugate is selected from CD1, CD1a, CD2, CD3, CD4, CD5, CD8, CD11A, CD14, CD15, CD16, CD18, CD19, CD20, CD25, TNFRSF5 (CD40), CD64, CD74, CD79, CD105, CD174, CD205, CD227, CD326, CD340, MUC16, EGP-1, EGP-2, EGF receptor (ErbB1), ErbB2, ErbB3, Factor H, FHL-1, Flt-3, folate receptor, Ga 733, GROB, HMGB-1, hypoxia inducible factor (HIF), HM1.24, HER-2/neu, insulin-like growth factor (ILGF), IFN-gamma, IFN-alpha, IFN-beta, IL2R, IL4R, IL6R, IL13R, IL15R, IL17R, IL18R, IL2, IL6, IL8, IL12, IL15, IL17, IL18, IL25, IP-10, IGF-1R, Ia, HM1.24, HCG, HLA-DR, ED-B, TMEFF2, EphB2, FAP (fibroblast activation protein), mesothelin, EGFR, TAG-72, GD2 (encoded by the B4GALNT1 gene), and 5T4.

In additional embodiments, a target bound by the immunoconjugate is a myeloid and hematopoietic target selected from CD33, CD64, TNFRSF5 (CD40), CD56, and CD138. In further embodiments, a target bound by the immunoconjugate is a carcinoma target selected from EpCam, GD2, EGFR, CD74, CD227, CD340, MUC16, GD2, GPNMB, PSMA, crypto, TMEFF2, EphB2, 5t4, mesothelin, TAG-72, and MN.

In other embodiments, a target bound by the immunoconjugate is a B cell target selected from CD19/CD21, CD20, CD22, TNFRSF5 (CD40), CD70, CD79a, CD79b, and CD205. In additional embodiments, a target bound by the immunoconjugate is a T cell target selected from CD25, CD30, TNFRSF5 (CD40), CD70, and CD205. In further embodiments, a target bound by an endothelial cell target selected from CD105, the stromal cell target FAP, and the vascular target ED-B.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The following embodiments are further provided for any of the above immunoconjugates. In one embodiment, an immunoconjugate has in vitro or in vivo cell killing activity. In one embodiment, the linker is attached to the antibody through a thiol group on the antibody. In one embodiment, the linker is cleavable by a protease. In one embodiment, the linker comprises a val-cit dipeptide. In one embodiment, the linker comprises a p-aminobenzyl unit. In one embodiment, the p-aminobenzyl unit is disposed between the drug and a protease cleavage site in the linker. In one embodiment, the p-aminobenzyl unit is p-aminobenzyloxycarbonyl (PAB). In one embodiment, the linker comprises 6-maleimidocaproyl. In one embodiment, the 6-maleimidocaproyl is disposed between the antibody and a protease cleavage site in the linker. The above embodiments may occur singly or in any combination with one another.

The MRD-containing antibody of the present invention may also be conjugating to a prodrug-activating enzyme which converts a prodrug (e.g., a peptidyl chemotherapeutic agent, see e.g., WO81/01145) to an active anti-cancer drug. See, for example, WO88/07378 and U.S. Pat. No. 4,975,278 the contents of which are herein incorporated by reference in its entirety. The enzyme component of the immunoconjugate is preferably capable of acting on a prodrug in such a way so as to convert it into its more active, cytotoxic form. See, for example, Pastan et al., Cell, 47:641 (1986), and Goldenberg et al., Cancer Journal for Clinicians, 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO93/21232.

In some embodiments, the multivalent and multispecific compositions of the invention (e.g., MRD-containing antibodies) are conjugated to a radioisotope, such as, $^{90}Y$, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$ using anyone of a number of well-known chelators or direct labeling. In other embodiments, the MRD-containing antibody is coupled to drugs, prodrugs or lymphokines such as, interferon. Compositions of the invention can be labeled with ligand reagents that bind, chelate or otherwise complex a radioisotope metal where the reagent is reactive with the engineered cysteine thiol of the antibody, using techniques known in the art such as, those described in Current Protocols in Immunology, Volumes 1 and 2, Coligen et al, Ed. Wiley-Interscience, New York, N.Y., Pubs. (1991). Chelating ligands which may complex a metal ion and that may have use in the compositions and methods of the invention include DOTA, DOTP, DOTMA, DTPA and TETA (Macrocyclics, Dallas, Tex.). Radionuclides can be targeted via complexation with the antibody-drug conjugates of the invention (Wu et al Nature Biotechnology 23(9): 1137-1146 (2005)). Linker reagents such as, DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al., Proc. Natl. Acad. Sci. USA 97(4):1802-1807 (2000)). DOTA-maleimide reagents react with the free cysteine amino acids of the cysteine engineered antibodies and provide a metal complexing ligand on the antibody (Lewis et al., Bioconj. Chem. 9:72-86 (1998)). Chelating linker labeling reagents such as, DOTA-NHS (1,4,7,10-tetraazacyclododecane-1,4, 7,10-tetraacetic acid mono (N-hydroxysuccinimide ester) are commercially available (Macrocyclics, Dallas, Tex.).

Conjugates of the multivalent and multispecific compositions of the invention (e.g., MRD-containing antibodies) and cytotoxin can routinely be made using a variety of bifunctional protein-coupling agents such as, N-succinimidyl-3-(2-pyridyidithiol) propionate (SPDP), iminothiolane (IT), bifunctional derivatives of imidoesters (such as, dimethyl adipimidate HCL), active esters (such as, disuccinimidyl suberate), aldehydes (such as, glutareldehyde), bis-azido compounds (such as, bis(p-azidobenzoyl) hexanediamine), bis-diazonium derivatives (such as, bis-(p-diazoniumbenzoyl)-ethylenediamine), diisocyanates (such as, tolyene 2,6-diisocyanate), and bis-active fluorine compounds (such as, 1,5-difluoro-2,4-dinitrobenzene). In specific embodiments, the toxin is conjugate to an MRD-containing antibody through an enzyme-cleavable linker system (e.g., such as, that present in SGN-35). Conjugates of an MRD-containing antibody and one or more small molecule toxins, such as, a calicheamicin, maytansinoids, a trichothene, and CC1065, and the derivatives of these toxins that have toxin activity, can also be used.

In some embodiments, the MRD-containing antibody can be complexed, or have MRDs that bind with other immunologically active ligands (e.g., chemokines, cytokines, and antibodies or fragments thereof) wherein the resulting molecule binds to the neoplastic cell or other target as well as the chemokine, cytokine, or an effector cell such as, a T cell. In certain embodiments, these conjugates can be generated as fusion proteins. The enzymes of this invention can be covalently bound to the antibody by techniques well-known in the art such as, the use of the heterobifunctional cross-linking reagents discussed above. Alternatively, fusion proteins comprising at least the antigen-binding region of an antibody of the invention linked to at least a functionally active portion of an enzyme of the invention can be constructed using recombinant DNA techniques known in the art.

In some embodiments, the N-terminus or C-terminus of the antibody to which an MRD is operably linked in the MRD-antibody fusions is truncated. In preferred embodiments, this truncation does not prevent or reduce the ability of the antibody to bind to its target antigen via its antigen binding domain. In other embodiments, the truncation does not prevent or reduce Fc effector function, half-life and/or ADCC activity. In other embodiments, MRDs are attached in the terminal region of the antibody chain. More particularly, in certain embodiments, the MRD is attached within 1, 2, 3, 4, 5, 10, 15, 20, 25, 30, 35, 40, 45, or 50 residues of the C-terminal amino acid of the heavy chain. In other embodiments, the MRD is attached within 1, 2, 3, 4, 5, 10, 15, 20, 25, 30, 35, 40, 45, or 50 residues of the C-terminal amino acid of the light chain. In additional embodiments, the MRD is attached within 1, 2, 3, 4, 5, 10, 15, 20, 25, 30, 35, 40, 45, or 50 residues of the N-terminal amino acid of the heavy chain. In other embodiments, the MRD is attached within 1, 2, 3, 4, 5, 10, 15, 20, 25, 30, 35, 40, 45, or 50 residues of the N-terminal amino acid of the light chain. Thus, for example, a MRD that is linked to the N-terminal end of the heavy chain can be linked to the first, second, third, fourth, fifth, or tenth amino acid of the N-terminal chain of the heavy chain. For example, an MRD-antibody fusion containing an MRD linked to the N-terminal of the heavy chain may contain amino acids 1-3 of the heavy chain sequence linked to the MRD, which is linked to amino acid 4 of the heavy chain sequence.

In certain embodiments, one or more MRDs are attached to an antibody at locations other than the termini of the antibody light and heavy chains. The MRD can be attached to any portion of the antibody that does not prevent the ability of the antibody to bind its target. Thus, in some embodiments, the MRD is located outside the antibody combining site. For example, the MRD can be located within a heavy chain sequence or within a light chain sequence. By way of example only, the MRD can be located between the Fc domain and the hinge region, between the hinge region and the CH1 domain of the heavy chain, between the CH1 domain and the variable region of the heavy chain, or between the constant region and the variable region of the light chain.

Angiogenesis inhibitors targeting the vascular endothelial growth factor (VEGF) signaling pathways have been observed to provide at best transitory therapeutic benefits followed by restoration of tumor growth and progression due to an apparent ability of angiogenic tumors to adapt to the presence of these inhibitors. Without being bound by theory, it is believed that the multivalent and multispecific properties of multivalent and multispecific compositions (e.g., MRD-containing antibodies) that bind an angiogenesis target provide these compounds with an ability to extend anti-angiogenic therapeutic benefits beyond those observed from for example, conventional monoclonal antibody therapies by binding multiple distinct angiogenesis related targets and thereby disrupting resistance mechanisms available to the angiogenic tumor.

In one embodiment, an MRD-containing antibody binds 2 or more targets selected from: VEGF (i.e., VEGFA), VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TIE2, TNFSF2 (TNFa), FGFR3, EFNa1, EFNa2, ANG1, ANG2, IL6, IL8, IL18, HGF, PDGFA, PLGF, PDGFB, CXCL12, KIT, GCSF, CXCR4, PTPRC, TIE2, VEGFR1, VEGFR2, VEGFR3, Notch 1, DLL4, EGFL7, α2β1 integrin, α4β1 integrin, α5β1 integrin, αvβ3 integrin, TGFb, MMP2, MMP7, MMP9, MMP12, PLAU, VCAM1, PDGFRA, and PDGFRB. Multivalent and multispecific compositions (e.g., MRD-containing antibodies) that bind VEGF and 2, 3, 4, 5 or more of these targets are also encompassed by the invention. In specific embodiments, the antibody component of the MRD-containing antibody binds VEGF. In further embodiments, the antibody component of the MRD-containing antibody is bevacizumab. Multivalent and multispecific compositions (e.g., MRD-containing antibodies) that bind VEGF and 2, 3, 4, 5 or more of these targets are also encompassed by the invention. In specific embodiments, the antibody component of the MRD-containing antibody binds VEGF. In further embodiments, the antibody component of the MRD-containing antibody is bevacizumab.

In one embodiment, an MRD-containing antibody binds VEGF (i.e., VEGFA) and additionally binds an angiogenic target selected from: VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TNFSF2 (TNFa), FGFR3, EFNa1, EFNa2, ANG1, ANG2, IL-6, IL-8, IL-18, HGF, TIE2, PDGFA, P1GF, PDGFB, CXCL12, KIT, GCSF, CXCR4, PTPRC, TIE2, VEGFR1, VEGFR2, VEGFR3, Notch 1, DLL4, EGFL7, α2β1 integrin, α4β1 integrin, α5β1 integrin, αvβ3 integrin, TGFb, MMP2, MMP7, MMP9, MMP12, PLAU, VCAM1, PDGFRA, and PDGFRB. Multivalent and multispecific compositions (e.g., MRD-containing antibodies) that bind VEGF and 2, 3, 4, 5 or more of these targets are also encompassed by the invention. In specific embodiments, the antibody component of the MRD-containing antibody binds VEGF. In further embodiments, the antibody component of the MRD-containing antibody is bevacizumab. In additional embodiments, the antibody component of the MRD-containing antibody competes for VEGF binding with bevacizumab.

In one embodiment, an MRD-containing antibody binds TNF alpha and additionally binds a target selected from: Te38, IL-12, IL-12p40, IL-13, IL-15, IL-17, IL-18, IL-1beta, IL-23, MIF, PEG2, PGE4, VEGF, TNF SF11 (RANKL), TNF (BLYS), GP130, CD-22, and CTLA-4. In another embodiment, an MRD-containing antibody binds TNF alpha, IL6, and TNFSF13B (BLYS). Multivalent and multispecific compositions (e.g., MRD-containing antibodies) that bind TNF and 2, 3, 4, 5 or more of these targets are also encompassed by the invention. In specific embodiments, the antibody component of the MRD-containing antibody binds TNF. In further embodiments, the antibody component of the MRD-containing antibody is adalimumab, certolizumab, golimumab or AME-527. In additional embodiments, the antibody component of the MRD-containing antibody competes for TNF binding with adalimumab, certolizumab, golimumab or AME-527.

In one embodiment, an MRD-containing antibody binds IL1 alpha and IL1 beta. In another embodiment, an MRD-containing antibody binds IL1 beta and TNFSF11 (RANKL). In an additional embodiment, an MRD-containing antibody binds IL1 beta and a target selected from IL13, IL17A, TNF, VEGF, PGE2, VEGFR1, VEGFR2, TNFSF12 (TWEAK) and TNF. Multivalent and multispecific compositions (e.g., MRD-containing antibodies) that bind IL1 beta and at least 1, 2, 3, 4, 5 or more of these targets are also encompassed by the invention. In specific embodiments, the antibody component of the MRD-containing antibody binds IL1 beta. In further embodiments, the antibody component of the MRD-containing antibody is catumaxomab, Xoma052, canakinumab or ACZ885. In additional embodiments, the antibody component of the MRD-containing antibody competes for IL1 alpha or IL1 beta binding with catumaxomab, Xoma052, canakinumab or ACZ885.

In another embodiment, an MRD-containing antibody binds IL12. In a further embodiment, an MRD-containing antibody binds IL12 and additionally binds IL18 or TNFSF12 (TWEAK). Multivalent and multispecific compositions (e.g., MRD-containing antibodies) that bind CTLA-4 and at least 1, 2, 3, 4, 5 or more of these targets are also encompassed by the invention. In specific embodiments, the antibody component of the MRD-containing antibody binds CTLA-4. In further embodiments, the antibody component of the MRD-containing antibody is briakinumab or ustekinumab. In additional embodiments, the antibody component of the MRD-containing antibody competes for IL12 binding with briakinumab or ustekinumab.

In another embodiment, an MRD-containing antibody binds CTLA-4. In a further embodiment, an MRD-containing antibody binds CTLA4 and additionally binds PDL-1 or BTNO2. Multivalent and multispecific compositions (e.g., MRD-containing antibodies) that bind CTLA-4 and one or both of these targets are also encompassed by the invention. In specific embodiments, the antibody component of the MRD-containing antibody binds CTLA-4. In further embodiments, the antibody component of the MRD-containing antibody is tremelimumab or iplimumab. In additional embodiments, the antibody component of the MRD-containing antibody competes for CTLA-4 binding with tremelimumab or iplimumab.

In an additional embodiment, an MRD-containing binds IL13. In a further embodiment, an MRD-containing antibody binds IL13 and additionally binds a target selected from: IL1beta, IL4, IL9, IL13, IL25, a LHR agonist, MDC, MIF, PED2, SPRR2a, SPRR2b; TARC, TGF-beta and IL25. In another embodiment, an MRD-containing antibody binds IL13 and a target selected from IL5, ADAMS, a LHR (agonist), IL23p19 and IgE. Multivalent and multispecific compositions (e.g., MRD-containing antibodies) that bind IL13 and at least 1, 2, 3, 4, 5 or more of these targets are also encompassed by the invention. In specific embodiments, the antibody component of the MRD-containing antibody binds IL13. In further embodiments, the antibody component of the MRD-containing antibody is TNX-650, lebrikizumab or CAT354. In additional embodiments, the antibody component of the MRD-containing antibody competes for IL13 binding with TNX-650, lebrikizumab or CAT354.

In a further embodiment, an MRD-containing antibody binds RGM A. In a further embodiment, an MRD-containing antibody binds RGM A and additionally binds a target selected from: RGM B, MAG, NgR, NogoA, OMGp and CSPGs. Multivalent and multispecific compositions (e.g., MRD-containing antibodies) that bind RGM A and at least 1, 2, 3, 4, 5 or more of these targets are also encompassed by the invention. In specific embodiments, the antibody component of the MRD-containing antibody binds RGM A.

In another embodiment, an MRD-containing antibody binds CD38 and additionally binds a target selected from CD20, TNFRSF5 (CD40) ALK1, TNF, VEGF, VEGFA, VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TNFSF2 (TNFa), FGFR3, VEGFR1, VEGFR2 and CD138. Multivalent and multispecific compositions (e.g., MRD-containing antibodies) that bind CD38 and at least 1, 2 or all 3 of these targets are also encompassed by the invention. In specific embodiments, the antibody component of the MRD-containing antibody binds CD38. In further embodiments, the antibody component of the MRD-containing antibody binds MOR202 or daratumumab. In additional embodiments, the antibody component of the MRD-containing antibody competes for CD38 binding with MOR202 or daratumumab.

In some embodiments an MRD-containing antibody binds ErbB1 (EGFR) and additionally binds ErbB3. In specific embodiments, the antibody component of the MRD-containing antibody binds ErbB1. In additional embodiments, the antibody component of the MRD-containing antibody is ERBITUX®. In additional embodiments, the antibody component, MRD component, and/or MRD-containing antibody competes for ErbB1-binding with ERBITUX®. In another embodiment, the antibody component of the MRD-containing antibody is an ErbB1-binding antibody selected from: nimotuzumab, zalutumumab, matuzumab, panitumumab, MEDX-214, and ABX-EGF. In additional embodiments, the antibody component, MRD component, and/or MRD-containing antibody competes for ErbB1-binding with an antibody selected from: nimotuzumab, zalutumumab, matuzumab, panitumumab, MEDX-214, and ABX-EGF.

In one embodiment, an MRD-containing antibody binds ErbB2 and IGF1R. In another embodiment, an MRD-containing antibody binds ErbB2, Ang2, and IGF1R. In specific embodiments, the antibody component of the MRD-containing antibody binds ErbB2. In additional embodiments, the antibody component of the MRD-containing antibody is HuMax-Her2™ or trastuzumab-DM1. In further embodiments, the antibody component of the MRD-containing antibody is trastuzumab. In additional embodiments, the antibody component, MRD component, and/or MRD-containing antibody competes for ErbB2-binding with trastuzumab.

In one embodiment, an MRD-containing antibody binds ErbB2 and additionally binds a target selected from: ErbB3, EGFR, IGF1R, cMet, VEGF, RON (MST1R), DLL4, PLGF, CDCP1 (CD318), NRP1, TNFRSF10A (DR4) and TNFRSF10B (DR5). In another embodiment, an MRD-containing antibody binds ErbB2 and additionally binds a target selected from: CD2, CD3, CD4 and NKG2D. In an additional embodiment, an MRD-containing antibody binds ErbB2 and IGF1, IGF2 or IGF1,2. Multivalent and multispecific compositions (e.g., MRD-containing antibodies) that bind ErbB2 and additionally bind 1, 2, 3, 4, 5 or more of these targets are also encompassed by the invention. In specific embodiments, the antibody component of the MRD-containing antibody binds ErbB2. In additional embodiments, the antibody component of the MRD-containing antibody is HuMax-Her2™ or trastuzumab-DM1. In further embodiments, the antibody component of the MRD-containing antibody is trastuzumab. In additional embodiments, the antibody component, MRD component, and/or MRD-containing antibody competes for ErbB2-binding with trastuzumab.

In some embodiments an MRD-containing antibody binds ErbB2 and additionally binds ErbB3. In specific embodiments, the antibody component of the MRD-containing antibody binds ErbB2. In additional embodiments, the antibody component of the MRD-containing antibody is HuMax-Her2™ or trastuzumab-DM1. In further embodiments, the antibody component of the MRD-containing antibody is trastuzumab. In additional embodiments, the antibody component, MRD component, and/or MRD-containing antibody competes for ErbB2-binding with trastuzumab. In another embodiment, the antibody component of the MRD-containing antibody is an ErbB2-binding antibody selected from: MDX-210 (Medarex), tgDCC-E1A (Targeted Genetics), MGAH22 (MacroGenics), and pertuzumab (OMNITARG™). In additional embodiments, the antibody component, MRD component, and/or MRD-containing antibody competes for ErbB2-binding with an antibody selected from: MDX-210, tgDCC-E1A, MGAH22, and pertuzumab.

In some embodiments, an MRD-containing antibody binds ErbB2 and HER2/3. In further embodiments, an MRD-containing antibody binds ErbB2 and HER2/3 simultaneously.

Angiogenesis inhibitors targeting the vascular endothelial growth factor (VEGF) signaling pathways have been observed to provide at best transitory therapeutic benefits followed by restoration of tumor growth and progression due to an apparent ability of angiogenic tumors to adapt the presence of these inhibitors. Without being bound by theory, it is believed that the multivalent and multispecific properties of MRD-containing antibodies that bind an angiogenesis target provide these compounds with an ability to extend anti-angiogenic therapeutic benefits beyond those observed from for example, conventional monoclonal antibody therapies by binding multiple distinct angiogenesis related targets and thereby disrupting resistance mechanisms available to the angiogenic tumor.

In another embodiment, an MRD-containing antibody binds PDGFRA and additionally binds an target selected from: VEGFA, VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TNFSF2 (TNFa), FGFR3, EFNa1, EFNa2, ANG1, ANG2, IL6, IL8, IL18, IGF1, IGF2, IGF1,2, HGF, TIE2, PDGFA, PLGF, PDGFB, CXCL12, KIT, GCSF, CXCR4, PTPRC, TIE2, VEGFR1, VEGFR2, VEGFR3, EGFR, cMET, Notch 1, DLL4, EGFL7, α2β1 integrin, α4β1 integrin, α5β1 integrin, αvβ3 integrin, TGFb, MMP2, MMP7, MMP9, MMP12, PLAU, VCAM1, and PDGFRB. Multivalent and multispecific compositions (e.g., MRD-containing antibodies) that bind PDGFRA and binds at least 1, 2, 3, 4, 5 or more of these targets are also encompassed by the invention. In specific embodiments, the antibody component of the MRD-containing antibody binds PDGFRA. In further embodiments, the antibody component of the MRD-containing antibody is olaratumab. In further embodiments, the antibody component, MRD component, and/or MRD-containing antibody competes for PDGFRA binding with olaratumab. In further embodiments, the antibody component of the MRD-containing antibody is MEDI-575. In further embodiments, the antibody component, MRD component, and/or MRD-containing antibody competes for PDGFRA binding with MEDI-575.

In another embodiment, an MRD-containing antibody binds PDGFRB and additionally binds an target selected from: VEGFA, VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TNFSF2 (TNFa), FGFR3, EFNa1, EFNa2, ANG1, ANG2, IL6, IL8, IL18, IGF1, IGF2, IGF1,2, HGF, TIE2, PDGFA, PLGF, PDGFB, CXCL12, KIT, GCSF, CXCR4, PTPRC, TIE2, VEGFR1, VEGFR2, VEGFR3, EGFR, cMET, Notch 1, DLL4, EGFL7, α2β1 integrin, α4β1 integrin, α5β1 integrin, αvβ3 integrin, TGFb, MMP2, MMP7, MMP9, MMP12, PLAU, VCAM1, and PDGFRA. Multivalent and multispecific compositions (e.g., MRD-containing antibodies) that bind PDGFRB and also bind at least 1, 2, 3, 4, 5 or more of these targets are also encompassed by the invention. In specific embodiments, the antibody component of the MRD-containing antibody binds PDGFRB.

In another embodiment, an MRD-containing antibody binds VEGFR1 and additionally binds an angiogenic target selected from: VEGF (i.e., VEGFA), VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TNFSF2 (TNFa), FGFR3, EFNa1, EFNa2, ANG1, ANG2, IL6, IL8, IL18, HGF, PDGFA, PLGF, PDGFB, CXCL12, KIT, GCSF, CXCR4, PTPRC, TIE2, VEGFR2, VEGFR3, Notch 1, DLL4, EGFL7, α2β1 integrin, α4β1 integrin, α5β1 integrin, αvβ3 integrin, TGFb, MMP2, MMP7, MMP9, MMP12, PLAU, VCAM1, PDGFRA, and PDGFRB. Multivalent and multispecific compositions (e.g., MRD-containing antibodies) that bind VEGFR1 and additionally bind 1, 2, 3, 4, 5 or more of these targets are also encompassed by the invention. In specific embodiments, the antibody component of the MRD-containing antibody binds VEGFR1. In further embodiments, the antibody component of the MRD-containing antibody is IMC-18F1. In additional embodiments, the antibody component, MRD component, and/or MRD-containing antibody competes for VEGFR1 binding with IMC-18F1.

In another embodiment, an MRD-containing antibody binds VEGFR2 and additionally binds a target selected from: VEGF (i.e., VEGFA), VEGFB, FGF1, FGF2, FGF4, FGF7, FGF8b, FGF19, FGFR1 (e.g., FGFR1-IIIC), FGFR2 (e.g., FGFR2-IIIa, FGFR2-IIIb, and FGFR2-IIIc), FGFR3, TNFSF2 (TNFa), FGFR3, NRP1, ROBO4, CD30, CD33, CD55 CD80, KIT, CXCL12, Notch1EFNa1, EFNa2, ANG1, ANG2, IL6, IL8, IL18, HGF, PDGFA, PLGF, PDGFB, CXCL12, KIT, GCSF, CXCR4, PTPRC, TIE2, VEGFR1, VEGFR3, Notch 1, DLL4, EGFL7, α2β1 integrin, α4β1 integrin, α5β1 integrin, αvβ3 integrin, TGFb, MMP2, MMP7, MMP9, MMP12, PLAU, VCAM1, PDGFRA, and PDGFRB. Multivalent and multispecific compositions (e.g., MRD-containing antibodies) that bind VEGFR2 and additionally bind 1, 2, 3, 4, 5 or more of these targets are also encompassed by the invention. In specific embodiments, the antibody component of the MRD-containing antibody binds VEGFR2. In further embodiments, the antibody component of the MRD-containing antibody is IMC-1C11 or DC101. In additional embodiments, the antibody component, MRD component, and/or MRD-containing antibody competes for VEGFR2 binding with IMC-1C11 or DC101.

In another embodiment, an MRD-containing antibody binds VEGFR2 and additionally binds ANG2 or TIE2. In specific embodiments, the antibody component of the MRD-containing antibody binds VEGFR2. In further embodiments, the antibody component of the MRD-containing antibody is IMC-1C11, DC101 or TTAC-0001. In additional embodiments, the antibody component, MRD component, and/or MRD-containing antibody competes for VEGFR2 binding with IMC-1C11, DC101 or TTAC-0001. In further embodiments, the TIE2 binding component comprises a fragment of ANG2 that binds TIE2. In particular embodiments, the TIE2 binding component comprises amino acids 283-449 of the human ANG2 disclosed in NCBI Ref. Seq. No. NP_001138.1.

In another embodiment, an MRD-containing antibody binds DLL4 and additionally binds a target selected from: EGFR, PLGF, VEGFR1, VEGFR2 and VEGF. Multivalent and multispecific compositions (e.g., MRD-containing antibodies) that bind DLL4 and at least 1, 2, 3, 4, 5 or more of these targets are also encompassed by the invention. In further embodiments, the antibody component of the MRD-containing antibody is REGN421. In additional embodiments, the antibody component, MRD component, and/or MRD-containing antibody competes for DLL4 binding with REGN421.

In additional embodiments, an MRD-containing antibody binds to an anti-angiogenic and a metastatic or invasive cancer target. In one embodiment, an MRD-containing antibody binds to an angiogenic target and also binds a metastatic or invasive cancer target selected from: CXCL12, CXCR4 (e.g., CXCR4b), CCR7 (e.g., CXCR7b), CD44 (e.g., CD44v3 and CD44v6), α2β1 integrin, α4β1 integrin, α5β1 integrin, αvβ1 integrin, αvβ3 integrin, TGFb, αvβ5 integrin, a9β1 integrin, α6β4 integrin, αMβ2 integrin, PD-1, HGF, cMET, MMP2, MMP-7, MMP-9, MMP-12, VEGFA, VEGFB, and IGF1. Multivalent and multispecific compositions (e.g., MRD-containing antibodies) that bind an angiogenic target and also bind 2, 3, 4, 5 or more of these metastatic or invasive cancer targets are also encompassed by the invention. In specific embodiments, the antibody component of the MRD-containing antibody binds VEGF. In further embodiments, the antibody component of the MRD-containing antibody is bevacizumab. In additional embodiments, the antibody component, MRD component, and/or MRD-containing antibody competes for VEGF binding with bevacizumab.

In one embodiment, an MRD-containing antibody binds to 2 or more targets associated with distinct cell signaling pathways. In additional embodiments, an MRD-containing antibody binds to 2 or more targets associated with redundant, overlapping or cross-talking signaling pathways. For example, in one embodiment, an MRD-containing antibody binds to 2 or more targets associated with PI3K/AKT/mTOR signaling (e.g., ErbB2, EGFR, IGF1R, Notch, FGFR1 (e.g., FGFR1-IIIC), FGFR2 (e.g., FGFR2-IIIa, FGFR2-IIIb, and FGFR2-IIIb), FGFR3, FGFR4, GPCR, and/or c-MET). In some embodiments, the multivalent and monovalent multispecific composition (e.g., MRD-containing antibody) binds 2, 3, 4, 5 or more of these targets.

In another embodiment, an MRD-containing antibody binds to 2 or more targets associated with receptor tyrosine Raf/MEK/MAPK signaling (e.g., VEGFR1, VEGFR2, VEGFR3, FGFR1 (e.g., FGFR1-IIIC), FGFR2 (e.g., FGFR2-IIIa, FGFR2-IIIb, and FGFR2-IIIb), FGFR3, FGFR4, CD28, RET, cMET, EGFR, ErbB2, Notch, Notch1, Notch3, Notch4, DLL1, DLL4, Jagged, Jagged1, Jagged2, and Jagged3. In some embodiments, the multivalent and multispecific compositions (e.g., MRD-containing antibodies) bind 1, 2, 3, 4, 5 or more of these targets.

In another embodiment, an MRD-containing antibody binds to 2 or more targets associated with SMAD signaling (e.g., Notch, TGFβ, TGFβR1, TGFβR2, and a BMP). In some embodiments, the multivalent and multispecific compositions (e.g., MRD-containing antibodies) bind 2, 3, 4, 5 or more of these targets.

In another embodiment, an MRD-containing antibody binds to 2 or more targets associated with JAK/STAT signaling (e.g., IFNgR1, IFNgR3, IFNG, IFN-AR2, IFN-AR1, IFN alpha, IFN beta, IL6a receptor (GP130), IL6, IL12RB1, IL12, and EGFR). Thus, the invention encompasses an MRD-containing antibody that binds to 2 or more targets selected from WNT1, WNT2, WNT2b, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16, FZD1, FZD2, FZD4, FZD5, FZD6, FZD7, FZD8, Notch, Notch1, Notch3, Notch4, DLL1, DLL4, Jagged, Jagged1, Jagged2, and Jagged3. In some embodiments, the multivalent and multispecific compositions (e.g., MRD-containing antibodies) bind 2, 3, 4, 5 or more of these targets.

In another embodiment, an MRD-containing antibody binds to 2 or more targets associated with NFkB signaling (e.g., BCR, TCR, IL1R, IL1, FZD1, FZD2, FZD4, FZD5, FZD6, FZD7, FZD8, Notch, Notch1, Notch3, Notch4, DLL4, Jagged, Jagged1, Jagged2, Jagged3, TNFSF1 (TNFb, LTa), TNFRSF1A (TNFR1, p55, p60), TNFRSF1B (TNFR2), TNFSF6 (Fas Ligand), TNFSF6 (Fas, CD95), TNFRSF6B (DcR3), TNFSF7 (CD27 Ligand, CD70), TNFRSF7 (CD27), TNFSF8 (CD30 Ligand), TNFRSF8 (CD30), TNFSF11 (RANKL), TNFRSF11A (RANK), TNFSF12 (TWEAK), TNFRSF12 (TWEAKR), TNFSF13 (APRIL), TNFSF13B (BLYS), TNFRSF13B (TACI), TNFRSF13C (BAFFR), TNFRSF15 (TL1A), TNFRSF17 (BCMA), TNFRSF19L (RELT), TNFRSF19 (TROY), TNFRSF21 (DR6), TNFRSF25 (DR3), TNFSF5 (CD40 Ligand), TNFRSF5 (CD40), TNFSF2 (TNFa), TNFSF3 (LTb), TNFRSF3 (LTBR), TNFSF14 (LIGHT, HVEM Ligand), TNFRSF14 (HVEM), TNFSF18 (GITR Ligand), TNFRSF18 (GITR), TNFSF4 (OX40 Ligand), TNFRSF4 (OX40), TNFSF9 (41BB Ligand), TNFRSF9 (41BB), a BMP, NGF, and TGF alpha). In some embodiments, the multivalent and multispecific compositions (e.g., MRD-containing antibodies) bind 2, 3, 4, 5 or more of these targets.

In another embodiment, an MRD-containing antibody binds to 2 or more targets associated with cell proliferation (e.g., FGF1, FGF2, FGF7, FGF4, FGF10, FGF18b, FGF19, FGF23, FGFR1 (e.g., FGFR1-IIIC), FGFR2 (e.g., FGFR1IIIB and FGFR-IIIC), FGFR3, FGFR4, TCR, TNFRSF5 (CD40), TLR1, TLR2, TLR3, TLR 4, TLR5, and TLR6). In some embodiments, the multivalent and multispecific compositions (e.g., MRD-containing antibodies) bind 2, 3, 4, 5 or more of these targets.

In another embodiment, an MRD-containing antibody binds to 2 or more targets associated with toll-like receptor signaling (e.g., TLR1, TLR2, TLR3, TLR 4, TLR5, and TLR6).

In another embodiment, an MRD-containing antibody binds to 2 or more targets associated with B cell signaling (e.g., mIg, Igα/Igβ (CD79a/CD79b) heterodimers (α/β), CD19, CD20, CD21, CD22, CD23, CD27, CD30, CD46, CD80, CD86, ICOSL (B7-H2), HLA-DR (CD74), PD1, PDL1, TNFRSF1A (TNFR1, p55, p60), TNFRSF1B (TNFR2), TNFRSF13B (TACI), TNFRSF13C (BAFFR), TNFRSF17 (BCMA), BTLA, TNFRSF5 (CD40), TLR4, TNFRSF14 (HVEM), Fc gamma RIIB, IL4R and CRAC. In a particular embodiment, the MRD-containing antibody binds to CD19 and CD20. In an additional embodiment, the MRD-containing antibody binds CD19, CD20, and CD22. In some embodiments, the multivalent and monovalent multispecific composition (e.g., MRD-containing antibodies) binds 2, 3, 4, 5 or more of these targets.

In a further embodiment, an MRD-containing antibody binds to 1 or more B cell surface markers selected from: CD10, CD24, CD37, CD53, CD72, CD75, CD77, CD79a, CD79b, CD81, CD82, CD83, CD84 (SLAMS) and CD85. In a further embodiment, an MRD-containing antibody binds to 1 or more B cell surface markers selected from: CD10, CD24, CD37, CD53, CD72, CD75, CD77, CD79a, CD79b, CD81, CD82, CD83, CD84 (SLAMS) and CD85. In some embodiments, the multivalent and multispecific compositions (e.g., MRD-containing antibodies) bind 2, 3, 4, 5 or more of these B cell surface markers.

In additional embodiments, an MRD-containing antibody binds CD19 and a target selected from: CD20, CD22, CD30, CD33, TNFRSF5 (CD40), CD52, CD74, CD80, CD138, VEGFR1, VEGFR2, EGFR, TNFRSF10A (DR4), TNFRSF10B (DR5), TNF, NGF, VEGF, IGF1,2, IGF2, IGF1 and TNFSF11 (RANKL). In additional embodiments, an MRD-containing antibody binds CD20 and a target selected from: CD3, CD4 and NKG2D. Multivalent and multispecific compositions (e.g., MRD-containing antibodies) that bind CD19 and also bind at least 2, 3, 4, 5 or more of these targets are also encompassed by the invention. In specific embodiments, the antibody component of the MRD-containing antibody binds CD19. In further embodiments, the antibody component of the MRD-containing antibody is MDX-1342, SGN-CD19A, XMAB®5574, SGN-19A, ASG- 5ME or MEDI-551. In additional embodiments, the antibody component, MRD component, and/or MRD-containing antibody competes for CD19 binding with MDX-1342, SGN-CD19A, XMAB®5574, SGN-19A, ASG-5ME or MEDI-551.

In additional embodiments, an MRD-containing antibody binds CD22 and a target selected from: CD19, CD20, CD23, CD30, CD33, TNFRSF5 (CD40), CD52, CD74, CD80, TNFRSF10A (DR4), TNFRSF10B (DR5), VEGF, TNF and NGF. In additional embodiments, an MRD-containing antibody binds CD22 and a target selected from: CD3, CD4 and NKG2D. Multivalent and multispecific compositions (e.g., MRD-containing antibodies) that bind CD22 and also bind 2, 3, 4, 5 or more of these targets are also encompassed by the invention. In specific embodiments, the antibody component of the MRD-containing antibody binds CD22. In further embodiments, the antibody component of the MRD-containing antibody is epratuzumab or inotuzumab. In additional embodiments, the antibody component, MRD component, and/or MRD-containing antibody competes for CD22 binding with epratuzumab or inotuzumab.

In additional embodiments, the antibody component of the MRD-containing antibody is moxetumomab (CAT-8015, Cambridge Antibody Technologies). In additional embodiments, the antibody component, MRD component, and/or MRD-containing antibody competes for CD22 binding with moxetumomab.

In additional embodiments, an MRD-containing antibody binds TNFRSF5 (CD40) and a target selected from: BCMA, TNFSF11 (RANKL), VEGFR1, VEGFR2, TNFRSF10A (DR4), TNFRSF10B (DR5), CD22, CD30, CD38, CD56 (NCAM), CD70, CD80, CD138, IL6, IGF1, IGF2, IGF1,2, BLyS, APRIL and NGF. In additional embodiments, an MRD-containing antibody binds CD40 and a target selected from: CD3, CD4 and NKG2D. Multivalent and multispecific compositions (e.g., MRD-containing antibodies) that bind CD40 and also bind 2, 3, 4, 5 or more of these targets are also encompassed by the invention. In specific embodiments, the antibody component of the MRD-containing antibody binds CD40. In further embodiments, the antibody component of the MRD-containing antibody is CP870893, dacetuzumab, ANTOVA®, lucatumumab, XMAB®5485 or teneliximab. In additional embodiments, the antibody component, MRD component, and/or MRD-containing antibody competes for CD40 binding with CP870893, dacetuzumab, ANTOVA®, lucatumumab, XMAB®5485 or teneliximab.

In some embodiments, an MRD-containing antibody binds CD33 and a target selected from: FLT3, CD44, TNFRSF10A (DR4), TNFRSF10B (DR5), CD80, MGC, VEGFR1, VEGFR2, IL1, IL6, TNF and VEGF. Multivalent and multispecific compositions (e.g., MRD-containing antibodies) that bind TNFRSF10B and also bind at least 2, 3, 4, 5 or more of these targets are also encompassed by the invention. In specific embodiments, the antibody component of the MRD-containing antibody binds CD33. In further embodiments, the antibody component of the MRD-containing antibody is gemtuzumab or lintuzumab. In additional embodiments the antibody component, MRD component, and/or MRD-containing antibody competes for CD33 binding with gemtuzumab or lintuzumab.

In another embodiment, an MRD-containing antibody binds to 2 or more targets associated with antigen presentation cell signaling (e.g., mIg, Igα/Igβ (CD79a/CD79b) heterodimers (α/β), CD19, CD20, CD21, CD22, CD23, CD27, CD28, CD30, CD30L, TNFSF14 (LIGHT, HVEM Ligand), CD70, ICOS, ICOSL (B7-H2), CTLA4, PD-1, PDL1 (B7-H1), B7-H4, B7-H3, PDL2 (B7-DC), BTLA, CD46, CD80 (B7-1), CD86 (B7-2), HLA-DR, CD74, PD1, TNFRSF4 (OX40), TNFRSF9 (41BB), TNFSF4 (OX40 Ligand), TNFSF9 (41BB Ligand), TNFRSF9 (41BB), TNFRSF1A (TNFR1, p55, p60), TNFRSF1B (TNFR2), TNFRSF13B (TACI), TNFRSF13C (BAFFR), TNFRSF17 (BCMA), BTLA, TNFRSF18 (GITR), TNFRSF5 (CD40), TLR4, TNFRSF14 (HVEM), Fcgamma RIIB, IL4R and CRAC). In some embodiments, the multivalent and multispecific compositions (e.g., MRD-containing antibodies) bind 2, 3, 4, 5 or more of these targets.

In another embodiment, an MRD-containing antibody binds to 2 or more targets associated with T cell receptor signaling (e.g., CD3, CD4, CD27, CD28, CD70, IL2R, LFA-1, C4, ICOS, CTLA-4, CD45, CD80, CD86, PG-1, TIM1, TIM2, TIM3, TIM4, galectin 9, TNFRSF1A (TNFR1, p55, p60), TNFRSF1B (TNFR2), TNFRSF21 (DR6), TNFRSF6 (Fas, CD95), TNFRSF25 (DR3), TNFRSF14 (HVEM), TNFSF18, TNFRSF18 (GITR), TNFRSF4 (OX40), TNFSF4 (OX40 Ligand), PD1, PDL1, CTLA4, TNFSF9 (41BB Ligand), TNFRSF9 (41BB), TNFSF14 (LIGHT, HVEM Ligand), TNFSF5 (CD40 Ligand), BTLA, and CRAC). In some embodiments, the multivalent and multispecific compositions (e.g., MRD-containing antibodies) bind 2, 3, 4, 5 or more of these targets.

In additional embodiments an MRD-containing antibody binds to a therapeutic target and a second target that is associated with an escape pathway for resisting the therapeutic effect resulting from targeting the therapeutic target. For example, in one embodiment, an MRD-containing antibody binds to EGFR and a target selected from MDR1, cMET, Notch, Notch1, Notch3, Notch4, DLL1, DLL4, Jagged, Jagged1, Jagged2, and Jagged3. In some embodiments, the multivalent and monovalent multispecific composition (e.g., MRD-containing antibodies) binds 2, 3, 4, 5 or more of these targets.

In specific embodiments, the MRD-containing antibody targets ErbB2 and an angiogenic factor. In specific embodiments, the MRD-containing antibody targets ErbB2 and IGF1R. In another embodiment, the antibody targets ErbB2 and at least one MRD targets an angiogenic factor and/or IGF1R. In one embodiment, an antibody that binds to the same ErbB2 epitope as trastuzumab is operably linked to at least one MRD that targets an angiogenic factor and/or IGF1R. In an additional embodiment, an antibody that competitively inhibits trastuzumab binding is operably linked to at least one MRD that targets an angiogenic factor and/or IGF1R. In additional embodiments, an antibody that comprises the sequences of SEQ ID NOS:59-64 is operably linked to at least one MRD that targets an angiogenic factor and/or IGF1R. In additional embodiments, the trastuzumab antibody is operably linked to at least one MRD that targets an angiogenic factor and/or IGF1R.

In some embodiments, an antibody that binds to ErbB2 is operably linked to an MRD that targets Ang2. In some embodiments, the antibody that binds to ErbB2 is linked to an Ang2 binding MRD that binds to the same Ang2 epitope as an MRD comprising the sequence of MGAQTNFMPM-DNDELLLYEQFILQQGLE SEQ ID NO:8. In some embodiments, the antibody that binds to ErbB2 is linked to an Ang2 binding MRD that competitively inhibits an MRD comprising the sequence of SEQ ID NO:8. In some embodiments, the antibody that binds to ErbB2 is linked to an MRD comprising the sequence of SEQ ID NO:8.

In some embodiments, at least one Ang2 binding MRD is operably linked to the C-terminus of the heavy chain of an antibody that binds to ErbB2. In some embodiments, at least one Ang2 binding MRD is operably linked to the N-terminus of the heavy chain of an antibody that binds to ErbB2. In some embodiments, at least one Ang2 binding MRD is operably linked to the C-terminus of the light chain of an antibody that binds to ErbB2. In some embodiments, at least one Ang2 binding MRD is operably linked to the N-terminus of the light chain of an antibody that binds to ErbB2.

In some embodiments, at least one Ang2 binding MRD is operably linked directly to an antibody that binds to ErbB2. In additional embodiments, at least one Ang2 binding MRD is operably linked to an antibody that binds to ErbB2 via a linker.

In some embodiments, an antibody that binds to ErbB2 is operably linked to an MRD that targets IGF1R. In some embodiments, the antibody that binds to ErbB2 is linked to an IGF1R binding MRD that binds to the same IGF1R epitope as an MRD comprising the sequence of SEQ ID NO:14. In some embodiments, the antibody that binds to ErbB2 is linked to an IGF1R binding MRD that competitively inhibits an MRD comprising the sequence of SEQ ID NO:14. In some embodiments, the antibody that binds to ErbB2 is linked to an MRD comprising the sequence of SEQ ID NO:14. In some embodiments, the antibody that binds ErbB2 is linked to an MRD encoding the sequence SLFVPRPERK (SEQ ID NO:103). In some embodiments, the antibody that binds ErbB2 is linked to an MRD encoding the sequence ESDVLHFTST (SEQ ID NO:104). In some embodiments, the antibody that binds ErbB2 is linked to an MRD encoding the sequence LRKYADGTL (SEQ ID NO:105).

In some embodiments, at least one IGF1R binding MRD is operably linked to the C-terminus of the heavy chain of an antibody that binds to ErbB2. In some embodiments, at least one IGF1R binding MRD is operably linked to the N-terminus of the heavy chain of an antibody that binds to ErbB2. In some embodiments, at least one IGF1R binding MRD is operably linked to the C-terminus of the light chain of an antibody that binds to ErbB2. In some embodiments, at least one IGF1R binding MRD is operably linked to the N-terminus of the light chain of an antibody that binds to ErbB2.

In some embodiments, at least one IGF1R binding MRD is operably linked directly to an antibody that binds to ErbB2. In additional embodiments, at least one IGF1R binding MRD is operably linked to an antibody that binds to ErbB2 via a linker.

In some embodiments, an MRD-containing antibody targets ErbB2 and HER2/3. In some embodiments, an MRD-containing antibody can bind to ErbB2 and HER2/3 simultaneously. In some embodiments, an antibody that binds to ErbB2 is operably linked to an MRD that targets HER2/3. In additional embodiments, at least one HER2/3-binding MRD is operably linked to the C-terminus of the heavy chain of an antibody that binds to ErbB2. In further embodiments, at least one HER2/3-binding MRD is operably linked to the N-terminus of the heavy chain of an antibody that binds to ErbB2. In additional embodiments, at least one HER2/3-binding MRD is operably linked to the C-terminus of the light chain of an antibody that binds to ErbB2. In additional embodiments, at least one HER2/3-binding MRD is operably linked to the N-terminus of the light chain of an antibody that binds to ErbB2.

In some embodiments, at least one HER2/3-binding MRD is operably linked directly to an antibody that binds to ErbB2. In additional embodiments, at least one HER2/3-binding MRD is operably linked to an antibody that binds to ErbB2 via a linker.

In some embodiments, an MRD-containing antibody targets ErbB2 and HER2/3. In some embodiments, an MRD-containing antibody can bind to ErbB2 and HER2/3 simultaneously. In some embodiments, an antibody that binds to HER2/3 is operably linked to an MRD that targets ErbB2. In additional embodiments, at least one ErbB2-binding MRD is operably linked to the C-terminus of the heavy chain of an antibody that binds to HER2/3. In further embodiments, at least one ErbB2-binding MRD is operably linked to the N-terminus of the heavy chain of an antibody that binds to HER2/3. In additional embodiments, at least one ErbB2-binding MRD is operably linked to the C-terminus of the light chain of an antibody that binds to HER2/3. In additional embodiments, at least one ErbB2-binding MRD is operably linked to the N-terminus of the light chain of an antibody that binds to HER2/3.

In some embodiments, at least one ErbB2-binding MRD is operably linked directly to an antibody that binds to HER2/3. In additional embodiments, at least one ErbB2-binding MRD is operably linked to an antibody that binds to HER2/3 via a linker.

In some embodiments, the MRD-containing antibody targets ErbB2, Ang2, and IGF1R. In some embodiments, the MRD-containing antibody comprises an antibody that targets ErbB2, an MRD that targets Ang2, and an MRD that targets IGF1R. In some embodiments, the Ang2 and IGF1R MRDs are attached to the same location on the anti-ErbB2 antibody. In some embodiments, the Ang2 and IGF1R MRDs are attached to different locations on the anti-ErbB2 antibody. In some embodiments, the Ang2 and IGF1R MRDs are on the light chain of the anti-ErbB2 antibody. In some embodiments, the Ang2 and IGF1R MRDs are on the heavy chain of the anti-ErbB2 antibody. In some embodiments, the Ang2 MRD is on the light chain of the ErbB2 antibody, and the IGF1R MRD is on the heavy chain of the anti-ErbB2 antibody. In some embodiments, the Ang2 MRD is on the heavy chain of the ErbB2 antibody, and the IGF1R MRD is on the light chain of the anti-ErbB2 antibody. In some embodiments, the Ang2 MRD is on the N-terminus of the heavy chain of the ErbB2 antibody, and the IGF1R MRD is on the C-terminus of the light chain of the anti-ErbB2 antibody. In some embodiments, the IGF1R MRD is on the N-terminus of the heavy chain of the ErbB2 antibody, and the Ang2 MRD is on the C-terminus of the light chain of the anti-ErbB2 antibody. Multivalent and multispecific compositions (e.g., MRD-containing antibodies) comprising an antibody that targets Ang2, an MRD that targets ErbB2, and an MRD that targets IGF1R; and multivalent and multispecific compositions (e.g., MRD-containing antibodies) comprising an antibody that targets IGF1R, an MRD that targets ErbB2, and an MRD that targets Ang2 are also encompassed by the invention.

In some embodiments, the MRD-containing antibody targets ErbB2, Ang2, and HER2/3. In some embodiments, the MRD-containing antibody comprises an antibody that targets ErbB2, an MRD that targets Ang2, and an MRD that targets HER2/3. In some embodiments, the Ang2 and HER2/3 MRDs are attached to the same location on the anti-ErbB2 antibody. In some embodiments, the Ang2 and HER2/3 MRDs are attached to different locations on the anti-ErbB2 antibody. In some embodiments, the Ang2 and HER2/3 MRDs are on the light chain of the anti-ErbB2 antibody. In some embodiments, the Ang2 and HER2/3 MRDs are on the heavy chain of the anti-ErbB2 antibody. In some embodiments, the Ang2 MRD is on the light chain of the ErbB2 antibody, and the HER2/3 MRD is on the heavy chain of the anti-ErbB2 antibody. In some embodiments, the Ang2 MRD is on the heavy chain of the ErbB2 antibody, and the HER2/3 MRD is on the light chain of the anti-ErbB2 antibody. In some embodiments, the Ang2 MRD is on the N-terminus of the heavy chain of the ErbB2 antibody, and the HER2/3 MRD is on the C-terminus of the light chain of the anti-ErbB2 antibody. In some embodiments, the HER2/3 MRD is on the N-terminus of the heavy chain of the ErbB2 antibody, and the Ang2 MRD is on the C-terminus of the light chain of the anti-ErbB2 antibody. Multivalent and multispecific compositions (e.g., MRD-containing antibodies) comprising an antibody that targets HER2/3, an MRD that targets ErbB2, and an MRD that targets Ang2; and multivalent and multispecific compositions (e.g., MRD-containing antibodies) comprising an antibody that targets Ang2, an MRD that targets ErbB2, and an MRD that targets HER2/3 are also encompassed by the invention.

In some embodiments, the MRD-containing antibody targets ErbB2, HER2/3, and IGF1R. In some embodiments, the MRD-containing antibody comprises an antibody that targets ErbB2, an MRD that targets HER2/3, and an MRD that targets IGF1R. In some embodiments, the HER2/3 and IGF1R MRDs are attached to the same location on the anti-ErbB2 antibody. In some embodiments, the HER2/3 and IGF1R MRDs are attached to different locations on the anti-ErbB2 antibody. In some embodiments, the HER2/3 and IGF1R MRDs are on the light chain of the anti-ErbB2 antibody. In some embodiments, the HER2/3 and IGF1R MRDs are on the heavy chain of the anti-ErbB2 antibody. In some embodiments, the HER2/3 MRD is on the light chain of the ErbB2 antibody, and the IGF1R MRD is on the heavy chain of the anti-ErbB2 antibody. In some embodiments, the HER2/3 MRD is on the heavy chain of the ErbB2 antibody, and the IGF1R MRD is on the light chain of the anti-ErbB2 antibody. In some embodiments, the HER2/3 MRD is on the N-terminus of the heavy chain of the ErbB2 antibody, and the IGF1R MRD is on the C-terminus of the light chain of the anti-ErbB2 antibody. In some embodiments, the IGF1R MRD is on the N-terminus of the heavy chain of the ErbB2 antibody, and the HER2/3 MRD is on the C-terminus of the light chain of the anti-ErbB2 antibody. Multivalent and multispecific compositions (e.g., MRD-containing antibodies) comprising an antibody that targets HER2/3, an MRD that targets ErbB2, and an MRD that targets IGF1R; and multivalent and multispecific compositions (e.g., MRD-containing antibodies) comprising an antibody that targets IGF1R, an MRD that targets ErbB2, and an MRD that targets HER2/3 are also encompassed by the invention.

In some embodiments, the MRD-containing antibody targets ErbB2, Ang2, HER2/3, and IGF1R. In some embodiments, the MRD-containing antibody comprises an antibody that targets ErbB2, an MRD that targets Ang2, an MRD that targets HER2/3, and an MRD that targets IGF1R. In some embodiments, the Ang2, HER2/3, and IGF1R MRDs are attached to the same chain of the anti-ErbB2 antibody. In some embodiments, the Ang2, HER2/3, and IGF1R MRDs are attached to different chains of the anti-ErbB2 antibody. In some embodiments, the Ang2, HER2/3, and IGF1R MRDs are on the light chain of the anti-ErbB2 antibody. In some embodiments, the Ang2, HER2/3, and IGF1R MRDs are on the heavy chain of the anti-ErbB2 antibody. In some embodiments, the Ang2, HER2/3, and IGF1R MRDs are attached to the same terminus of the anti-ErbB2 antibody. In some embodiments, the Ang2, HER2/3, and IGF1R MRDs are attached to different termini of the anti-ErbB2 antibody. Multivalent and multispecific compositions (e.g., MRD-containing antibodies) comprising: an antibody that targets HER2/3, an MRD that targets ErbB2, an MRD that targets Ang2, and an MRD that targets IGF1R; multivalent and multispecific compositions (e.g., MRD-containing antibodies) comprising an antibody that targets Ang2, an MRD that targets ErbB2, an MRD that targets HER2/3, and an MRD that targets IGF1R; and multivalent and multispecific compositions (e.g., MRD-containing antibodies) comprising an antibody that targets IGF1R, an MRD that targets ErbB2, an MRD that targets HER2/3, and an MRD that targets Ang2 are also encompassed by the invention.

In some embodiments, the anti-ErbB2 antibody operably linked to an Ang2 binding MRD binds to both ErbB2 and Ang2 simultaneously. In some embodiments, the anti-ErbB2 antibody operably linked to an IGF1R binding MRD binds to both ErbB2 and IGF1R simultaneously. In some embodiments, the anti-ErbB2 antibody operably linked to a HER2/3 binding MRD binds to both ErbB2 and HER2/3 simultaneously. In some embodiments, the anti-ErbB2 antibody operably linked to an Ang2 MRD, an IGF1R MRD, and/or a HER2/3 MRD binds to ErbB2, Ang2, IGF1R, and/or HER2/3 simultaneously. In some embodiments, the anti-ErbB2 antibody operably linked to an Ang2, IGF1R and/or HER2/3 binding MRD(s) exhibits ADCC activity. In additional embodiments, the anti-ErbB2 antibody operably linked to an Ang2, IGF1R, and/or HER2/3 binding MRD(s) down-regulates Akt signaling. In additional embodiments, the anti-ErbB2 antibody operably linked to an Ang2 binding MRD inhibits Ang2 binding to TIE2. In additional embodiments, the anti-ErbB2 antibody operably linked to an IGF1R binding MRD(s) down-regulates IGF1R signaling. In additional embodiments, the anti-ErbB2 antibody operably linked to an Ang2, IGF1R and/or HER2/3 binding MRD(s) inhibits cell proliferation. In additional embodiments, the anti-ErbB2 antibody operably linked to an Ang2, IGF1R, and/or HER2/3 binding MRD(s) inhibits tumor growth.

In specific embodiments, the MRD-containing antibody targets VEGF and an angiogenic factor. In specific embodiments, the MRD-containing antibody targets VEGF and IGF1R. In another embodiment, the antibody targets VEGF and at least one MRD targets an angiogenic factor and/or IGF1R. In one embodiment, an antibody that binds to the same VEGF epitope as bevacizumab is operably linked to at least one MRD that targets an angiogenic factor and/or IGF1R. In an additional embodiment, an antibody that competitively inhibits bevacizumab binding is operably linked to at least one MRD that targets an angiogenic factor and/or IGF1R. In additional embodiments, an antibody that comprises the sequences of SEQ ID NOS:78-79 is operably linked to at least one MRD that targets an angiogenic factor and/or IGF1R. In additional embodiments, the bevacizumab antibody is operably linked to at least one MRD that targets an angiogenic factor and/or IGF1R.

In some embodiments, an antibody that binds to VEGF is operably linked to an MRD that targets Ang2. In some embodiments, the antibody that binds to VEGF is linked to an Ang2 binding MRD that binds to the same Ang2 epitope as an MRD comprising the sequence of SEQ ID NO:8. In some embodiments, the antibody that binds to VEGF is linked to an Ang2 binding MRD that competitively inhibits an MRD comprising the sequence of SEQ ID NO:8. In some embodiments, the antibody that binds to VEGF is linked to an MRD comprising the sequence of SEQ ID NO:8.

In some embodiments, at least one Ang2 binding MRD is operably linked to the C-terminus of the heavy chain of an antibody that binds to VEGF. In some embodiments, at least one Ang2 binding MRD is operably linked to the N-terminus of the heavy chain of an antibody that binds to VEGF. In some embodiments, at least one Ang2 binding MRD is operably linked to the C-terminus of the light chain of an antibody that binds to VEGF. In some embodiments, at least one Ang2 binding MRD is operably linked to the N-terminus of the light chain of an antibody that binds to VEGF.

In some embodiments, at least one Ang2 binding MRD is operably linked directly to an antibody that binds to VEGF. In additional embodiments, at least one Ang2 binding MRD is operably linked to an antibody that binds to VEGF via a linker.

In some embodiments, an antibody that binds to VEGF is operably linked to an MRD that targets IGF1R. In some embodiments, the antibody that binds to VEGF is linked to an IGF1R binding MRD that binds to the same IGF1R epitope as an MRD comprising the sequence of SEQ ID NO:14. In some embodiments, the antibody that binds to VEGF is linked to an IGF1R binding MRD that competitively inhibits an MRD comprising the sequence of SEQ ID NO:14. In some embodiments, the antibody that binds to VEGF is linked to an MRD comprising the sequence of SEQ ID NO:14. In some embodiments, the antibody that binds ErbB2 is linked to an MRD encoding the sequence SLFVPRPERK (SEQ ID NO:103). In some embodiments, the antibody that binds ErbB2 is linked to an MRD encoding the sequence ESDVLHFTST (SEQ ID NO:104). In some embodiments, the antibody that binds ErbB2 is linked to an MRD encoding the sequence LRKYADGTL (SEQ ID NO:105).

In some embodiments, at least one IGF1R binding MRD is operably linked to the C-terminus of the heavy chain of an antibody that binds to VEGF. In some embodiments, at least one IGF1R binding MRD is operably linked to the N-terminus of the heavy chain of an antibody that binds to VEGF. In some embodiments, at least one IGF1R binding MRD is operably linked to the C-terminus of the light chain of an antibody that binds to VEGF. In some embodiments, at least one IGF1R binding MRD is operably linked to the N-terminus of the light chain of an antibody that binds to VEGF.

In some embodiments, at least one IGF1R binding MRD is operably linked directly to an antibody that binds to VEGF. In additional embodiments, at least one IGF1R binding MRD is operably linked to an antibody that binds to VEGF via a linker.

In some embodiments, the MRD-containing antibody targets VEGF, Ang2, and IGF1R. In some embodiments, the MRD-containing antibody comprises an antibody that targets VEGF, an MRD that targets Ang2, and an MRD that targets IGF1R. In some embodiments, the Ang2 and IGF1R MRDs are attached to the same location on the anti-VEGF antibody. In some embodiments, the Ang2 and IGF1R MRDs are attached to different locations on the anti-VEGF antibody. In some embodiments, the Ang2 and IGF1R MRDs are on the light chain of the anti-VEGF antibody. In some embodiments, the Ang2 and IGF1R MRDs are on the heavy chain of the anti-VEGF antibody. In some embodiments, the Ang2 MRD is on the light chain of the anti-VEGF antibody, and the IGF1R MRD is on the heavy chain of the anti-VEGF antibody. In some embodiments, the Ang2 MRD is on the heavy chain of the anti-VEGF antibody, and the IGF1R MRD is on the light chain of the anti-VEGF antibody. In some embodiments, the Ang2 MRD is on the N-terminus of the heavy chain of the anti-VEGF antibody, and the IGF1R MRD is on the C-terminus of the light chain of the anti-VEGF antibody. In some embodiments, the IGF1R MRD is on the N-terminus of the heavy chain of the anti-VEGF antibody, and the Ang2 MRD is on the C-terminus of the light chain of the anti-VEGF antibody.

In some embodiments, the anti-VEGF antibody operably linked to an Ang2 binding MRD binds to both anti-VEGF and Ang2 simultaneously. In some embodiments, the anti-VEGF antibody operably linked to an IGF1R binding MRD binds to both anti-VEGF and IGFR1 simultaneously. In some embodiments, the anti-VEGF antibody operably linked to an Ang2 binding MRD and an IGF1R binding MRD binds to VEGF, Ang2, and IGF1R simultaneously. In some embodiments, the anti-VEGF antibody operably linked to an Ang2 and/or IGF1R binding MRD(s) exhibits ADCC activity. In additional embodiments, the anti-VEGF antibody operably linked to an Ang2 and/or IGF1R binding MRD(s) down-regulates VEGF signaling. In additional embodiments, the anti-VEGF antibody operably linked to an Ang2 binding MRD inhibits Ang2 binding to TIE2. In additional embodiments, the anti-VEGF antibody operably linked to an IGF1R binding MRD inhibits IGF1R signaling. In additional embodiments, the anti-VEGF antibody operably linked to an Ang2 and/or IGF1R binding MRD(s) inhibits cell proliferation. In additional embodiments, the anti-VEGF antibody operably linked to an Ang2 and/or IGF1R binding MRD(s) inhibits tumor growth.

In some embodiments, the anti-ErbB2 antibody or the VEGF antibody contains and MRD that inhibits the binding of pertuzumab to ErbB2. In some embodiments, an anti-ErbB2 antibody contains at least one MRD that binds to Ang2 or IGF1R and one MRD that inhibits the binding of pertuzumab to ErbB2. In some embodiments, an anti-VEGF antibody contains at least one MRD that binds to Ang2 or IGF1R and one MRD that inhibits the binding of pertuzumab to ErbB2. In some embodiments, an anti-ErbB2 antibody contains an MRD that binds Ang2, an MRD that binds IGF1R, and an MRD that inhibits the binding of pertuzumab to ErbB2. In some embodiments, an anti-VEGF antibody contains an MRD that binds Ang2, an MRD that binds IGF1R, and an MRD that inhibits the binding of pertuzumab to ErbB2.

In specific embodiments, the MRD-containing antibody targets TNF and an angiogenic factor. In another embodiment, the antibody targets TNF, and at least one MRD targets an angiogenic factor. In one embodiment, an antibody that binds to the same TNF epitope as adalimumab is operably linked to at least one MRD that targets an angiogenic factor. In an additional embodiment, an antibody that competitively inhibits adalimumab binding is operably linked to at least one MRD that targets an angiogenic factor. In additional embodiments, an antibody that comprises the sequences of SEQ ID NOS:80-85 is operably linked to at least one MRD that targets an angiogenic factor. In additional embodiments, the adalimumab antibody is operably linked to at least one MRD that targets an angiogenic factor. In one embodiment, an antibody that binds to the same TNF epitope as golimumab is operably linked to at least one MRD that targets an angiogenic factor. In an additional embodiment, an antibody that competitively inhibits golimumab binding is operably linked to at least one MRD that targets an angiogenic factor. In additional embodiments, the golimumab antibody is operably linked to at least one MRD that targets an angiogenic factor.

In some embodiments, an antibody that binds to TNF is operably linked to an MRD that targets Ang2. In some embodiments, the antibody that binds to TNF is linked to an Ang2 binding MRD that binds to the same Ang2 epitope as an MRD comprising the sequence of SEQ ID NO:8. In some embodiments, the antibody that binds to TNF is linked to an Ang2 binding MRD that competitively inhibits an MRD comprising the sequence of SEQ ID NO:8. In some embodiments, the antibody that binds to TNF is linked to an MRD comprising the sequence of SEQ ID NO:8.

In some embodiments, at least one Ang2 binding MRD is operably linked to the C-terminus of the heavy chain of an antibody that binds to TNF. In some embodiments, at least one Ang2 binding MRD is operably linked to the N-terminus of the heavy chain of an antibody that binds to TNF. In some embodiments, at least one Ang2 binding MRD is operably linked to the C-terminus of the light chain of an antibody that binds to TNF. In some embodiments, at least one Ang2 binding MRD is operably linked to the N-terminus of the light chain of an antibody that binds to TNF.

In some embodiments, at least one Ang2 binding MRD is operably linked directly to an antibody that binds to TNF. In additional embodiments, at least one Ang2 binding MRD is operably linked to an antibody that binds to TNF via a linker.

In some embodiments, the anti-TNF antibody operably linked to an Ang2 binding MRD binds to both TNF and Ang2 simultaneously. In some embodiments, the anti-TNF antibody operably linked to an Ang2 binding MRD exhibits ADCC activity. In additional embodiments, the anti-TNF antibody operably linked to an Ang2 binding MRD inhibits binding of TNF to the p55 and p75 cell surface TNF receptors. In additional embodiments, the anti-TNF antibody operably linked to an Ang2 binding MRD lyses surface TNF-expressing cells in vitro in the presence of complement. In additional embodiments, the anti-TNF antibody operably linked to an Ang2 binding MRD inhibits Ang2 binding to TIE2. In additional embodiments, the anti-TNF antibody operably linked to an Ang2 binding MRD reduces the signs and symptoms of arthritis.

In some embodiments, the MRD-containing antibody targets TNF and IL6. In some embodiments, the MRD-containing antibody is capable of binding TNF and IL6 simultaneously. Thus, in some embodiments, an antibody that binds to TNF is operably linked to an MRD that targets IL6. In other embodiments, an antibody that binds to IL6 is operably linked to an MRD that targets TNF.

In some embodiments, at least one IL6-binding MRD is operably linked to the C-terminus of the heavy chain of an antibody that binds TNF. In some embodiments, at least one IL6-binding MRD is operably linked to the N-terminus of the heavy chain of an antibody that binds to TNF. In some embodiments, at least one IL6-binding MRD is operably linked to the C-terminus of the light chain of an antibody that binds to TNF. In some embodiments, at least one IL6-binding MRD is operably linked to the N-terminus of the light chain of an antibody that binds to TNF.

In some embodiments, at least one TNF-binding MRD is operably linked to the C-terminus of the heavy chain of an antibody that binds IL6. In some embodiments, at least one TNF-binding MRD is operably linked to the N-terminus of the heavy chain of an antibody that binds to IL6. In some embodiments, at least one TNF-binding MRD is operably linked to the C-terminus of the light chain of an antibody that binds to IL6. In some embodiments, at least one TNF-binding MRD is operably linked to the N-terminus of the light chain of an antibody that binds to IL6.

In some embodiments, at least one IL6-binding MRD is operably linked directly to an antibody that binds to TNF. In additional embodiments, at least one IL6-binding MRD is operably linked to an antibody that binds to TNF via a linker.

In some embodiments, at least one TNF-binding MRD is operably linked directly to an antibody that binds to IL6. In additional embodiments, at least one TNF-binding MRD is operably linked to an antibody that binds to IL6 via a linker.

In some embodiments, the MRD-containing antibody targets TNF and BLyS. In some embodiments, the MRD-containing antibody is capable of binding TNF and BLyS simultaneously. In some embodiments, an antibody that binds to TNF is operably linked to an MRD that targets BLyS. In other embodiments, an antibody that binds to BLyS is operably linked to an MRD that targets TNF.

In some embodiments, at least one BLyS-binding MRD is operably linked to the C-terminus of the heavy chain of an antibody that binds TNF. In some embodiments, at least one BLyS-binding MRD is operably linked to the N-terminus of the heavy chain of an antibody that binds to TNF. In some embodiments, at least one BLyS-binding MRD is operably linked to the C-terminus of the light chain of an antibody that binds to TNF. In some embodiments, at least one BLyS-binding MRD is operably linked to the N-terminus of the light chain of an antibody that binds to TNF.

In some embodiments, at least one TNF-binding MRD is operably linked to the C-terminus of the heavy chain of an antibody that binds BLyS. In some embodiments, at least one TNF-binding MRD is operably linked to the N-terminus of the heavy chain of an antibody that binds to BLyS. In some embodiments, at least one TNF-binding MRD is operably linked to the C-terminus of the light chain of an antibody that binds to BLyS. In some embodiments, at least one TNF-binding MRD is operably linked to the N-terminus of the light chain of an antibody that binds to BLyS.

In some embodiments, at least one BLyS-binding MRD is operably linked directly to an antibody that binds to TNF. In additional embodiments, at least one BLyS-binding MRD is operably linked to an antibody that binds to TNF via a linker.

In other embodiments, at least one TNF-binding MRD is operably linked directly to an antibody that binds to BLyS. In additional embodiments, at least one TNF-binding MRD is operably linked to an antibody that binds to BLyS via a linker.

In some embodiments, the MRD-containing antibody targets Ang2, TNF, and IL6. In some embodiments, the MRD-containing antibody is capable of binding Ang2, TNF, and IL6 simultaneously. In some embodiments, an antibody that binds to TNF is operably linked to an MRD that targets Ang2 and an MRD that targets IL6. In some embodiments, the Ang2 and IL6-binding MRDs are located on the same antibody chain. In some embodiments, the Ang2 and IL6-binding MRDs are located on the same antibody terminus. In some embodiments, the Ang2 and IL6-binding MRDs are located on different antibody chains. In some embodiments, the Ang2 and IL6-binding MRDs are located on different antibody termini.

In some embodiments, an antibody that binds to Ang2 is operably linked to an MRD that targets TNF and an MRD that targets IL6. In some embodiments, the TNF and IL6-binding MRDs are located on the same antibody chain. In some embodiments, the TNF and IL6-binding MRDs are located on the same antibody terminus. In some embodiments, the TNF and IL6-binding MRDs are located on different antibody chains. In some embodiments, the TNF and IL6-binding MRDs are located on different antibody termini.

In some embodiments, an antibody that binds to IL6 is operably linked to an MRD that targets Ang2 and an MRD that targets TNF. In some embodiments, the Ang2 and TNF-binding MRDs are located on the same antibody chain. In some embodiments, the Ang2 and TNF-binding MRDs are located on the same antibody terminus. In some embodiments, the Ang2 and TNF-binding MRDs are located on different antibody chains. In some embodiments, the Ang2 and TNF-binding MRDs are located on different antibody termini.

In some embodiments, the MRD-containing antibody targets Ang2, TNF, and BLyS. In some embodiments, the MRD-containing antibody is capable of binding Ang2, TNF, and BLyS simultaneously. In some embodiments, an antibody that binds to TNF is operably linked to an MRD that targets Ang2 and an MRD that targets BLyS. In other embodiments, an antibody that binds to BLyS is operably linked to an MRD that targets TNF and an MRD that targets Ang2. In other embodiments, an antibody that binds to Ang2 is operably linked to an MRD that targets TNF and an MRD that targets BLyS. In some embodiments, the Ang2, BLyS, and/or TNF-binding MRDs are located on the same antibody chain. In some embodiments, Ang2, BLyS, and/or TNF-binding MRDs are located on the same antibody terminus. In some embodiments, the Ang2, BLyS, and/or TNF-binding MRDs are located on different antibody chains. In some embodiments, the Ang2, BLyS, and/or TNF-binding MRDs are located on different antibody termini.

In some embodiments, the MRD-containing antibody targets Ang2, TNF, IL6, and BLyS. In some embodiments, the MRD-containing antibody is capable of binding Ang2, TNF, IL6 and BLyS simultaneously. In some embodiments, an antibody that binds to TNF is operably linked to an MRD that targets Ang2, an MRD that targets IL6, and an MRD that targets BLyS. In some embodiments, an antibody that binds to Ang2 is operably linked to an MRD that targets TNF, an MRD that targets IL6, and an MRD that targets BLyS. In some embodiments, an antibody that binds to IL6 is operably linked to an MRD that targets Ang2, an MRD that targets TNF, and an MRD that targets BLyS. In some embodiments, an antibody that binds to BLyS is operably linked to an MRD that targets Ang2, an MRD that targets IL6, and an MRD that targets TNF. In some embodiments, the TNF, Ang2, IL6, and/or BLyS-binding MRDs are located on the same antibody chain. In some embodiments, the TNF, Ang2, IL6 and/or BLyS-binding MRDs are located on the same antibody terminus. In some embodiments, the TNF, Ang2, IL6, and/or BLyS-binding MRDs are located on different antibody chains. In some embodiments, the TNF, Ang2, IL6 and/or BLyS-binding MRDs are located on different antibody termini.

VI. Methods of Making Antibody-MRD Fusions

The multivalent and multispecific compositions of the invention (e.g., MRD-containing antibodies) and MRDs can be produced by any method known in the art for the synthesis of antibodies, polypeptides, immunoconjugates, and cytotoxins, in particular, by chemical synthesis or by recombinant expression techniques. An advantage of multivalent and multispecific compositions (e.g., MRD-containing antibodies) is that they can be produced using protocols that are known in the art for producing antibodies. The antibody-MRD fusion molecules can be encoded by a polynucleotide comprising a nucleotide sequence. Thus, the polynucleotides described herein can encode an MRD, an antibody heavy chain, an antibody light chain, a fusion protein comprising an antibody heavy chain and at least one MRD, and/or a fusion protein comprising an antibody light chain and at least one MRD.

Accordingly, the invention provides vector constructs comprising a polynucleotide sequence(s) encoding multivalent and multispecific compositions (e.g., MRD-containing antibodies) and a host cell comprising these vector constructs. Standard techniques for cloning and transformation may be used in the preparation of cell lines expressing the multivalent and multispecific compositions (e.g., MRD-containing antibodies) of the invention.

Recombinant expression vectors containing a polynucleotide sequence(s) encoding multivalent and multispecific compositions (e.g., MRD-containing antibodies) of the invention can be prepared using well known techniques. The expression vectors include a polynucleotide coding sequence operably linked to suitable transcriptional or translational regulatory nucleotide sequences such as, those derived from mammalian, microbial, viral, or insect genes. Exemplary regulatory sequences present in the expression vector constructs include transcriptional promoters, operators, enhancers, mRNA ribosomal binding sites, and/or other appropriate sequences which control transcription and translation initiation and termination. Nucleotide sequences are "operably linked" when the regulatory sequence functionally relates to the nucleotide sequence for the appropriate polypeptide. Thus, a promoter sequence is operably linked to, for example, an antibody heavy chain-MRD sequence if the promoter nucleotide sequence controls the transcription of the appropriate nucleotide sequence.

The polynucleotide coding sequence in the expression vector can include additional heterologous sequences encoding polypeptides such as, signal peptides that are not naturally associated with antibody heavy and/or light chain sequences. For example, a nucleotide sequence for a signal peptide (secretory leader) can be fused in-frame to the polypeptide sequence so that the MRD-containing antibody is secreted to the periplasmic space or into the medium. A signal peptide that is functional in the intended host cells enhances extracellular secretion of the appropriate antibody. The signal peptide can be cleaved from the polypeptide upon secretion of antibody from the cell. Examples of sequences encoding secretory signals that can be included in the expression vectors include those described in for example, U.S. Pat. Nos. 5,698,435, 5,698,417, and 6,204,023.

A variety of host-expression vector systems can be utilized to express the coding sequence an MRD-containing antibody.

Host cells useful in the present invention include but are not limited to microorganisms such as, bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing MRD-containing antibody coding sequences. In particular embodiments, the mammalian cell systems are used to produce the multivalent and multispecific compositions of the invention (e.g., MRD-containing antibodies). Mammalian cell systems typically utilize recombinant expression constructs containing promoters derived from the genome of mammalian cells (e.g., metallothionein promoter) or from mammalian viruses (e.g., the adenovirus late promoter; the vaccinia virus 7.5K promoter). Examples of mammalian host cells useful for producing the multivalent and multispecific compositions of the invention include, CHO cells, BHK cells, NS0 cells, SP2/0 cells, YO myeloma cells, P3X63 mouse myeloma cells, PER cells, PER.C6 cells, COS cells, 293 cells, 3T3 cells and hybridoma cells.

Vectors containing the polynucleotides encoding the multivalent and multispecific compositions of the invention (e.g., MRD containing antibodies) or portions or fragments thereof, include plasmid vectors, a single and double-stranded phage vectors, as well as single and double-stranded RNA or DNA viral vectors. The vectors can be routinely introduced into host cells using known techniques for introducing DNA and RNA into cells. Phage and viral vectors may also be introduced into host cells in the form of packaged or encapsulated virus using known techniques for infection and transduction. Moreover, viral vectors may be replication competent or alternatively, replication defective. Alternatively, cell-free translation systems may also be used to produce the protein using RNAs derived from the DNA expression constructs of the invention (see, e.g., Intl. Appl. Publ. WO86/05807 and WO89/01036; and U.S. Pat. No. 5,122,464).

Also provided herein, are methods of producing an MRD-containing antibody, the method comprising: culturing a host cell comprising one or more polynucleotides or an expression vector comprising one or more isolated polynucleotides in a medium under conditions allowing the expression of said one or more polynucleotide, wherein said one or more polynucleotides encodes one or more polypeptides that form part of MRD-containing antibody; and recovering said MRD-containing antibody.

Prokaryotes useful as host cells in producing the compositions of the invention (e.g., MRDs) include gram negative or gram positive organisms such as, *E. coli* and *B. subtilis*. Expression vectors for use in prokaryotic host cells generally contain one or more phenotypic selectable marker genes (e.g., genes encoding proteins that confer antibiotic resistance or that supply an autotrophic requirement). Examples of useful prokaryotic host expression vectors include the pKK223-3 (Pharmacia, Uppsala, Sweden), pGEM1 (Promega, Wis., USA), pET (Novagen, Wis., USA) and pRSET (Invitrogen, Calif., USA) series of vectors (see, e.g., Studier, J. Mol. Biol. 219:37 (1991) and Schoepfer, Gene 124:83 (1993)). Exemplary promoter sequences frequently used in prokaryotic host cell expression vectors include T7, (Rosenberg et al., Gene 56: 125-135 (1987)), beta-lactamase (penicillinase), lactose promoter system (Chang et al., Nature 275:615 (1978)); and Goeddel et al., Nature 281:544 (1979)), tryptophan (trp) promoter system (Goeddel et al., Nucl. Acids Res. 8:4057, (1980)), and tac promoter (Sambrook et al., 1990, Molecular Cloning, A Laboratory Manual, 2d Ed., Cold Spring Harbor Laboratory, Cold Spring Harbor, N.Y.).

In alternative embodiments, eukaryotic host cell systems can be used, including yeast cells transformed with recombinant yeast expression vectors containing the coding sequence of an MRD-containing antibody of the present invention, such as, the expression systems taught in U.S. Pat. Appl. No. 60/344,169 and WO03/056914 (methods for producing human-like glycoprotein in a non-human eukaryotic host cell) (the contents of each of which are incorporated by reference in their entirety). Exemplary yeast that can be used to produce compositions of the invention, such as, MRDs, include yeast from the genus *Saccharomyces, Pichia*, Actinomycetes and *Kluyveromyces*. Yeast vectors typically contain an origin of replication sequence from a 2mu yeast plasmid, an autonomously replicating sequence (ARS), a promoter region, sequences for polyadenylation, sequences for transcription termination, and a selectable marker gene. Examples of promoter sequences in yeast expression constructs include, promoters from metallothionein, 3-phosphoglycerate kinase (Hitzeman et al., J. Biol. Chem. 255:2073, (1980)) and other glycolytic enzymes, such as, enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Additional suitable vectors and promoters for use in yeast expression as well as yeast transformation protocols are known in the art. See, e.g., Fleer et al., Gene, 107:285-195 (1991) and Hinnen et al., Proc. Natl. Acad. Sci., 75:1929 (1978).

Insect and plant host cell culture systems are also useful for producing the compositions of the invention. Such host cell systems include for example, insect cell systems infected with recombinant virus expression vectors (e.g., baculovirus) containing the coding sequence of an MRD-containing antibody; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of an MRD-containing antibody, including, but not limited to, the expression systems taught in U.S. Pat. No. 6,815,184, WO2004/057002, WO2004/024927, U.S. Pat. Appl. Nos. 60/365,769, 60/368, 047, and WO2003/078614, the contents of each of which is herein incorporated by reference in its entirety.

In alternate embodiments, other eukaryotic host cell systems may be used, including animal cell systems infected with recombinant virus expression vectors (e.g., adenovirus, vaccinia virus) including cell lines engineered to contain multiple copies of the DNA encoding an MRD-containing antibody either stably amplified (CHO/dhfr) or unstably amplified in double-minute chromosomes (e.g., murine cell lines). In one embodiment, the vector comprising the polynucleotide(s) encoding the MRD-containing antibody of the invention is polycistronic.

Exemplary mammalian cells useful for producing these compositions include 293 cells (e.g., 293T and 293F), CHO cells, BHK cells, NS0 cells, SP2/0 cells, YO myeloma cells, P3X63 mouse myeloma cells, PER cells, PER.C6 (Crucell, Netherlands) cells or hybridoma cells, other mammalian cells. Additional exemplary mammalian host cells that are useful in practicing the invention include but are not limited, to VERY, Hela, COS, MDCK, 3T3, W138, BT483, Hs578T, HTB2, BT20 and T47D, CRL7O3O and HsS78Bst cells. Some examples of expression systems and selection methods are described in the following references and references cited therein: Borth et al., Biotechnol. Bioen. 71(4):266-73 (2000-2001), in Werner et al., Arzneimittelforschung/Drug Res. 48(8):870-80 (1998), in Andersen and Krummen, Curr. Op. Biotechnol. 13:117-123 (2002), in Chadd and Chamow, Curr. Op. Biotechnol. 12:188-194 (2001), and in Giddings, Curr. Op. Biotechnol. 12: 450-454 (2001). Additional examples of expression systems and selection methods are described in Logan & Shenk, Proc. Natl. Acad. Sci. USA, 81:355-359 (1984), Bittner et al., Methods in Enzymol. 153:51-544(1987)). Transcriptional and translational control sequences for mammalian host cell expression vectors are frequently derived from viral genomes. Commonly used promoter sequences and enhancer sequences in mammalian expression vectors include, sequences derived from Polyoma virus, Adenovirus 2, Simian Virus 40 (SV40), and human cytomegalovirus (CMV). Exemplary commercially available expression vectors for use in mammalian host cells include pCEP4 (Invitrogen®) and pcDNA3 (Invitrogen®).

A number of selection systems can be used in mammalian host-vector expression systems, including, but not limited to, the herpes simplex virus thymidine kinase, hypoxanthine-guanine phosphoribosyltransferase and adenine phosphoribosyltransferase (Lowy et al., Cell 22:817 (1980)) genes, which can be employed in tk, hgprt⁻ or aprt⁻ cells, respectively. Additionally, antimetabolite resistance can be used as the basis of selection for e.g., dhfr, gpt, neo, hygro, trpB, hisD, ODC (ornithine decarboxylase), and the glutamine synthase system.

Methods which are well known to those skilled in the art can be used to construct expression vectors containing the coding sequence of an MRD-containing antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989) and Ausubel et al., CURRENT PROTOCOLS IN MOLECULAR BIOLOGY, Greene Publishing Associates and Wiley Interscience, N.Y (1989).

A variety of host-expression vector systems may be utilized to express the coding sequence an MRD-containing antibody. A host cell strain can be chosen which modulates the expression of inserted antibody sequences, or modifies and processes the antibody gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used.

Stable expression typically achieves more reproducible results than transient expression and also is more amenable to large-scale production; however, it is within the skill of one in the art to determine whether transient expression is better for a particular situation. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

In some embodiments, the multivalent and multispecific compositions (e.g., MRD-containing antibodies) are expressed at levels (titers) comparable to those of antibodies. In some embodiments, the multivalent and multispecific compositions (e.g., MRD-containing antibodies) are expressed at least about 10 µg/ml, at least about 20 µg/ml, or at least about 30 µg/ml. In some embodiments, the multivalent and multispecific compositions (e.g., MRD-containing antibodies) are expressed at least about 40 µg/ml or at least about 50 µg/ml. In some embodiments, the multivalent and multispecific compositions (e.g., MRD-containing antibodies) are expressed at least about 60 µg/ml, at least about 70 µg/ml, at least about 80 µg/ml, at least about 90 µg/ml, at least about 95 µg/ml, at least about 100 µg/ml, at least about 110 µg/ml, at least about 120 µg/ml, at least about 130 µg/ml, at least about 140 µg/ml, at least about 150 µg/ml, at least about 160 µg/ml, at least about 170 µg/ml, at least about 180 µg/ml, at least about 190 µg/ml, or at least about 200 µg/ml. The expression levels of an antibody molecule can be increased by vector amplification and the use recombinant methods and tools known in the art, including chromatin remodeling strategies to enhance transgene expression.

The present invention is further directed to a method for modifying the glycosylation profile of an MRD-containing antibody that is produced by a host cell, comprising expressing in said host cell a nucleic acid encoding an MRD-containing antibody and a nucleic acid encoding a polypeptide with a glycosyltransferase activity, or a vector comprising such nucleic acids. Genes with glycosyltransferase activity include β(1,4)-N-acetylglucosaminyltransferase III (GnTIII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). In one embodiment, a combination of genes with glycosyltransferase activity are expressed in the host cell (e.g., GnTIII and Man II). Likewise, the method also encompasses expression of one or more polynucleotide(s) encoding the MRD-containing antibody in a host cell in which a glycosyltransferase gene has been disrupted or otherwise deactivated (e.g., a host cell in which the activity of the gene encoding α1-6 core fucosyltransferase has been knocked out). In another embodiment, the MRD-containing antibody can be produced in a host cell that further expresses a polynucleotide encoding a polypeptide having GnTIII activity to modify the glycosylation pattern. In a specific embodiment, the polypeptide having GnTIII activity is a fusion polypeptide comprising the Golgi localization domain of a Golgi resident polypeptide. In another embodiment, the expression of the MRD-containing antibody in a host cell that expresses a polynucleotide encoding a polypeptide having GnTIII activity results in an MRD-containing antibody with increased Fc receptor binding affinity and increased effector function. Accordingly, in one embodiment, the present invention is directed to a host cell comprising (a) an isolated nucleic acid comprising a sequence encoding a polypeptide having GnTIII activity; and (b) an isolated polynucleotide encoding an MRD-containing antibody of the present invention, such as, a chimeric, primatized or humanized antibody. In another embodiment, the polypeptide having GnTIII activity is a fusion polypeptide comprising the catalytic domain of GnTIII and the Golgi localization domain is the localization domain of mannosidase II. Methods for generating such fusion polypeptides and using them to produce antibodies with increased effector functions are disclosed in U.S. Provisional Pat. Appl. No. 60/495,142 and U.S. Pat. Appl. Publ. No. 2004/0241817, each of which is herein incorporated by reference.

The multivalent and multispecific compositions (e.g., MRD-containing antibodies) with altered glycosylation produced by the host cells of the invention typically exhibit increased Fc receptor binding affinity and/or increased effector function as a result of the modification of the host cell (e.g., by expression of a glycosyltransferase gene). The increased Fc receptor binding affinity can be increased binding to an Fcγ activating receptor, such as, the FcγRIIIa receptor. The increased effector function can be an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming.

Once a multivalent and monovalent multispecific composition (e.g., MRD-containing antibody) of the invention has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In additional embodiments, the multivalent and multispecific compositions of the present invention or fragments thereof are optionally fused to heterologous polypeptide sequences described herein or otherwise known in the art to facilitate purification. In additional embodiments, the multivalent and multispecific compositions or fragments thereof are optionally fused to heterologous polypeptide sequences described herein or otherwise known in the art to facilitate purification. More particularly, it is envisioned that ligands (e.g., antibodies and other affinity matrices) for MRDs or other components of the multivalent and multispecific compositions can be used in affinity columns for affinity purification and that optionally, the MRDs or other components of the multivalent and monovalent multispecific composition that are bound by these ligands are removed from the composition prior to final preparation of the multivalent and multispecific compositions using techniques known in the art.

VII. Uses of Antibody-MRD Fusions

The multivalent and multispecific compositions (e.g., MRD-containing antibodies) described herein are useful in a variety of applications including, but not limited to, therapeutic treatment methods, such as, the treatment of cancer. In certain embodiments, the multivalent and multispecific compositions (e.g., MRD-containing antibodies) are useful for inhibiting tumor growth, reducing neovascularization, reducing angiogenesis, inducing differentiation, reducing tumor volume, and/or reducing the tumorigenicity of a tumor. The methods of use may be in vitro, ex vivo, or in vivo methods. Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. The 2006 edition of the Physician's Desk Reference (PDR) discloses the mechanism of action and preferred doses of treatment and dosing schedules for thalidomide (p 979-983), VELCADE® (p 2102-2106) and melphalan (p 976-979).

The multivalent and multispecific compositions (e.g., MRD-containing antibodies) are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The dosage ranges for the administration of the multivalent and multispecific compositions of the invention are those large enough to produce the desired effect in which the disease symptoms mediated by the target molecule are ameliorated. The dosage should not be so large as to cause adverse side effects, such as, hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

The preparation of a pharmacological composition that contains active ingredients dissolved or dispersed therein is well understood in the art. Typically such compositions are prepared as sterile injectables either as liquid solutions or suspensions, aqueous or nonaqueous. However, solid forms suitable for solution, or suspensions, in liquid prior to use can also be prepared. The preparation can also be emulsified. Thus, an antibody-MRD containing composition can take the form of solutions, suspensions, tablets, capsules, sustained release formulations or powders, or other compositional forms.

In some embodiments, the compositions of the invention (e.g., multivalent and multispecific compositions (e.g., MRD-containing antibodies)) are formulated to ensure or optimize distribution in vivo. For example, the blood-brain barrier (BBB) excludes many highly hydrophilic compounds and if so desired, the compositions are prepared so as to increase transfer across the BBB, by for example, formulation in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade Clin. Pharmacol. 29:685 (1989)).

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. Physiologically tolerable carriers are well known in the art. Likewise, composition of the present invention can include pharmaceutically acceptable salts of the components therein. Pharmaceutically acceptable salts include the acid addition salts (formed with the free amino groups of the polypeptide) that are formed with inorganic acids for example, hydrochloric or phosphoric acids, or such organic acids as acetic, tartaric, mandelic and the like. Salts formed with the free carboxyl groups can also be derived from inorganic bases for example, sodium, potassium, ammonium, calcium or ferric hydroxides, and such organic bases as isopropylamine, trimethylamine, 2-ethylamino ethanol, histidine, procaine and the like Liquid compositions can also contain liquid phases in addition to and to the exclusion of water. Exemplary of such additional liquid phases are glycerin, vegetable oils such as, cottonseed oil, organic esters such as, ethyl oleate, and water-oil emulsions.

In one embodiment, a therapeutic composition contains a multivalent and monovalent multispecific composition (e.g., MRD-containing antibody) of the present invention, typically in an amount of at least 0.1 weight percent of MRD-containing antibody fusion per weight of total therapeutic composition. A weight percent is a ratio by weight of MRD-containing antibody per total composition. Thus, for example, 0.1 weight percent is 0.1 grams of MRD-containing antibody per 100 grams of total composition.

The MRD-containing antibody are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The dosage schedule and amounts effective for therapeutic and prophylactic uses, i.e., the "dosing regimen", will depend upon a variety of factors, including the cause, stage and severity of the disease or disorder, the health, physical status, age of the mammal being treated, and the site and mode of the delivery of the MRD-containing antibody. Therapeutic efficacy and toxicity of the complex and formation can be determined by standard pharmaceutical, pharmacological, and toxicological procedures in cell cultures or experimental animals. Data obtained from these procedures can likewise be used in formulating a range of dosages for human use. Moreover, therapeutic index (i.e., the dose therapeutically effective in 50 percent of the population divided by the dose lethal to 50 percent of the population ($ED_{50}/LD_{50}$)) can readily be determined using known procedures. The dosage is preferably within a range of concentrations that includes the $ED_{50}$ with little or no toxicity, and may vary within this range depending on the dosage form employed, sensitivity of the patient, and the route of administration.

The dosage regimen also takes into consideration pharmacokinetics parameters known in the art, such as, drug absorption rate, bioavailability, metabolism and clearance (see, e.g., Hidalgo-Aragones, J. Steroid Biochem. Mol. Biol. 58:611-617 (1996); Groning et al., Pharmazie 51:337-341 (1996); Fotherby Contraception 54:59-69 (1996); and Johnson et al., J. Pharm. Sci. 84:1144-1146 (1995)). It is well within the state of the art for the clinician to determine the dosage regimen for each subject being treated. Moreover, single or multiple administrations of a multivalent and monovalent multispecific composition (e.g., MRD-containing antibody) containing compositions can be administered depending on the dosage and frequency as required and tolerated by the subject. The duration of prophylactic and therapeutic treatment will vary depending on the particular disease or condition being treated. Some diseases are amenable to acute treatment whereas others require long-term, chronic therapy. When treating with an additional therapeutic agent, MRD-containing antibody) can be administered serially, or simultaneously with the additional therapeutic agent.

Therapeutically effective amounts of MRD-containing antibody of the invention vary according to, for example, the targets of the MRD-containing antibody and the potency of conjugated cytotoxic agents encompassed by various embodiments of the invention Thus, for example therapeutically effective dose of an a multivalent and monovalent multispecific composition (e.g., MRD-containing antibody) that "mops up" a soluble ligand, such as, TNF alpha, is expected to be higher than that for an a multivalent and monovalent multispecific composition (e.g., MRD-containing antibody) that redirects T cell effector function to a target on a hematological malignancy. Likewise, therapeutically effective amounts of a multivalent and multispecific compositions (e.g., MRD-containing antibodies) comprising a maytansinoid cytotoxic agent are likely to be lower than the dosage of an a multivalent and monovalent multispecific composition (e.g., MRD-containing antibody) comprising a less potent chemotherapeutic, such as, taxol, or the counterpart a multivalent and monovalent multispecific composition does not contain a cytotoxic agent.

According to one embodiment, a therapeutically effective dose of an a multivalent and monovalent multispecific composition (e.g., MRD-containing antibody) is an amount selected from about 0.00001 mg/kg to about 20 mg/kg, from about 0.00001 mg/kg to about 10 mg/kg, from about 0.00001 mg/kg to about 5 mg/kg, from about 0.0001 mg/kg to about 20 mg/kg, from about 0.0001 mg/kg to about 10 mg/kg, from about 0.0001 mg/kg to about 5 mg/kg, from about 0.001 mg/kg to about 20 mg/kg, from about 0.001 mg/kg to about 10 mg/kg, and from about 0.001 mg/kg to about 5 mg/kg of the patient's body weight, in one or more dose administrations daily, for one or several days.

According to another embodiment, a therapeutically effective amount of an a multivalent and monovalent multispecific composition (e.g., MRD-containing antibody) is an amount such that when administered in a physiologically tolerable composition is sufficient to achieve a plasma concentration of from about 0.1 microgram (µg) per milliliter (ml) to about 100 µg/ml, from about 1 µg/ml to about 5 µg/ml, and usually about 5 µg/ml. Stated differently, in another embodiment, the dosage can vary from about 0.1 mg/kg to about 300 mg/kg, from about 0.2 mg/kg to about 200 mg/kg, from about 0.5 mg/kg to about 20 mg/kg, in one or more dose administrations daily, for one or several days.

In some embodiments, the a multivalent and monovalent multispecific composition (e.g., MRD-containing antibody) is administered at about 1 mg/kg to about 50 mg/kg, about 1 mg/kg to about 25 mg/kg, about 1 mg/kg to about 20 mg/kg, about 1 mg/kg to about 15 mg/kg, about 1 mg/kg to about 10 mg/kg, or about 1 mg/kg to about 5 mg/kg.

In additional embodiments, the interval between dose administration of the multivalent and monovalent multispecific composition (e.g., an MRD-containing antibody) is about daily, about twice a week, about every week, about every other week, or about every three weeks. In some embodiments, the multivalent and monovalent multispecific composition is administered first at a higher loading dose and subsequently at a lower maintenance dose.

In further embodiments, therapeutic composition comprise multivalent and multispecific compositions (e.g., MRD-containing antibodies) in an amount of at least 0.1 weight percent of antibody per weight of total therapeutic composition. A weight percent is a ratio by weight of antibody/total composition. Thus, for example, 0.1 weight percent is 0.1 grams of antibody-MRD per 100 grams of total composition. According to some embodiments, a therapeutic composition comprising a multivalent and monovalent multispecific composition contains about 10 micrograms (µg) per milliliter (ml) to about 100 milligrams (mg) per ml of antibody as active ingredient per volume of composition. In additional embodiments, a therapeutic composition comprising a multivalent and monovalent multispecific composition contains about 1 mg/ml to about 10 mg/ml (i.e., about 0.1 to 1 weight percent) of antibody as active ingredient per volume of composition.

As shown in the examples herein, a multivalent and multispecific composition (e.g., an MRD containing antibody) can have a similar PK profile to a corresponding antibody. Thus, in some embodiments, an antibody-MRD is administered in a dosing concentration and regimen that is the same as the antibody component of the antibody-MRD molecule alone (e.g., a commercial antibody, or a so-called "biosimilar" or a "biobetter" thereof). Likewise, the multivalent and multispecific composition can have a different PK profile from a corresponding antibody. For example, in embodiments where the multivalent and multispecific compositions redirect a T cell response and/or include a cytotoxic agent, the dosing concentration is expected to be less than that of the corresponding antibody. In these instances, therapeutically effective dosing concentrations and regimens for these compositions can routinely be determined using factors and criteria known in the art.

The multivalent and multispecific compositions (e.g., MRD-containing antibodies) need not be, but optionally are, formulated with one or more agents currently used to prevent or treat the disorder in question. The effective amount of such other agents depends on the amount of multivalent and monovalent multispecific composition present in the formulation, the type of disorder or treatment, and other factors discussed above.

As discussed above, the appropriate dosage of the multivalent and monovalent multispecific composition (e.g., MRD-containing antibody) will depend on the type of disease to be treated, as defined above, the severity and course of the disease, previous therapy, the patient's clinical history, and the discretion of the attending physician. The multivalent and monovalent multispecific composition is suitably administered to the patient at one time or over a series of treatments. Preferably, the multivalent and monovalent multispecific composition is administered by intravenous infusion or by subcutaneous injections. According to some embodiments, the multivalent and monovalent multispecific composition is administered parenterally by injection or by gradual infusion over time. Although the target molecule can typically be accessed in the body by systemic administration and therefore most often treated by intravenous administration of therapeutic compositions, other tissues and delivery means are contemplated where there is likelihood that the tissue targeted contains the target molecule. Thus, the multivalent and monovalent multispecific composition can be administered intravenously, intraperitoneally, intramuscularly, subcutaneously, intracavity, transdermally, and can be delivered by peristaltic means. Multivalent and multispecific compositions can also be delivered by aerosol to airways and lungs. In some embodiments, the antibody-MRD molecule is administered by intravenous infusion. In some embodiments, the antibody-MRD molecule is administered by subcutaneous injection.

The therapeutic compositions containing a multivalent and monovalent multispecific composition (e.g., MRD-containing antibody) can conventionally be administered intravenously, as by injection of a unit dose, for example. The term "unit dose" when used in reference to a therapeutic composition of the present invention refers to physically discrete units suitable as unitary dosage for the patient, each unit containing a predetermined quantity of active material calculated to produce the desired therapeutic effect in association with the required diluent; i.e., carrier, or vehicle. In a specific embodiment, the therapeutic compositions containing a human monoclonal antibody or a polypeptide are administered subcutaneously.

The compositions of the invention are administered in a manner compatible with the dosage formulation, and in a therapeutically effective amount. The quantity to be administered depends on the patient to be treated, capacity of the patient's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In other embodiments, the invention provides a method for treating or preventing a disease, disorder, or injury comprising administering a therapeutically effective amount or prophylactically effective amount of antibody-MRD molecule to a patient in need thereof. In some embodiments, the disease, disorder or injury is cancer. In other embodiments, the disease, disorder or injury is a disease or disorder of the immune system, such as, inflammation or an autoimmune disease.

Multivalent and multispecific compositions (e.g., MRD-containing antibodies) are expected to have at least the same therapeutic efficacy as the antibody contained in the MRD antibody containing antibody when administered alone. Accordingly, it is envisioned that the multivalent and multispecific compositions (e.g., MRD-containing antibodies) can be administered to a patient to treat or prevent a disease, disorder, or injury for which the antibody contained in the MRD-containing antibody, or an antibody that functions in the same way as the antibody contained in the MRD-containing antibody, demonstrates a reasonably correlated beneficial activity in treating or preventing such disease, disorder or injury. This beneficial activity can be demonstrated in vitro, in an in vivo animal model, or in human clinical trials. In one embodiment, an MRD-containing antibody is administered to a patient to treat or prevent a disease, disorder or injury for which the antibody component of the MRD-containing antibody, or an antibody that functions in the same way as the antibody contained in the MRD-containing antibody, demonstrates therapeutic or prophylactic efficacy in vitro or in an animal model. In another embodiment, an MRD-containing antibody is administered to a patient to treat or prevent a disease, disorder or injury for which the antibody component of the MRD-containing antibody, or an antibody that functions in the same way as the antibody contained in the MRD-containing antibody, demonstrates therapeutic or prophylactic efficacy in humans. In another embodiment, an MRD-containing antibody is administered to a patient to treat or prevent a disease, disorder or injury for which the antibody component of the MRD-containing antibody, or an antibody that functions in the same way as the antibody contained in the MRD-containing antibody, has been approved by a regulatory authority for use in such treatment or prevention.

In another embodiment, an MRD-containing antibody is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, demonstrates therapeutic or prophylactic efficacy in vitro or in an animal model. In another embodiment, an MRD-containing antibody is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, demonstrates therapeutic or prophylactic efficacy in humans. In another embodiment, an MRD-containing antibody, is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, has been approved by a regulatory authority for use in such treatment or prevention. The administration of an MRD-containing antibody in combination with more than one therapeutic as described above is also encompassed by the invention.

According to one embodiment, an MRD-containing antibody is administered in combination with a compound that promotes apoptosis, inhibits apoptosis, promotes cell survival, inhibits cell survival, promotes senescence of diseased or aberrant cells, inhibits cell senescence, promotes cell proliferation, inhibits cell proliferation, promotes cell differentiation, inhibits cell differentiation, promotes cell activation, inhibits cell activation, promotes cell metabolism, inhibits cell metabolism, promotes cell adhesion, inhibits cell adhesion, promotes cell cycling or cell division, inhibits cell cycling or cell division, promotes DNA replication or repair, inhibits DNA replication or repair, promotes transcription or translation, or inhibits transcription or translation.

According to one embodiment, an MRD-containing antibody is administered in combination with a compound that promotes apoptosis or senescence of diseased or aberrant cells. In some embodiments, the MRD-containing antibody is administered in combination with a compound that agonizes, antagonizes or reduces the activity of: EGFR, ErbB2, cMET, TNFa, TGFb, integrin $\alpha v \beta 3$, TLR2, TLR3, TLR4, TLR5, TLR7, TLR8, TLR9, TNFR1, TNFRSF10A (TRAIL R1 DR4), TNFRSF10B (TRAIL R2 DR5), TNF, TRAIL, IFN beta, MYC, Ras, BCR, ABL, JNK, CKH2, CHK1, CDK1, RAC1, MEK, MOS, mTOR, AKT, NFkB, Ikk, IAP1, IAP2, XIAP, b-catenin, survivin, HDAC, HSP70, HSP90, proteasome 20S, topoisomerase 1, MDM2, E2F, or E2F1.

According to one embodiment, an MRD-containing antibody is administered in combination with a compound that inhibits cell survival. In some embodiments, the MRD-containing antibody is administered in combination with a compound that antagonizes or reduces the activity of: VEGF, VEGFR1, VEGFR2, IGF1R, IGF1, IGF2, PDGF-A, PDGF-B, PDGF-CC, PDGF-C, PDGF-D, PDGFRA, PDGFRB, TFGa, TGFB3, PI3K, TNFSF13B (BLYS), TNFRSF13C (BAFFR), JNK, NFKB, SIP, integrin $\alpha v \beta 3$, or survivin.

According to one embodiment, an MRD-containing antibody is administered in combination with a compound that regulates cell proliferation. In some embodiments, the MRD-containing antibody is administered in combination with a compound that antagonizes or reduces the activity of: VEGF, VEGFR, EGFR, ErbB2, NFKB, HIF, MUC1, MUC2, or HDAC.

According to one embodiment, an MRD-containing antibody is administered in combination with a compound that regulates cell adhesion. In some embodiments, the MRD-containing antibody is administered in combination with a compound that inhibits or reduces the activity of: MMP1, MMP2, MMP7, MMP9, MMP12, PLAU, $\alpha v \beta 1$ integrin, $\alpha v \beta 3$ integrin, $\alpha v \beta 5$ integrin, TGFb, EPCAM, $\alpha 1 \beta 1$ integrin, $\alpha 2 \beta 1$ integrin, $\alpha 4 \beta 1$ integrin, $\alpha 2 \beta 1$ integrin, $\alpha 5 \beta 1$ integrin, a9$\beta 1$ integrin, $\alpha 6 \beta 4$ integrin, $\alpha M \beta 2$ integrin, CEA, L1, Mel-CAM, or HIF1. In one embodiment the MRD-containing antibody is administered in combination with a compound that inhibits or reduces the activity of $\alpha v \beta 3$ integrin, $\alpha v \beta 5$ integrin, or $\alpha 5 \beta 1$ integrin. In specific embodiments the MRD-containing antibody is administered in combination with: MEDI-522 (VITAXIN, Abegrin; MedImmune), ATN-161 (Attenuon), EMD 121974 (Merck KGaA), CNTO 95 (Cenotocor), or velociximab (M200, Protein Design Labs).

According to one embodiment, an MRD-containing antibody is administered in combination with a compound that regulates cell activation. In some embodiments, the MRD-containing antibody is administered in combination with a compound that promotes, inhibits or reduces the activity of: CD80, CD86, MHC, PDL2 (B7-DC), B7-H1, B7-H2 (ICOSL), B7-H3, B7-H4, CD28, CTLA4, TCR, PD1, CD80, or ICOS.

According to one embodiment, an MRD-containing antibody is administered in combination with a compound that regulates cell cycling, cell division or mitosis. In some embodiments, the MRD-containing antibody is administered in combination with a compound that antagonizes or reduces the activity of: PI3K, SMO, Ptch, HH, SHH, plk1, plk2, plk3, plk4, aurora A, aurora B, aurora C, CDK1, CDK2, CDK4, CHK1, CHK2, GSK3B, PAK, NEK2A, ROCK 2, MDM2, EGF (KSP), proteasome 20S, HDAC, or survivin.

According to one embodiment, an MRD-containing antibody is administered in combination with a compound that regulates DNA replication or repair. In some embodiments, the MRD-containing antibody is administered in combination with a compound that antagonizes or reduces the activity of: BRCA1, CHK1, CHK2, E2F, E2FL, MDM2, MDM4, or PARP1.

According to one embodiment, an MRD-containing antibody is administered in combination with a compound that regulates transcription or translation. In some embodiments, the MRD-containing antibody is administered in combination with a compound that antagonizes or reduces the activity of: IGF1R, IGF1, IGF2, PDGFRA, PDGFRB, PDGF-A, PDGF-B, PDGF-CC, PDGF-C, PDGF-D, KIT, MYC, CD28, CDK4, CDK6, mTOR, MDM2, HDAC, E2F, E2F1, or HIF1.

According to one embodiment, an MRD-containing antibody is administered in combination with a compound that regulates migration, invasion or metastasis. In some embodiments, the MRD-containing antibody is administered in combination with a compound that inhibits or reduces the activity of: c-MET, RON, CXCR4, PI3K, AKT, MMP2, FN1, CATHD, AMF, $\alpha v \beta 1$ integrin, $\alpha v \beta 3$ integrin, $\alpha v \beta 5$ integrin, TGFb, $\alpha 1 \beta 1$ integrin, $\alpha 2 \beta 1$ integrin, $\alpha 4 \beta 1$ integrin, $\alpha 2 \beta 1$ integrin, $\alpha 5 \beta 1$ integrin, a9$\beta 1$ integrin, $\alpha 6 \beta 4$ integrin, $\alpha M \beta 2$ integrin, or HIF1.

According to one embodiment, an MRD-containing antibody is administered in combination with a compound that regulates cell metabolism. In some embodiments, the MRD-containing antibody is administered in combination with a compound that inhibits or reduces the activity of: ErbB2, EGFR, IGF1R, IGF1, IGF2, TGFa, ICOS, PI3K, VEGFR1, VEGFR2, mTOR, HIF1, or HDAC.

According to one embodiment, an MRD-containing antibody is administered in combination with an inhibitor of one or more protein kinases. In one embodiment, the protein kinase inhibitor inhibits a target of the MRD containing antibody (e.g., by either one or more MRDs or the antibody of the MRD containing antibody). In an alternative embodiment, the protein kinase inhibitor inhibits a protein kinase that is not a target of the MRD containing antibody. In some embodiments, the protein kinase inhibitor inhibits one protein kinase. In other embodiments, the protein kinase inhibitor inhibits more than one protein kinase.

In some embodiments, an MRD containing antibody is administered in combination with an inhibitor (e.g., small molecule, antibody, etc.) of a protein kinase selected from: EGFR, FGFR1 (e.g., FGFR1-IIIC), FGFR2 (e.g., FGFR2-IIIa, FGFR2-IIIb, and FGFR2-IIIb), FGFR3, ErbB2, VEGFR1, VEGFR2, VEGFR3, Tie-2, PDGFR, PDGFRB, RON, and c-Met. In other embodiments, the inhibitor inhibits a protein kinase that is not targeted by the MRD containing antibody. In an additional embodiment, an MRD-containing antibody is administered in combination with an inhibitor of one or more protein kinases selected from: EGFR, FGFR1 (e.g., FGFR1-IIIC), FGFR2 (e.g., FGFR2-IIIa, FGFR2-IIIb, and FGFR2-IIIb), FGFR3, ErbB2, VEGFR1, VEGFR2, VEGFR3, Tie-2, PDGFRA, PDGFRB, FIT3, ALK, RET, Kit, raf, p38, RON, c-Met, PI3K, ERK, FAK, AKT, SYK, JAK1, JAK2, JAK3, TYK2, S1P, FAK, PTK7, PKD1, PKA, PKC, PKG, PRKDC, Pim, CDK, p1k, p38MAPK, SRC, ABL, FGR, FYN, HCK, LCK, LYN, YES, EPH4, BMK1, ERK5, mTOR, CHK1, CHK2, CSNK1G1, CSNK1G2, CSNK1G3, GSK3, BTK, JNK, Aurora Kinase, Aurora Kinase A, Aurora Kinase B, and Aurora Kinase C.

In an additional embodiment, an MRD-containing antibody is administered in combination with a protein kinase inhibitor selected from: imatinib mesylate (e.g., GLEEVEC™), gefitinib (e.g., IRESSA™, Astra Zeneca), vandetanib (e.g., ZACTIMA™, Astra Zeneca), erlotinib (e.g., TARCEVA™, Genentech/OSI), sunitinib (e.g., SUTENT™, Pfizer), lapatanib (GSK), and sorafenib (e.g., NEXAVAR™, Bayer).

In a further embodiment, an MRD-containing antibody is administered in combination with a protein kinase inhibitor selected from: nilotinib (e.g., AMN107, Novartis), dasatinib (e.g., BMS 354825, BMS), ABT-869, botsutinib (e.g., SKI-606, Wyeth), cediranib, recentib, captastatin, AEE788 (Novartis), AZD0530 (AstraZeneca) Exel 7646/Exel 0999 Exelixis), cabozantinib (e.g., XL184; Exelixis), XL880/GSK1363089 (Exelixis/GSK), ARQ-197 (Arqule and Daiichi Sankyo), Inno-406 (Innovive), SGS523 (SGX), PF-2341066 (Pfizer), CI-1033 (Pfizer), motesanib (e.g., AMG-706, Amgen), AG-013736 (Axitinib), AMG-705 (Amgen), pegaptanib (OSI/Pfizer), lestaurtinib, ruxolitinib, SB1518, CYT387, LY3009104, TG101348 JANEX-1, tofacitinib (Pfizer), INCB18424, LFM-A13, pazopanib (e.g., GW786034B, GlaxoSmithKline), GW-572016, EKB-569 (Wyeth-Ayerst), vatalanib (e.g., PTK787/ZK), AZD2171, MK-0457 (VX-680, Merck), PHA 739358 (Nerviano), mubritinib (Takeda), E7080 (Eisai), fostamatinib (Rigel/AstraZeneca), SGX523, SNS-032 (Sunesis), XL143, SNS-314 (Sunesis), SU6668 (Pfizer), AV-951 (AVEO), AV-412 (AVEO), tivozanib (AVEO), PX-866 (Oncothyreon), canertinib (CI-1033), NSC 109555, VRX0466617, UCN-01, CHK2 inhibitor II, EXEL-9844, XL844, CBP501, PF-004777736, debromohymerialdisine, Go6976, AEG3482, cediranib (e.g., RECENTIN™, AstraZeneca), semaxanib (SU5416), SU5616, CGP, 53716, mastinib, and ZD6474 (AstraZeneca).

In a further embodiment, an MRD-containing antibody is administered in combination with a FGFR protein kinase inhibitor selected from: sunitinib, SU5402, PD173074, TKI258 (Novartis), BIM 1120 (Boehringer Ingelheim), brivanib (BMS-582,664), E7080 (Eisai), and TSU-68 (Taiho).

In an additional embodiment, an MRD-containing antibody is administered in combination with a protein kinase inhibitor of JAK1, JAK2, JAK3, or SYK. In a further embodiment the protein kinase inhibitor is selected from: lestaurtinib, tofacitinib, ruxolitinib, SB1518, CYT387, LY3009104, TG101348, fostamatinib, BAY 61-3606, and sunitinib.

In one embodiment, an ErbB2 (HER2) binding MRD-containing antibody (e.g., an MRD-binding antibody that binds ErbB2 by either one or more MRDs or the antibody of the MRD containing antibody) is administered in combination with a protein kinase inhibitor of ErbB2. In another specific embodiment a trastuzumab antibody-based MRD-containing antibody is administered in combination with a protein kinase inhibitor of ErbB2. In one embodiment, an ErbB2-binding MRD-containing antibody is administered in combination with lapatinib. In a specific embodiment a trastuzumab antibody-based MRD-containing antibody is administered in combination with lapatinib. In one embodiment, an ErbB2-binding MRD-containing antibody is administered in combination with sunitinib. In a specific embodiment a trastuzumab antibody-based MRD-containing antibody is administered in combination with sunitinib. In one embodiment, an ErbB2-binding MRD-containing antibody is administered in combination with neratinib. In a specific embodiment a trastuzumab antibody-based MRD-containing antibody is administered in combination with neratanib. In one embodiment, an ErbB2-binding MRD-containing antibody is administered in combination with iapatinib. In a specific embodiment a trastuzumab antibody-based MRD-containing antibody is administered in combination with iapatinib. In an additional embodiment, an ErbB2 (HER2) binding MRD-containing antibody is administered in combination with a protein kinase inhibitor selected from: canertinib (GW-572016), AV-412 (AVEO), tivozanib (AVEO), vandetanib (e.g., ZACTIMA™, AstraZeneca), AEE788 (Novartis), Exel 7646/Exel 0999 (Exelixis), CI-1033 (Pfizer), and EKB-569 (Wyeth-Ayerst). In a specific embodiment a trastuzumab antibody-based MRD-containing antibody is administered in combination with a protein kinase inhibitor selected from: canertinib (GW-572016), AV-412 (AVEO), tivozanib (AVEO), vandetanib (e.g., ZACTIMA™, AstraZeneca), AEE788 (Novartis), Exel 7646/Exel 0999 (Exelixis), CI-1033 (Pfizer), PX-866 (Oncothyreon), and EKB-569 (Wyeth-Ayerst).

In another embodiment, an EGFR binding MRD-containing antibody (e.g., an MRD-binding antibody that binds EGFR by either one or more MRDs or the antibody of the MRD containing antibody) is administered in combination with a protein kinase inhibitor of EGFR. In a specific embodiment a cetuximab antibody-based MRD-containing antibody is administered in combination with a protein kinase inhibitor of EGFR. In one embodiment, an EGFR binding MRD-containing antibody is administered in combination with gefitinib (e.g., IRESSA™, AstraZeneca). In a specific embodiment a cetuximab antibody-based MRD-containing antibody is administered in combination with gefitinib (e.g., IRESSA™, AstraZeneca). In one embodiment, an EGFR binding MRD-containing antibody is administered in combination with erlotinib (e.g., TARCEVA™, Genentech/OSI). In a specific embodiment a cetuximab antibody-based MRD-containing antibody is administered in combination with erlotinib (e.g., TARCEVA™, Genentech/OSI). In one embodiment, an EGFR binding MRD-containing antibody is administered in combination with lapatinib. In a specific embodiment a cetuximab antibody-based MRD-containing antibody is administered in combination with lapatinib. In one embodiment, an EGFR binding MRD-containing antibody is administered in combination with sorafenib (e.g., NEXAVAR™, Bayer). In a specific embodiment a cetuximab antibody-based MRD-containing antibody is administered in combination with sorafenib (e.g., NEXAVAR™, Bayer). In another embodiment, an EGFR binding MRD-containing antibody is administered in combination with a protein kinase inhibitor selected from: canertinib (GW-572016), ZD6474, AV-412 (AVEO), tivozanib (AVEO), vandetanib (ZACTIMA, AstraZeneca), AEE788 (Novartis), Exel 7646/Exel 0999 (Exelixis), CI-1033 (Pfizer), and EKB-569 (Wyeth-Ayerst). In a specific embodiment a cetuximab antibody-based MRD-containing antibody is administered in combination with a protein kinase inhibitor selected from: canertinib (GW-572016), ZD6474, AV-412 (AVEO), tivozanib (AVEO), vandetanib (ZACTIMA, AstraZeneca), AEE788 (Novartis), Exel 7646/Exel 0999 (Exelixis), CI-1033 (Pfizer), PX-866 (Oncothyreon), and EKB-569 (Wyeth-Ayerst).

In one embodiment, a VEGFA, VEGFR1, or VEGFR2 binding MRD-containing antibody (e.g., an MRD-binding antibody that binds VEGFR1 by either one or more MRDs or the antibody of the MRD containing antibody) is administered in combination with a protein kinase inhibitor of VEGR1, VEGFR2, or VEGFR3. In one embodiment, the VEGFA, VEGFR1 or VEGFRr2 binding MRD-containing antibody is administered in combination with: sunitinib, sorafenib, pazopanib (e.g., GW786034B), AZD2171, vatalanib, ZD6474, AMG-706, or AC013736.

In a further embodiment, an MRD-containing antibody is administered in combination with a proteasome inhibitor. In a specific embodiment, the inhibitor is bortezomib (e.g., VELCADE™). In another specific embodiment, the inhibitor is PR-171 (Proteolix).

In a further embodiment, an MRD-containing antibody is administered in combination with a HDAC inhibitor.

In a further embodiment, an MRD-containing antibody is administered in combination with a mTOR inhibitor.

In a further embodiment, an MRD-containing antibody is administered in combination with a NFKB inhibitor.

In one embodiment, the invention provides a method of treating cancer comprising administering a therapeutically effective amount of a VEGFA or VEGFR binding MRD-containing antibody to a patient in need thereof. In a specific embodiment, the invention provides a method of treating cancer comprising administering a therapeutically effective amount of bevacizumab comprising at least one MRD to a patient in need thereof. In one embodiment, the invention provides a method of treating colorectal cancer by administering a therapeutically effective amount of bevacizumab comprising at least one MRD to a patient having colorectal cancer. In another embodiment, the invention provides a method of treating breast cancer by administering a therapeutically effective amount of bevacizumab comprising at least one MRD to a patient having breast cancer. In another embodiment, the invention provides a method of treating non-small cell lung carcinoma by administering a therapeutically effective amount of bevacizumab comprising at least one MRD to a patient having non-small cell lung carcinoma. In other embodiments, therapeutic effective amounts of bevacizumab comprising at least one MRD are administered to a patient to treat metastatic colorectal cancer, metastatic breast cancer, metastatic pancreatic cancer, or metastatic non-small cell lung carcinoma. In another embodiment, the invention provides a method of treating cancer by administering to a patient a therapeutically effective amount of bevacizumab comprising at least one MRD to a patient having renal cell carcinoma, glioblastoma multiforme, ovarian cancer, prostate cancer, liver cancer or pancreatic cancer.

Combination therapy and compositions including multivalent and multispecific compositions (e.g., MRD-containing antibodies) of the invention and another therapeutic are also encompassed by the invention, as are methods of treatment using these compositions. In other embodiments, compositions of the invention are administered alone or in combination with one or more additional therapeutic agents. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the therapeutic compounds or agents given first, followed by the second. Accordingly, in one embodiment, a VEGFA or VEGFR binding MRD-containing antibody is administered in combination with 5-fluorouracil, carboplatin, paclitaxel, or interferon alpha. In another embodiment, bevacizumab comprising at least one MRD is administered in combination with 5-fluorouracil, carboplatin, paclitaxel, or interferon alpha.

In another embodiment, the invention provides a method of treating macular degeneration comprising administering a therapeutically effective amount of a VEGFA or VEGFR binding MRD-containing antibody to a patient in need thereof. In a specific embodiment, the invention provides a method of treating macular degeneration comprising administering a therapeutically effective amount of bevacizumab comprising at least one MRD to a patient in need thereof. In a specific embodiment, the invention provides a method of treating macular degeneration comprising administering a therapeutically effective amount of ranibizumab comprising at least one MRD to a patient in need thereof.

In some embodiments, the invention provides a method of treating cancer comprising administering a therapeutically effective amount of an ErbB2 (HER2) binding MRD-containing antibody to a patient in need thereof. In various embodiments, the ErbB2-binding multivalent and multispecific compositions (e.g., MRD-containing antibodies) are administered to patients who have been previously shown to respond to another ErbB2-based therapy (e.g., HERCEPTIN, chemotherapy and/or radiation) or are predicted to respond to another ErbB2-based therapy. In other embodiments, the ErbB2-binding multivalent and multispecific compositions (e.g., MRD-containing antibodies) are administered to patients who have previously failed to respond to another ErbB2-based therapy or are predicted to fail to respond to another ErbB2-based therapy.

In a specific embodiment, the invention provides a method of treating cancer comprising administering a therapeutically effective amount of trastuzumab comprising at least one MRD to a patient in need thereof. In one embodiment, the invention provides a method of treating breast cancer by administering a therapeutically effective amount of trastuzumab comprising at least one MRD to a patient having breast cancer. In other embodiments, therapeutic effective amounts of trastuzumab comprising at least one MRD are administered to a patient to treat metastatic breast cancer.

In another embodiment, an ErbB2 (HER2) binding MRD-containing antibody is administered in combination with cyclophosphamide, paclitaxel, docetaxel, carboplatin, anthracycline, or a maytansinoid. In a specific embodiment, trastuzumab comprising at least one MRD is administered in combination with cyclophosphamide, paclitaxel, docetaxel, carboplatin, anthracycline, or a maytansinoid.

In another embodiment, the invention provides a method of treating cancer comprising administering a therapeutically effective amount of a CD20-binding MRD-containing antibody to a patient in need thereof. In a specific embodiment, the invention provides a method of treating a hematologic cancer comprising administering a therapeutically effective amount of rituximab comprising at least one MRD to a patient in need thereof. In one embodiment, the invention provides a method of treating CD20 positive NHL by administering a therapeutically effective amount of bevacizumab comprising at least one MRD to a patient having CD20 positive NHL. In one embodiment, the invention provides a method of treating CD20 positive CLL by administering a therapeutically effective amount of bevacizumab comprising at least one MRD to a patient having CD20 positive CLL.

In another embodiments, a therapeutically effective amount of a CD20-binding MRD-containing antibody is administered in combination with: ludarabine, cyclophosphamide, FC (fludarabine and cyclophosphamide), anthracycline based chemotherapy regimen (e.g., CHOP (cyclophosphamide, adriamycin, vincristine and prednisone)), or CVP (cyclophosphamide, prednisone, and vincristine) chemotherapy. In a specific embodiment, a therapeutically effective amount of bevacizumab comprising at least one MRD is administered in combination with: ludarabine, cyclophosphamide, FC (fludarabine and cyclophosphamide), anthracycline based chemotherapy regimen (e.g., CHOP (cyclophosphamide, adriamycin, vincristine and prednisone)), or CVP (cyclophosphamide, prednisone, and vincristine) chemotherapy.

Any of the antibody-MRD fusions containing antibodies and/or MRDs that bind CD20 can be used according to the methods of treating a disorder associated with CD20, or that can be treated by targeting cells that express CD20 (e.g., hematological cancers and autoimmune disease). In some embodiments, the antibody component of the antibody-MRD-fusion is selected from rituximab, ocrelizumab, GA101, and PF-5,230,895.

The invention also provides a method of treating a disorder of the immune system comprising administering a therapeutically effective amount of an MRD-containing antibody. In some embodiments, the administered MRD-containing antibody binds a target selected from: CD20, TNFRSF5 (CD40), CD45RB, CD52, CD200, CCR2, PAFR, IL6R, TNFRSF1A, VLA4, CSF2, TNFSF5 (CD40 LIGAND), TLR2, TLR4, GPR44, FASL, TREM1, IL1, IL1 beta, IL1RN, tissue factor, MIF, MIP2, IL6, IL8, IL10, IL12, IL13, IL15, IL17, IL18, IL23, TNF, TNFSF12 (TWEAK), LP S, CXCL13, VEGF, IFN alpha, IFN gamma, GMCSF, FGF, TGFb, C5, and CCR3. Multivalent and multispecific compositions (e.g., MRD-containing antibodies) that bind 2, 3, 4, 5 or more of these targets are also encompassed by the invention.

In particular embodiments, the invention provides a method of treating a disorder of the immune system comprising administering a therapeutically effective amount of an MRD-containing antibody that binds TNF and ANG2.

In additional embodiments, the invention provides a method of treating a disorder of the immune system comprising administering a therapeutically effective amount of an MRD-containing antibody that binds IL1, IL12, and TNF. In further embodiments, the MRD-containing antibody binds IL1, IL12, TNF and ANG2.

In additional embodiments, the administered MRD-containing antibody binds IL1, IL6 and TNF. In further embodiments, the MRD-containing antibody binds IL1, IL6, TNF and ANG2.

target selected from: CD20, TNFRSF5 (CD40), CD45RB, CD52, CD200, CCR2, PAFR, IL6R, TNFRSF1A, VLA4, CSF2, TNFSF5 (CD40 LIGAND), TLR2, TLR4, GPR44, FASL, TREM1, IL1, IL1 beta, IL1RN, tissue factor, MIF, MIP2, IL6, IL8, IL10, IL12, IL13, IL15, IL17, IL18, IL23, TNF, TNF (TWEAK), LPS, CXCL13, VEGF, IFN alpha, IFN gamma, GMCSF, FGF, TGFb, C5, and CCR3. Multivalent and multispecific compositions (e.g., MRD-containing antibodies) that bind 2, 3, 4, 5 or more of these targets are also encompassed by the invention.

In additional embodiments, the invention provides a method of treating an autoimmune disease comprising administering a therapeutically effective amount of an MRD-containing antibody. In a specific embodiment, the administered MRD-containing antibody binds a target selected from: CD1C, CD3, CD4, CD19, CD20, CD21, CD22, CD23, CD24, CD28, CD37, CD38, CD45RB, CD52, CD69, CD72, CD74, CD75, CD79A, CD79B, CD80, CD81, CD83, CD86, CD200, IL2RA, IL1R2, IL6R, VLA4, HLA-DRA, HLA-A, ITGA2, ITGA3, CSF2, TLR2, TLR4, GPR44, TREM1, TIE2, TNF, FASL, tissue factor, MIF, MIP2, IL1, IL1 beta, IL1RN, IL2, IL4, IL6, IL8, IL10, IL11, IL12, IL13, IL15, IL17, IL18, IL23, TNFRSF1A, TNFRSF5 (CD40), TNFRSF6 (Fas, CD95), TNFRSF7 (CD27), TNFRSF8 (CD30), TNFRSF13C (BAFFR), TNFSF5 (CD40 Ligand), TNFSF6 (Fas Ligand), TNFSF8 (CD30 Ligand), TNFSF12 (TWEAK), TNFSF13B (BLyS), ANG2, ICOSL (B7-H2), MS4A1, IFN alpha, IFN beta1, IFN gamma, TNFSF7 (CD27 Ligand, CD70), PAFR, INHA, INHBA, DPP4, NTSE, CTLA4, B7.1/B7.2, LPS, VEGF, GMCSF, FGF, C5, CXCL13, CXCR4, CCR2 and CCR3. In further embodiments, the multivalent and multispecific compositions (e.g., MRD-containing antibodies) are administered to treat rheumatoid arthritis and the multivalent and multispecific compositions bind a target selected from: CD19, CD20, CD45RB, CD52CD200, IL1, IL6, IL12, IL15, IL17, IL18, IL23, TNF, TNF (TWEAK), TNFRSF5 (CD40), TNF (CD40 Ligand), TNF (BLyS), VEGF, VLA4, IFN gamma, IFN alpha, GMCSF, FGF, C5, CXCL13 and CCR2. In additional embodiments, the multivalent and multispecific compositions (e.g., MRD-containing antibodies) are administered to treat systemic lupus erythematous and the multivalent and multispecific compositions bind IFN alpha and TNFSF13B (BLyS). In further embodiments, the multivalent and multispecific compositions (e.g., MRD-containing antibodies) are administered to treat multiple sclerosis and the multivalent and multispecific compositions bind a target selected from: ANG2, IL1, IL12, IL18, IL23, CXCL13, TNF, TNFRSF5 (CD40), TNFSF5 (CD40 Ligand), VEGF, VLA4, TNF, CD45RB, CD200, IFN gamma, GM-CSF, FGF, C5, CD52, TNFRSF1A, TNFRSF5 (CD40), TNFRSF6 (Fas, CD95), TNFRSF7 (CD27), TNFRSF8 (CD30), TNFSF12 (TWEAK), TNFRSF13C (BAFFR), TNFSF5 (CD40 Ligand), TNFSF6 (Fas Ligand), TNFSF8 (CD30 Ligand), TNFRSF21 (DR6), TNF SF12 (TWEAK), TNF (BLyS), ANG2, AGE (S100 A, amphoterin), ICOSL (B7-H2), MS4A 1, IFN alpha, IFN beta1, IFN gamma, TNFSF7 (CD27 Ligand, CD70), MCP1, CCR2 and CXCL13. Multivalent and multispecific compositions that bind at least 2, 3, 4, 5 or more of these targets are also encompassed by the invention.

In a further embodiment, the invention provides a method of treating a disorder of the immune system comprising administering a therapeutically effective amount of a CD20-binding MRD-containing antibody to a patient in need thereof. In a specific embodiment, the invention provides a method of treating an autoimmune disease comprising administering a therapeutically effective amount of a CD20-binding MRD-containing antibody to a patient in need thereof. In one embodiment, the invention provides a method of treating an autoimmune disease comprising administering a therapeutically effective amount of a rituximab-MRD-containing antibody to a patient in need thereof. In another embodiment, the invention provides a method of treating rheumatoid arthritis comprising administering a therapeutically effective amount of a rituximab-MRD-containing antibody to a patient in need thereof. In another embodiment, the invention provides a method of treating systemic lupus erythematous comprising administering a therapeutically effective amount of a rituximab-MRD-containing antibody to a patient in need thereof. In another embodiment, the invention provides a method of treating multiple sclerosis comprising administering a therapeutically effective amount of a rituximab-MRD-containing antibody to a patient in need thereof.

In an additional embodiment, the invention provides a method of treating an autoimmune disease comprising administering a therapeutically effective amount of an ocrelizumab-MRD-containing antibody to a patient in need thereof. In one embodiment, the invention provides a method of treating rheumatoid arthritis comprising administering a therapeutically effective amount of an ocrelizumab-MRD-containing antibody to a patient in need thereof. In a further embodiment, the invention provides a method of treating systemic lupus erythematous comprising administering a therapeutically effective amount of a ocrelizumab-MRD-containing antibody to a patient in need thereof. In another embodiment, the invention provides a method of treating multiple sclerosis comprising administering a therapeutically effective amount of an ocrelizumab-MRD-containing antibody to a patient in need thereof.

In another embodiment, the invention provides a method of treating an autoimmune disease comprising administering a therapeutically effective amount of a PF5,230,895-MRD-containing antibody to a patient in need thereof. In one embodiment, the invention provides a method of treating rheumatoid arthritis comprising administering a therapeutically effective amount of a PF5,230,895-MRD-containing antibody to a patient in need thereof. In a further embodiment, the invention provides a method of treating systemic lupus erythematous comprising administering a therapeutically effective amount of a PF5,230,895-MRD-containing antibody to a patient in need thereof. In another embodiment, the invention provides a method of treating multiple sclerosis comprising administering a therapeutically effective amount of an PF5,230,895-MRD-containing antibody to a patient in need thereof.

In some embodiments, the invention provides a method of treating a disorder of the immune system comprising administering a therapeutically effective amount of an MRD-containing antibody that binds CD20. In further embodiments, the administered MRD-containing antibody binds CD20 and a target selected from: TNF, TNFRSF5 (CD40), TNFSF5 (CD40 LIGAND), TNFSF12 (TWEAK), TNFRSF1A, CD45, RB, CD52, CD200, CCR2, PAFR, IL6R, VLA4, CSF2, RAGE, TLR2, TLR4, GPR44, FASL, TREM1, TIE2, tissue factor, MIF, MIP2, LPS, IL1, IL1 beta, IL1RN, IL6, IL6R, IL8, IL10, IL12, IL13, IL15, IL17, IL18, IL23, CXCL13, VEGF, IFN alpha, IFN gamma, GMCSF, FGF, C5, and CCR3. Multivalent and multispecific compositions (e.g., MRD-containing antibodies) that bind CD20 and also bind at least 1, 2, 3, 4, 5 or more of these targets are also encompassed by the invention. In specific embodiments, the antibody component of the MRD-containing antibody binds CD20. In further embodiments, the antibody component of the MRD-containing antibody is a rituximab, ocrelizumab, GA101 or PF-5,230,895.

In some embodiments, the invention provides a method of treating an autoimmune disease comprising administering a therapeutically effective amount of an MRD-containing antibody that binds CD20. In a specific embodiment, the administered MRD-containing antibody binds CD20 and a target selected from: CD1C, CD3, CD4, CD19, CD21, CD22, CD23, CD24, CD28, CD37, CD38, CD45RB, CD52, CD69, CD72, CD74, CD75, CD79A, CD79B, CD80, CD81, CD83, CD86, CD200, IL2RA, IL1R2, IL6R, VLA4, HLA-DRA, HLA-A, ITGA2, ITGA3, CSF2, TLR2, TLR4, GPR44, TREM1, TIE2, TNF, FASL, tissue factor, MIF, MIP2, IL1, IL1 beta, IL1RN, IL2, IL4, IL6, IL8, IL10, IL11, IL12, IL13, IL15, IL17, IL18, IL23, TIE2, TNFRSF1A, TNFRSF5 (CD40), TNFRSF6 (Fas, CD95), TNFRSF7 (CD27), TNFRSF8 (CD30), TNFRSF13C (BAFFR), TNFSF5 (CD40 Ligand), TNFSF6 (Fas Ligand), TNFSF8 (CD30 Ligand), TNFSF12 (TWEAK), TNFSF13B (BLyS), ANG2, ICOSL (B7-H2), MS4A1, IFN alpha, IFN beta1, IFN gamma, TNFSF7 (CD27 Ligand, CD70), PAFR, INHA, INHBA, DPP4, NT5E, CTLA4, B7.1/B7.2, LPS, VEGF, GMCSF, FGF, C5, CXCL13, CXCR4, CCR2 and CCR3. In further embodiments, the multivalent and multispecific compositions (e.g., MRD-containing antibodies) are administered to treat rheumatoid arthritis and the multivalent and multispecific compositions bind CD20 and a target selected from: CD19, CD45RB, CD52, CD200, IL12, IL15, IL17, IL18, IL23, TNF, TNFSF12 (TWEAK), TNFRSF5 (CD40), TNFSF5 (CD40 Ligand), VEGF, VLA4, IFN gamma, interferon alpha, GMCSF, FGF, C5, CXCL13 and CCR2. In further embodiments, the multivalent and multispecific compositions (e.g., MRD-containing antibodies) are administered to treat multiple sclerosis and the multivalent and multispecific compositions bind CD20 and a target selected from: ANG2, IL12, IL18, IL23, CXCL13, TNFRSF5 (CD40), TNFSF5 (CD40 Ligand), VEGF, VLA4, TNF, CD45RB, CD200, IFN gamma, GM-CSF, FGF, C5, CD52, TIE2, TNFRSF1A, TNFRSF5 (CD40), TNFRSF6 (Fas, CD95), TNFRSF7 (CD27), TNFRSF8 (CD30), TNFSF12 (TWEAK), TNFRSF13C (BAFFR), TNFSF5 (CD40 Ligand), TNFSF6 (Fas Ligand), TNFSF8 (CD30 Ligand), TNFRSF21 (DR6), TNF (TWEAK), TNF (BLyS), ICOSL (B7-H2), MS4A 1, IFN alpha, IFN beta1, IFN gamma, TNFSF7 (CD27 Ligand, CD70), CCR2 and CXCL13. Multivalent and multispecific compositions that bind at least 1, 2, 3, 4, 5 or more of these targets are also encompassed by the invention. In specific embodiments, the antibody component of the MRD-containing antibody binds TNF. In further embodiments, the antibody component of the MRD-containing antibody is selected from rituximab, ocrelizumab, GA101 and PF-5,230,895.

In some embodiments, the invention provides a method of treating a disorder of the immune system comprising administering a therapeutically effective amount of a TNF-binding MRD-containing antibody to a patient in need thereof. In various embodiments, the TNF-binding multivalent and multispecific compositions (e.g., MRD-containing antibodies) are administered to patients who have been previously shown to respond to another TNF-based therapy or are predicted to respond to another TNF-based therapy (e.g., TNF antagonists such as, anti-TNFs (e.g., HUMIRA), EMBREL, CD28 antagonists, CD20 antagonists, and IL6/IL6R antagonists). In other embodiments, the TNF-binding multivalent and multispecific compositions (e.g., MRD-containing antibodies) are administered to patients who have previously failed to respond to another TNF-based therapy or are predicted to fail to respond to another TNF-based therapy.

In some embodiments, the invention provides a method of treating a disorder of the immune system comprising administering a therapeutically effective amount of an MRD-containing antibody that binds TNF.

In further embodiments, the administered MRD-containing antibody binds TNF and a target selected from: CD20, TNFRSF5 (CD40), CD45RB, CD52, CD200, CCR2, PAFR, IL6R, TNFRSF1A, VLA4, CSF2, TNFSF5 (CD40 LIGAND), TLR2, TLR4, GPR44, FASL, TREM1, IL1, IL1 beta, IL1RN, tissue factor, MIF, MIP2, IL6, IL8, IL10, IL12, IL13, IL15, IL17, IL18, IL23, TNFSF12 (TWEAK), LPS, CXCL13, VEGF, IFN gamma, GMCSF, FGF, C5, and CCR3. Multivalent and multispecific compositions (e.g., MRD-containing antibodies) that bind TNF and at least 1, 2, 3, 4, 5 or more of these targets are also encompassed by the invention. In specific embodiments, the antibody component of the MRD-containing antibody binds TNF. In further embodiments, the antibody component of the MRD-containing antibody is selected from adalimumab, certolizumab, golimumab and AME-527.

In some embodiments, the invention provides a method of treating an autoimmune disease comprising administering a therapeutically effective amount of an MRD-containing antibody that binds TNF. In a specific embodiment, the administered MRD-containing antibody binds TNF and a target selected from: CD1C, CD3, CD4, CD19, CD20, CD21, CD22, CD23, CD24, CD28, CD37, CD38, CD45RB, CD52, CD69, CD72, CD74, CD75, CD79A, CD79B, CD80, CD81, CD83, CD86, CD200, IL2RA, IL1R2, IL6R, VLA4, HLA-DRA, HLA-A, ITGA2, ITGA3, CSF2, TLR2, TLR4, GPR44, TREM1, TIE2, FASL, tissue factor, MIF, MIP2, IL1, IL1 beta, IL1RN, IL2, IL4, IL6, IL8, IL10, IL11, IL12, IL13, IL15, IL17, IL18, IL23, TIE2, TNFRSF1A, TNFRSF5 (CD40), TNFRSF6 (Fas, CD95), TNFRSF7 (CD27), TNFRSF8 (CD30), TNFRSF13C (BAFFR), TNFSF5 (CD40 Ligand), TNFSF6 (Fas Ligand), TNFSF8 (CD30 Ligand), TNFSF12 (TWEAK), TNFSF13B (BLyS), ANG2, ICOSL (B7-H2), MS4A1, IFN alpha, IFN beta1, IFN gamma, TNFSF7 (CD27 Ligand, CD70), PAFR, INHA, INHBA, DPP4, NT5E, CTLA4, B7.1/B7.2, LPS, VEGF, GMCSF, FGF, C5, CXCL13, CXCR4, CCR2 and CCR3. In further embodiments, the multivalent and multispecific compositions (e.g., MRD-containing antibodies) are administered to treat rheumatoid arthritis and the multivalent and multispecific compositions bind TNF and a target selected from: CD19, CD20, CD45RB, CD52CD200, IL12, IL15, IL17, IL18, IL23, TNFSF12 (TWEAK), TNFRSF5 (CD40), TNFSF5 (CD40 Ligand), TNFSF13B (BLyS), VEGF, VLA4, IFN gamma, interferon alpha, GMCSF, FGF, C5, CXCL13 and CCR2. In further embodiments, the multivalent and multispecific compositions (e.g., MRD-containing antibodies) are administered to treat multiple sclerosis and the multivalent and multispecific compositions bind TNF and a target selected from: ANG2, IL12, IL18, IL23, CXCL13, TNFRSF5 (CD40), TNFSF5 (CD40 Ligand), VEGF, VLA4, TNF, CD45RB, CD200, IFN gamma, GM-CSF, FGF, C5, CD52, TNFRSF1A, TNFRSF5 (CD40), TIE2, TNFRSF6 (Fas, CD95), TNFRSF7 (CD27), TNFRSF8 (CD30), TNFSF12 (TWEAK), TNFRSF13C (BAFFR), TNFSF5 (CD40 Ligand), TNFSF6 (Fas Ligand), TNFSF8 (CD30 Ligand), TNFRSF21 (DR6), TNFSF12 (TWEAK), TNFSF13B (BLyS), ICOSL (B7-H2), MS4A 1, IFN alpha, IFN beta1, IFN gamma, TNFSF7 (CD27 Ligand, CD70), CCR2 and CXCL13. Multivalent and multispecific compositions that bind a least 1, 2, 3, 4, 5 or more of these targets are also encompassed by the invention. In specific embodiments, the antibody component of the MRD-containing antibody binds TNF. In further embodiments, the antibody component of the MRD-containing antibody selected from adalimumab, certolizumab, golimumab and AME-527.

In other embodiments, the TNF-binding multivalent and multispecific compositions (e.g., MRD-containing antibodies) are administered to patients who have been previously shown to respond to an autoimmune disease based therapy or are predicted to respond to other autoimmune disease based therapies (e.g., TNF antagonists such as, Anti-TNFs (e.g., HUMIRA®), ENBREL®, CD28 antagonists, CD20 antagonists, BLyS antagonists, and IL6/IL6R antagonists). In other embodiments, the TNF-binding multivalent and multispecific compositions (e.g., MRD-containing antibodies) are administered to patients who have previously failed to respond to another autoimmune disease based therapy or are predicted to fail to respond to another autoimmune disease based therapy.

In a specific embodiment, the invention provides a method of treating a disorder of the immune system comprising administering a therapeutically effective amount of adalimumab comprising at least one MRD to a patient in need thereof. In one embodiment, the invention provides a method of treating an autoimmune disease by administering a therapeutically effective amount of adalimumab comprising at least one MRD to a patient in need thereof. In one embodiment, the invention provides a method of treating rheumatoid arthritis, by administering a therapeutically effective amount of adalimumab comprising at least one MRD to a patient in need thereof. In one embodiment, the invention provides a method of treating an inflammatory disorder, by administering a therapeutically effective amount of adalimumab comprising at least one MRD to a patient in need thereof. In another embodiment, the invention provides a method of treating Crohn's disease, by administering a therapeutically effective amount of adalimumab comprising at least one MRD to a patient in need thereof. In another embodiment, the invention provides a method of treating ulcerative colitis, by administering a therapeutically effective amount of adalimumab comprising at least one MRD to a patient in need thereof. In another embodiment, the invention provides a method of treating psoriatic arthritis, ankylosing spondylitis, psoriasis, or juvenile idiopathic arthritis by administering a therapeutically effective amount of adalimumab comprising at least one MRD to a patient in need thereof.

In an additional embodiment, the invention provides a method of treating a disorder of the immune system comprising administering a therapeutically effective amount of ATN-103 comprising at least one MRD to a patient in need thereof. In one embodiment, the invention provides a method of treating an inflammatory disorder, by administering a therapeutically effective amount of ATN-103 comprising at least one MRD to a patient in need thereof. In another embodiment, the invention provides a method of treating an autoimmune disease, by administering a therapeutically effective amount of ATN-103 comprising at least one MRD to a patient in need thereof. In a further embodiment, the invention provides a method of treating rheumatoid arthritis, by administering a therapeutically effective amount of ATN-103 comprising at least one MRD to a patient in need thereof. In another embodiment, the invention provides a method of treating Crohn's disease, by administering a therapeutically effective amount of ATN-103 comprising at least one MRD to a patient in need thereof. In an additional embodiment, the invention provides a method of treating ulcerative colitis, by administering a therapeutically effective amount of ATN-103 comprising at least one MRD to a patient in need thereof. In another embodiment, the invention provides a method of treating psoriatic arthritis, ankylosing spondylitis, psoriasis, or juvenile idiopathic arthritis by administering a therapeutically effective amount of ATN-103 comprising at least one MRD to a patient in need thereof.

In a specific embodiment, the invention provides a method of treating a disorder of the immune system comprising administering a therapeutically effective amount of infliximab comprising at least one MRD to a patient in need thereof. In one embodiment, the invention provides a method of treating an inflammatory disorder, by administering a therapeutically effective amount of infliximab comprising at least one MRD to a patient in need thereof. In one embodiment, the invention provides a method of treating an autoimmune disease, by administering a therapeutically effective amount of infliximab comprising at least one MRD to a patient in need thereof. In one embodiment, the invention provides a method of treating rheumatoid arthritis, by administering a therapeutically effective amount of infliximab comprising at least one MRD to a patient in need thereof. In another embodiment, the invention provides a method of treating Crohn's disease, by administering a therapeutically effective amount of infliximab comprising at least one MRD to a patient in need thereof. In another embodiment, the invention provides a method of treating ulcerative colitis, by administering a therapeutically effective amount of infliximab comprising at least one MRD to a patient in need thereof. In another embodiment, the invention provides a method of treating psoriatic arthritis, ankylosing spondylitis, psoriasis, or juvenile idiopathic arthritis by administering a therapeutically effective amount of infliximab comprising at least one MRD to a patient in need thereof.

In some embodiments, the invention provides a method of treating a disorder of the immune system comprising administering a therapeutically effective amount of an MRD-containing antibody that binds TNFSF15 (TL1A).

In further embodiments, the administered MRD-containing antibody binds TL1A and a target selected from: TNF, IFN gamma, IL1, IL1beta, IL6, IL8, IL12, IL15, IL17, IL18, IL23 and IL32. Multivalent and multi specific compositions (e.g., MRD-containing antibodies) that bind TL1A and at least 1, 2, 3, 4, 5 or more of these targets are also encompassed by the invention. In specific embodiments, the antibody component of the MRD-containing antibody binds TL1A.

In an additional embodiment, the invention provides a method of treating a disorder of the immune system comprising administering a therapeutically effective amount of a IL22-binding MRD-containing antibody to a patient in need thereof. In a specific embodiment, the invention provides a method of treating a disorder of the immune system comprising administering a therapeutically effective amount of PF5,212,367 (ILV-094) comprising at least one MRD to a patient in need thereof. In one embodiment, the invention provides a method of treating an autoimmune disease by administering a therapeutically effective amount of PF5,212,367 comprising at least one MRD to a patient in need thereof. In one embodiment, the invention provides a method of treating rheumatoid arthritis, by administering a therapeutically effective amount of PF5,212,367 comprising at least one MRD to a patient in need thereof. In one embodiment, the invention provides a method of treating an inflammatory disorder, by administering a therapeutically effective amount of PF5,212,367 comprising at least one MRD to a patient in need thereof. In another embodiment, the invention provides a method of treating Crohn's disease, by administering a therapeutically effective amount of PF5,212,367 comprising at least one MRD to a patient in need thereof. In a further embodiment, the invention provides a method of treating ulcerative colitis, by administering a therapeutically effective amount of PF5,212,367 comprising at least one MRD to a patient in need thereof. In another embodiment, the invention provides a method of treating psoriatic arthritis, ankylosing spondylitis, psoriasis, or juvenile idiopathic arthritis by administering a therapeutically effective amount of PF5,212,367 comprising at least one MRD to a patient in need thereof.

In an additional embodiment, the invention provides a method of treating a disorder of the immune system comprising administering a therapeutically effective amount of a alpha4 integrin-binding MRD-containing antibody to a patient in need thereof. In a specific embodiment, the invention provides a method of treating a disorder of the immune system comprising administering a therapeutically effective amount of natalizumab comprising at least one MRD to a patient in need thereof. In one embodiment, the invention provides a method of treating an autoimmune disease by administering a therapeutically effective amount of natalizumab comprising at least one MRD to a patient in need thereof. In another embodiment, the invention provides a method of treating rheumatoid arthritis, by administering a therapeutically effective amount of natalizumab comprising at least one MRD to a patient in need thereof. In a further embodiment, the invention provides a method of treating systemic lupus erythematous comprising administering a therapeutically effective amount of a natalizumab-MRD-containing antibody to a patient in need thereof. In another embodiment, the invention provides a method of treating multiple sclerosis comprising administering a therapeutically effective amount of a natalizumab-MRD-containing antibody to a patient in need thereof. In a further embodiment, the invention provides a method of treating an inflammatory disorder, by administering a therapeutically effective amount of natalizumab comprising at least one MRD to a patient in need thereof. In another embodiment, the invention provides a method of treating Crohn's disease, by administering a therapeutically effective amount of natalizumab comprising at least one MRD to a patient in need thereof. In an additional embodiment, the invention provides a method of treating ulcerative colitis, by administering a therapeutically effective amount of natalizumab comprising at least one MRD to a patient in need thereof. In another embodiment, the invention provides a method of treating multiple sclerosis, by administering a therapeutically effective amount of natalizumab comprising at least one MRD to a patient in need thereof. In an additional embodiment, the invention provides a method of treating psoriatic arthritis, ankylosing spondylitis, psoriasis, or juvenile idiopathic arthritis by administering a therapeutically effective amount of natalizumab comprising at least one MRD to a patient in need thereof.

In an additional embodiment, the invention provides a method of treating a disorder of the immune system comprising administering a therapeutically effective amount of a TNFSF5 (CD40 LIGAND)-binding MRD-containing antibody to a patient in need thereof. In a specific embodiment, the invention provides a method of treating a disorder of the immune system comprising administering a therapeutically effective amount of CDP7657 comprising at least one MRD to a patient in need thereof. In one embodiment, the invention provides a method of treating an autoimmune disease by administering a therapeutically effective amount of CDP7657 comprising at least one MRD to a patient in need thereof. In another embodiment, the invention provides a method of treating rheumatoid arthritis, by administering a therapeutically effective amount of CDP7657 comprising at least one MRD to a patient in need thereof. In a further embodiment, the invention provides a method of treating systemic lupus erythematous comprising administering a therapeutically effective amount of a CDP7657-MRD-containing antibody to a patient in need thereof. In another embodiment, the invention provides a method of treating multiple sclerosis comprising administering a therapeutically effective amount of a CDP7657-MRD-containing antibody to a patient in need thereof. In one embodiment, the invention provides a method of treating an inflammatory disorder, by administering a therapeutically effective amount of CDP7657 comprising at least one MRD to a patient in need thereof. In another embodiment, the invention provides a method of treating Crohn's disease, by administering a therapeutically effective amount of CDP7657 comprising at least one MRD to a patient in need thereof. In a further embodiment, the invention provides a method of treating ulcerative colitis, by administering a therapeutically effective amount of CDP7657 comprising at least one MRD to a patient in need thereof. In an additional embodiment, the invention provides a method of treating psoriatic arthritis, ankylosing spondylitis, psoriasis, or juvenile idiopathic arthritis by administering a therapeutically effective amount of CDP7657 comprising at least one MRD to a patient in need thereof.

In another embodiment, the invention provides a method of treating a disorder of the immune system comprising administering a therapeutically effective amount of a TNFSF12 (TWEAK)-binding MRD-containing antibody to a patient in need thereof. In a specific embodiment, the invention provides a method of treating a disorder of the immune system comprising administering a therapeutically effective amount of the Biogen TNFSF12 (TWEAK) antibody (that has entered phase 1 clinical trials) comprising at least one MRD to a patient in need thereof. In one embodiment, the invention provides a method of treating an autoimmune disease by administering a therapeutically effective amount of the Biogen TNFSF12 (TWEAK) antibody comprising at least one MRD to a patient in need thereof. In one embodiment, the invention provides a method of treating rheumatoid arthritis, by administering a therapeutically effective amount of the Biogen TNFSF12 (TWEAK) antibody comprising at least one MRD to a patient in need thereof. In a further embodiment, the invention provides a method of treating systemic lupus erythematous comprising administering a therapeutically effective amount of the Biogen TNFSF12 (TWEAK) antibody comprising at least one MRD to a patient in need thereof. In another embodiment, the invention provides a method of treating multiple sclerosis comprising administering a therapeutically effective amount of the Biogen TNFSF12 (TWEAK) antibody comprising at least one MRD to a patient in need thereof. In another embodiment, the invention provides a method of treating an inflammatory disorder, by administering a therapeutically effective amount of the Biogen TNFSF12 (TWEAK) antibody comprising at least one MRD to a patient in need thereof. In an additional embodiment, the invention provides a method of treating Crohn's disease, by administering a therapeutically effective amount of the Biogen TNFSF12 (TWEAK) antibody comprising at least one MRD to a patient in need thereof. In another embodiment, the invention provides a method of treating ulcerative colitis, by administering a therapeutically effective amount of the Biogen TNFSF12 (TWEAK) antibody comprising at least one MRD to a patient in need thereof. In a further embodiment, the invention provides a method of treating psoriatic arthritis, ankylosing spondylitis, psoriasis, or juvenile idiopathic arthritis by administering a therapeutically effective amount of the Biogen TNFSF12 (TWEAK) antibody comprising at least one MRD to a patient in need thereof.

In an additional embodiment, the invention provides a method of treating a disorder of the immune system comprising administering a therapeutically effective amount of a CD25-binding MRD-containing antibody to a patient in need thereof. In a specific embodiment, the invention provides a method of treating a disorder of the immune system comprising administering a therapeutically effective amount of daclizumab comprising at least one MRD to a patient in need thereof. In one embodiment, the invention provides a method of treating an autoimmune disease by administering a therapeutically effective amount of daclizumab comprising at least one MRD to a patient in need thereof. In another embodiment, the invention provides a method of treating rheumatoid arthritis, by administering a therapeutically effective amount of daclizumab comprising at least one MRD to a patient in need thereof. In a further embodiment, the invention provides a method of treating systemic lupus erythematous comprising administering a therapeutically effective amount of a daclizumab-MRD-containing antibody to a patient in need thereof. In another embodiment, the invention provides a method of treating multiple sclerosis comprising administering a therapeutically effective amount of a daclizumab-MRD-containing antibody to a patient in need thereof. In one embodiment, the invention provides a method of treating an inflammatory disorder, by administering a therapeutically effective amount of daclizumab comprising at least one MRD to a patient in need thereof. In another embodiment, the invention provides a method of treating Crohn's disease, by administering a therapeutically effective amount of daclizumab comprising at least one MRD to a patient in need thereof. In a further embodiment, the invention provides a method of treating ulcerative colitis, by administering a therapeutically effective amount of daclizumab comprising at least one MRD to a patient in need thereof. In an additional embodiment, the invention provides a method of treating psoriatic arthritis, ankylosing spondylitis, psoriasis, or juvenile idiopathic arthritis by administering a therapeutically effective amount of daclizumab comprising at least one MRD to a patient in need thereof.

Antibody-MRD fusion proteins having antibodies and/or MRDs that bind cancer antigens or other targets associated with cancer establishment, progression, and/or metastasis are described herein or otherwise known in the art and may be used according to the methods of the invention to treat cancer. In specific embodiments the antibody-MRD fusion proteins comprise an antibody and/or MRD that bind to a target identified herein.

In another embodiment, the invention provides a method of treating cancer comprising administering a therapeutically effective amount of an EGFR-binding MRD-containing antibody to a patient in need thereof. In a specific embodiment, the invention provides a method of treating cancer comprising administering a therapeutically effective amount of cetuximab comprising at least one MRD to a patient in need thereof. In one embodiment, the invention provides a method of treating cancer by administering a therapeutically effective amount of cetuximab comprising at least one MRD to a patient having colorectal cancer. In another embodiment, therapeutic effective amounts of cetuximab comprising at least one MRD are administered to a patient to treat metastatic colorectal cancer, metastatic breast cancer, metastatic pancreatic cancer, or metastatic non-small cell lung carcinoma. In one embodiment, the invention provides a method of treating cancer by administering a therapeutically effective amount of cetuximab comprising at least one MRD to a patient having squamous cell carcinoma of the head and neck.

In another embodiment, a therapeutically effective amount of an EGFR-binding MRD-containing antibody is administered in combination with irinotecan, FOLFIRI, platinum-based chemotherapy, or radiation therapy. In a specific embodiment, a therapeutically effective amount of cetuximab comprising at least one MRD is administered in combination with irinotecan, FOLFIRI, platinum-based chemotherapy, or radiation therapy.

In certain embodiments, the invention provides a method of treating cancer comprising administering a therapeutically effective amount of an MRD-antibody described herein to a patient in need thereof.

In one embodiment, the invention provides a method of treating a solid cancer by administering a therapeutically effective amount of a solid cancer binding MRD-antibody described herein (e.g., an MRD-antibody that binds a validated solid tumor associated target as described herein to a patient in need thereof.

In some embodiments, the invention provides a method of treating a solid cancer by administering a therapeutically effective amount of an MRD-antibody that binds to a member selected from the group consisting of: IGFR1, ALK1, p-cadherin, CRYPTO, and alpha5 b1 integrin. In other embodiments, the antibody component of the administered MRD-antibody is a member selected from: figitumumab, CP-870893, PF-3,732,010, PF-3,446,962, volociximab, BIIB022, and the Biogen CRYPTO antibody.

In some embodiments, the multivalent and multispecific compositions (e.g., MRD-containing antibodies) described herein are useful for treating cancer. Thus, in some embodiments, the invention provides methods of treating cancer comprise administering a therapeutically effective amount of a MRD-containing antibody to a patient (e.g., a patient (subject) in need of treatment). In certain embodiments, the cancer is a cancer selected from the group consisting of colorectal cancer, pancreatic cancer, lung cancer, ovarian cancer, liver cancer, breast cancer, brain cancer, kidney cancer, prostate cancer, gastrointestinal cancer, melanoma, cervical cancer, bladder cancer, glioblastoma, and head and neck cancer. In certain embodiments, the cancer is breast cancer. In certain embodiments, the patient is a human.

Other examples of cancers or malignancies that may be treated with MRD containing antibodies and MRDs include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extra cranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extra cranial Germ Cell Tumor, Extra gonadal Germ Cell Tumor, Extra hepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/ Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, and Wilms' Tumor.

In some embodiments, multivalent and multispecific compositions (e.g., MRD-containing antibodies) are useful for inhibiting tumor growth. In certain embodiments, the method of inhibiting the tumor growth comprises contacting the cell with a MRD-containing antibody in vitro. For example, an immortalized cell line or a cancer cell line that expresses an MRD target and/or an antibody target is cultured in medium to which is added the MRD-containing antibody to inhibit tumor growth. In some embodiments, tumor cells are isolated from a patient sample for example, a tissue biopsy, pleural effusion, or blood sample and cultured in medium to which is added a MRD-containing antibody to inhibit tumor growth.

In some embodiments, the method of inhibiting tumor growth comprises contacting the tumor or tumor cells with a therapeutically effective amount of the MRD-containing antibody in vivo. In certain embodiments, contacting a tumor or tumor cell is undertaken in an animal model. For example, multivalent and multispecific compositions (e.g., MRD-containing antibodies) can be administered to xenografts in immunocompromised mice (e.g., NOD/SCID mice) to inhibit tumor growth. In some embodiments, cancer stem cells are isolated from a patient sample for example, a tissue biopsy, pleural effusion, or blood sample and injected into immunocompromised mice that are then administered a MRD-containing antibody to inhibit tumor cell growth. In some embodiments, the MRD-containing antibody is administered at the same time or shortly after introduction of tumorigenic cells into the animal to prevent tumor growth. In some embodiments, the MRD-containing antibody is administered as a therapeutic after the tumorigenic cells have grown to a specified size.

In certain embodiments, the method of inhibiting tumor growth comprises administering to a patient (subject) a therapeutically effective amount of a MRD-containing antibody. In certain embodiments, the patient is a human. In certain embodiments, the patient has a tumor or has had a tumor removed. In certain embodiments, the tumor expresses an antibody target. In certain embodiments, the tumor overexpresses the MRD target and/or the antibody target.

In certain embodiments, the inhibited tumor growth is selected from the group consisting of brain tumor, colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a breast tumor.

In additional embodiments, multivalent and multispecific compositions (e.g., MRD-containing antibodies) are useful for reducing tumorigenicity. Thus, in some embodiments, the method of reducing the tumorigenicity of a tumor in a patient, comprises administering a therapeutically effective amount of a multivalent and monovalent multispecific composition (e.g., MRD-containing antibody) to the patient. In certain embodiments, the tumor comprises cancer stem cells. In certain embodiments, the frequency of cancer stem cells in the tumor is reduced by administration of the multivalent and monovalent multispecific composition (e.g., MRD-containing antibody).

In other embodiments, multivalent and multispecific compositions (e.g., MRD-containing antibodies) are useful for diagnosing, treating or preventing a disorder of the immune system. In one embodiment, the disorder of the immune system is inflammation or an inflammatory disorder. In a more specific embodiment, the inflammatory disorder is selected from the group consisting of asthma, allergic disorders, and rheumatoid arthritis. In further embodiment, the disorder of the immune system is an autoimmune disease. Autoimmune disorders, diseases, or conditions that may be diagnosed, treated or prevented using multivalent and multispecific compositions (e.g., MRD-containing antibodies) include, but are not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), multiple sclerosis, neuritis, uveitis ophthalmia, polyendocrinopathies, purpura (e.g., Henloch-scoenlein purpura), Reiter's Disease, Stiff-Man Syndrome, autoimmune pulmonary inflammation, myocarditis, IgA glomerulonephritis, dense deposit disease, rheumatic heart disease, Guillain-Barre Syndrome, insulin dependent diabetes mellitus, and autoimmune inflammatory eye, autoimmune thyroiditis, hypothyroidism (i.e., Hashimoto's thyroiditis, systemic lupus erythematous, discoid lupus, Goodpasture's syndrome, Pemphigus, Receptor autoimmunities for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as, primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulomatous, degenerative, and atrophic disorders.

In another embodiment the disorder of the immune system diagnosed, treated or prevented using multivalent and multispecific compositions (e.g., MRD-containing antibodies) is selected from the group consisting of: Crohn's disease, Systemic lupus erythematous (SLE), inflammatory bowel disease, psoriasis, diabetes, ulcerative colitis, multiple sclerosis, and rheumatoid arthritis. In a preferred embodiment, the autoimmune disease is rheumatoid arthritis.

In other embodiments, a therapeutically effective amount of a multivalent and monovalent multispecific composition (e.g., MRD-containing antibody) is administered to a patient to treat a metabolic disease or disorder.

In other embodiments, a therapeutically effective amount of a multivalent and monovalent multispecific composition (e.g., MRD-containing antibody) is administered to a patient to treat a cardiovascular disease or disorder. In one embodiment, the multivalent and multispecific compositions (e.g., MRD-containing antibodies) is administered to a patient to treat thrombosis, atherosclerosis, heart attack, or stroke.

In another embodiments, a therapeutically effective amount of a multivalent and monovalent multispecific composition (e.g., MRD-containing antibodies) is administered to a patient to treat a musculoskeletal disease or disorder.

In further embodiments, a therapeutically effective amount of a multivalent and monovalent multispecific composition (e.g., MRD-containing antibody) is administered to a patient to treat a skeletal disease or disorder. In one embodiment, the multivalent and monovalent multispecific composition (e.g., MRD-containing antibody) is administered to a patient to treat osteoporosis.

In additional embodiments, the multivalent and monovalent multispecific composition binds (1) a target on a cell or tissue of interest (e.g., a tumor antigen on a tumor cell) and (2) a target on a leukocyte, such as, a T-cell receptor molecule. According to one embodiment, the binding of one or more targets by the multivalent and monovalent multispecific composition is used to direct an immune response to an infectious agent, cell, tissue, or other location of interest in a patient. For example, in some embodiments an MRD of the multivalent and monovalent multispecific composition binds a target on the surface of an effector cell. Thus, in some embodiments, an MRD of the multivalent and monovalent multispecific composition binds a target on the surface of a T cell. In specific embodiments an MRD of the multivalent and monovalent multispecific composition binds CD3. In other embodiments, an MRD of the multivalent and monovalent multispecific composition binds CD2. In further embodiments, an MRD of the multivalent and monovalent multispecific composition binds the T-cell receptor (TCR). According to additional embodiments, an MRD of the multivalent and monovalent multispecific composition binds a target on the surface of a Natural Killer Cell. Thus, in some embodiments, an MRD of the multivalent and monovalent multispecific composition binds a NKG2D (Natural Killer Group 2D) receptor. In additional embodiments an MRD of the multivalent and monovalent multispecific composition binds CD16 (i.e., Fc gamma RIII) CD64 (i.e., Fc gamma RI), or CD32 (i.e., Fc gamma RII). In additional embodiments, the multispecific composition contains more than one monospecific binding site for different targets.

Thus, in some embodiments, a multivalent and monovalent multispecific composition (e.g., an MRD-containing antibody) binds a target on a leukocyte and a tumor antigen on a tumor cell. In some embodiments, the MRD-containing antibody binds NKG2D. In further embodiments, an MRD-containing antibody binds NKG2D and a target selected from ErbB2, EGFR, IGF1R, CD19, CD20, CD80 and EPCAM. In some embodiments, the MRD-containing antibody binds CD3. In particular embodiments, the MRD-containing antibody binds CD3 epsilon. In further embodiments, an MRD-containing antibody binds CD3 and a target selected from ErbB2, EGFR, IGF1R, CD19, CD20, CD80 and EPCAM. In some embodiments, the MRD-containing antibody binds CD4. In further embodiments, an MRD-containing antibody binds CD4 and a target selected from ErbB2, EGFR, IGF1R, CD19, CD20, CD80 and EPCAM.

In further embodiments, the multivalent and monovalent multispecific composition has a single binding site (i.e., is monospecific) for a target. In some embodiments, the multivalent and monovalent multispecific composition has a single binding site (i.e., is monospecific) for a target on a leukocyte, such as, a T-cell (e.g., CD3) and binds a target on a cell or tissue of interest (e.g., a tumor antigen on a tumor cell, such as, a target disclosed herein).

In further embodiments, the invention is directed to treating a disease or disorder by administering a therapeutically effective amount of a multivalent and monovalent multispecific composition that has a single binding site (i.e., is monospecific) for a target. In some embodiments, the administered multivalent and monovalent multispecific composition has a single binding site (i.e., is monospecific) for a target on a leukocyte, such as, a T-cell (e.g., CD3) and binds a target on a cell or tissue of interest (e.g., a tumor associated antigen on a tumor cell). In some embodiments, the tumor cell is from a cancer selected from breast cancer, colorectal cancer, endometrial cancer, kidney (renal cell) cancer, lung cancer, melanoma, Non-Hodgkin Lymphoma, leukemia, prostate cancer, bladder cancer, pancreatic cancer, and thyroid cancer.

Additional embodiments are directed to administering a therapeutically effective amount of a multivalent and monovalent multispecific composition to treat a neurological disease or disorder selected from brain cancer, a neurodegenerative disease, schizophrenia, epilepsy, Alzheimer's disease, Parkinson's disease, Huntington's disease, ALS, multiple sclerosis, Neuromyelitis optica and Neuro-AIDS (e.g., HIV-associated dementia). In another embodiment, the multivalent and monovalent multispecific composition is administered to a patient to treat a brain cancer, metastatic cancer of the brain, or primary cancer of the brain. In a further embodiment, the multivalent and monovalent multispecific composition is administered to a patient to treat brain injury, stroke, spinal cord injury, or pain management. In further embodiments, the multivalent and monovalent multispecific composition is administered to a patient to treat brain injury, stroke, or spinal cord injury, or for pain management.

In one embodiment, a therapeutically effect amount of the multivalent and monovalent multispecific composition is administered to a patient to treat an infection or a symptom associated with an infection caused by an infectious agent. In some embodiments, the infection is caused by a member selected from apovavirus (e.g., JC polyomavirus), trypanosomes, West Nile virus, HIV, *Streptococcus pneumoniae* and *Haemophilus influenzae*, bovine spongiform encephalopathy, meningitis, Progressive multifocal leukoencephalopathy (PML), Late-stage neurological trypanosomiasis, Encephalitis, and rabies.

According to some embodiments, the multivalent and monovalent multispecific composition (e.g., MRD-containing antibody) is able to cross the blood brain barrier (BBB) and bind a target located on the brain side of the BBB. In additional embodiments, the multivalent and monovalent multispecific composition has a single binding site that binds a target (e.g., ligand, receptor, or accessory protein) associated with an endogenous BBB receptor mediated transport system. In some embodiments, a single binding site of the composition is an MRD. In other embodiments, a single binding site of the composition is an antibody antigen binding domain. In some embodiments, the multivalent and monovalent multispecific composition contains 1, 2, 3, 4, 5, or more single binding sites (i.e., monovalently binds) for a target associated with an endogenous BBB receptor mediated transport system and the composition is able to cross to the cerebrospinal fluid side of the BBB. In additional embodiments, the multivalent and monovalent multispecific composition contains 1, 2, 3, 4, 5, or more multiple binding sites (i.e., multivalently binds) for a target associated with an endogenous BBB receptor mediated transport system and the composition is able to cross to the cerebrospinal fluid side of the BBB. In additional embodiments, a therapeutically effective amount of an MRD-containing antibody is administered to a patient to treat a neurological disease or disorder selected from brain cancer, a neurodegenerative disease, schizophrenia, epilepsy, Alzheimer's disease, Parkinson's disease, Huntington's disease, ALS, multiple sclerosis, neuromyelitis optica and beuro-AIDS (e.g., HIV-associated dementia). In some embodiments, the multivalent and monovalent multispecific composition has a single binding site (i.e., is monovalent for binding a particular target (antigen)) or two or more binding sites (i.e., is monovalent for binding a particular target) for a target selected from alpha-synuclein, RGM A, NOGO A, NgR, OMGp MAG, CSPG, neurite inhibiting semaphorins (e.g., Semaphorin 3A and Semaphorin 4) an ephrin, A-beta, AGE (S100 A, amphoterin), NGF, soluble A-B, aggrecan, midkine, neurocan, versican, phosphacan, Te38 and PGE2. In some embodiments, the multivalent and monovalent multispecific composition additionally has a single binding site or multiple binding sites for a target selected from IL1, IL1R, IL6, IL6R, IL12, IL18, IL23, TNFSF12 (TWEAK), TNFRSF5 (CD40), TNFSF5 (CD40 LIGAND), CD45RB, CD52, CD200, VEGF, VLA4, TNF alpha, Interferon gamma, GMCSF, FGF, C5, CXCL13, CCR2, CB2, MIP 1a, and MCP-1.

In additional embodiments, the multivalent and monovalent multispecific composition is capable of transferring to the cerebrospinal fluid side of the BBB and is administered to a patient to treat a neurological disease or disorder selected from: brain cancer, a neurodegenerative disease, schizophrenia, epilepsy, Alzheimer's disease, Parkinson's disease, Huntington's disease, ALS, multiple sclerosis, neuromyelitis optica and neuro-AIDS (e.g., HIV-associated dementia). In further embodiments, the invention is directed to treating a disease or disorder by administering an MRD-containing antibody that has a single binding site (i.e., is monospecific) for a target to a patient in need thereof. In some embodiments, the administered MRD-containing antibody has a single binding site (i.e., is monospecific) for a target on a leukocyte, such as, a T-cell (e.g., CD3) and binds a target on a cell or tissue of interest (e.g., a tumor associated antigen on a tumor cell).

In some embodiments, the multivalent and monovalent multispecific composition is administered to a patient to treat a neurological disease or disorder selected from brain cancer, a neurodegenerative disease, schizophrenia, epilepsy, Alzheimer's disease, Parkinson's disease, Huntington's disease, ALS, multiple sclerosis, Neuromyelitis optica and Neuro-AIDS (e.g., HIV-associated dementia). In additional embodiments, the multivalent and monovalent multispecific composition is administered to a patient to treat a brain cancer, metastatic cancer of the brain, or primary cancer of the brain. In additional embodiments, the multivalent and monovalent multispecific composition is administered to a patient to treat brain injury, stroke, spinal cord injury, or pain. Thus, according to some embodiments, the disease, disorder, or injury treated or prevented with an MRD-containing antibody or MRD of the invention is neurological. In one embodiment, the neurological disease, disorder or injury is associated with pain such as, acute pain or chronic pain.

In some embodiments the multivalent and monovalent multispecific composition binds at least 1, 2, 3, 4, or 5 targets associated with a neurological disease or disorder. In one embodiment, the multivalent and monovalent multispecific composition (e.g., MRD-containing antibody) binds 1, 2, or all 3 of the targets RGM A; NgR, and NogoA. In another embodiment, the multivalent and monovalent multispecific composition binds 1, 2, 3, or all 4 of RGM A, RGM B, and Semaphorin 3A or Semaphorin 4. In a further embodiment, the multivalent and monovalent multispecific composition binds at least 1, 2, 3, 4 or 5 targets selected from aggrecan, midkine, neurocan, versican, phosphacan, Te38, TNF alpha, NogoA, RGM A, MAG, and OMGp. In another embodiment, the multivalent and monovalent multispecific composition binds at least 1, 2, 3, 4 or 5 targets selected from aggrecan, midkine, neurocan, versican, phosphacan, Te38 and TNF alpha. In an alternative embodiment, the multivalent and monovalent multispecific composition binds at least 1, 2, 3, 4 or 5 targets selected from NgR-p75, NgR-Troy, NgR-Nogo66 (Nogo), NgR-Lingo, Lingo-Troy, Lingo-p75, MAG and Omgp. In another embodiment, the multivalent and monovalent multispecific composition binds at least 1, 2, 3, 4 or 5 targets selected from NGF, prostaglandin E2 (PGE2), TNF-alpha, IL1 beta, and IL6R.

In an additional embodiment, the multivalent and monovalent multispecific composition binds at least 1, 2, 3, 4 or 5 targets selected from alpha-synuclein, RGM A and one or more pro-inflammatory mediators (e.g., TNF alpha, ILL and MCP-1). Such compositions have applications in, for example, treating neurodegenerative diseases such as, Parkinson's.

In another embodiment, the multivalent and monovalent multispecific composition binds and antagonizes (i.e., is an antagonist of e.g., inhibits the activity of) 1, 2, 3, 4 or 5 targets selected from RGM A, NOGO A, neurite inhibiting semaphorins (e.g., Semaphorin 3A and Semaphorin 4), ephrins and pro-inflammatory targets (e.g., IL12, TNFSF12 (TWEAK), IL23, CXCL13, TNFRSF5 (CD40), TNFSF5 (CD40 LIGAND), IL18, VEGF, VLA4, TNF alpha, CD45RB, CD200, interferon gamma, GMCSF, FGF, C5, CD52, and CCR2). In an additional embodiment, the multivalent and monovalent multispecific composition binds and antagonizes 1, 2, 3, 4 or 5 targets selected from CD3, IL2, IL2R, IL6, IL6R, IL10, IL12p40, IL23, TGF beta, TNFRSF21 (DR6), fn14, CD20, LINGO, CXCL13 and CCL2. The compositions have applications in treating for example, inflammation, neuroregeneration and neurodegenerative disorders, such as MS). Multivalent and multispecific compositions (e.g., MRD-containing antibodies) that bind at least 1, 2, 3, 4, 5 or more of these targets are also encompassed by the invention. In specific embodiments, the antibody component of the MRD-containing antibody binds CD3, CD20, CD52, VLA4, TNF, TNFRSF21 (DR6), LINGO, CD3, interferon gamma or IL6.

In another embodiment, the multivalent and monovalent multispecific composition binds and antagonizes (i.e., is an antagonist of) 1, 2, 3, 4 or 5 targets selected from AGE (S100 A, amphoterin), pro-inflammatory cytokines (e.g., IL1, IL6, and TNF), chemokines (e.g., MCP 1), and molecules that inhibit neural regeneration (e.g., Nogo and RGM A). These compositions have applications in treating, for example, chronic neurodegenerative diseases such as, Alzheimer's. In an additional embodiment, the composition of the invention binds at least 1, 2, 3, 4 or 5 targets that influence neural generation and survival including, for example, NGF agonists, IL1 or IL1R antagonists, and A-beta. These compositions have applications in treating, for example, chronic neurodegenerative diseases such as, Alzheimer's.

In an additional embodiment, the composition of the invention binds to and antagonizes 1, 2, 3, 4, or 5 targets that targets that interfere with neural regeneration or recovery, including NogoA, OMgp MAG, RGM A, CSPG, one or more astrocyte inhibiting semaphorins (e.g., Semaphorin 3A and Semaphorin 4), ephrins, and pro-inflammatory cytokines (e.g., IL1, IL6, and TNF). These compositions have applications in treating neurodegenerative diseases and neural injury or trauma.

In additional embodiment, the multivalent and monovalent multispecific composition binds and antagonize (i.e., is an antagonist of) 1, 2, 3, 4, or 5 targets associated with pain, including, but not limited to, NGF and SCN9A/NAV1.7. Such compositions have applications in for example, treating or alleviating pain and pain associated conditions.

In additional embodiments, the targets bound by the compositions of the invention binds and antagonizes 1, 2, 3, 4, 5 or more mediators and or soluble or cell surface targets implicated in the inhibition of neurite growth or recovery. In specific embodiments, compositions of the invention bind to and antagonizes 1, 2, 3, 4, 5 or more targets selected from Nogo, Ompg, MAG, RGM A, semaphorins, ephrins, soluble A-b, pro-inflammatory cytokines (e.g., IL1 and TNF alpha), chemokines (e.g., MIP 1a).

In some embodiments, the invention provides a method of treating or ameliorating pain by administering a therapeutically effective amount of a pain target binding MRD-antibody, to a patient in need thereof. In additional embodiments, the invention provides a method of treating or ameliorating pain by administering a therapeutically effective amount of an NGF binding MRD-antibody, to a patient in need thereof. In further embodiments, the invention provides a method of treating or ameliorating pain by administering a therapeutically effective amount of tanezumumab (e.g., Pfizer) comprising an MRD, to a patient in need thereof.

In additional embodiments, the invention provides a method of treating or ameliorating Alzheimer's by administering a therapeutically effective amount of an Alzheimer's target binding MRD-antibody, to a patient in need thereof. In additional embodiments, the invention provides a method of treating or ameliorating Alzheimer's by administering a therapeutically effective amount of a beta amyloid binding MRD-antibody, to a patient in need thereof. In additional embodiments, the invention provides a method of treating or ameliorating Alzheimer's by administering a therapeutically effective amount of RN1219 (PF-4,360,365; Pfizer) comprising an MRD, to a patient in need thereof.

In additional embodiments, the invention provides a method of treating or ameliorating multiple sclerosis by administering a therapeutically effective amount of a multiple sclerosis target binding MRD-antibody, to a patient in need thereof. In additional embodiments, the invention provides a method of treating or ameliorating multiple sclerosis by administering a therapeutically effective amount of a LINGO binding MRD-antibody, to a patient in need thereof. In another embodiment, the invention provides a method of treating or ameliorating multiple sclerosis by administering a therapeutically effective amount of an MRD-antibody that binds LINGO and TNFRSF21 (DR6) to a patient in need thereof. In additional embodiments, the invention provides a method of treating or ameliorating multiple sclerosis by administering a therapeutically effective amount of the Biogen LINGO antibody comprising an MRD, to a patient in need thereof. In further embodiments, the invention provides a method of treating or ameliorating multiple sclerosis by administering a therapeutically effective amount of the natalizumab (e.g., TYSABRI®; Biogen) comprising an MRD, to a patient in need thereof. In an additional embodiment, the invention provides a method of treating or ameliorating multiple sclerosis by administering a therapeutically effective amount of the Biogen LINGO antibody comprising an MRD, to a patient in need thereof.

In an additional embodiment, the invention provides a method of treating or ameliorating multiple sclerosis by administering a therapeutically effective amount of a CD20 binding MRD-antibody, to a patient in need thereof. In one embodiment, the invention provides a method of treating or ameliorating multiple sclerosis by administering a therapeutically effective amount of the ocrelizumab (Biogen Idec) comprising an MRD, to a patient in need thereof.

In other embodiments, the multivalent and multispecific compositions (e.g., MRD-containing antibodies) are useful for treating or preventing an infectious disease. Infectious diseases that may be treated or prevented with multivalent and multispecific compositions (e.g., MRD-containing antibodies) include, but are not limited to, diseases associated with yeast, fungal, viral and bacterial infections. Viruses causing viral infections which can be treated or prevented with multivalent and multispecific compositions (e.g., MRD-containing antibodies) include, but are not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and cytomegalovirus), adenoviruses (e.g., lassa fever virus), paramyxoviruses (e.g., morbilbivirus virus, human respiratory syncytial virus, mumps, and pneumovirus), adrenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C (including avian influenza, e.g., H5N1 subtype)), papovaviruses (e.g., papillomaviruses), picomaviruses (e.g., rhinoviruses, enteroviruses and hepatitis A viruses), poxviruses, reoviruses (e.g., rotaviruses), togaviruses (e.g., rubella virus), rhabdoviruses (e.g., rabies virus). Microbial pathogens causing bacterial infections include, but are not limited to, *Streptococcus pyogenes, Streptococcus pneumoniae, Neisseria gonorrhoea, Neissetia meningitidis, Corynebacterium diphtheriae, Clostridium botulinum, Clostridium pefringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigellaflexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia Lsutsugumushi, Chlamydia* spp., and *Helicobacter pylori.*

In a preferred embodiment, the he multivalent and multispecific compositions (e.g., MRD-containing antibodies) are administered to a patient to treat or prevent human immunodeficiency virus (HIV) infection or AIDS, botulism, anthrax, or *Clostridium difficile.*

VIII MRD Linked Compounds that are not Antibodies

In a distinct group of embodiments, one or more MRDs of the invention are operably linked to the amino and/or carboxy terminus of an immunoglobulin fragment, such as Fab, Fab', F(ab')2, pFc', or Fc. In some embodiments, the MRDs are operably linked to a Fab or Fc polypeptide containing an additional Ig domain. In some embodiments, the MRDs are operably linked to the amino and/or carboxy terminus of an immunoglobulin fragment that is also operably linked to an scFv. In other embodiments, the MRDs of the invention are operably linked to an Fc-fusion protein.

According to this group of embodiments, one two, three, four, five, six, seven to ten, or more than ten MRDs are operably linked to the amino terminus and/or carboxy terminus of the immunoglobulin fragment. These MRDs are optionally linked to one another or to the immunoglobulin fragment via a linker. In one embodiment, one, two, three, four, five, six, seven to ten, or more than ten, of the MRDs operably linked to the amino terminus and/or carboxy terminus of the immunoglobulin fragment are the same. In another embodiment, one, two, three, four, five, six, seven to ten, or more than ten, of the MRDs operably linked to the amino terminus and/or carboxy terminus of the immunoglobulin fragment are different.

The MRDs operably linked to the immunoglobulin fragment can be monomeric (i.e., containing one MRD at the terminus of a peptide chain optionally connected by a linker) or multimeric (i.e., containing more than one MRD in tandem optionally connected by a linker). The MRDs can be homo-multimeric (i.e., containing more than one of the same MRD in tandem optionally connected by linker(s) (e.g., homodimers, homotrimers, homotetramers etc.)) or heteromultimeric (i.e., containing two or more MRDs in which there are at least two different MRDs optionally connected by linker(s) where all or some of the MRDs linked to a particular terminus are different (e.g., heterodimer)). In one embodiment, two different monomeric MRDs are located at different termini of the immunoglobulin fragment. In another embodiment, three, four, five, six, or more different monomeric MRDs are located at different termini of the immunoglobulin fragment.

In an alternative embodiment, the MRD-containing antibody contains at least one dimeric and one monomeric MRD located at different immunoglobulin termini. In another alternative embodiment, the MRD-containing antibody contains at least one homodimeric and one monomeric MRD located at different immunoglobulin termini. In another alternative embodiment, the MRD-containing antibody contains at least one heterodimeric and one monomeric MRD located at different immunoglobulin termini.

In an alternative embodiment, the MRD-containing antibody contains at least one multimeric and one monomeric MRD located at different immunoglobulin termini. In another alternative embodiment, the MRD-containing antibody contains at least one homomultimeric and one monomeric MRD located at different immunoglobulin termini. In another alternative embodiment, the MRD-containing antibody contains at least one heteromultimeric and one monomeric MRD located at different immunoglobulin termini.

Multiple MRDs that are operably linked to the immunoglobulin fragment can target the same target binding site, or two or more different target binding sites. Where the MRDs bind to different target binding sites, the binding sites may be on the same or different targets. Similarly, one or more of the MRDs may bind to the same target as the immunoglobulin fragment.

In some embodiments, at least one of the MRDs and if applicable, the immunoglobulin fragment (e.g., where the immunoglobulin fragment is an Fab), bind to their targets simultaneously. In additional embodiments, two, three, four, five, six, seven, eight, nine, ten, or more than ten MRDs, and if applicable the immunoglobulin fragment, bind to their targets simultaneously.

The synthesis of MRDs operably linked to an immunoglobulin fragment and the assay of these MRDs and immunoglobulin fragment for their ability to bind, or compete for binding with one or more targets simultaneously can be routinely accomplished using methods disclosed herein or otherwise known in the art.

In a specific embodiment, one or more of the operably linked MRDs or the immunoglobulin fragment, binds to VEGF. In another specific embodiment, one or more of the operably linked MRDs or the immunoglobulin fragment, binds to the same epitope as ranibizumab (LUCENTIS®, Genentech). In another specific embodiment, one or more of the operably linked MRDs or the immunoglobulin fragment, competitively inhibits ranibizumab binding to VEGF. In an additional embodiment, the immunoglobulin fragment is a Fab. In a further specific embodiment, the immunoglobulin fragment is ranibizumab.

In another embodiment, the invention provides a method of treating macular degeneration comprising administering a therapeutically effective amount of a VEGFA or VEGFR binding MRD-immunoglobulin fragment fusion to a patient in need thereof. In a specific embodiment, the invention provides a method of treating macular degeneration comprising administering a therapeutically effective amount of a VEGFA or VEGFR binding MRD-Fab fusion to a patient in need thereof. In a specific embodiment, the invention provides a method of treating macular degeneration comprising administering a therapeutically effective amount of MRD-ranibizumab to a patient in need thereof.

In other embodiments the one or more MRDs of the invention are operably linked to the amino and/or carboxyl terminus of an Fc fusion protein. The Fc fusion protein can contain fusions to any protein or polypeptide sequence of therapeutic value, for example, any of the targets or receptors of the targets described herein. For example, the fusions can contain the extracellular domain of receptors or ligands that typically function or display improved cognate-partner binding in multimeric form, including for example, receptors corresponding to the TNF-R superfamily (e.g., TNFR2, TACI, BCMA, HVEM, etc.), IL receptor superfamily (e.g., IL1-R-IL6R), VEGFR superfamily (e.g., VEGFR1-VEGR3), FGFR superfamily (e.g., FGFR1-FGFR4), and B7 superfamily (e.g., CTLA)).

In a specific embodiment, one, two, three, four, five, six, or more MRDs are operably linked to a VEGR1/VEGFR2-Fc fusion protein. In another specific embodiment, one or more of the operably linked MRDs bind to the same epitope as aflibercept (Regeneron). In another specific embodiment, one or more of the operably linked MRDs competitively inhibit aflibercept binding to VEGFA or PLGF. In a further specific embodiment, the MRDs are operably linked to aflibercept.

In another embodiment, the invention provides a method of treating cancer comprising administering a therapeutically effective amount of an MRD-VEGFR1/VEGFR2-Fc fusion protein to a patient in need thereof. In a specific embodiment, the invention provides a method of treating colorectal cancer, prostate cancer, or non-small cell lung cancer comprising administering a therapeutically effective amount of a VEGFA or PLGF binding MRD-Fc fusion protein to a patient in need thereof. In a specific embodiment, the invention provides a method of treating macular degeneration comprising administering a therapeutically effective amount of a VEGFA or PLGF binding MRD-Fc fusion protein and irinotecan, 5FU, oxaliplatin, doxetaxel, or FOLFOX6, to a patient in need thereof.

In another embodiment, the invention provides a method of treating cancer comprising administering a therapeutically effective amount of MRD-aflibercept to a patient in need thereof. In a specific embodiment, the invention provides a method of treating colorectal cancer, prostate cancer, or non-small cell lung cancer comprising administering a therapeutically effective amount of MRD-aflibercept to a patient in need thereof. In a specific embodiment, the invention provides a method of treating macular degeneration comprising administering a therapeutically effective amount of MRD-aflibercept and irinotecan, 5FU, oxaliplatin, doxetaxel, or FOLFOX6, to a patient in need thereof.

In a specific embodiment, one, two, three, four, five, six, or more MRDs are operably linked to a CTLA4-Fc fusion protein. In another specific embodiment, one or more of the operably linked MRDs bind to the same epitope as abatacept (ORENCIA®). In another specific embodiment, one or more of the operably linked MRDs competitively inhibits abatacept binding to CD80 (B7-1) or CD86 (B7-2). In a further specific embodiment, the MRDs are operably linked to abatacept. In another specific embodiment, one or more of the operably linked MRDs bind to the same epitope as belatacept (Bristol Myers Squibb). In another specific embodiment, one or more of the operably linked MRDs competitively inhibits belatacept binding to CD80 (B7-1) or CD86 (B7-2). In an additional embodiment, the immunoglobulin fragment is a Fab. In a further specific embodiment, the MRDs are operably linked to belatacept.

In another embodiment, the invention provides a method of suppressing an immune response comprising administering a therapeutically effective amount of an MRD-CTLA4-Fc fusion protein to a patient in need thereof. In a specific embodiment, the invention provides a method suppressing an immune response comprising administering a therapeutically effective amount of MRD-abatacept to a patient in need thereof. In another specific embodiment, the invention provides a method of treating rheumatoid arthritis comprising administering a therapeutically effective amount of MRD-abatacept to a patient in need thereof. In another specific embodiment, the invention provides a method of suppressing an immune response to a graft rejection comprising administering a therapeutically effective amount of MRD-abatacept to a patient in need thereof.

In a specific embodiment, the invention provides a method of suppressing an immune response comprising administering a therapeutically effective amount of MRD-belatacept to a patient in need thereof. In another specific embodiment, the invention provides a method of suppressing an immune response to a graft rejection comprising administering a therapeutically effective amount of MRD-belatacept to a patient in need thereof.

In another specific embodiment, one, two, three, four, five, six, or more MRDs are operably linked to a TNFR2-Fc fusion protein. In another specific embodiment, one or more of the operably linked MRDs bind to the same epitope as etanercept (ENBREL®). In another specific embodiment, one or more of the operably linked MRDs competitively inhibits etanercept binding to TNF alpha. In another embodiment, one or more of the operably linked MRDs binds ANG2. In a further specific embodiment, the MRDs are operably linked to etanercept.

In another embodiment, the invention provides a method of suppressing an immune response comprising administering a therapeutically effective amount of a MRD-TNFR2-Fc fusion protein to a patient in need thereof. In one embodiment, the invention provides a method of treating an autoimmune disease by administering a therapeutically effective amount of a MRD-TNFR2-Fc fusion protein to a patient in need thereof. In one embodiment, the invention provides a method of treating rheumatoid arthritis, by administering a therapeutically effective amount of an MRD-TNFR2-Fc fusion protein to a patient in need thereof. In one embodiment, the invention provides a method of treating an inflammatory disorder, by administering a therapeutically effective amount of an MRD-TNFR2-Fc fusion protein to a patient in need thereof. In another embodiment, the invention provides a method of treating Crohn's disease, by administering a therapeutically effective amount of an MRD-TNFR2-Fc fusion protein to a patient in need thereof. In another embodiment, the invention provides a method of treating ulcerative colitis, by administering a therapeutically effective amount of an MRD-TNFR2-Fc fusion protein to a patient in need thereof. In another embodiment, the invention provides a method of treating psoriatic arthritis, ankylosing spondylitis, psoriasis, or juvenile idiopathic arthritis by administering a therapeutically effective amount of an MRD-TNFR2-Fc fusion protein to a patient in need thereof.

In another embodiment, the invention provides a method of suppressing an immune response comprising administering a therapeutically effective amount of a MRD-etanercept-Fc fusion protein to a patient in need thereof. In one embodiment, the invention provides a method of treating an autoimmune disease by administering a therapeutically effective amount of MRD-etanercept to a patient in need thereof. In one embodiment, the invention provides a method of treating rheumatoid arthritis, by administering a therapeutically effective amount of MRD-etanercept to a patient in need thereof. In one embodiment, the invention provides a method of treating an inflammatory disorder, by administering a therapeutically effective amount of MRD-etanercept to a patient in need thereof. In another embodiment, the invention provides a method of treating Crohn's disease, by administering a therapeutically effective amount of MRD-etanercept to a patient in need thereof. In another embodiment, the invention provides a method of treating ulcerative colitis, by administering a therapeutically effective amount of MRD-etanercept to a patient in need thereof. In another embodiment, the invention provides a method of treating psoriatic arthritis, ankylosing spondylitis, psoriasis, or juvenile idiopathic arthritis by administering a therapeutically effective amount of MRD-etanercept to a patient in need thereof.

In another specific embodiment, one, two, three, four, five, six, or more MRDs are operably linked to a TACI-Fc fusion protein. In another specific embodiment, one or more of the operably linked MRDs bind to the same epitope as atacicept (Merck/Serono). In another specific embodiment, one or more of the operably linked MRDs competitively inhibits atacicept binding to BLyS or APRIL. In a further specific embodiment, the MRDs are operably linked to atacicept.

In another embodiment, the invention provides a method of suppressing an immune response comprising administering a therapeutically effective amount of a MRD-TACI-Fc fusion protein to a patient in need thereof. In one embodiment, the invention provides a method of treating an autoimmune disease by administering a therapeutically effective amount of a MRD-TACI-Fc fusion protein to a patient in need thereof. In one embodiment, the invention provides a method of treating rheumatoid arthritis, by administering a therapeutically effective amount of a MRD-TACI-Fc fusion protein to a patient in need thereof. In one embodiment, the invention provides a method of treating systemic lupus erythematous by administering a therapeutically effective amount of a MRD-TACI-Fc fusion protein to a patient in need thereof. In another embodiment, the invention provides a method of suppressing an immune response comprising administering a therapeutically effective amount of an MRD-atacicept fusion protein to a patient in need thereof. In one embodiment, the invention provides a method of treating an autoimmune disease by administering a therapeutically effective amount of an MRD-atacicept fusion protein to a patient in need thereof. In one embodiment, the invention provides a method of treating rheumatoid arthritis, by administering a therapeutically effective amount of an MRD-atacicept protein fusion protein to a patient in need thereof. In one embodiment, the invention provides a method of treating systemic lupus erythematous, by administering a therapeutically effective amount of an MRD-atacicept fusion protein to a patient in need thereof.

In another specific embodiment, one, two, three, four, five, six, or more MRDs are operably linked to an IL1R-Fc fusion protein. In another specific embodiment, one or more of the operably linked MRDs bind to the same epitope as rilonacept (Regeneron). In another specific embodiment, one or more of the operably linked MRDs competitively inhibits rilonacept binding to IL1R. In a further specific embodiment, the MRDs are operably linked to rilonacept.

In another embodiment, the invention provides a method of preventing gout comprising administering a therapeutically effective amount of a MRD-IL1R-Fc fusion protein to a patient in need thereof. In a specific embodiment, the invention provides a method of preventing gout comprising administering a therapeutically effective amount of an MRD-rilonacept-Fc fusion protein to a patient in need thereof.

In some embodiments, the invention encompasses a complex comprising an antibody and at least one modular recognition domain (MRD), wherein the MRD comprises at least two cysteines, wherein a first cysteine is located within the first ten amino acids of the MRD, a second cysteine is located within the last ten amino acids of the MRD, and wherein the MRD comprises at least five amino acids between said first cysteine and said second cysteine. In additional embodiments, the MRD comprises at least 10, 15, 20, or 25 amino acids between the first cysteine and the second cysteine. In some embodiments, the MRD comprises at least one proline between the first cysteine and the second cysteine. In other embodiments, the MRD comprises at least two proline between the first cysteine and the second cysteine. In some embodiments, the first cysteine is no more than 5, 3, 3, 2, or 1 amino acids away from the N-terminus of the complex. In some embodiments, the second cysteine is no more than 5, 3, 3, 2, or 1 amino acids away from the C-terminus of the complex. In some embodiments, the in vivo half-life of an MRD in a complex of the invention is increased compared to the half-life of an MRD in a corresponding complex wherein at least one of the cysteines is mutated or deleted. In some embodiments, the binding affinity of the MRD is at least equal to the binding affinity of an MRD in a corresponding complex wherein at least one of the cysteines is mutated or deleted.

In some embodiments, the invention encompasses a complex comprising an antibody and at least one modular recognition domain (MRD), wherein the antibody and the MRD bind to different targets or epitopes on the same cell or molecule, wherein the MRD binding agonizes or antagonizes the MRD target under physiological conditions, and wherein said MRD does not bind to and agonize or antagonize said MRD target under physiological conditions in the absence of said antibody. In some embodiments, an MRD in the complex of the invention binds the MRD target in the absence of the antibody with an EC50 of greater than 0.01 nM, 0.1 nM, 0.5 nM, or 0.7 nM under physiological conditions.

In some embodiments, the invention encompasses a complex comprising an antibody and at least one MRD, wherein the antibody and the MRD bind to different targets or epitopes on a heteromeric or homomeric protein, wherein the MRD binding agonizes or antagonizes the MDR target under physiological conditions, and wherein said MRD does not bind to and agonize or antagonize said MRD target under physiological conditions in the absence of the antibody. In some embodiments, an MRD in the complex of the invention binds the MRD target with an EC50 of greater than 0.01 nM, 0.1 nM, 0.5 nM, or 0.7 nM under physiological conditions.

In some embodiments, the invention encompasses a method for inhibiting the growth of a cell comprising contacting the cell with a multispecific and multivalent complex comprising an antibody and at least one modular recognition domain (MRD), and a protein kinase inhibitor. In some embodiments, the antibody binds to a target selected from: VEGF, VEGFR1, EGFR, ErbB2, IGF-IR, cMET, FGFR1, and FGFR2. In some embodiments, the protein kinase inhibitor inhibits a target of the MRD containing antibody. In some embodiments, the protein kinase inhibitor inhibits a different target than the MRD containing antibody. In some embodiments, the protein kinase inhibitor inhibits more than one protein kinase. In some embodiments, the protein kinase inhibitor is a member selected from: imatinib, gefitinib, vandetanib, erlotinib, sunitinib, lapatinib, and sorafenib.

In some embodiments, the invention encompasses a method for inhibiting angiogenesis in a patient comprising administering to said patient a therapeutically effective amount of a multispecific and multivalent complex comprising an antibody and at least one modular recognition domain (MRD), and a protein kinase inhibitor. In some embodiments, the antibody binds to a target selected from: VEGF, VEGFR1, EGFR, ErbB2, IGF-IR, cMET, FGFR1, and FGFR2. In some embodiments, the protein kinase inhibitor inhibits a target of the MRD containing antibody. In some embodiments, the protein kinase inhibitor inhibits a different target than the MRD containing antibody. In some embodiments, the protein kinase inhibitor inhibits more than one protein kinase. In some embodiments, the protein kinase inhibitor is a member selected from: imatinib, gefitinib, vandetanib, erlotinib, sunitinib, lapatinib, and sorafenib.

In some embodiments, the invention encompasses a method for treating a patient having cancer comprising administering to said patient a therapeutically effective amount of a multispecific and multivalent complex comprising an antibody and at least one modular recognition domain (MRD), and a protein kinase inhibitor. In some embodiments, the antibody binds to a target selected from: VEGF, VEGFR1, EGFR, ErbB2, IGF-IR, cMET, FGFR1, and FGFR2. In some embodiments, the protein kinase inhibitor inhibits a target of the MRD containing antibody. In some embodiments, the protein kinase inhibitor inhibits a different target than the MRD containing antibody. In some embodiments, the protein kinase inhibitor inhibits more than one protein kinase. In some embodiments, the protein kinase inhibitor is a member selected from: imatinib, gefitinib, vandetanib, erlotinib, sunitinib, lapatinib, and sorafenib.

In some embodiments, the invention encompasses a method for treating a patient having a disease or disorder of the immune system comprising administering to said patient a therapeutically effective amount of a multispecific and multivalent complex comprising an antibody and at least one modular recognition domain (MRD), and a protein kinase inhibitor. In some embodiments, the disease or disorder of the immune system is inflammation or an autoimmune disease. In further embodiments, the autoimmune disease is rheumatoid arthritis, Crohn's disease, systemic lupus erythematous, inflammatory bowel disease, psoriasis, diabetes, ulcerative colitis, or multiple sclerosis. In additional embodiments, the antibody binds TNF. In some embodiments, the protein kinase inhibitor inhibits a target that is not a target of the MRD-containing antibody. In some embodiments, the protein kinase inhibitor inhibits more than one protein kinase. In further embodiments, the protein kinase inhibitor is a member selected from: lestaurtinib, tofacitinib, ruxolitinib, SB1518, CYT387, LY3009104, TG101348, fostamatinib, BAY 61-3606, and sunitinib.

In some embodiments, the invention encompasses a multivalent and multispecific complex comprising an antibody and at least one modular recognition domain (MRD), wherein the complex has a single binding site for a cell surface target. In some embodiments, the multivalent and multispecific complex comprises 2 single binding sites for different epitopes on the same target. In some embodiments, the multivalent and multispecific complex has 2, 3, 4, 5 or more single binding sites for different targets. In some embodiments, the multivalent and multispecific complex has a single binding site for a target on a leukocyte. In some embodiments, the multivalent and multispecific complex has a single binding site for a target on a T-cell. In some embodiments, the multivalent and multispecific complex has a single binding site for CD3. In further embodiments, complex has a single binding site for CD3 epsilon. In additional embodiments, the complex has a single binding site for a target on a natural killer cell. In additional embodiments, the complex has multiple binding sites for a target on a diseased cell. In some embodiments, the complex has multiple binding sites for 2, 3, 4, 5 or more targets on a diseased cell. In additional embodiments, the complex has multiple binding sites for a target on a tumor cell. In further embodiments, the complex has multiple binding sites for 2, 3, 4, 5 or more targets on a tumor cell. In some embodiments, the complex has multiple binding sites for a target on an immune cell. In further embodiments, the complex has multiple binding sites for 2, 3, 4, 5 or more targets on an immune cell. In some embodiments, the complex has a single binding site for a target on a natural killer cell. In some embodiments, the complex binds a target on a leukocyte and a target on a tumor cell. In some embodiments, the complex binds CD3 and CD19. In further embodiments, the complex has multiple binding sites for a target on an infectious agent or a cell infected with an infectious agent. In further embodiments, the complex has multiple binding sites for 2, 3, 4, 5 or more targets on an infectious agent or a cell infected with an infectious agent. In some embodiments, the complex has a single binding site for a target associated with an endogenous blood brain barrier (BBB) receptor mediated transport system. In further embodiments, the complex has multiple binding sites for a target associated with an endogenous BBB receptor mediated transport system. In some embodiments, the complex has multiple binding sites for 2, 3, 4, 5 or more targets associated with an endogenous BBB receptor mediated transport system. In some embodiments, the single binding site is an MRD. In some embodiments, the single binding site is an antigen binding domain.

In some embodiments, the complexes of the invention comprise a cytotoxic agent.

Polynucleotide encoding a heavy chain or light chain of the MRD containing antibody of the invention, vectors comprising these polynucleotides and host cells containing these vectors and/or polynucleotides are also encompassed by the invention The following examples are intended to illustrate but not limit the invention.

EXAMPLES

Example 1. Integrin Targeting Antibody-MRD Molecules

Novel antibody-MRD fusion molecules were prepared by fusion of an integrin αvβ3-targeting peptides to catalytic antibody 38C2. Fusions at the N-termini and C-termini of the light chain and the C-termini of the heavy chain were most effective. Using flow cytometry, the antibody conjugates were shown to bind efficiently to integrin αvβ3-expressing human breast cancer cells. The antibody conjugates also retained the retro-aldol activity of their parental catalytic antibody 38C2, as measured by methodol and doxorubicin prodrug activation. This demonstrates that cell targeting and catalytic antibody capability can be efficiently combined for selective chemotherapy.

Example 2. Angiogenic Cytokine Targeting Antibody-MRD Molecules

Angiogenic cytokine targeting antibody-MRD fusion molecules were constructed. The antibody used was 38C2, which was fused with a MRD containing the 2xCon4 peptide (AQQEECEWDPWTCEH-MGSGSATGGSGSTASSGSGSATHQEECEWDPWTCE-HMLE (SEQ ID NO:10)). The MRD-containing peptide was fused to either the N- or C-terminus of the light chain and the C-terminus of the heavy chain. Similar results were found with the other Ang2 MRD peptides. Additional Ang2 MRD peptides include: MGAQTNFMPMDNDELLL YEQ-FILQQGLEGGSGSTASSGSGSSLGAQTNFMPMDN-DELLLY (SEQ ID NO:20) (LM-2x-32); and AQQEECE-WDPWTCEHMGSGSATGGSGSTASSGSGSATHQEEC-EWDPWTCEH MLE (SEQ ID NO:10) (2xCon4).

One of skill in the art, given the teachings herein, will appreciate that other such combinations will create functional Ang2 binding MRDs as described herein.

Example 3. Antibody-MRD Fusions with Non-Catalytic Antibodies

A humanized mouse monoclonal antibody, LM609, directed towards human integrin αvβ3 has been previously described (Rader, C. et. al., PNAS 95:8910-5 (1998)).

Figure 3:
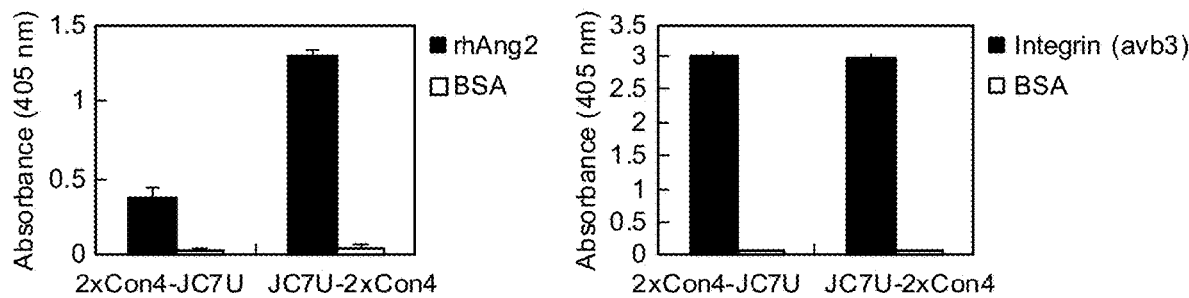
FIG. 3 depicts the results of an enzyme linked immunosorbent assay (ELISA) in which integrin and Ang2 were bound by an anti-integrin antibody (JC7U) fused to an Ang2 targeting MRD (2xCon4).
Figure 4:
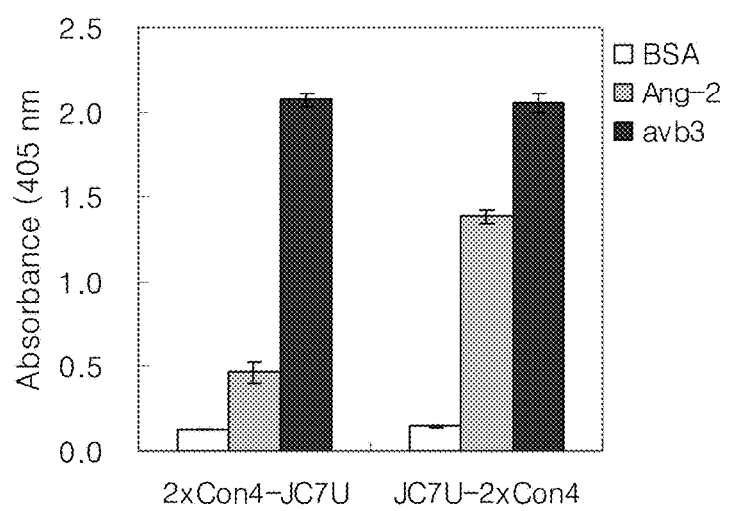
FIG. 4 depicts the results of an ELISA in which integrin and Ang2 were bound by an anti-integrin antibody (JC7U) fused to an Ang2 targeting MRD (2xCon4).

A human non-catalytic monoclonal Ab, JC7U was fused to an anti-Ang2 MRD containing 2xCon4 (AQQEECEWD-PWTCEHMGSGSATGGSGSTASSGSGSATHQEECE-WDPWTCEH MLE (SEQ ID NO:10)) at either the N- or C-terminus of the light chain. 2xCon4 (AQQEECEWDP-WTCEHMGSGSATGGSGSTASSGSGSATHQEECEWD-PWTCEHMLE (SEQ ID NO:10)) was studied as an N-terminal fusion to the Kappa chain of the antibody (2xCon4-JC7U) and as a C-terminal fusion (JC7U-2xCon4). Both fusions maintained integrin and Ang2 binding. As shown in the left panel of FIG. 3, both antibody constructs (2xCon4-JC7U and JC7U-2xCon4) specifically bound to recombinant Ang2 as demonstrated by ELISA studies. Binding to Ang2, however, is significantly higher with JC7U-2xCon4, which has the 2xCon4 (SEQ ID NO:10) fusion at the C-terminus of the light chain of the antibody. The right panel of FIG. 3 depicts the binding of Ang2-JC7U and JC7U-Ang2 to integrin αvβ3. The results show that fusion of 2xCon4 (SEQ ID NO:10) to either the N- or the C-light chain terminus does not affect mAb JC7U binding to integrin αvβ3. FIG. 4 depicts another ELISA study using the same antibody-MRD fusion constructs.

Example 4. HERCEPTIN®-MRD Fusion Molecules

Another example of MRD fusions to a non-catalytic antibody are HERCEPTIN®-MRD fusion constructs. The HERCEPTIN®-MRD fusions are multifunctional, both small molecule αv integrin antagonists and the chemically programmed integrin-targeting antibody show remarkable efficacy in preventing the breast cancer metastasis by interfering with αv-mediated cell adhesion and proliferation. MRD fusions containing HERCEPTIN®-2xCon4 (which targets ErbB2 and Ang2) and HERCEPTIN®-V114 (which targets ErbB2 and VEGF targeting) and HERCEPTIN®-RGD-4C-2xCon4 (which targets ErbB2, ang2, and integrin targeting) are effective.

Example 5. VEGF Targeting Antibody-MRD Molecules

An antibody containing an MRD that targets VEGF was constructed. A MRD which targets v1 14 (SEQ ID NO:13) was fused at the N-terminus of the kappa chain of 38C2 and HERCEPTIN® using a linker. Expression and testing of the resulting antibody-MRD fusion constructs demonstrated strong VEGF binding.

Example 6. IGF1R Targeting Antibody-MRD Molecules

Fusion of an MRD which targets IGF1R (SFYSCLESLVNGPAEKSRG QWDGCRKK (SEQ ID NO:14)) to the N-terminus of the kappa chain of 38C2 and HERCEPTIN® using the long linker sequence as a connector was studied. Expression and testing of the resulting antibody-MRD fusion constructs demonstrated strong IGF1R binding. Additional clones showing high binding to IGR1R were identified after several rounds of mutagenesis and screening of the regions described in Table 4. The preferred sequences listed in Table 5 bind IGF1R and show no significant or no binding affinity to the insulin receptor, thereby suggesting specificity for IGF1R.

TABLE 4

Template for further mutagenesis.

| Name | DNA | AA |
|---|---|---|
| Rm2-2-218 | GTGGAGTGCAGGGCG CCG (SEQ ID NO: 50) | VECRAP (SEQ ID NO: 51) |
| Rm2-2-316 | GCTGAGTGCAGGGCT GGG (SEQ ID NO: 52) | AECRAG (SEQ ID NO: 53) |
| Rm2-2-319 | CAGGAGTGCAGGACG GGG (SEQ ID NO: 54) | QECRTG (SEQ ID NO: 55) |

TABLE 5

| Mutant | Amino acid sequence | Template | SEQ ID NO |
|---|---|---|---|
| Rm4-31 | NFYQCIEMLASHPAEKSRGQWQECRTGG | Rm2-2-319 | 35 |
| Rm4-33 | NFYQCIEQLALRPAEKSRGQWQECRTGG | Rm2-2-319 | 36 |
| Rm4-39 | NFYQCIDLLMAYPAEKSRGQWQECRTGG | Rm2-2-319 | 37 |
| Rm4-310 | NFYQCIERLVTGPAEKSRGQWQECRTGG | Rm2-2-319 | 38 |
| Rm4-314 | NFYQCIEYLAMKPAEKSRGQWQECRTGG | Rm2-2-319 | 39 |
| Rm4-316 | NFYQCIEALQSRPAEKSRGQWQECRTGG | Rm2-2-319 | 40 |
| Rm4-319 | NFYQCIEALSRSPAEKSRGQWQECRTGG | Rm2-2-319 | 41 |
| Rm4-44 | NFYQCIEHLSGSPAEKSRGQWQECRTG | Rm2-2-319 | 42 |
| Rm4-45 | NFYQCIESLAGGPAEKSRGQWQECRTG | Rm2-2-319 | 43 |
| Rm4-46 | NFYQCIEALVGVPAEKSRGQWQECRTG | Rm2-2-319 | 44 |
| Rm4-49 | NFYQCIEMLSLPPAEKSRGQWQECRTG | Rm2-2-319 | 45 |
| Rm4-410 | NFYQCIEVFWGRPAEKSRGQWQECRTG | Rm2-2-319 | 46 |
| Rm4-411 | NFYQCIEQLSSGPAEKSRGQWQECRTG | Rm2-2-319 | 47 |
| Rm4-415 | NFYQCIELLSARPAEKSRGQWAECRAG | Rm2-2-316 | 48 |
| Rm4-417 | NFYQCIEALARTPAEKSRGQWVECRAP | Rm2-2-218 | 49 |

Example 7. ErbB2 Binding, Ang2-Targeting Antibody-MRD Molecules

Figure 5:
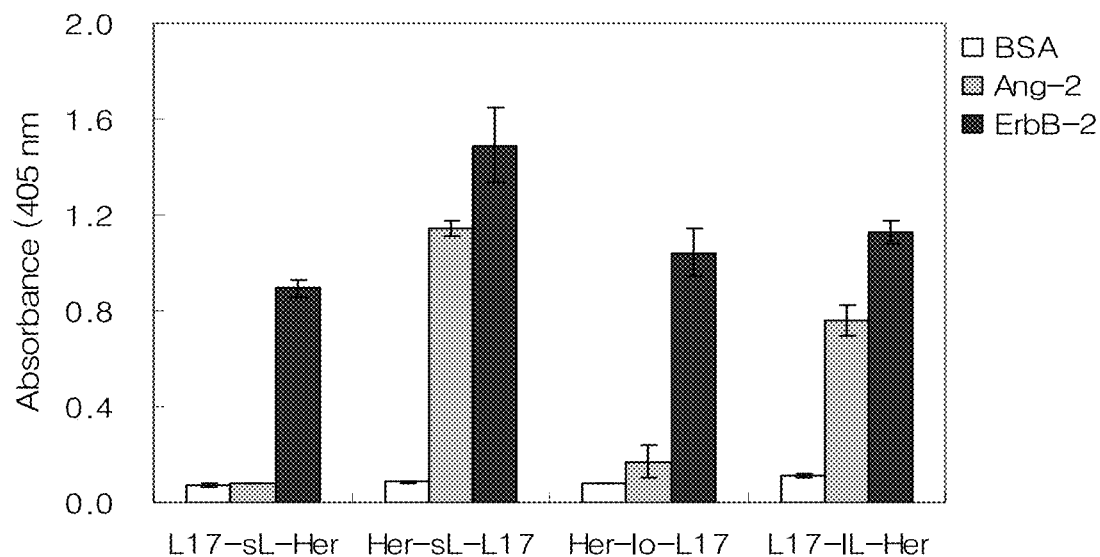
FIG. 5 depicts the results of an ELISA in which an anti-ErbB2 antibody was fused to an MRD which targets Ang2.

An antibody was constructed which contains an MRD that targets Ang2 (L17) (SEQ ID NO:7) fused to the light chain of an antibody which binds to ErbB2. Either the short linker sequence, the long linker sequence, or the 4th loop in the light chain constant region was used as a linker. FIG. 5 depicts the results of an ELISA using constructs containing an N-terminal fusion of an Ang2 targeting MRD with the ErbB2 antibody with the short linker peptide (GGGS (SEQ ID NO:1)) (L17-sL-Her), a C-terminal fusion of Ang2 targeting MRD with the ErbB2 antibody with the short linker peptide (Her-sL-L17), a C-terminal fusion of Ang2 targeting MRD with the ErbB2 antibody with the 4th loop in the light chain constant region (Her-lo-L17), or an N-terminal fusion of Ang2 targeting MRD with the ErbB2 antibody with the long linker peptide (SSGGGGSGGGGGGSSRSS (SEQ ID NO:19)) (L17-1L-Her). ErbB2 was bound with varying degrees by all of the constructs. However, Ang2 was bound only by Her-sL-L17 and L17-1L-Her.

Figure 6:
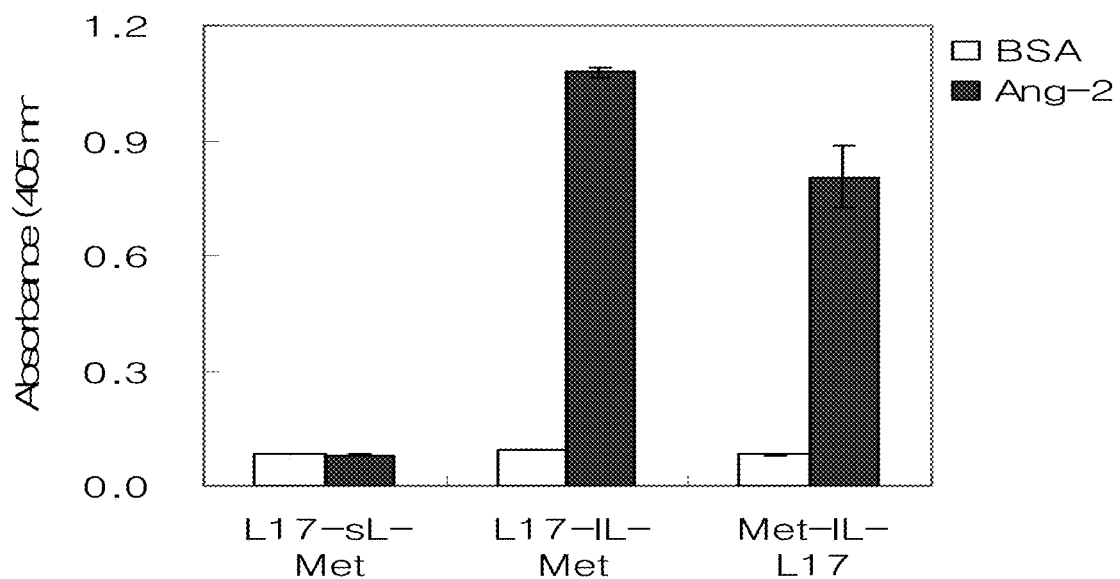
FIG. 6 depicts the results of an ELISA in which an Ang2 targeting MRD was fused to a hepatocyte growth factor receptor (cMET) binding antibody.

Example 8. Hepatocyte Growth Factor Receptor Binding, Ang2-Targeting Antibody-MRD Molecules Fusion of an MRD which targets Ang2 (L17) (SEQ ID NO:7) was made to either the N-terminus or C-terminus of the light chain of the Met antibody, which binds to hepatocyte growth factor receptor. Either the short linker sequence or the long linker sequence were used as a connector. FIG. 6 depicts the results of an ELISA using constructs containing N-terminal fusion of Ang2 targeting MRD with the Met antibody with the short linker peptide (GGGS (SEQ ID NO:1)) (L17-sL-Met), N-terminal fusion of Ang2 targeting MRD with the Met antibody with the long linker peptide (SSGGGGSGGGGGSSRSS (SEQ ID NO:19)) (L17-1L-Met), and C-terminal fusion of Ang2 targeting MRD with the Met antibody with the long linker peptide (Met-lLL17). Expression and testing of the resulting antibody-MRD fusion constructs demonstrated strong Ang2 binding when the long linker peptide was used. Fusion of the Ang2 targeting MRD to the C-light chain terminus of the antibody resulted in slightly higher binding to Ang2 then fusion of the Ang2 targeting to the N-light chain terminus of the antibody.

Example 9. ErbB2 Binding, Integrin-Targeting Antibody-MRD Molecules

Figure 7:
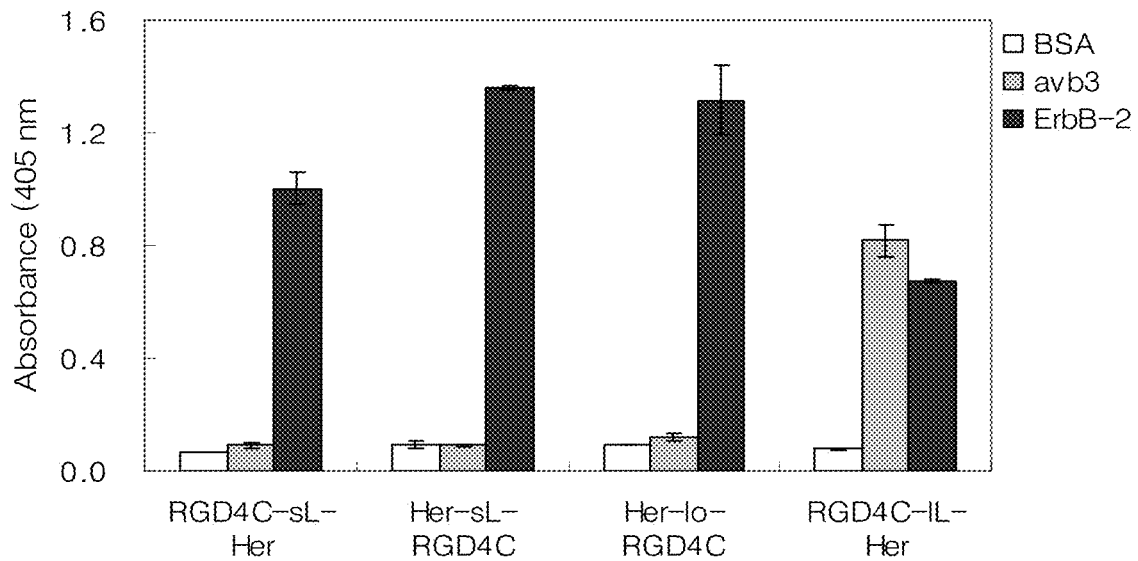
FIG. 7 depicts the results of an ELISA in which an integrin targeting MRD was fused to an ErbB2-binding antibody.

An antibody was constructed which contains an MRD that targets integrin αvβ3 (RGD4C) with the sequence CDCRGDCFC (SEQ ID NO:106) fused to the light chain of an antibody HERCEPTIN® which binds to ErbB2 (Her). Either the short linker sequence, the long linker sequence, or the 4th loop in the light chain constant region was used as a linker. FIG. 7 depicts the results of an ELISA using constructs containing an N-terminal fusion of integrin αvβ3 targeting MRD with the ErbB2 antibody with the short linker peptide (GGGS (SEQ ID NO:1)) (RGD4C-sL-Her), a C-terminal fusion of integrin αvβ3 targeting MRD with the ErbB2 antibody with the short linker peptide (Her-sL-RGD4C), a C-terminal fusion of integrin αvβ3 targeting MRD with the ErbB2 antibody with the 4th loop in the light chain constant region (Her-lo-RGD4C), or an N-terminal fusion of integrin αvβ3 targeting MRD with the ErbB2 antibody with the long linker peptide (SSGGGGSGGGGGSSRSS (SEQ ID NO:19)) (RGD4C-1L-Her). ErbB2 was bound with varying degrees by all of the constructs. However, integrin αvβ3 was bound only by RGD4C-1L-Her.

Figure 8:
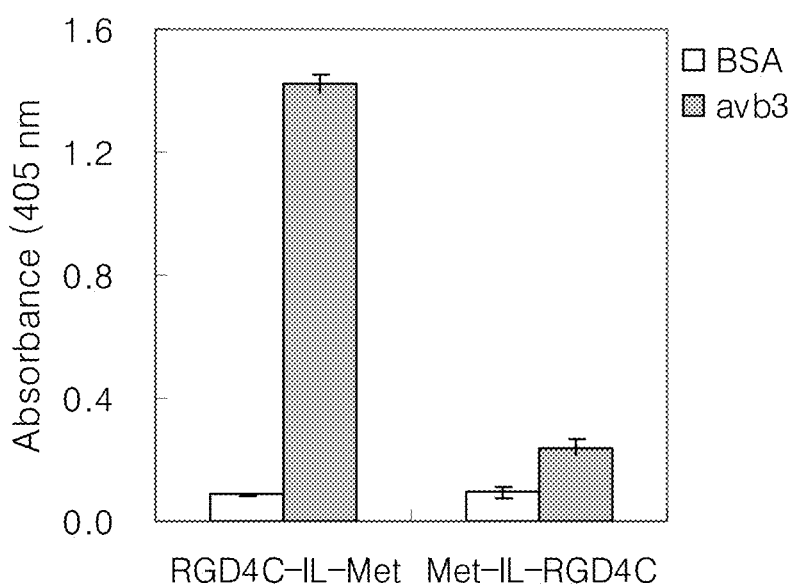
FIG. 8 depicts the results of an ELISA in which an integrin targeting MRD was fused to a hepatocyte growth factor receptor binding antibody.

Example 10. Hepatocyte Growth Factor Receptor Binding, Integrin-Targeting Antibody-MRD Molecules An antibody was constructed which contains an MRD that targets integrin αvβ3 (RGD4C) (SEQ ID NO:106) fused to the light chain of an antibody which binds to the hepatocyte growth factor receptor (Met). Antibody-MRD constructs containing the long linker sequence were used. FIG. 8 depicts the results of an ELISA using constructs containing an N-terminal fusion of integrin αvβ3 targeting MRD with the hepatocyte growth factor receptor antibody (RGD4C-1L-Met), or a C-terminal fusion of integrin αvβ3 targeting MRD with the hepatocyte growth factor receptor antibody (Met-1L-RGD4C). The RGD4C-1L-Met demonstrated strong integrin αvβ3 binding.

Figure 9:
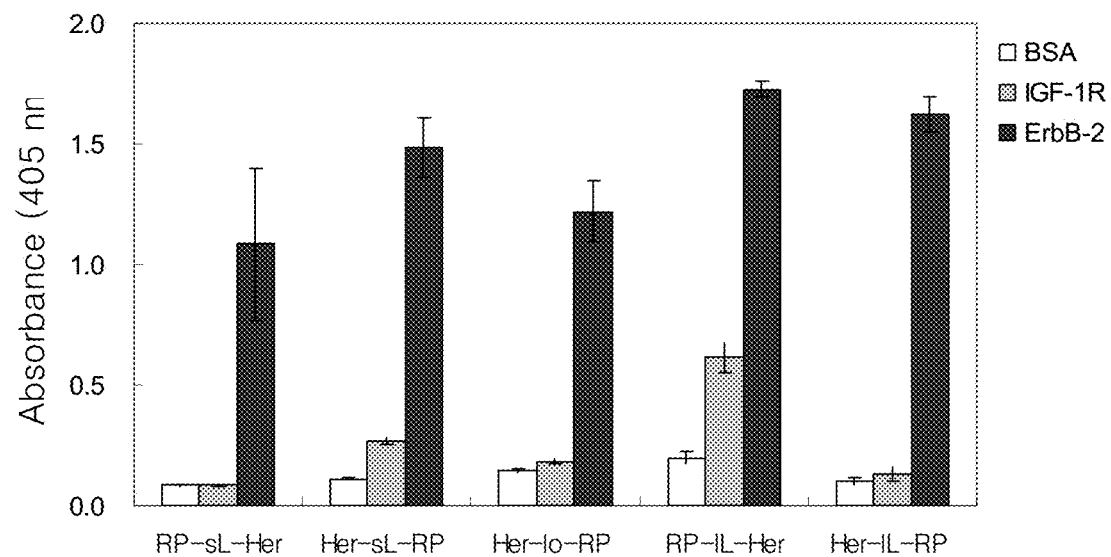
FIG. 9 depicts the results of an ELISA in which an insulin-like growth factor-I receptor targeting MRD was fused to an ErbB2-binding antibody.

Example 11. ErbB2 Binding, Insulin-Like Growth Factor-I Receptor-Targeting Antibody-MRD Molecules Antibodies were constructed which contains an MRD that targets insulin-like growth factor-I receptor (RP) (SEQ ID NO:14) fused to the light chain of an antibody which binds to ErbB2 (Her). Either the short linker peptide, the long linker peptide, or the 4th loop in the light chain constant region was used as a linker (Carter et al., Proc. Natl. Acad. Sci. USA 89:4285-4289 (1992); U.S. Pat. No. 5,677,171; and ATCC Deposit 10463, each of which is herein incorporated by reference). FIG. 9 depicts the results of an ELISA using constructs containing an N-terminal fusion of insulin-like growth factor-I receptor targeting MRD with the ErbB2 antibody with the short linker peptide (RP-sL-Her), a C-terminal fusion of insulin-like growth factor-I receptor targeting MRD with the ErbB2 antibody and the short linker peptide (Her-sL-RP), a C-terminal fusion of insulin-like growth factor-I receptor targeting MRD with the ErbB2 antibody with the 4th loop in the light chain constant region (Her-lo-RP), an N-terminal fusion of insulin-like growth factor-I receptor targeting MRD with the ErbB2 antibody with the long linker peptide (RP-1L-Her), or a C-terminal fusion of insulin-like growth factor-I receptor targeting MRD with the ErbB2 antibody with the long linker peptide (Her-1L-RP). ErbB2 was bound with varying degrees by all of the constructs. Insulin-like growth factor-I receptor was bound by RP-1L-Her.

Example 12. ErbB2 Binding. VEGF-Targeting Antibody-MRD Molecules

Figure 10:
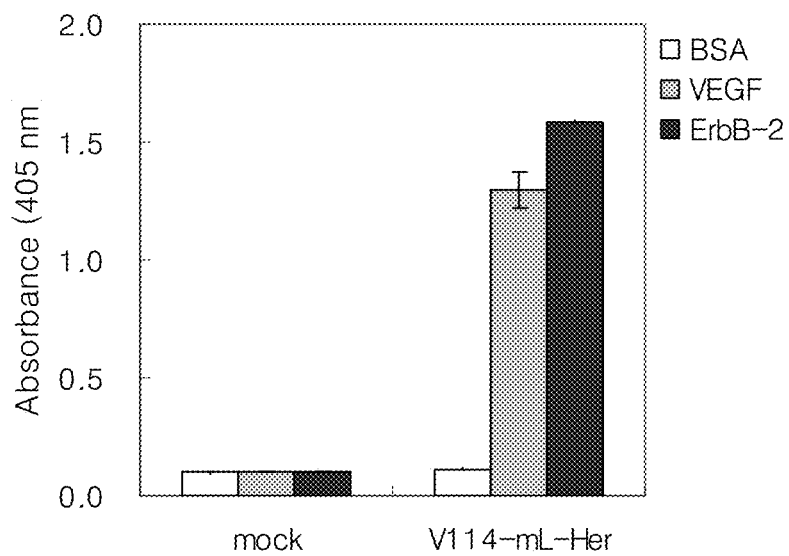
FIG. 10 depicts the results of an ELISA in which a VEGF-targeting MRD was fused to an ErbB2-binding antibody.

Fusion of an MRD which targets VEGF (VI 14) (SEQ ID NO:13) (Fairbrother W. J., et al., Biochemistry 37:177754-177764 (1998)) was made to the N-terminus of the light chain of a ErbB2-binding antibody (Her). A medium linker peptide (SSGGGGSGGGGGSS (SEQ ID NO:2)) was used as a connector. FIG. 10 depicts the results of an ELISA using a construct containing an N-terminal fusion of VEGF targeting MRD with the ErbB2-binding antibody with the medium linker peptide (V1 14-mL-Her). Expression and testing of the resulting antibody-MRD fusion construct demonstrated strong VEGF and ErbB2 binding.

Example 13. Integrin Targeting Antibody-MRD Molecules

Figure 11:
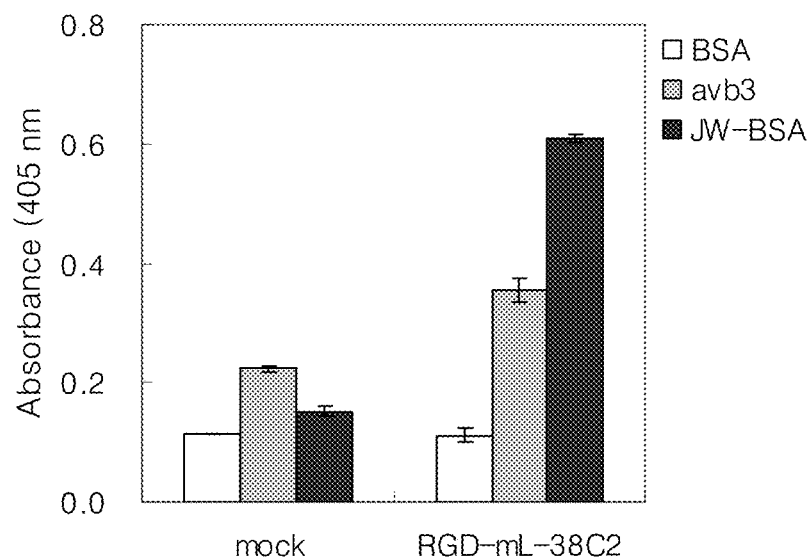
FIG. 11 depicts the results of an ELISA in which an integrin targeting MRD was fused to a catalytic antibody.

Fusion of an MRD which targets integrin αvβ3 (RGD) (SEQ ID NO:106) to the N-terminus of the light chain of 38C2 using the medium linker peptide as a connector was studied. FIG. 11 demonstrates that expression and testing of the resulting antibody-MRD fusion construct had strong integrin αvβ3 binding.

Example 14. Ang2 Targeting Antibody-MRD Molecules

Figure 12:
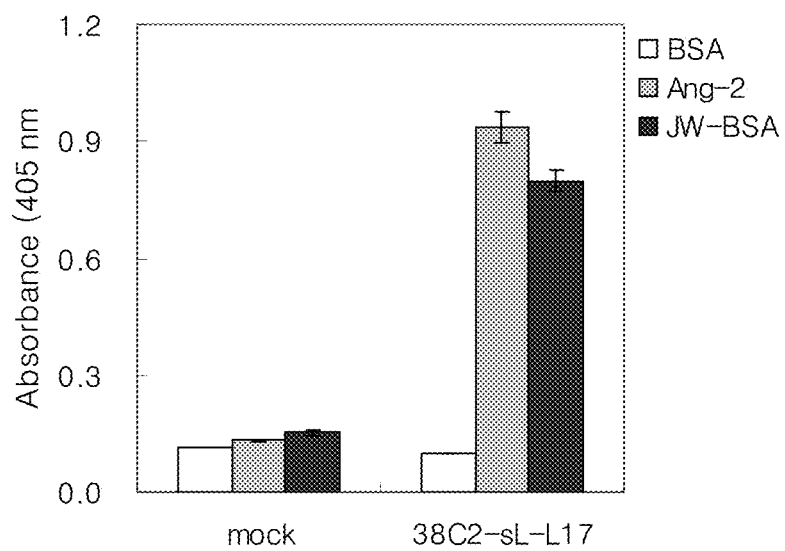
FIG. 12 depicts the results of an ELISA in which an Ang2-targeting MRD was fused to a catalytic antibody.

Fusion of an MRD which targets Ang2 (L 17) (SEQ ID NO:7) to the C-terminus of the light chain of 38C2 using the short linker sequence as a connector was studied. FIG. 12 demonstrates that expression and testing of the resulting antibody-MRD fusion construct had strong Ang2 binding.

Example 15. ErbB2 Binding, Integrin and Ang2 Targeting Antibody-MRD Molecules

Figure 13:
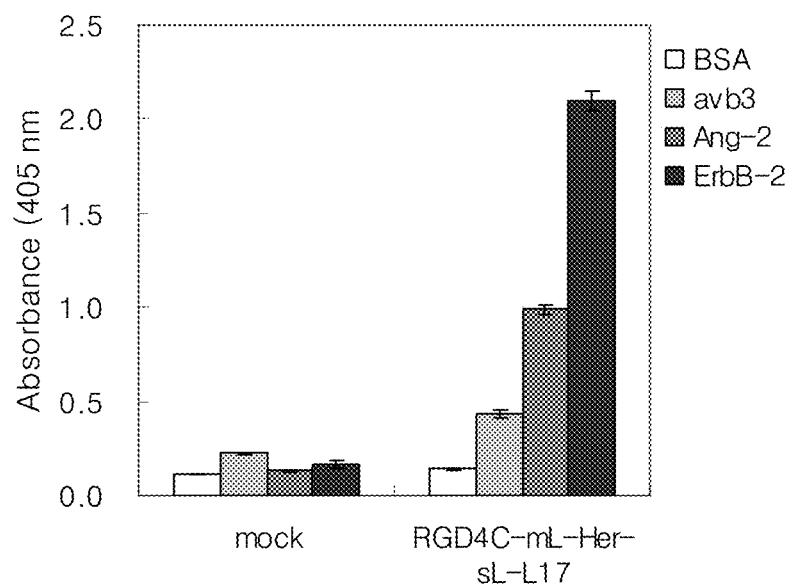
FIG. 13 depicts the results of an ELISA in which an integrin targeting MRD and an Ang2 targeting MRD were fused to an ErbB2-binding antibody.

An MRD which targets integrin αvβ3 (RGD4C) was connected to the N-terminus of the light chain of an ErbB2 targeting antibody (Her) with a medium linker, and an Ang2 (L17) targeting MRD was connected by a short linker to the C-terminus of the same ErbB2 targeting antibody (RGD4C- mL-Her-sL-L17). FIG. 13 demonstrates that the resulting antibody-MRD fusion construct bound to integrin, Ang2, and ErbB2.

Similarly, ErbB2 targeting antibodies (e.g., Her) with an IGF-1R MRD fused to the C-terminus of the heavy chain or the N-terminus of the light chain bound to immobilized IGF-1R at comparable rates. In addition, ErbB2 targeting antibodies containing an IGF-1R MRD fused to the N-terminus of the light chain and an Ang2 MRD fused to the C-terminus of the heavy chain bound to immobilized IGF-1R at comparable rates. Each of these three multivalent and multispecific compositions (e.g., MRD-containing antibodies) also inhibited the binding of IGF-1 to immobilized IGF-1R. The trispecific molecule (HERCEPTIN with IGF-1R and Ang2 MRDs) bound to both cell surface ErbB2 and soluble Ang2.

Example 16. ErbB2 Binding, Integrin-Targeting Antibody-MRD Molecules

Figure 14:
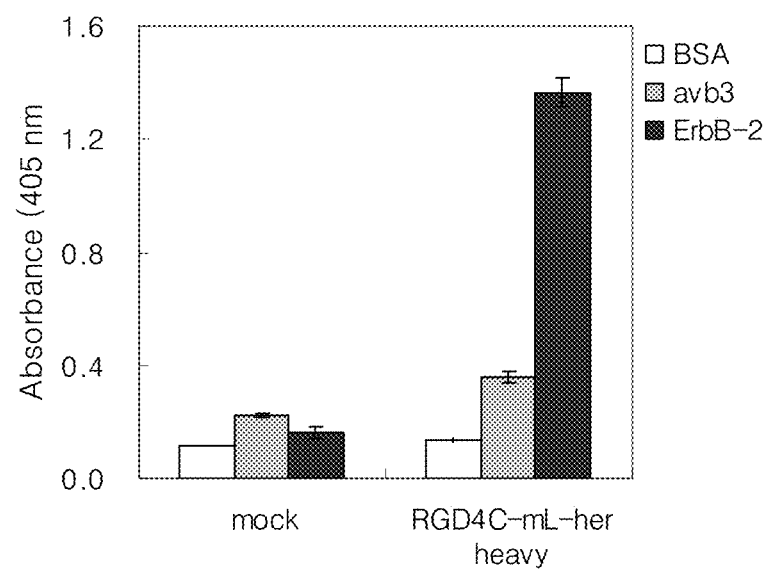
FIG. 14 depicts the results of an ELISA in which an integrin targeting MRD was fused to an ErbB2-binding antibody.

An antibody was constructed which contains an MRD that targets integrin $\alpha v\beta 3$ (RGD4C) fused to the N-terminus of the heavy chain of an antibody which binds to ErbB2 (Her) using the medium linker as a connector (RGD4C-mL-her-heavy). FIG. 14 depicts the results of an ELISA using the construct. Both integrin and ErbB2 were bound by the construct.

Figure 15:
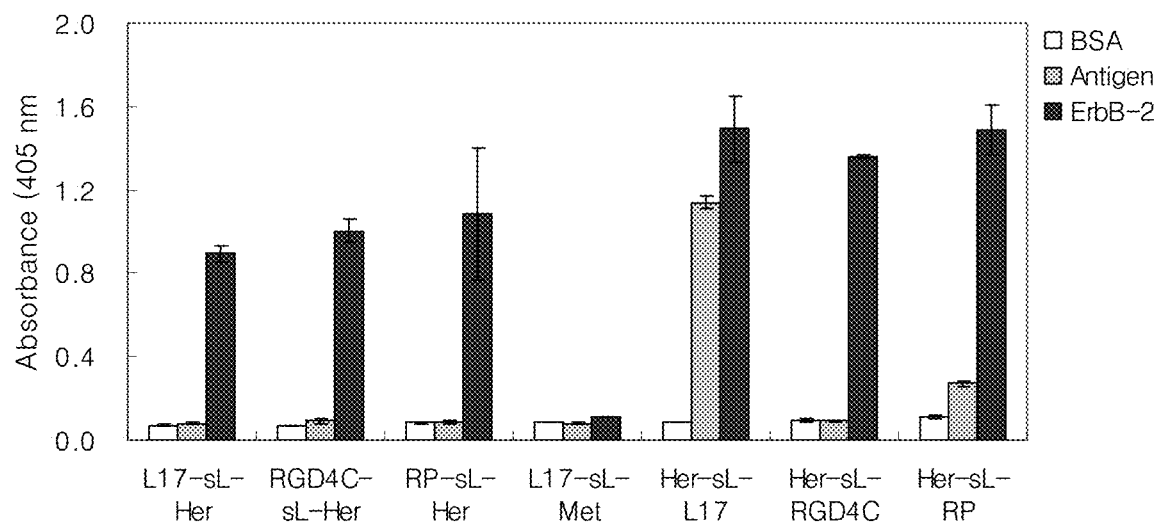
FIG. 15 depicts the results of an ELISA in which an integrin, Ang2, or insulin-like growth factor-I receptor-targeting MRD was fused to an ErbB2 or hepatocyte growth factor receptor-binding antibody with a short linker peptide.

Example 17. ErbB2 or Hepatocyte Growth Factor Receptor Binding, and Integrin, Ang2 or Insulin-Like Growth Factor-I Receptor-Targeting Antibody-MRD Molecules with the Short Linker Peptide Antibody-MRD molecules were constructed which contain ErbB2 or hepatocyte growth factor receptor binding antibodies, and integrin $\alpha v\beta 3$, Ang2 or insulin-like growth factor-I receptor-targeting MRD regions were linked with the short linker peptide to the light chain of the antibody. FIG. 15 depicts the results of an ELISA using constructs containing an N-terminal fusion of Ang2 targeting MRD fused to the ErbB2 antibody (L17-sL-Her), an N-terminal fusion of integrin-targeting MRD with the ErbB2 antibody (RGD4C-sL-Her), an N-terminal fusion of insulin-like growth factor-I receptor targeting MRD with the ErbB2-binding antibody (RP-sL-Her), a C-terminal fusion of Ang2 targeting MRD with the hepatocyte growth factor receptor binding antibody (L17-sL-Met), a C-terminal fusion of Ang2 targeting MRD with the ErbB2-binding antibody (Her-sL-L17), a C-terminal fusion of integrin targeting MRD with the ErbB2-binding antibody (Her-sL-RGD4C), or a C-terminal fusion of insulin-like growth factor-I receptor targeting MRD with the ErbB2-binding antibody (Her-sL-RP). ErbB2 was bound with varying degrees by the antibody-MRD constructs, with the exception of the construct containing the hepatocyte growth factor receptor-binding antibody. Antigen was bound only by the Her-sL-L17 construct.

Figure 16:
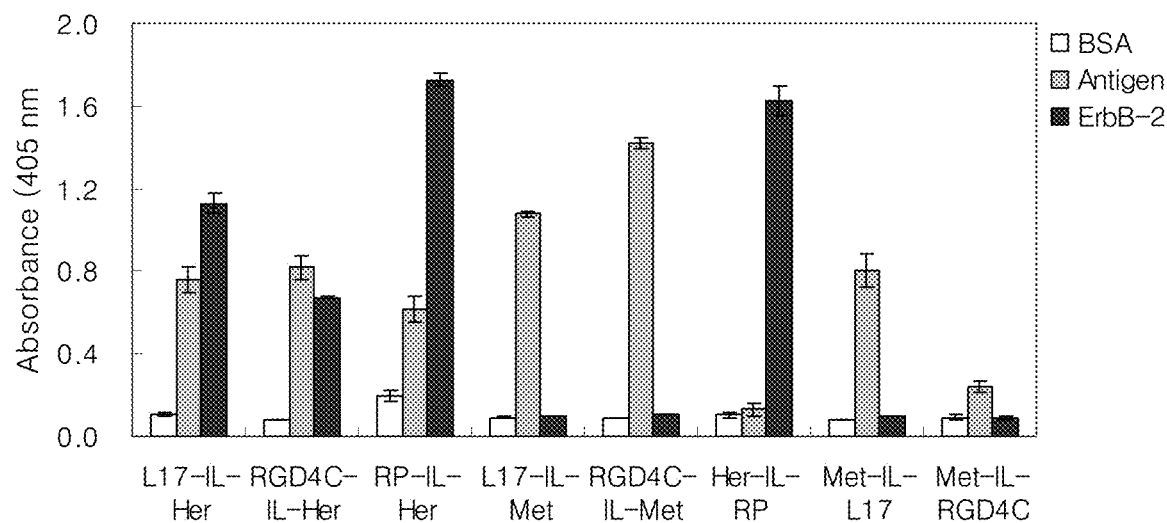
FIG. 16 depicts the results of an ELISA in which an integrin, Ang2, or insulin-like growth factor-I receptor-targeting MRD was fused to an ErbB2 or hepatocyte growth factor receptor-binding antibody with a long linker peptide.

Example 18. ErbB2 or Hepatocyte Growth Factor Receptor Binding, and Integrin, Ang2 or Insulin-Like Growth Factor-I Receptor-Targeting Antibody-MRD Molecules with the Long Linker Peptide Antibody-MRD molecules were constructed which contain ErbB2 or hepatocyte growth factor receptor binding antibodies, and integrin $\alpha v\beta 3$, Ang2 or insulin-like growth factor-I receptor-targeting MRD regions linked with the long linker peptide to the light chain of the antibody. FIG. 16 depicts the results of an ELISA using constructs containing an N-terminal fusion of Ang2 targeting MRD fused to the ErbB2 antibody (L17-1L-Her), an N-terminal fusion of integrin-targeting MRD with the ErbB2 antibody (RGD4C-1L-Her), an N-terminal fusion of insulin-like growth factor-I receptor-targeting MRD with the ErbB2-binding antibody (RP-1L-Her), a C-terminal fusion of Ang2 targeting MRD with the hepatocyte growth factor receptor binding antibody (L17-1L-Met), a C-terminal fusion of integrin targeting MRD with the hepatocyte growth factor receptor binding antibody (RGD4C-1L-Met), a C-terminal fusion of Ang2 targeting MRD with the insulin-like growth factor-I receptor binding antibody (Her-1L-RP), a C-terminal fusion of Ang2 targeting MRD with the hepatocyte growth factor receptor binding antibody (Met-1L-L17), or a C-terminal fusion of integrin targeting MRD with the hepatocyte growth factor receptor binding antibody (Met-1L-RGD4C). As shown in FIG. 16, antibody-MRD fusions are effective to bind antigen and ErbB2. Lu et al., J. Biol. Chem. 20:280(20):19665-19672 (2005); Lu et al., J. Biol. Chem. 2004 Jan. 23:279 (4):2856-65.

Example 19: Cloning and Expression of Ang2 MRDs Fused to Maltose Binding Protein A. Cloning of MBP Fusions Monomer and dimer peptides were expressed as protein fusions to maltose binding protein (MBP) using a modified form of the pMAL-p2 vector and expression system from New England Biolabs (NEB; Beverly, Mass.) The PCR-generated MRD sequence was inserted into a pMAL vector down-stream from the malE gene, which encodes MBP. This results in a vector that encodes an MRD-MBP-fusion protein. The pMAL vector contains a strong Ptac promoter and is inducible by IPTG. The pMAL-p2 series contains the normal malE signal sequence, which directs the fusion protein through the cytoplasmic membrane. pMAL-p2 fusion proteins capable of being exported can be purified from the periplasm through osmotic shock. Further purification can be performed, for example by binding to amylose resin.

B. Expression of MBP Fusion Proteins and Osmotic Shock Fractionation

For expression of fusion proteins, bacterial cultures grown overnight were back-diluted into fresh media to an OD A600 of approximately 0.1. Cultures were grown to an OD of approximately 0.8 and induced with IPTG at a concentration of 0.3 mM. Cultures were incubated with shaking for approximately 4 hours, after which bacteria were centrifuged for 15 minutes at 4700 g. Pelleted bacteria were resuspended in 30 mM Tris-HCL pH 7.4, 20% sucrose, 1 mM EDTA. Cells were incubated for 20 minutes at room temperature (RT) prior to centrifugation for 15 minutes at 4700 g. Pelleted bacteria were then resuspended in ice cold $MgSO_4$, and incubated for 20 minutes on ice, with periodic mixing. Cell suspensions were sonicated (Misonix XL2020) for 90 seconds. Cells were centrifuged at 4° C. for 20 minutes at 4700 g. The supernatant ("osmotic shock fraction") was adjusted to 1×PBS using 10×PBS (Quality Biologics, cat #119-069-131) and filtered through 0.2 micron filter. These osmotic shock fractions were assayed directly for binding to Ang2.

C. Direct Binding of MBP Fusion Proteins

For detection of direct binding of MRD-MBP fusions to Ang2, the following ELISA was performed. Ninety-six-well plates were coated overnight with rhAng2 (R&D cat#623-AN) at 320 ng/ml (100 µl/well). Wells were blocked for 3.25 hours with 250 µl Blocking buffer (Thermo Cat# N502), followed by 4 washes with 300 µl wash buffer (PBS, 0.1% tween). MBP fusion proteins were serially diluted in Blocking buffer and added to wells for 2 hours at RT. After washing (8×300 µl wash buffer), samples were treated with HRP-mouse anti MBP mAb (NEB, cat # E8038S), diluted 1:4000 in Blocking buffer. After incubation for 1 hour at RT, wells were washed (8×300 µl wash buffer) prior to receiving 100 µl of TMB substrate (KPL Laboratories). Color development was stopped with 100 µl of $H_2SO_4$, and absorbance was read at 450 nm.

D. Results

Figure 17B:
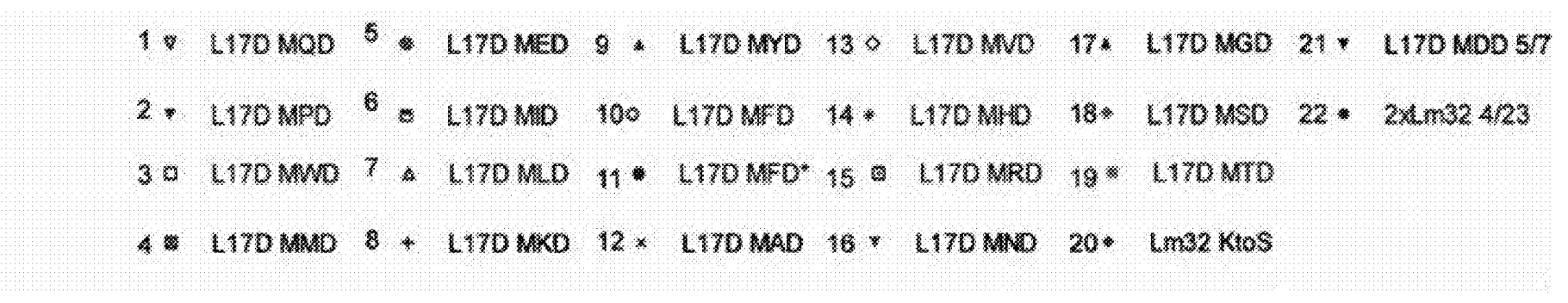

MRD-MBP fusions were assayed for direct binding to Ang2. Osmotic shock fractions of induced bacterial cultures were serially diluted and added to Ang2 coated wells. Bound fusion proteins were detected with anti-MBP mAb. The dose response curves are presented in FIGS. 17A and 17B. Assayed proteins represent mutational variants of the sequence MGAQTNFMPMDDDE LLLYEQFILQQGLE (L17D) (SEQ ID NO:107). In this series, the motif MDD within L17D was mutated at the first D to all other possible amino acids (except cysteine). Other MRDs tested were "Lm32 KtoS" and a dimer of Lm32 (2×Lm32). As presented in FIG. 17C, several MXD mutants exhibit binding in the 0.1 to 100 nm range. The Lm32 dimer (2×Lm32) exhibits greater than 10 fold higher affinity for Ang2 than either L17D or "Lm32 KtoS".

Example 21: Expression and Purification of Antibodies Containing MRDs

Molecular recognition domains were constructed and expressed in a pcDNA 3.3 vector as fusion proteins with either the heavy or light chains of antibodies. For protein production, plasmid DNAs encoding the heavy and light chains of the antibodies containing MRDs were first transformed into chemically competent bacteria in order to produce large amounts of DNA for transient transfection. Single transformants were propagated in LB media and purified using Qiagen's Endotoxin Free Plasmid Kits. Briefly, cells from an overnight culture were lysed; lysates were clarified and applied to an anion-exchange column, and then subjected to a wash step and eluted with high salt. Plasmids were precipitated, washed, and resuspended in sterile water.

HEK293T cells were expanded to the desired final batch size (about 5 L) prior to transfection. The purified plasmid (1 mg per liter of production) was complexed with the polyethylenimine (PEI) transfection reagent, added to the shake flask culture, and incubated at 37° C. The culture was monitored daily for cell count, cell diameter, and viability. The conditioned medium was harvested and stored at −80° C. until purification.

Antibodies containing MRDs were purified from the conditioned medium using affinity chromatography. Culture supernatant was filter clarified and applied directly to a chromatography column containing recombinant Protein A Sepharose (GE Healthcare). The column was washed, and bound antibodies containing MRDs were eluted by lowering buffer pH. Following elution, eluate fractions were immediately adjusted to physiologic pH. Following Protein A affinity purification, an additional optional polishing chromatographic step can be performed as needed.

Purified proteins were dialyzed into PBS, concentrated to ~1-4 mg/ml, sterile filtered, aliquoted aseptically, and stored frozen at −80° C. All steps of the purification were monitored by SDS-PAGE-Coomassie, and precautions were taken during the purification to keep endotoxin levels as minimal as possible.

The final product was analyzed for endotoxin levels (EndoSafe), purity (SDS-PAGE-coomassie, analytical SEC-HPLC), protein identity (Western blot), and yield (Bradford assay). An additional size exclusion HPLC analysis was performed to assess the level of aggregates.

The data presented in Table 6 indicate that the antibodies containing MRDs can be expressed and purified using conventional techniques.

TABLE 6

| Zybody | Yield (mg) | Purity | Aggregates (%) | Endotoxin (EU/ml) |
|---|---|---|---|---|
| HER2xCon4(H) | 36 | >90% | 4.6 | <1 |
| HER-lm32(H) | 57 | >90% | 1 | 2.02 |
| HER-lm32(L) | 98 | >90% | 2 | 3.26 |
| AVA-lm32(H) | 12 | >90% | 0 | <1 |

Example 22: Simultaneous Binding of HER Lm32(H) and HER Lm32 (L) to Her2 and Ang2

A. Methods

Ninety-six-well plates were coated overnight with rHER2-Fc (R&D cat#1129-ER-050) at 20 ng/ml (100W/well). Wells are blocked for 3.25 hours with 250 μl Blocking buffer (Thermo Cat# N502), followed by 4 washes with 300 μl wash buffer (PBS, 0.1% tween). Antibodies containing MRDs (HER-lm32(H), HER-lm32(L), and AVA-lm32(H)) and antibodies (HERCEPTIN®) were serially diluted in Blocking buffer, containing 1.94 μg/ml biotinylated Ang2 (R&D cat#BT633) and added to wells for 2 hours at RT. After washing (8×300 μl wash buffer), parallel samples received either HRP-conjugated anti-human kappa chain mAb-(Abeam, cat # ab79115-1) diluted 1:1000 in Blocking buffer or HRP-conjugated streptavidin (Thermo Scientific cat#N100) diluted 1:4000 diluted in Blocking buffer. After incubation for 1 hour at RT, wells were washed (8×300 μl wash buffer) prior to receiving 100 μl of TMB substrate (KPL Laboratories). Color development was stopped with 100 μl of $H_2SO_4$, and absorbance was read at 450 nm.

B. Results

As detected with anti-human kappa chain mAb, both a HERCEPTIN®-based antibody or HERCEPTIN®-based antibodies containing MRDs bind to Her2 Fc in the presence of Ang2 in a dose dependent manner (FIG. 18A). Only the HERCEPTIN®-based antibodies containing MRDs (HER-lm32(H) and HER-lm32(L)) exhibit simultaneous binding to Her2 Fc and Ang2, as detected by HRP-conjugated streptavidin (FIG. 18B).

Example 23: Simultaneous Binding of AVA-Lm32(H) to VEGF and Ang2

A. Methods:

Ninety-six-well plates were coated overnight with human VEGF (PeproTech, Inc. cat#100-20) at 30 ng/ml (100 μl/well). Wells were blocked for 3.25 hours with 250 μl Blocking buffer (Thermo Cat# N502), followed by 4 washes with 300 µl wash buffer (PBS, 0.1% tween). Antibodies containing MRDs (HER-lm32(H) and AVA-lm32(H)) and antibodies (AVASTIN®) were serially diluted in Blocking buffer, containing 3.876 µg/ml biotinylated Ang2 (R&D cat#BT633) and added to wells for 2 hours at RT. After washing (8×300 µl wash buffer), parallel samples received either HRP-conjugated anti-human kappa chain mAb (Abcam, cat # ab79115) diluted 1:1000 in Blocking buffer or HRP-conjugated streptavidin (Thermo Scientific cat#N100) diluted 1:4000 diluted in Blocking buffer. After incubation for 1 hour at RT, wells were washed (8×300 µl wash buffer) prior to receiving 100 µl of TMB substrate (KPL Laboratories). Color development was stopped with 100 µl of $H_2SO_4$, and absorbance was read at 450 nm.

B. Results

As detected with anti-human kappa chain mAb, both AVASTIN® and AVASTIN®-based antibodies containing MRDs bind to VEGF in the presence of Ang2 in a dose dependent manner (FIG. 19A). Only the AVASTIN®-based antibodies containing MRDs (AVA-lm32(H)) exhibited simultaneous binding to VEGF and Ang2, as detected by HRP-conjugated streptavidin (FIG. 19B).

Example 24: Simultaneous Binding of HER-Lm32 (H) and HER-Lm32 (L) to HER2 and Angiopoietin-2

The ability of HER-lm32 (H) and HER-lm32 (L) simultaneously bind to Her2 expressed on the surface of breast carcinoma cells BT-474, and to Ang2 in solution, was determined by flow cytometry. Mouse anti-human Ig-FITC was used for detection of the heavy chain of the antibodies containing MRDs, and Ang2-biotin/streptavidin-PE was used for detection of the lm32 MRD. Cells that bind Her2 and Ang2 simultaneously are expected to be detected as double positive for FITC and PE fluorescence.

One million HER2 positive breast carcinoma cells BT-474 were incubated with 1 HER-lm32(H) or HER-lm32 (L) for 25 minutes at RT. After washing, cells were incubated with 200 ng/mL Ang2 biotin (R&D systems) for 25 minutes at RT and then with 20 µL of mouse anti-human Ig-FITC and Streptavidin-PE for 15 minutes. After washing with 2 mL buffer, cells were analyzed by flow cytometry (FACS Canto II, BD).

In order to confirm the specificity of binding of HER-lm32(H) and HER-lm32(L) to HER2 on BT-474 cells, binding was determined in the presence of 10-fold excess of HERCEPTIN®. In these experiments, antibodies containing MRDs (1 µg) were incubated with one million BT-474 cells in the absence or presence of 10 µg HERCEPTIN® for 25 minutes at RT. Binding of antibodies containing MRDs to HER2 was determined by incubating with 200 ng/mL Ang2 biotin followed by detection with streptavidin-PE.

The data presented in FIGS. 20A and 20B demonstrate that both HER-lm32(H) and HER-lm32(L), bind simultaneously to HER2 and Ang2. In both cases, the cells exhibited bright dual fluorescence in the FITC and PE fluorescence channels. The fact that HER-lm32(H) and HER-lm32(L) binding to HER2 is completely inhibited by HERCEPTIN® (FIGS. 20C-20F) indicates that the binding is specific.

In addition, tri-specific binding was demonstrated using an antibody containing two distinct MRDs. An EGFR-binding affibody and an Ang2-binding peptide (LM32) were fused to the C-terminus of the light and heavy chains of HERCEPTIN, respectively. The MRD-containing antibody was incubated with the EGFR+, Her2-A431 human epithelial cell line. Cell-bound MRD-containing antibody was detected with biotinylated Ang2/strepavidin-PE, alexafluor labeled ErbB2-Fc, or the combination of Ang2/strepavidin-PE and alexafluor labeled ErbB2-Fc. The results demonstrated that the MRD-containing antibody simultaneously bound EGFR cell surface receptor and two soluble ligands (ErbB2 and Ang2).

Additional experiments demonstrated that a fusion of lm32 to the C-terminus of the heavy chain of HERCEPTIN retained the binding specificity and Fc function of HERCEPTIN. HERCEPTIN and the HERCEPTIN-lm32 fusion bound to FcRn with similar affinities (EC50s for HERCEPTIN and HERCEPTIN lm-32 were 2.17 and 2.84 µg/ml, respectively). The HERCEPTIN and the HERCEPTIN-lm32 fusion displayed comparable ADCC activity on SK-BR-3 cells. The HERCEPTIN-lm32 fusion and HERCEPTIN bound to Fcγ-RI and Fcγ-RIII with similar affinities. The HERCEPTIN-lm32 fusion and HERCEPTIN bound to complement receptor C1q with similar affinities. In addition, the HERCEPTIN-lm32 fusion bound Ang2 with subnanomolar affinity and antagonized Ang2 binding to the Tie-2 receptor. The HERCEPTIN-lm32 fusion bound the extracellular domain of ErbB2 and also inhibited Ang2-induced proliferation of primary bovine lymphoendothelial cells. The HERCEPTIN-lm32 fusion and HERCEPTIN bound to the extracellular domain of Her2 with similar kinetic parameters. Additional experiments demonstrated that the HERCEPTIN-lm32 fusion was as effective as HERCEPTIN in inhibiting the proliferation of several cultured breast cancer cell lines (BT-474, MDA-MB-361 and SK-BR-3). The antiproliferative effect of the HERCEPTIN-lm32 fusion on SK-BR-3 cells was not affected by the presence of Ang2 (2 µg/ml) in the culture.

Simultaneous target binding has been observed for other multivalent and multispecific compositions (e.g., multivalent and multispecific compositions (e.g., MRD-containing antibodies)). For example, a fusion of lm32 to the C-terminus of HUMIRA heavy chain (HUM-lm32(H)) was able to simultaneously bind to Ang2 and TNFα. The same fusion was able to bind 293 cells transiently transfected with full length human TNFα with similar affinity to the HUMIRA antibody. HUM-lm32(H) was also able to inhibit the interaction of TNF with its receptors. HUM-lm32(H) also bound to cell surface expressed and plate bound FcRn as well as to Fcγ-RI and Fcγ-RIII Example 25: Antibody-MRDs Containing Heavy Chain Fusions Bind to Targets To assess the ability of lm32-containing antibodies to block the interaction of Ang2 with its receptor TIE2, their effect on the binding of soluble TIE2 to plate-bound Ang2 was determined by ELISA.

Ang2 (R&D Systems, catalog#623-AN) was coated on a 96-well plate (Thermo Electron, cat#3855) at 200 ng/mL in PBS overnight at 4° C. The plate was then incubated with 100 µL of blocking solution (Thermo Scientific, cat#N502) for 1 hour at RT. After washing the plate 4 times with 0.1% Tween-20 in PBS, the plate bound Ang2 was incubated with 0.5 µg/mL soluble TIE2 (R&D Systems, cat#313-TI) in the absence or presence of various concentrations of serially diluted antibodies containing MRDs for 1 hour at RT. After washing 4 times, 100 µL of 0.5 µg/mL anti TIE2 antibody (cat#BAM3313, R&D Systems) was added and incubated at RT for 1 hour. TIE2 binding to Ang2 was detected by incubation with 1:1000 diluted goat anti-mouse-HRP (BD Pharmingen, cat#554002) for 1 hour at RT. The plate was washed 4 times and incubated with 100 µL TMB reagent for 10 minutes at RT. After stopping the reaction with 100 µL of 0.36N $H_2SO_4$, the plate was read at 450 nm using a spectrophotometer.

As presented in FIG. 21, HER-lm32(H), HER-lm32(L), and AVA-lm32(H) inhibited TIE2 binding to plate-bound Ang2 in a dose-dependent fashion. All tested lm32-containing antibodies demonstrated comparable inhibitory effects with IC-50 values of 4 nM for HER-lm32 (H), 8 nM for HER-lm32(L) and 3.3 nM for AVA-lm32(H).

Example 26: Antibody-MRDs Containing Heavy Chain Fusions Bind to Targets

To determine the specificity and relative affinity of AVA-lm32 (H) binding to VEGF, a competitive binding assay was performed using biotin labeled AVASTIN®.

AVASTIN® was labeled with biotin using EZ-Link NHS-LC-Biotin (Pierce, cat#21336). VEGF (Peprotech, cat#100-20) was coated on a 96-well plate (Thermo Electron, cat#3855) at 100 ng/mL in PBS overnight at 4° C. The plate was then incubated with 100 of blocking solution (Thermo Scientific, cat#N502) for 1 hour at RT. After washing the plate 4 times with 0.1% Tween 20 in PBS, 50 µL of AVASTIN®-biotin at 150 ng/mL and 50 of various concentrations of AVA-lm32(H) or unlabeled AVASTIN® were added and incubated at RT for 1 hour. The plate was washed 4 times and incubated with Streptavidin-HRP (Thermo, cat#N100) at 1:1000 dilution for 1 hour at RT. The plate was washed 4 times and 100 µL of TMB reagent was added. After 10 minutes incubation at RT, 100 µL of 0.36N $H_2SO_4$ was added to stop the reaction and the plate was read at 450 nm.

The data presented in FIG. 22 demonstrate that AVA-lm32 (H) specifically binds to VEGF-2. It inhibits binding of biotinylated AVASTIN® to VEGF in a dose dependent manner. The dose response curves generated by AVA-lm32 (H) and unlabeled AVASTIN® are superimposable and indicate similar binding affinities.

Example 27: Binding of HER-Lm32(H) and HER-Lm32(L) to HER2 Expressed on Breast Cancer Cells To determine the relative binding affinity of HERCEPTIN®-based antibodies containing MRDs to cell surface HER2 compared to HERCEPTIN®, a competitive binding assay was performed with Eu-labeled HERCEPTIN®.

HERCEPTIN® was labeled with Eu3+ using a dissociation-enhanced lanthanide fluorescence immunoassay (DEL-FIA) Europium-labeling kit (Perkin Elmer Life Sciences, cat#1244-302) following the manufacturer's instructions. The labeling agent is the Eu-chelate of N1-(p-isothiocynateobenzyl) diethylenetriamine N1, N2, N3, N3-tetraacetic acid (DTTA). The DTTA group forms a stable complex with Eu3+, and the isothiocynate group reacts with amino groups on the protein at alkaline pH to form a stable, covalent thio-urea bond. HERCEPTIN® (0.2 mg in 200 mL sodium bicarbonate buffer pH 9.3) was labeled with 0.2 mg of labeling agent at 4° C. overnight. Eu-labeled HERCEPTIN® was purified by spin column using 50 mmol/L tris-HCl pH 7.5 and 0.9% NaCl elution buffer.

The Eu-HERCEPTIN® binding assay was performed by incubating 0.5-1 million BT-474 or SK-BR3 breast cancer cells per well in a 96-well plate with 2-5 nM Eu-HERCEPTIN® in the presence of various concentrations of unlabeled HERCEPTIN®-based antibodies containing MRDs or HERCEPTIN® for 1 hour at RT. Unbound Eu-HERCEPTIN® was removed by washing using 200 µL complete medium. Cells were then resuspended in 100 µL complete medium and 80 µL of cell suspension transferred to a 96-well isoplate. Cells were incubated with 100 µL Delfia enhancer solution at RT for 10 minutes and cell bound Eu-HERCEPTIN® was detected by Envison (Perkin Elmer).

The inhibition of binding curves obtained using BT-474 cells are presented in FIG. 23. Eu-HERCEPTIN® binding to BT-474 was inhibited by HERCEPTIN® and HERCEPTIN®-based antibodies containing MRDs in a dose-dependent fashion. Comparable IC-50 values were observed: 4.7 nM for HER-lm32(H), 5.7 nM for HER-lm32(L), and 3.7 nM for unlabeled HERCEPTIN®.

Example 28: Inhibition of Breast Cancer Cells Proliferation by HERCEPTIN®-Based Antibodies Containing MRDs HERCEPTIN sensitive breast cancer cells SK-BR-3 expressing HER2neo receptor were also tested in a bioassay. SK-BR-3 cells (2000 cell/well) were plated in 96 well plates (Costar) in complete McCoy's growth medium containing 2 mM glutamine, pen/strep (Invitrogen) and 10% FBS (Hy-Clone). The cells were cultured for 24 hours at 37° C., 5% $CO_2$, 85% humidity. On the following day, the growth medium was replaced with starvation medium (McCoy's medium containing 2 mM glutamine, pen/strep, 0.5% FBS). Nine serial dilutions (concentration range 5000-7.8 ng/ml) of HERCEPTIN® and HERCEPTIN®-based antibodies containing MRDs were prepared in complete growth medium. After 24 hours of incubation, the starvation medium was removed, and the serial dilutions of HERCEPTIN® and HERCEPTIN®-based antibodies containing MRDs were transferred to the plates in triplicates. The cells were cultured for 6 days. The proliferation was quantified using the CellTiter Glo luminescence method.

The IC50 values determined using a four-parameter logistic model were as follows: 0.49+/−0.17 nm for HER-lm32 (H), 0.81+/−0.19 nm for HER-lm32(L), and 0.67+/−0.15 nm for HER-con4(H). All tested HERCEPTIN®-based antibodies containing MRDs were able to inhibit the proliferation of the SK-BR-3 breast carcinoma cells with subnanomolar IC-50 values. The representative fitted dose response curves shown in FIGS. 24A-24C demonstrate that HERCEPTIN®-based antibodies containing MRDs inhibit cell proliferation with similar potency to HERCEPTIN®.

Example 29: Antibody Dependent Cytotoxicity of HERCEPTIN®-Based Antibodies Containing MRDs To assess the ability of antibodies containing MRDs to mediate ADCC in vitro, a cytotoxicity assay based on the "DELFIA EUTDA Cytotoxicity reagents AD0116" kit (PerkinElmer) was used. In this assay, the target cells were labeled with a hydrophobic fluorescence enhancing ligand (BADTA, bis (acetoxymethyl) 2,2':6',2"-terpyridine-6,6"-dicarboxylate). Upon entering the cells, BADTA is converted to a hydrophilic compound (TDA, 2,2':6',2"-terpyridine-6,6"-dicarboxylic acid) by cytoplasmic esterases mediated cleavage and no longer can cross the membrane. After cell lysis, TDA is released into a medium containing Eu3+ solution to form a fluorescent chelate (EuTDA). The fluorescence intensity is directly proportional to the number of lysed cells.

HERCEPTIN® and HERCEPTIN®-based antibodies containing MRDs can mediate ADCC on Her2 positive breast cancer cells by binding to the HER2 receptor on the surface of the target cells and activating the effector cells present in human PBMCs by interacting with their FcγRIII receptors. A HER2 positive human breast cancer cell line SK-BR-3 was used as a target cell line in the ADCC assay to demonstrate this.

SK-BR-3 cells were detached with 0.05% trypsin-versene and resuspended at $1\times10^6$ cells/mL in RPMI1640 medium containing 2 mM glutamine, pen/strep and 10% FBS (complete growth medium). $2\times10^6$ cells in 2 mL of media were transferred into 15 mL tube and 10 μl of BADTA reagent was added. The cell suspension was mixed gently and placed in the incubator at 37° C., 5% $CO_2$ and 85% humidity for 15 minutes. Seven 10× serial dilutions starting with 5 μg/mL of HERCEPTIN® or HERCEPTIN®-based antibodies containing MRDs were prepared during cell labeling.

After incubation with BADTA, cells were washed 4 times in complete growth medium containing 2.5 mM Probenecid. Between washes, cells were spun down by centrifugation at 1000 rpm for 3 minutes. After the last wash, labeled SK-BR-3 cells were resuspended in 10 mL complete growth medium and 50 μl of cells were added to each well of 96 well plate, except background wells. 50 μl of serial dilutions of HERCEPTIN® or HERCEPTIN®-based antibodies containing MRDs were added to the designated wells. The plates were transferred to the incubator at 37° C., 5% $CO_2$ and 85% humidity for 30 minutes.

PBMCs that were purified from human peripheral blood one day prior the ADCC assay, were washed once in RPMI1640 with 2 mM glutamine, pen/strep, 10% FBS. 10 mL of the PBMCs suspension with $2.5\times10^6$ cells/mL was prepared. 100 μl of PBMC suspension was transferred into wells containing target cells and HERCEPTIN® or HERCEPTIN®-based antibodies containing MRDs in triplicate. The following controls were placed in designated wells: Spontaneous release (target cells without effector cells), Maximum release (lysed target cells) and Background (media without cells). The plates were incubated for 2.5 hours an incubator with 37° C., 5% $CO_2$ and 85% humidity.

After incubation 20 μl of the supernatant was transferred to another plate and 200 μl of Europium solution was added. The plates were incubated on a plate shaker at RT for 15 minutes. The time resolved fluorescence was measured using PerkinElmer EnVision 2104 Multilabel Reader.

The following formula was used to calculate percentage of Specific release:

$$\frac{\text{Experimental release (counts)} - \text{Spontaneous release (counts)}}{\text{Maximum release (counts)} - \text{Spontaneous release (counts)}} \times 100$$

The IC50 values calculated by a four-parameter logistic model were as follows: 0.213+/−0.077 nM for HER-lm32 (H), 0.204+/−0.036 nM for HER-lm32(L), and 0.067+/−0.015 nM for HER-con4(H). All tested antibodies containing MRDs demonstrated robust ADCC activity with subnanomolar IC-50 values. The representative fitted dose response curves shown in FIGS. 25A and 25B demonstrate that antibodies containing MRDs are able to mediate cell dependent cytotoxicity with comparable potency to HERCEPTIN®.

A similar experiment was conducted in the presence of Ang2. Human PBMCs were activated with 20 ng/ml of IL2 overnight and added to freshly plated (10,000 cells/well) BADTA labeled SK-BR-3 cells. The effector/target ratio was 25/1. After a 4-hour incubation with serial dilutions of HER-lm32(H) or HUMIRA in the presence of 2 μg/ml Ang2, Eu was added to the medium and TRFI measured on Envision reader (Perkin-Elmer). HER-lm32 was more potent in mediating ADCC in the presence of Ang2.

Example 30: Inhibition of Endothelial Cell Proliferation by AVA-Lm32(H)

The biological activities of the AVASTIN®-based antibodies containing MRDs AVA-lm32(H) were tested to determine if they could inhibit VEGF-induced proliferation of Human Umbilical Vein Endothelial Cells (HUVEC) assay.

HUVEC were obtained from GlycoTech (Gaithersburg, Md.) and Lonza on passage 1 and passage 3 respectively. Cells were grown on Endothelial cell basal medium (EBM-2) with addition of 2% fetal bovine serum (FBS) and single quotes (Lonza) at 37° C., 5% $CO_2$, 85% humidity. For inhibition of proliferation experiments, cells were plated in 96-well plates (Costar) at 2000 cells per well in EBM-2 medium with 2% FBS and cultivated for 24 hours. Nine serial dilutions of AVASTIN® or AVA-lm32(H) were prepared starting with 5 μg/mL on EBM-2 medium with 2% FBS. VEGF (R & D Systems) was added at a final concentration of 10 ng/mL to all serial dilutions. After incubation for 15 minutes at 37° C., 5% $CO_2$, 85% humidity, serial dilutions were added to the cells. After 96 hours, CellTiter Glo was added to the cells. After incubation at RT for 15 minutes, the cell suspension was transferred into 96 well white opaque plates, and luminescence was measured using PerkinElmer EnVision 2104 Multilabel Reader.

As shown in FIGS. 26A and 26B, AVA-lm32(H) exhibited dose dependent anti-proliferative activity on HUVECs from both sources. IC50 values calculated from 4 PL fitted curves indicate similar potency for AVA-lm32(H) and AVASTIN® (IC50 values 0.36+/−0.42 nM and 0.33+/−0.38 nM, respectively).

Example 31: MRD-Containing Antibodies Inhibit Tumor Proliferation In Vivo

In order to determine the effectiveness of multivalent and multispecific compositions (e.g., MRD-containing antibodies) in vivo, their efficacy in a mouse Colo5 tumor model was assessed. In these experiments, tumors were implanted into the right flank of six-week old female athymic nude mice by injecting $5\times10^6$ Colo205 cells suspended in 100 μL PBS. Three groups of eight animals each received intraperitoneal injections of 5 mg/kg of antibody (HERCEPTIN, Rituxan) or an MRD-containing antibody (HER-2xCon4; "H2xCon4") in 100 μL PBS every third day starting at day 6 after tumor implantation. The results, shown in FIG. 27, demonstrate that the MRD-containing antibody was more efficient at inhibiting tumor growth than either Rituximab® or HERCEPTIN®.

HERCEPTIN with lm32 fused to the C-terminus of the heavy chain also inhibited tumor growth in both Her2 dependent and angiogenesis dependent xenograft tumor models. The HERCEPTIN-lm32 fusion had a similar PK to HERCEPTIN in both mice and monkeys after single dose injections. Furthermore, the HERCEPTIN-lm32 fusion was stable in whole blood at 37° C. for up to 72 hours.

Example 32: Molecular Assays to Evaluate MRD-Containing Antibodies

Novel multivalent and multispecific compositions (e.g., MRD-containing antibodies) are generated by altering the sequence of the MRD and/or the antibody, by altering the location at which the antibody is linked to the MRD, and/or by altering the linker through which the MRD is connected to the antibody. The binding potential, structure, and functional properties of the multivalent and multispecific compositions (e.g., MRD-containing antibodies) are evaluated using known techniques to measure protein binding and function. The multivalent and multispecific compositions (e.g., MRD-containing antibodies) are compared to the MRD alone, the antibody alone, and to other multivalent and multispecific compositions (e.g., MRD-containing antibodies).

An MRD-containing antibody is tested using a solid phase assay in which a target of the MRD and/or antibody is immobilized on a solid surface and then exposed to increasing concentrations of a flourescently labeled MRD-containing antibody. The solid surface is washed to remove unbound MRD-containing antibody and the amount of target-bound MRD-containing antibody is determined directly by quantitating fluorescence. In another experiment, the immobilized target is exposed to increasing concentrations of an unlabeled MRD-containing antibody and the amount of target-bound MRD-containing antibody is determined indirectly by use of a labeled reagent that binds to the MRD-containing antibody An MRD-containing antibody is tested using a liquid phase assay in which a target of the MRD and/or antibody is added to various concentrations of an MRD-containing antibody is a solution. The interaction of the target with the MRD-containing antibody is detected by the appearance of a molecular complex comprised of a target and MRD-containing antibody that differs in molecular mass (and mobility) from unbound target and unbound MRD-containing antibody.

An MRD-containing antibody is also assayed in a cell based assay in which target-expressing cells are incubated in the presence of increasing concentrations of MRD-containing antibody. The binding of the MRD-containing antibody is detected by fluorescence activated cell sorting. In addition, cellular proliferation, cellular differentiation, protein phosphorylation, protein expression, mRNA expression, membrane composition, signaling pathway activity, and cellular viability are assessed.

Useful multivalent and multispecific compositions (e.g., MRD-containing antibodies) bind to both the MRD target and to the antibody target. In addition, useful multivalent and multispecific compositions (e.g., MRD-containing antibodies) affect at least one cellular process.

Example 33: Identification of MRDs with Improved Characteristics

Two potential T cell epitopes were identified in LM32. In order to identify LM32 variants that did not contain T cell epitopes, and therefore, were less likely to produce immunogenic responses, mutational and deletional variants of the LM32 peptide were created. The LM32 variants listed in Table 7 MRDs were expressed as MBP fusion proteins and tested for the ability to bind Ang2.

TABLE 7

| MRD expressed as a MBP fusion protein | EC50 (nM) | SEQ ID NO |
|---|---|---|
| KSLSLSPGSGGGSMGAQTNFMP MDNDELLLYEQFI | 1.080 | 32 |
| KSLSLSPGSGGGSMGAQTNFMP MDN[illegible]ELLLYEQFI | 20.700 | 33 |
| KSLSLSPGSGGGSMGAQTNFMP MDNDE[illegible]LLYEQFILQQGLE | 1.040 | 88 |
| KSLSLSPGSGGGSMGAQTNFMP MDNDEL[illegible]LYEQFILQQGLE | na | 89 |
| KSLSLSPGSGGGSMGAQTNFMP MDNDE[illegible]LLYEQFILQQGLE | 0.182 | 90 |
| KSLSLSPGSGGGSMGAQTNFMP MDNDEL[illegible]LYEQFILQQGLE | 1.420 | 91 |
| KSLSLSPGSGGGSMGAQTNFMP MDNDELLLYEQFI[illegible]QQGLE | na | 92 |
| KSLSLSPGSGGGSMGAQTNFMP MDNDE[illegible]LLYEQFI[illegible]QQGLE | 0.902 | 93 |
| KSLSLSPGSGGGSMGAQTNFMP MDNDE[illegible]LLYEQFI[illegible]QQGLE | 0.392 | 94 |
| KSLSLSPGSGGGSMGAQTNFMP MDN[illegible]EL[illegible]LYEQFI[illegible]QQG | na | 95 |
| KSLSLSPGSGGGSMGAQTNFMP MDNDE[illegible]LLYE[illegible]FILQQGLE | 0.922 | 96 |
| KSLSLSPGSGGGSMGAQTNFMP MDNDE[illegible]LLYE[illegible]FILQQGLE | 0.426 | 97 |
| KSLSLSPGSGGGSMGAQTNFMP MDN[illegible]EL[illegible]LYE[illegible]FILQQGLE | na | 98 |
| KSLSLSPGSGGGSMGAQTNFMP MD[illegible]DELLLYEQFILQQGLE | 0.383 | 99 |
| KSLSLSPGSGGGSMGAQTNFMP MD[illegible]DELLLYEQFILQQGLE | 0.240 | 100 |

The LM32 variants are then tested for their ability to induce proliferation and/or cytokine release. LM32 variants that are functionally active and have reduced immunogenic potential are identified. An MRD-containing antibody comprising the LM32 variant fused to the light chain of HERCEPTIN®, an MRD-containing antibody comprising the LM32 variant fused to the heavy chain of HERCEPTIN®, an MRD-containing antibody comprising the LM32 variant fused to the light chain of HUMIRA®, an MRD-containing antibody comprising the LM32 variant fused to the heavy chain of HUMIRA®, MRD-containing antibody comprising the LM32 variant fused to the light chain of AVASTIN®, and an MRD-containing antibody comprising the LM32 variant fused to the heavy chain of AVASTIN® are created. The LM32-variant containing antibodies are administered to animal models and the plasma protein representation and plasma and tissue residence are measured and compared to those of HERCEPTIN®, HUMIRA®, and AVASTIN®. In addition, the effects of the LM32-variant containing antibodies on cellular proliferation, angiogenesis, tumorigenicity, arthritic indicators are compared to the effects of HERCEPTIN®, HUMIRA®, and AVASTIN®.

Example 34: In Vivo Assays to Evaluate MRD-Containing Antibodies

In order to determine the efficacy of multivalent and multispecific compositions (e.g., MRD-containing antibodies) in vivo, animal models are treated with an antibody and an MRD-containing antibody and the results are compared.

MRD-containing anti-HER2 antibodies are tested in the following in vivo model. NIH 3T3 cells transfected with a HER2 expression plasmid are injected into nu/nu athymic mice subcutaneously at a dose of $10^6$ cells in 0.1 ml of phosphate-buffered saline as described in U.S. Pat. No. 6,399,063, which is herein incorporated by reference in its entirety. On days, 0, 1, 5, and every 4 days thereafter 100 µg of a HER2 antibody, an ang2-containing HER2 antibody, an igf1r-containing HER2 antibody and an ang2-igf1r-containing HER2 antibody are injected intraperitoneally. Tumor occurrence and size are monitored for one month. Increases in efficacy of multivalent and multispecific compositions (e.g., MRD-containing antibodies) compared to antibodies are observed.

MRD-containing anti-VEGF antibodies are tested in the following in vivo model. RIP-TβAg mice are provided with high-sugar chow and 5% sugar water as described in U.S. Published Application No. 2008/0248033, which is herein incorporated by reference in its entirety. At 9-9.5 or 11-12 weeks of age, the mice are treated twice-weekly with intra-peritoneal injections of 5 mg/kg of an anti-VEGF antibody, ang2-containing VEGF antibody, ifg1r-containing VEGF antibody or ang2- and igf1r-containing antibody. The 9-9.5 week mice are treating for 14 days and then examined. The 11-12 week mice are examined after 7, 14, and 21 days of treatment. The pancreas and spleen of the mice are removed and analyzed. Tumor number is determined by a dissecting out each spherical tumor and counting. Tumor burden is determined by calculating the sum of the volume of all tumors within the pancreas of a mouse. The effect on angiogenesis is determined by calculating the mean number of angiogenic islets observed. Increases in efficacy of multivalent and multispecific compositions (e.g., MRD-containing antibodies) compared to antibodies are observed.

MRD-containing anti-TNF antibodies are tested in the following in vivo model. Transgenic mice (Tg197) are treated with three intra-peritoneal injections of anti-TNF antibody or ang2-containing TNF antibody at 1.5 µg/g, 15 µg/g, or 30 µg/g as in U.S. Pat. No. 6,258,562, which is incorporated herein by reference in its entirety. Injections continue for about 10 weeks and macroscopic changes in joint morphology are recorded each week. At 10 weeks, mice are sacrificed and microscopic examination of tissue is performed. Joint size is established as an average measurement on the hind right ankle using a micrometer device and arthritic scores are recorded as follows: 1=no arthritis; +/−=mild (joint distortion); ++=moderate arthritis (swelling, joint deformation); and +++=heavy arthritis (ankylosis detected on flexion and severely impaired movement). Histopathological scoring based on haematoxylinleosin staining of joint sections is based as follows; 0=No detectable disease; 1=proliferation of the synovial membrane; 2=heavy synovial thickening 3=cartilage destruction and bone erosion. Increases in efficacy of multivalent and multispecific compositions (e.g., MRD-containing antibodies) compared to antibodies are observed.

Example 35: MRD-Containing Antibodies are Superior to Combinations of Antibodies and MRDs In order to compare the efficacy of multivalent and multispecific compositions (e.g., MRD-containing antibodies) to combinations of antibodies and MRDs, their effect on SK-BR-3 cells treated with EGF was studied.

SK-BR-3 cells were treated with HERCEPTIN, HERCEPTIN containing an EGFR-MRD, HUMIRA containing an EGFR-MRD ("MRD alone"), or HERCEPTIN in combination with HUMIRA containing an EGFR-MRD ("antibody plus MRD alone") for 10 minutes or 3 hours and stimulated with EGF for 5 minutes. Cell lysates were collected and western blots were used to determine phosphotyrosine or phospho-Akt levels. The results are shown in FIGS. 28A and 28B. The HERCEPTIN containing an EGFR-MRD completely inhibited EGF-induced receptor phosphorylation and Akt activation, whereas HERCEPTIN, the MRD alone, and the HERCEPTIN antibody plus MRD alone had little or no effect.

In addition, the effect of multivalent and multispecific compositions (e.g., MRD-containing antibodies) on cellular proliferation was compared to the effect of the combination of antibodies and MRDs. In these experiments, MCF-7 derived breast carcinoma cells were treated with a HERCEPTIN antibody containing an igf1r-targeting MRD fused to the C-terminus of the light chain, HERCEPTIN alone, or a HUMIRA antibody containing the same igf1r-targeting MRD ("MRD alone"). As shown in FIG. 29A, the MRD-containing antibody inhibited cell proliferation better than HERCEPTIN alone or the MRD alone.

MCF-7 cells were also treated with a penta-specific MRD-containing antibody. First, these penta-specific multivalent and multispecific compositions (e.g., MRD-containing antibodies) were shown to bind to five targets. An Ang2-targeting MRD (lm32), and an EGFR-targeting MRD were fused to the N- and C-termini, respectively of a HERCEPTIN antibody. In addition, a αvβ3-targeting MRD (eeti) and an igf1r-targeting MRD were fused to the N- and C-termini, respectively of the same HERCEPTIN antibody. Ang2, ErbB2, EGFR, IGF1R and αvβ3 were coated on separate wells of a 96-well plate and incubated with serial dilutions of the MRD-containing antibody. Bound MRD-containing antibody was detected using anti-human IgG-kappa detector. The results demonstrated that the MRD-containing antibody bound to Ang2, ErbB2, EGFR, IGF1R and αvβ3 with low nanomolar or sub-nanomolar affinities that are comparable to the binding-affinities of the MRDs or antibodies individually.

Then, the ability of these penta-specific multivalent and multispecific compositions (e.g., MRD-containing antibodies) to inhibit proliferation of MCF-7 cells was tested as described above. The results, shown in FIG. 29B, demonstrate that the HERCEPTIN penta-specific multivalent and multispecific compositions (e.g., MRD-containing antibodies) decrease proliferation more efficiently than the HERCEPTIN antibody.

Example 36: MRD-Containing Anti-TNF Antibodies

An MRD-containing antibody that targets TNF was created by fusing an Ang2-binding MRD (lm32) to the C-terminus of HUMIRA heavy chain and was expressed in both transient and stable expression systems. The MRD-containing antibody bound simultaneously to TNFα and Ang2. The MRD-containing antibody bound soluble and cell surface TNFα and retained the binding specificity and Fc functions of HUMIRA (e.g., FcRn, FcgammaR1 and FcgammaR3 binding) and also inhibited Ang2 mediated signaling through Tie-2 receptor in a dose dependent manner with sub-nanomolar affinities.

The HUMIRA-lm32 fusion also inhibited TNFα mediated cytotoxicity in L929 cells. The cells were cultured in 96-well plates overnight and treated with 1 ng/mL TNF plus 1 µg/ml of Actinomycin D in the presence of HUMIRA or HUMIRA-lm32 for 24 hours at 37° C. After incubation, 100 µL of cell Titer-Glow reagent was added, and luminescence was measured using InVision (Perkin-Elmer) after 15 minutes at room temperature. The results demonstrated that HUMIRA and HUMIRA-lm32 displayed equal potency in inhibiting TNFα-mediated cytotoxicity in L929 cells (HUMIRA IC50=19.0 ng/ml; HUMIRA-lm32 IC50=18.9 ng/ml).

Furthermore, the HUMIRA-lm32 fusion displayed a dose-dependent protection of hTNF-transgenic mice from clinical signs of arthritis in a well-established mouse model. See, e.g., Keffer et al., EMBO J. 10:4025-4031 (1991). A single-dose PK study in mice demonstrated that the HUMIRA-lm32 fusion and HUMIRA have similar PK and immunogenicity profiles. However, the HUMIRA-lm32 fusion showed increased efficacy in this model compared to that of HUMIRA alone both when measured by clinical symptoms or by histology. See FIGS. 30A and 30B.

Example 37: Zybodies Inhibit EGF-Induced Signaling

SK-BR3 cells were plated at $0.5 \times 10^6$ cells/well in 6-well plates and incubated (37° C., 5% $CO_2$) for 24 hours at which time cells were treated with 10 µg/mL bi- and tri-specific zybodies or Herceptin in 1 mL complete DMEM medium with 10% FBS for 24 hr. at 37° C. Cells were then stimulated with 100 ng/mL EGF for 5 minutes. After stimulation, cells were was disrupted in 200 µL cell lysis buffer (10 mM Tris-HCl (pH 7.5), 1% Triton X-100, 150 mM NaCl, 10% Glycerol, 1 mM sodium vanadate, 5 mM EDTA and protease inhibitors). The cell lysates were centrifuged at 14000 RPM for 10 minutes at 4° C. to remove cell debris. Equal volume of 2× sample buffer and cell lysates were mixed and boiled at 100° C. for 5 minutes, proteins were resolved on a 10% SDS-PAGE and transferred to PVDF (catalog#LC2005, Invitrogen) membranes. Membranes were block with 3% BSA, 0.1% Tween 20 overnight and incubated with antibodies to phospho-AKT (catalog#AF887, R&D systems), phospho-ERK (Catalog#AF1018, R&D systems), and total ERK (MAB1576, R&D system). Horseradish or AP conjugated anti-rabbit and anti-mouse secondary antibodies (Invitrogen) were used to visualize immune-reactive proteins using chemiluminescence or AP detection reagents respectively.

One bispecific antibody used in this example comprised Herceptin and an EGFR-binding MRD (Her-egfr). Another bispecific antibody comprised Herceptin with a Pertuzumab-scfv (which targets a different HER2 epitope than the Herceptin antibody) on the C-terminus of the heavy chain (Her-Pertuzumab(H)). One trispecific antibody comprised Herceptin with an EGFR-binding MRD on the C-terminus of the heavy chain and a Pertuzumab-scfv on the C-terminus of the light chain. Another trispecific antibody comprised Herceptin with an EGFR-binding MRD on the C-terminus of the light chain and a Pertuzumab-scfv on the C-terminus of the heavy chain (Her-zEGFR(L)-Pert(H)). Another trispecific antibody comprised an EGFR-binding MRD, and a Pertuzumab-scfv which targets a different HER2 epitope than the Herceptin antibody (Her-Pert(L)zEGFR(H) and Her-zEGFR(L)-Pert(H).

SK-BR3 cells express very high levels of HER2 and are sensitive to anti-proliferative effects of Herceptin. Inhibition of constitutively activated AKT is one of the mechanisms for the anti-proliferative effects of Herceptin in HER2 overexpressing cells. Such inhibition can be overcome by the addition of growth factors such as EGF, IGF-1 and Heregulin (HRG) through the induction of intracellular pro-mitogenic signaling. As shown in FIG. 31, EGF-induced activation of AKT and ERK pathways in SK-BR3 cells as shown by increase in phoshorylated AKT and ERK levels. Herceptin had no effect on EGF-induced activation of signaling pathways in SK-BR3 cells whereas Her-egfr and the two tri-specific zybodies with an EGFR targeting peptide inhibited EGF effects. Compared to the bi-specific antibody which inhibited only EGF-induced signaling, tri-specific antibodies also inhibited constitutively active levels of Akt and ERK in SK-BR3 cells.

Example 38: Zybodies Inhibit Heregulin-Induced Signaling

SK-BR3 cells were plated at $0.5 \times 10^6$ cells/well in 6-well plates and cultured overnight. The next day, cells were treated with 10 µg/mL bi- and tri-specific zybodies or Herceptin in 1 mL complete DMEM medium with 10% FBS for 24 hr. at 37° C. Cells were then stimulated with 200 ng/mL Heregulin for 10 minutes. Western blot analysis was performed to detect phosphorylated and total Akt and ERK levels as described in Example 37.

Heregulin binds to HER3 and induces activation of signaling pathways via HER2-HER3 heterodimer formation. As shown in FIG. 32, Heregulin induced activation of Akt and ERK in SK-BR3 cells. Herceptin and HER-egfr had no effect on Heregulin-induced Akt activation. Pertuzumab, but not Herceptin, blocks Heregulin mediated HER2-HER3 heterodimer formation and signaling. FIG. 32 shows that bi- and tri-specific zybodies comprising a Pertuzumab-scfv completely inhibited Heregulin-induced Akt activation in SK-BR3 cells.

Example 39: Zybodies Inhibit EGF- and Heregulin-Induced Signaling

SK-BR3 cells were plated at $0.5 \times 10^6$ cells/well in 6-well plates and cultured overnight. The next day, cells were treated with 10 µg/mL bi and tri-specific zybodies or Herceptin in 1 mL complete DMEM medium with 10% FBS for 24 hr. at 37° C. Cells were then stimulated with 100 ng/mL EGF and 200 ng/mL Heregulin for 10 minutes. Western blot analysis was performed to detect phosphorylated and total Akt and ERK levels as described in Example 37.

Combined stimulation of SK-BR3 cells with EGF and Heregulin resulted in both AKT and ERK activation (FIG. 33). Herceptin, HER-efgr and HER-pertuzuScfv were ineffective in blocking the combined effects of EGF and Heregulin. Tri-specific zybodies that contained both an EGFR targeting peptide and a Pertuzumab-scfv completely inhibited EGF and Heregulin induced Akt and ERK activation in SK-BR3 cells.

Example 40: Zybodies Down-Regulate Cell-Surface EGFR

SK-BR3 cells were plated at $0.5 \times 10^6$ cells/well in 6-well plates and cultured overnight. The next day, cells were treated with 10 µg/mL bi- and tri-specific zybodies, Herceptin, Erbitux, EGF, and combinations thereof in 1 mL complete DMEM medium with 10% FBS for 24 hr. at 37° C. as indicated. Cells were detached and the levels of EGFR on the cells were determined by Flow cytometry using PE conjugated anti-EGFR antibody.

The zybodies used in this experiment were a Herceptin antibody with an EGFR-binding MRD on the C-terminal of the heavy chain (HER-egfr(H)); a Humira antibody with an EGFR-binding MRD on the C-terminal of the heavy chain (HUM-egfr(H)); Herceptin with a Pertuzumab-scfv on the C-terminal of the heavy chain (HER-perscfv(H)); Humira with a Pertuzumab-scfv on the C-terminal of the heavy chain (HUM-perscfv(H)); Herceptin with a Pertuzumab-scfv on the C-terminal of the light chain and an EGFR-binding MRD on the C-terminal of the heavy chain (HER-perscfv (L)-egfr(H)); Herceptin with a Pertuzumab-scfv on the C-terminal of the heavy chain and an EGFR-binding MRD on the C-terminal of the light chain (HER-perscfv(H)-egfr (L)); and a Humira antibody with an EGFR-binding MRD (HUM-egfr).

Erbitux, EGF, and bi- and tri-specific zybodies containing egfr-targeting peptides down regulated EGFR receptor levels on the cell surface (FIGS. 34A-34M). Treatment with HER-egfr for 24 hr. was more effective (61%) than HUM-egfr alone (27%) or in combination of HUM-egfr plus Herceptin (41%) and Erbitux plus Herceptin (51%) (FIGS. 34A-34M). This indicates that simultaneous targeting of EGFR and HER2 in zybody format was more effective in down regulating EGFR than a combination of two individual antibodies. Also, treatment with tri-specific antibodies that target EGFR and two different epitopes of HER2 completely down regulated (99%) EGFR levels on SK-BR3 cells.

Example 41: Zybodies Down-Regulate EGFR Expression

SK-BR3 cells were plated at 0.5×10⁶ cells/well in 6-well plates and cultured overnight. The next day, cells were treated with 10 μg/mL bi and tri-specific zybodies or Herceptin in 1 mL complete DMEM medium with 10% FBS for 24 hr. at 37° C. Cell lysates were prepared and Western blot analysis was performed to detect EGFR using EGFR antibody (catalog# MAB10951, R&D system) and total ERK levels as described in Example 37.

Treatment with Herceptin and Her-Pertuzumab scfv had no effect on EGFR levels in SK-BR3 cells. HER-egfr partially down regulated EGFR protein and almost complete degradation of EGFR was observed in cells treated with tri-specific zybodies.

Example 42: Zybodies Increase MRD Potency

The following experiments were performed to examine the effect that antibody fusion has on MRD potency. Individual wells of a 96-well plate were coated with IGF1R and ErbB2-Fc (HER2) (1 ug/ml) at varying ratios. Wells were washed, and then serial dilutions of zybodies were added in the presence of biotin-labeled IGF-1. The zybodies used were a Herceptin antibody containing an IGFR-targeting MRD on the C-terminus of the heavy chain (HER-igfr(H)) and a Humira antibody containing an IGFR-targeting MRD on the C-terminus of the heavy chain (HUM-igfr(H)). Bound IGF-1 was quantitated by addition of streptavidin-HRP. The results are shown in the table below.

TABLE 8

Inhibition of IGF-1 Binding, $IC_{50}$ (nM)

| Zybody | Ratio of IGF1R:HER2 | | | |
|---|---|---|---|---|
| | 1:0 | 3:1 | 1:1 | 1:3 |
| HER-igfr(H) | 220 | 20.91 | 1.44 | 0.14 |
| HUM-igfr(H) | 240 | 189.9 | 186 | 111 |

The inhibition of IGF-1 binding was similar for both zybodies tested when the plates did not contain ErbB2-Fc (HER2) (IC50 HER-igfr(H)=220 nM; IC50 HUM-igfr(H)=240 nM). When the plates contained both the antibody target and the MRD target, binding to MRD target drastically decreased. For example, using the HER-igfr(H) zybody, inhibition of IGF-1 binding dropped from $IC_{50}$=220 nm when the antibody target was not on the plates (ratio of IGF1R:HER2=1:0) to $IC_{50}$=1.44 when the antibody target and MRD target were present on the plates in equivalent amounts (ratio of IGFR1R:HER2=1:1). The data indicate that engagement of both antibody and MRD targets by HER-igf1r(H) enhances the potency of the low affinity IGF-1R MRD>1000-fold. In contrast, this drastic effect was not observed when the same experiment was performed using a zybody containing the Humira antibody, which does not bind to HER2 even though the zybody contained the same IGF1R-targeting MRD. Thus, bi-specific zybodies display enhanced MRD potency through heterotypic avidity-driven binding.

Example 43: Conformational Constraints can Increase MRD Binding and Stability

In order to determine the effect of conformational constraints on MRDs in the context of an MRD-containing antibody, several modified MRD constructs containing cysteines at various locations were developed. The cysteines form intermolecular disulfide bonds and therefore contain the three-dimensional conformation of the proteins. The MRD that was altered in this experiment was MPM. The sequence of MPM, which is shown in the table below, is similar to the sequence of lm32 (described above), but contains four amino acid changes: MSG, N16Q, L19A, and Q24E. The G at position five in MPM minimizes potential oxidation of the methionine residue, and L19A and Q24E remove potentially immunogenic sequences. In these experiments, all MRDs were fused to the C-terminus of the Herceptin heavy chain.

The resulting multivalent and multispecific compositions (e.g., MRD-containing antibodies) were then tested for target binding and stability. Stability was determined by administering the MRD-containing antibody by IV injection to mice and comparing the levels of MRD in the plasma 15 minutes post-injection to the levels of MRD in the plasma 2, 3, or 4 days post-injection. The results are shown below in Table 9.

TABLE 9

Binding and Stability of Constrained MRDs

| Construct | Sequence | EC50 nm | MRD % 48 hrs |
|---|---|---|---|
| HER-2x-con4 | AQQEECEWDPWTCEHM GSGSATGGSGSTASSG SGSATHQEECEWDPWT CEHMILE (SEQ ID NO: 136) | 0.018 | 70 |

TABLE 9-continued

Binding and Stability of Constrained MRDs

| Construct | Sequence | EC50 nm | MRD % 48 hrs |
|---|---|---|---|
| HER-1m32(H) | KSLSLSPGKGGGSMGAQTNFMPMDNDELLLYEQFILQQGLE (SEQ ID NO: 34) | 0.033 | 23 |
| HER-mpm(H) | KSLSLSPGSGGGSGGAQTNFMPMDQDEALLYEEFILQQGLE (SEQ ID NO: 56) | | 19 |
| HER-1m32 (MPM Q8C G30C) (H) | KSLSLSPGSGGGSGGACTNFMPMDQDEALLYEEFILQQCLE (SEQ ID NO: 57) | 4.06 | |
| HER-1m32 (MPM T9C G30C) (H) | KSLSLSPGSGGGSGGAQCNFMPMDQDEALLYEEFILQQCLE (SEQ ID NO: 58) | 0.598 | 38 |
| HER-1m32 (MPM N10C G30C) (H) | KSLSLSPGSGGGSGGAQTCFMPMDQDEALLYEEFILQQCLE (SEQ ID NO: 67) | 0.177 | 9 |
| HER-1m32 (MPM F11C G30C) (H) | KSLSLSPGSGGGSGGAQTNCMPMDQDEALLYEEFILQQCLE (SEQ ID NO: 68) | 5.91 | |
| HER-1m32 (MPM N10C L28C) (H) | KSLSLSPGSGGGSGGAQTCFMPMDQDEALLYEEFICQQGLE (SEQ ID NO: 69) | 0.403 | 33 |
| HER-1m32 (MPM MSC G30C) (H) | KSLSLSPGSGGGSCGAQTNFMPMDQDEALLYEEFILQQCLE (SEQ ID NO: 70) | 0.0641 | 60 |
| HER-1m32 (MPM MSC L28C) (H) | KSLSLSPGSGGGSCGAQTNFMPMDQDEALLYEEFICQQGLE (SEQ ID NO: 101) | 0.109 | 14 |
| HER-1m32 MPM A7C G30C) (H) | KSLSLSPGSGGGSGGCQTNFMPMDQDEALLYEEFILQQCLE (SEQ ID NO: 108) | 0.174 | 82 |
| HER-1m32 (MPM P13C G30C) (H) | KSLSLSPGSGGGSGGAQTNFMCMDQDEALLYEEFILQQCLE (SEQ ID NO: 109) | | |
| HER-1m32 (MPM MSC N10C) (H) | KSLSLSPGSGGGSCGAQTCFMPMDQDEALLYEEFILQQGLE (SEQ ID NO: 110) | 0.2 | 13 |
| HER-1m32 (MPM MSC F11C) (H) | KSLSLSPGSGGGSCGAQTNCMPMDQDEALLYEEFILQQGLE (SEQ ID NO: 111) | | |
| HER-1m32 (MPM D5 N10C G30C) (H) | KSLSLSPGSGGGSCFMPMDQDEALLYEEFILQQCLE (SEQ ID NO: 112) | 0.751 | 3 |
| HER-1m32 (MPM D5 N10C L28C) (H) | KSLSLSPGSGGGSCFMPMDQDEALLYEEFICQQGLE (SEQ ID NO: 113) | 0.697 | 36 |

The results demonstrated that adding two cysteine residues outside the core target-binding domain (e.g., PMDQDEALLY in MPM) of an MRD can increase the MRD half-life without substantially decreasing the binding affinity.

Constructs containing one cysteine located near the terminus of the molecule (e.g., about two amino acids away from the terminus) and one cysteine located on the opposite end of the target-binding domain (e.g., at least about 3 or about 4-7 amino acids outside of the core binding domain) and near the protein fusion (e.g., about 4-6 amino acids away from the linker or antibody sequence) can show increased MRD half-life without substantially decreasing the binding affinity. Furthermore, MRDs that include cysteines within the target-binding site, in particular on either end of the target-binding site can be MRDs that have both high stability and efficient target binding.

Novel multivalent and multispecific compositions (e.g., MRD-containing antibodies) in which the MRDs have a long half-life in vivo and efficient target-binding can be identified by altering the sequence of the MRD to include at least two cysteines. The cysteines can be at least about 6, about 7, about 8, about 9, about 10, about 11, about 12, about 13, about 14, about 15, about 16, about 17, about 18, about 19, or about 20 amino acids away from each other. The binding potential and half-life of the MRD in the MRD-containing antibody is evaluated using known techniques and the methods described herein. MRD-containing antibodies are administered to mice intravenously. Plasma is collected from mice shortly after administration (e.g., 15 minutes after administration) and at a later time point (e.g., 2, 3, or 4 days after administration). Useful multivalent and multispecific compositions (e.g., MRD-containing antibodies) that both bind efficiently to the MRD target and are stable in vivo (e.g., at least about 50% of the MRD is present 48 hours after administration) are identified.

Example 44: MRD-Containing Antibodies for Redirected T-Cell Killing

Antibody MRD-fusion molecules were prepared by fusion of a CD3-targeting peptide to an anti-CD19 antibody and by fusion of a CD19-targeting peptide to an anti-CD3 antibody. The resulting MRD-containing antibodies are analyzed by flow cytometric analysis on CD3-positive Jurkat cells, human PBMCs and a number of different CD19-positive B cell lymphoma cell lines (e.g., SKW6.4, Blin I, BJAB, Daudi and Raji) to determine their specific binding affinities to each target. Since BL60 and the plasmacytoma cell lines NCI and L363 are negative for both CD3 and CD19, they are used as negative control cells to determine the specificity MRD-containing antibodies. CD3-negative Jurkat cells can also be used as a negative control cell population. Cell lines are cultured in complete RPMI 1640 (Invitrogen) with 10% FCS (GIBCO).

Cells are washed with PBS and blocked by resuspension in PBS with 10% human IgG (Innovative Research) and 0.1% $NaN_3$ (blocking buffer) for 30 min at 4° C. Cells are then pelleted by centrifugation (100×g for 5 min) followed by incubation with the MRD-containing antibodies in blocking buffer for 30 min at 4° C. The cells are washed three times with PBS, and cell-surface bound MRD-containing antibodies are detected. Flow cytometry can be performed with a BD FACScan.

Example 45: In Vitro Cytotoxicity of MRD-Containing Antibodies for Redirected T-Cell Killing The bispecific CD19/CD3 MRD-containing antibodies are assayed with respect to their abilities to induce redirected T-cell killing of CD19-positive lymphoma cells. Human peripheral blood mononuclear cells (PBMCs) are isolated as effector cells from fresh buffy coats of random donors using Lymphoprep™ (Nycomed/Axis-Shield PoC) gradient centrifugation with subsequent centrifugation at 100×g to remove platelets. CD19-positive B cells are depleted using Dynabeads® CD19 Pan B (Life Technologies). The PBMC populations are analyzed by flow cytometry before and after CD19-positive B cell depletion by labeling with FITC-conjugated mouse antibody against human CD19 and counter-labeled with a PE-conjugated anti-CD45 antibody. The PBMCs are incubated overnight at 37° C. under 5% $CO_2$. CD19-positive B cell lines (e.g., SKW6.4, Blin I, BJAB, Daudi and Raji) were used as target cells.

Target cells are incubated in 96-well plates using RPMI 1640 complete medium (Invitrogen) with 10% FCS (GIBCO) at different densities, such that addition of the same number of unstimulated PBMCs resulted in different effector-to-target cell (E:T) ratios. Various concentrations of bispecific CD19/CD3 MRD-containing antibodies are then added to each well followed by the addition of unstimulated PBMCs. Plates are incubated at 37° C. under 5% $CO_2$ for 3 hrs. Cytotoxicity can be measured using the DELFIA® EuTDA cytotoxicity assay (PerkinElmer) in round-bottom 96-well-plates following manufacturer's instructions. Spontaneous cell death is measured by incubating the target cells without effector cells or MRD-containing antibodies, and maximal cell death is determined by incubating the target cells with 10% Triton X-100. The fraction of specific cell lysis is calculated as the ratio between effector mediated cytotoxicity ([experimental cell death]–[spontaneous cell death]) and the maximum expected cytotoxicity ([maximal cell death]–[spontaneous cell death]).

Example 45: In Vivo Efficacy of MRD-Containing Antibodies for Redirected T-Cell Killing Raji B lymphoma cells are removed from routine cell culture, washed in PBS, and prepared as $1 \times 10^7$ cells/ml. NOD/SCID mice are then inoculated subcutaneously with $1 \times 10^6$ Raji cells with or without $5 \times 10^6$ PBMCs (as prepared above) in a 50% Matrigel solution. Bispecific CD19/CD3 MRD-containing antibodies are administered intravenously 1 hr after lymphoma cell inoculation. As negative controls, bispecific MRD-containing antibodies directed to HER2 and CD3 (i.e., a CD3-binding MRD fused to an anti-HER2 antibody and a HER2-binding MRD fused to an anti-CD3 antibody) and HER2 and CD19 ((i.e., a CD19-binding MRD fused to an anti-HER2 antibody and a HER2-binding MRD fused to an anti-CD19 antibody) and PBS are also administered intravenously 1 hr after lymphoma cell inoculation. MRD-containing antibodies or PBS are administered once per day for four days after the initial dose. Subcutaneous tumors are measured by caliper to determine growth rate for each treatment group. Body weight of mice is also determined twice per week as an indicator of treatment tolerability.

Although the invention has been described with reference to the above examples, it will be understood that modifications and variations are encompassed within the spirit and scope of the invention. Accordingly, the invention is limited only by the following claims This Application claims the benefit under 35 U.S.C. § 119(e) to Provisional Application Nos. 61/489,249, filed May 24, 2011; 61/597,714, filed Feb. 10, 2012; and 61/610,831 filed Mar. 14, 2012; each of which is herein incorporated by reference in its entirety. Additionally, the disclosure of U.S. Appl. Publ. No. 2012/0100166 is herein incorporated by reference in its entirety.

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

What is claimed is:

1. A complex comprising an antibody linked to a modular recognition domain (MRD) capable of binding angiopoietin-2 (ANG-2), wherein the antibody binds to tumor necrosis factor alpha (TNF), and wherein the MRD comprises amino acid sequence DCAVYPNPPWCYKMEFGK (SEQ ID NO: 16).

2. The complex of claim 1, wherein the antibody is selected from the group consisting of: adalimumab, golimumab, and infliximab.

3. A pharmaceutical composition comprising the complex of claim 1 and a pharmaceutically acceptable carrier.

4. A method for inhibiting angiogenesis in a patient comprising administering to said patient a therapeutically effective amount of the complex of claim 1.

5. The complex of claim 1, wherein the MRD is linked to the antibody directly.

6. The complex of claim 1, wherein the MRD is linked to the antibody through a linker.

7. A complex comprising an antibody linked to an MRD capable of binding angiopoietin-2 (ANG-2), wherein the antibody is adalimumab and the MRD comprises the amino acid sequence DCAVYPNPPWCYKMEFGK (SEQ ID NO: 16).

8. The complex of claim 7, wherein the MRD is linked to the antibody directly.

9. The complex of claim 7, wherein the MRD is linked to the antibody through a linker.

10. A pharmaceutical composition comprising the complex of claim 7 and a pharmaceutically acceptable carrier.

11. A complex comprising an antibody linked to an MRD capable of binding angiopoietin-2 (ANG-2), wherein the antibody is golimumab and the MRD comprises the amino acid sequence DCAVYPNPPWCYKMEFGK (SEQ ID NO: 16).

12. The complex of claim 11, wherein the MRD is linked to the antibody through a linker.

13. The complex of claim 11, wherein the MRD is linked to the antibody directly.

14. A pharmaceutical composition comprising the complex of claim 11 and a pharmaceutically acceptable carrier.

15. A complex comprising an antibody linked to an MRD capable of binding angiopoietin-2 (ANG-2), wherein the antibody is infliximab and the MRD comprises the amino acid sequence DCAVYPNPPWCYKMEFGK (SEQ ID NO: 16).

16. The complex of claim 15, wherein the MRD is linked to the antibody through a linker.

17. The complex of claim 15, wherein the MRD is linked to the antibody directly.

18. A pharmaceutical composition comprising the complex of claim 15 and a pharmaceutically acceptable carrier.

19. A peptide capable of binding angiopoietin-2 (ANG-2), wherein the peptide comprises the amino acid sequence of SEQ ID NO: 16.

20. A fusion peptide comprising the peptide of claim 19 and a heterologous peptide.

* * * * *

SEQUENCE LISTING

```
<160> NUMBER OF SEQ ID NOS: 135

<210> SEQ ID NO 1
<211> LENGTH: 4
<212> TYPE: PRT
<213> ORGANISM: Artificial Sequence
<220> FEATURE:
<223> OTHER INFORMATION: linker peptide

<400> SEQUENCE: 1

Gly Gly Gly Ser
1

<210> SEQ ID NO 2
<211> LENGTH: 15
<212> TYPE: PRT
<213> ORGANISM: Artificial Sequence
```

```
<220> FEATURE:
<223> OTHER INFORMATION: linker peptide

<400> SEQUENCE: 2

Ser Ser Gly Gly Gly Ser Gly Gly Gly Gly Gly Ser Ser
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: integrin targeting MRD

<400> SEQUENCE: 3

Tyr Cys Arg Gly Asp Cys Thr
1               5

<210> SEQ ID NO 4
<211> LENGTH: 7
<212> TYPE: PRT
<213> ORGANISM: Artificial Sequence
<220> FEATURE:
<223> OTHER INFORMATION: integrin targeting MRD

<400> SEQUENCE: 4

Pro Cys Arg Gly Asp Cys Leu
1               5

<210> SEQ ID NO 5
<211> LENGTH: 7
<212> TYPE: PRT
<213> ORGANISM: Artificial Sequence
<220> FEATURE:
<223> OTHER INFORMATION: integrin targeting MRD

<400> SEQUENCE: 5

Thr Cys Arg Gly Asp Cys Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: integrin targeting MRD

<400> SEQUENCE: 6

Leu Cys Arg Gly Asp Cys Phe
1               5

<210> SEQ ID NO 7
<211> LENGTH: 28
<212> TYPE: PRT
<213> ORGANISM: Artificial Sequence
<220> FEATURE:
<223> OTHER INFORMATION: cytokine targeting MRD

<400> SEQUENCE: 7

Met Gly Ala Gln Thr Asn Phe Met Pro Met Asp Asp Leu Glu Gln Arg
1               5                   10                  15

Leu Tyr Glu Gln Phe Ile Leu Gln Gln Gly Leu Glu
            20                  25

<210> SEQ ID NO 8
<211> LENGTH: 28
```

<212> TYPE: PRT
<213> ORGANISM: Artificial Sequence
<220> FEATURE:
<223> OTHER INFORMATION: lm 32MRD

<400> SEQUENCE: 8

Met Gly Ala Gln Thr Asn Phe Met Pro Met Asp Asn Asp Glu Leu Leu
1               5                   10                  15

Leu Tyr Glu Gln Phe Ile Leu Gln Gln Gly Leu Glu
            20                  25

<210> SEQ ID NO 9
<211> LENGTH: 27
<212> TYPE: PRT
<213> ORGANISM: Artificial Sequence
<220> FEATURE:
<223> OTHER INFORMATION: ANGa

<400> SEQUENCE: 9

Gly Ala Gln Thr Asn Phe Met Pro Met Asp Asp Leu Glu Gln Arg Leu
1               5                   10                  15

Tyr Glu Gln Phe Ile Leu Gln Gln Gly Leu Glu
            20                  25

<210> SEQ ID NO 10
<211> LENGTH: 54
<212> TYPE: PRT
<213> ORGANISM: Artificial Sequence
<220> FEATURE:
<223> OTHER INFORMATION: 2xCon4

<400> SEQUENCE: 10

Ala Gln Gln Glu Glu Cys Glu Trp Asp Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Trp Asp Pro Trp Thr
        35                  40                  45

Cys Glu His Met Leu Glu
    50

<210> SEQ ID NO 11
<211> LENGTH: 18
<212> TYPE: PRT
<213> ORGANISM: Artificial Sequence
<220> FEATURE:
<223> OTHER INFORMATION: ANGb

<400> SEQUENCE: 11

Leu Trp Asp Asp Cys Tyr Phe Phe Pro Asn Pro Pro His Cys Tyr Asn
1               5                   10                  15

Ser Pro

<210> SEQ ID NO 12
<211> LENGTH: 18
<212> TYPE: PRT
<213> ORGANISM: Artificial Sequence
<220> FEATURE:
<223> OTHER INFORMATION: ANGc

<400> SEQUENCE: 12

Leu Trp Asp Asp Cys Tyr Ser Tyr Pro Asn Pro Pro His Cys Tyr Asn
1               5                   10                  15

Ser Pro

<210> SEQ ID NO 13
<211> LENGTH: 19
<212> TYPE: PRT
<213> ORGANISM: Artificial Sequence
<220> FEATURE:
<223> OTHER INFORMATION: VEGF targeting MRD

<400> SEQUENCE: 13

Val Glu Pro Asn Cys Asp Ile His Val Met Trp Glu Trp Glu Cys Phe
1               5                   10                  15

Glu Arg Leu

<210> SEQ ID NO 14
<211> LENGTH: 27
<212> TYPE: PRT
<213> ORGANISM: Artificial Sequence
<220> FEATURE:
<223> OTHER INFORMATION: MRD which targets IGF1R

<400> SEQUENCE: 14

Ser Phe Tyr Ser Cys Leu Glu Ser Leu Val Asn Gly Pro Ala Glu Lys
1               5                   10                  15

Ser Arg Gly Gln Trp Asp Gly Cys Arg Lys Lys
            20                  25

<210> SEQ ID NO 15
<211> LENGTH: 18
<212> TYPE: PRT
<213> ORGANISM: Artificial Sequence
<220> FEATURE:
<223> OTHER INFORMATION: ANGd

<400> SEQUENCE: 15

Leu Trp Asp Asp Cys Tyr Ser Phe Pro Asn Pro His Cys Tyr Asn
1               5                   10                  15

Ser Pro

<210> SEQ ID NO 16
<211> LENGTH: 18
<212> TYPE: PRT
<213> ORGANISM: Artificial Sequence
<220> FEATURE:
<223> OTHER INFORMATION: ANGe

<400> SEQUENCE: 16

Asp Cys Ala Val Tyr Pro Asn Pro Pro Trp Cys Tyr Lys Met Glu Phe
1               5                   10                  15

Gly Lys

<210> SEQ ID NO 17
<211> LENGTH: 18
<212> TYPE: PRT
<213> ORGANISM: Artificial Sequence
<220> FEATURE:
<223> OTHER INFORMATION: ANGf

<400> SEQUENCE: 17

Pro His Glu Glu Cys Tyr Phe Tyr Pro Asn Pro His Cys Tyr Thr
1               5                   10                  15

Met Ser

<210> SEQ ID NO 18
<211> LENGTH: 18
<212> TYPE: PRT
<213> ORGANISM: Artificial Sequence
<220> FEATURE:
<223> OTHER INFORMATION: ANGg

<400> SEQUENCE: 18

Pro His Glu Glu Cys Tyr Ser Tyr Pro Asn Pro Pro His Cys Tyr Thr
1               5                   10                  15

Met Ser

<210> SEQ ID NO 19
<211> LENGTH: 18
<212> TYPE: PRT
<213> ORGANISM: Artificial Sequence
<220> FEATURE:
<223> OTHER INFORMATION: long linker peptide

<400> SEQUENCE: 19

Ser Ser Gly Gly Gly Gly Ser Gly Gly Gly Gly Gly Ser Ser Arg
1               5                   10                  15

Ser Ser

<210> SEQ ID NO 20
<211> LENGTH: 60
<212> TYPE: PRT
<213> ORGANISM: Artificial Sequence
<220> FEATURE:
<223> OTHER INFORMATION: LM-2x-32

<400> SEQUENCE: 20

Met Gly Ala Gln Thr Asn Phe Met Pro Met Asp Asn Asp Glu Leu Leu
1               5                   10                  15

Leu Tyr Glu Gln Phe Ile Leu Gln Gln Gly Leu Glu Gly Gly Ser Gly
                20                  25                  30

Ser Thr Ala Ser Ser Gly Ser Gly Ser Ser Leu Gly Ala Gln Thr Asn
            35                  40                  45

Phe Met Pro Met Asp Asn Asp Glu Leu Leu Leu Tyr
        50                  55                  60

<210> SEQ ID NO 21
<211> LENGTH: 26
<212> TYPE: PRT
<213> ORGANISM: Artificial Sequence
<220> FEATURE:
<223> OTHER INFORMATION: fusion protein

<400> SEQUENCE: 21

Gly Tyr Tyr Val Cys Tyr Pro Arg Gly Ser Lys Pro Glu Asp Ala Asn
1               5                   10                  15

Phe Tyr Leu Tyr Leu Arg Ala Arg Val Cys
                20                  25

<210> SEQ ID NO 22
<211> LENGTH: 7
<212> TYPE: PRT
<213> ORGANISM: Artificial Sequence
<220> FEATURE:
<223> OTHER INFORMATION: fusion protein

<400> SEQUENCE: 22

Tyr Leu Tyr Leu Arg Ala Arg
1               5

<210> SEQ ID NO 23
<211> LENGTH: 23
<212> TYPE: PRT
<213> ORGANISM: Artificial Sequence
<220> FEATURE:
<223> OTHER INFORMATION: fusion protein

<400> SEQUENCE: 23

Tyr Arg Cys Asn Gly Thr Asp Ile Tyr Lys Asp Lys Glu Ser Thr Val
1               5                   10                  15

Gln Val His Tyr Arg Met Cys
            20

<210> SEQ ID NO 24
<211> LENGTH: 9
<212> TYPE: PRT
<213> ORGANISM: Artificial Sequence
<220> FEATURE:
<223> OTHER INFORMATION: fusion protein

<400> SEQUENCE: 24

Asp Lys Glu Ser Thr Val Gln Val His
1               5

<210> SEQ ID NO 25
<211> LENGTH: 78
<212> TYPE: PRT
<213> ORGANISM: Artificial Sequence
<220> FEATURE:
<223> OTHER INFORMATION: human CD3 delta mature ECD

<400> SEQUENCE: 25

Lys Ile Pro Ile Glu Glu Leu Glu Asp Arg Val Phe Val Asn Cys Asn
1               5                   10                  15

Thr Ser Ile Thr Trp Val Glu Gly Thr Val Gly Thr Leu Leu Ser Asp
            20                  25                  30

Ile Thr Arg Leu Asp Leu Gly Lys Arg Ile Leu Asp Pro Arg Gly Ile
        35                  40                  45

Tyr Arg Cys Asn Gly Thr Asp Ile Tyr Lys Asp Lys Glu Ser Thr Val
    50                  55                  60

Gln Val His Tyr Arg Met Cys Gln Ser Cys Val Glu Leu Asp
65                  70                  75

<210> SEQ ID NO 26
<211> LENGTH: 89
<212> TYPE: PRT
<213> ORGANISM: Artificial Sequence
<220> FEATURE:
<223> OTHER INFORMATION: human CD3 gamma mature ECD

<400> SEQUENCE: 26

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn
            85

<210> SEQ ID NO 27
<211> LENGTH: 105
<212> TYPE: PRT
<213> ORGANISM: Artificial Sequence
<220> FEATURE:
<223> OTHER INFORMATION: human CD3 epsilon mature ECD

<400> SEQUENCE: 27

Gly Asn Glu Glu Met Gly Gly Ile Thr Gln Thr Pro Tyr Lys Val Ser
1               5                   10                  15

Ile Ser Gly Thr Thr Val Ile Leu Thr Cys Pro Gln Tyr Pro Gly Ser
            20                  25                  30

Glu Ile Leu Trp Gln His Asn Asp Lys Asn Ile Gly Gly Asp Glu Asp
        35                  40                  45

Asp Lys Asn Ile Gly Ser Asp Glu Asp His Leu Ser Leu Lys Glu Phe
    50                  55                  60

Ser Glu Leu Glu Gln Ser Gly Tyr Tyr Val Cys Tyr Pro Arg Gly Ser
65                  70                  75                  80

Lys Pro Glu Asp Ala Asn Phe Tyr Leu Tyr Leu Arg Ala Arg Val Cys
                85                  90                  95

Glu Asn Cys Met Glu Met Asp Val Met
            100                 105

<210> SEQ ID NO 28
<211> LENGTH: 9
<212> TYPE: PRT
<213> ORGANISM: Artificial Sequence
<220> FEATURE:
<223> OTHER INFORMATION: human CD3 zeta mature ECD

<400> SEQUENCE: 28

Gln Ser Phe Gly Leu Leu Asp Pro Lys
1               5

<210> SEQ ID NO 29
<211> LENGTH: 27
<212> TYPE: PRT
<213> ORGANISM: Artificial Sequence
<220> FEATURE:
<223> OTHER INFORMATION: MRD-binding polypeptide

<400> SEQUENCE: 29

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25

<210> SEQ ID NO 30
<211> LENGTH: 10
<212> TYPE: PRT
<213> ORGANISM: Artificial Sequence
<220> FEATURE:
<223> OTHER INFORMATION: MRD-binding polypeptide

<400> SEQUENCE: 30

Gln Asp Gly Asn Glu Glu Met Gly Gly Ile
1               5                   10

<210> SEQ ID NO 31

```
<211> LENGTH: 9
<212> TYPE: PRT
<213> ORGANISM: Artificial Sequence
<220> FEATURE:
<223> OTHER INFORMATION: MRD-binding polypeptide

<400> SEQUENCE: 31

Gln Asp Gly Asn Glu Glu Met Gly Gly
1               5

<210> SEQ ID NO 32
<211> LENGTH: 35
<212> TYPE: PRT
<213> ORGANISM: Artificial Sequence
<220> FEATURE:
<223> OTHER INFORMATION: MRD expressed as a MBP fusion protein

<400> SEQUENCE: 32

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Leu Leu Leu Tyr Glu
                20                  25                  30

Gln Phe Ile
        35

<210> SEQ ID NO 33
<211> LENGTH: 35
<212> TYPE: PRT
<213> ORGANISM: Artificial Sequence
<220> FEATURE:
<223> OTHER INFORMATION: MRD expressed as a MBP fusion protein

<400> SEQUENCE: 33

Lys Ser Leu Ser Leu Ser Pro Gly Ser Gly Gly Gly Ser Met Gly Ala
1               5                   10                  15

Gln Thr Asn Phe Met Pro Met Asp Asn Glu Glu Leu Leu Leu Tyr Glu
                20                  25                  30

Gln Phe Ile
        35

<210> SEQ ID NO 34
<211> LENGTH: 41
<212> TYPE: PRT
<213> ORGANISM: Artificial Sequence
<220> FEATURE:
<223> OTHER INFORMATION: HER-lm32(H)

<400> SEQUENCE: 34

Lys Ser Leu Ser Leu Ser Pro Gly Lys Gly Gly Gly Ser Met Gly Ala
1               5                   10                  15

Gln Thr Asn Phe Met Pro Met Asp Asn Asp Glu Leu Leu Leu Tyr Glu
                20                  25                  30

Gln Phe Ile Leu Gln Gln Gly Leu Glu
        35                  40

<210> SEQ ID NO 35
<211> LENGTH: 28
<212> TYPE: PRT
<213> ORGANISM: Artificial Sequence
<220> FEATURE:
<223> OTHER INFORMATION: Rm4-31

<400> SEQUENCE: 35

Asn Phe Tyr Gln Cys Ile Glu Met Leu Ala Ser His Pro Ala Glu Lys
```

```
               1               5                  10                15
Ser Arg Gly Gln Trp Gln Glu Cys Arg Thr Gly Gly
            20                  25
```

<210> SEQ ID NO 36
<211> LENGTH: 28
<212> TYPE: PRT
<213> ORGANISM: Artificial Sequence
<220> FEATURE:
<223> OTHER INFORMATION: Rm4-33

<400> SEQUENCE: 36

```
Asn Phe Tyr Gln Cys Ile Glu Gln Leu Ala Leu Arg Pro Ala Glu Lys
1               5                  10                 15
Ser Arg Gly Gln Trp Gln Glu Cys Arg Thr Gly Gly
            20                  25
```

<210> SEQ ID NO 37
<211> LENGTH: 28
<212> TYPE: PRT
<213> ORGANISM: Artificial Sequence
<220> FEATURE:
<223> OTHER INFORMATION: Rm4-39

<400> SEQUENCE: 37

```
Asn Phe Tyr Gln Cys Ile Asp Leu Leu Met Ala Tyr Pro Ala Glu Lys
1               5                  10                 15
Ser Arg Gly Gln Trp Gln Glu Cys Arg Thr Gly Gly
            20                  25
```

<210> SEQ ID NO 38
<211> LENGTH: 28
<212> TYPE: PRT
<213> ORGANISM: Artificial Sequence
<220> FEATURE:
<223> OTHER INFORMATION: Rm4-310

<400> SEQUENCE: 38

```
Asn Phe Tyr Gln Cys Ile Glu Arg Leu Val Thr Gly Pro Ala Glu Lys
1               5                  10                 15
Ser Arg Gly Gln Trp Gln Glu Cys Arg Thr Gly Gly
            20                  25
```

<210> SEQ ID NO 39
<211> LENGTH: 28
<212> TYPE: PRT
<213> ORGANISM: Artificial Sequence
<220> FEATURE:
<223> OTHER INFORMATION: Rm4-314

<400> SEQUENCE: 39

```
Asn Phe Tyr Gln Cys Ile Glu Tyr Leu Ala Met Lys Pro Ala Glu Lys
1               5                  10                 15
Ser Arg Gly Gln Trp Gln Glu Cys Arg Thr Gly Gly
            20                  25
```

<210> SEQ ID NO 40
<211> LENGTH: 28
<212> TYPE: PRT
<213> ORGANISM: Artificial Sequence
<220> FEATURE:
<223> OTHER INFORMATION: Rm4-316

<400> SEQUENCE: 40

```
Asn Phe Tyr Gln Cys Ile Glu Ala Leu Gln Ser Arg Pro Ala Glu Lys
1               5                   10                  15

Ser Arg Gly Gln Trp Gln Glu Cys Arg Thr Gly Gly
            20                  25
```

<210> SEQ ID NO 41
<211> LENGTH: 28
<212> TYPE: PRT
<213> ORGANISM: Artificial Sequence
<220> FEATURE:
<223> OTHER INFORMATION: Rm4-319

<400> SEQUENCE: 41

```
Asn Phe Tyr Gln Cys Ile Glu Ala Leu Ser Arg Ser Pro Ala Glu Lys
1               5                   10                  15

Ser Arg Gly Gln Trp Gln Glu Cys Arg Thr Gly Gly
            20                  25
```

<210> SEQ ID NO 42
<211> LENGTH: 27
<212> TYPE: PRT
<213> ORGANISM: Artificial Sequence
<220> FEATURE:
<223> OTHER INFORMATION: Rm4-44

<400> SEQUENCE: 42

```
Asn Phe Tyr Gln Cys Ile Glu His Leu Ser Gly Ser Pro Ala Glu Lys
1               5                   10                  15

Ser Arg Gly Gln Trp Gln Glu Cys Arg Thr Gly
            20                  25
```

<210> SEQ ID NO 43
<211> LENGTH: 27
<212> TYPE: PRT
<213> ORGANISM: Artificial Sequence
<220> FEATURE:
<223> OTHER INFORMATION: Rm4-45

<400> SEQUENCE: 43

```
Asn Phe Tyr Gln Cys Ile Glu Ser Leu Ala Gly Gly Pro Ala Glu Lys
1               5                   10                  15

Ser Arg Gly Gln Trp Gln Glu Cys Arg Thr Gly
            20                  25
```

<210> SEQ ID NO 44
<211> LENGTH: 27
<212> TYPE: PRT
<213> ORGANISM: Artificial Sequence
<220> FEATURE:
<223> OTHER INFORMATION: Rm4-46

<400> SEQUENCE: 44

```
Asn Phe Tyr Gln Cys Ile Glu Ala Leu Val Gly Val Pro Ala Glu Lys
1               5                   10                  15

Ser Arg Gly Gln Trp Gln Glu Cys Arg Thr Gly
            20                  25
```

<210> SEQ ID NO 45
<211> LENGTH: 27
<212> TYPE: PRT
<213> ORGANISM: Artificial Sequence
<220> FEATURE:
<223> OTHER INFORMATION: Rm4-49

<400> SEQUENCE: 45

```
Asn Phe Tyr Gln Cys Ile Glu Met Leu Ser Leu Pro Pro Ala Glu Lys
1               5                   10                  15

Ser Arg Gly Gln Trp Gln Glu Cys Arg Thr Gly
            20                  25
```

<210> SEQ ID NO 46
<211> LENGTH: 27
<212> TYPE: PRT
<213> ORGANISM: Artificial Sequence
<220> FEATURE:
<223> OTHER INFORMATION: Rm4-410

<400> SEQUENCE: 46

```
Asn Phe Tyr Gln Cys Ile Glu Val Phe Trp Gly Arg Pro Ala Glu Lys
1               5                   10                  15

Ser Arg Gly Gln Trp Gln Glu Cys Arg Thr Gly
            20                  25
```

<210> SEQ ID NO 47
<211> LENGTH: 27
<212> TYPE: PRT
<213> ORGANISM: Artificial Sequence
<220> FEATURE:
<223> OTHER INFORMATION: Rm4-411

<400> SEQUENCE: 47

```
Asn Phe Tyr Gln Cys Ile Glu Gln Leu Ser Ser Gly Pro Ala Glu Lys
1               5                   10                  15

Ser Arg Gly Gln Trp Gln Glu Cys Arg Thr Gly
            20                  25
```

<210> SEQ ID NO 48
<211> LENGTH: 27
<212> TYPE: PRT
<213> ORGANISM: Artificial Sequence
<220> FEATURE:
<223> OTHER INFORMATION: Rm4-415

<400> SEQUENCE: 48

```
Asn Phe Tyr Gln Cys Ile Glu Leu Leu Ser Ala Arg Pro Ala Glu Lys
1               5                   10                  15

Ser Arg Gly Gln Trp Ala Glu Cys Arg Ala Gly
            20                  25
```

<210> SEQ ID NO 49
<211> LENGTH: 27
<212> TYPE: PRT
<213> ORGANISM: Artificial Sequence
<220> FEATURE:
<223> OTHER INFORMATION: Rm4-417

<400> SEQUENCE: 49

```
Asn Phe Tyr Gln Cys Ile Glu Ala Leu Ala Arg Thr Pro Ala Glu Lys
1               5                   10                  15

Ser Arg Gly Gln Trp Val Glu Cys Arg Ala Pro
            20                  25
```

<210> SEQ ID NO 50
<211> LENGTH: 18
<212> TYPE: DNA
<213> ORGANISM: Artificial Sequence
<220> FEATURE:
<223> OTHER INFORMATION: Rm2-2-218

```
<400> SEQUENCE: 50
gtggagtgca gggcgccg                                             18

<210> SEQ ID NO 51
<211> LENGTH: 6
<212> TYPE: PRT
<213> ORGANISM: Artificial Sequence
<220> FEATURE:
<223> OTHER INFORMATION: Rm2-2-218

<400> SEQUENCE: 51

Val Glu Cys Arg Ala Pro
1               5

<210> SEQ ID NO 52
<211> LENGTH: 18
<212> TYPE: DNA
<213> ORGANISM: Artificial Sequence
<220> FEATURE:
<223> OTHER INFORMATION: Rm2-2-316

<400> SEQUENCE: 52
gctgagtgca gggctggg                                             18

<210> SEQ ID NO 53
<211> LENGTH: 6
<212> TYPE: PRT
<213> ORGANISM: Artificial Sequence
<220> FEATURE:
<223> OTHER INFORMATION: Rm2-2-316

<400> SEQUENCE: 53

Ala Glu Cys Arg Ala Gly
1               5

<210> SEQ ID NO 54
<211> LENGTH: 18
<212> TYPE: DNA
<213> ORGANISM: Artificial Sequence
<220> FEATURE:
<223> OTHER INFORMATION: Rm2-2-319

<400> SEQUENCE: 54
caggagtgca ggacgggg                                             18

<210> SEQ ID NO 55
<211> LENGTH: 6
<212> TYPE: PRT
<213> ORGANISM: Artificial Sequence
<220> FEATURE:
<223> OTHER INFORMATION: Rm2-2-319

<400> SEQUENCE: 55

Gln Glu Cys Arg Thr Gly
1               5

<210> SEQ ID NO 56
<211> LENGTH: 41
<212> TYPE: PRT
<213> ORGANISM: Artificial Sequence
<220> FEATURE:
<223> OTHER INFORMATION: HER-mpm(H)

<400> SEQUENCE: 56

Lys Ser Leu Ser Leu Ser Pro Gly Ser Gly Gly Gly Ser Gly Gly Ala
1               5                   10                  15
```

Gln Thr Asn Phe Met Pro Met Asp Gln Asp Glu Ala Leu Leu Tyr Glu
                20                  25                  30

Glu Phe Ile Leu Gln Gln Gly Leu Glu
        35                  40

<210> SEQ ID NO 57
<211> LENGTH: 41
<212> TYPE: PRT
<213> ORGANISM: Artificial Sequence
<220> FEATURE:
<223> OTHER INFORMATION: HER-1m32 (MPM Q8C G30C) (H)

<400> SEQUENCE: 57

Lys Ser Leu Ser Leu Ser Pro Gly Ser Gly Gly Gly Ser Gly Gly Ala
1               5                   10                  15

Cys Thr Asn Phe Met Pro Met Asp Gln Asp Glu Ala Leu Leu Tyr Glu
                20                  25                  30

Glu Phe Ile Leu Gln Gln Cys Leu Glu
        35                  40

<210> SEQ ID NO 58
<211> LENGTH: 41
<212> TYPE: PRT
<213> ORGANISM: Artificial Sequence
<220> FEATURE:
<223> OTHER INFORMATION: HER-1m32 (MPM T9C G30C) (H)

<400> SEQUENCE: 58

Lys Ser Leu Ser Leu Ser Pro Gly Ser Gly Gly Gly Ser Gly Gly Ala
1               5                   10                  15

Gln Cys Asn Phe Met Pro Met Asp Gln Asp Glu Ala Leu Leu Tyr Glu
                20                  25                  30

Glu Phe Ile Leu Gln Gln Cys Leu Glu
        35                  40

<210> SEQ ID NO 59
<211> LENGTH: 12
<212> TYPE: PRT
<213> ORGANISM: Artificial Sequence
<220> FEATURE:
<223> OTHER INFORMATION: VL-CDR1

<400> SEQUENCE: 59

Arg Ala Ser Gln Asp Val Asn Thr Ala Val Ala Trp
1               5                   10

<210> SEQ ID NO 60
<211> LENGTH: 7
<212> TYPE: PRT
<213> ORGANISM: Artificial Sequence
<220> FEATURE:
<223> OTHER INFORMATION: VL-CDR2

<400> SEQUENCE: 60

Ser Ala Ser Phe Leu Tyr Ser
1               5

<210> SEQ ID NO 61
<211> LENGTH: 9
<212> TYPE: PRT
<213> ORGANISM: Artificial Sequence
<220> FEATURE:
<223> OTHER INFORMATION: VL-CDR3

```
<400> SEQUENCE: 61

Gln Gln His Tyr Thr Thr Pro Pro Thr
1               5

<210> SEQ ID NO 62
<211> LENGTH: 10
<212> TYPE: PRT
<213> ORGANISM: Artificial Sequence
<220> FEATURE:
<223> OTHER INFORMATION: VH-CDR1

<400> SEQUENCE: 62

Gly Arg Asn Ile Lys Asp Thr Tyr Ile His
1               5                   10

<210> SEQ ID NO 63
<211> LENGTH: 17
<212> TYPE: PRT
<213> ORGANISM: Artificial Sequence
<220> FEATURE:
<223> OTHER INFORMATION: VH-CDR2

<400> SEQUENCE: 63

Arg Ile Tyr Pro Thr Asn Gly Tyr Thr Arg Tyr Ala Asp Ser Val Lys
1               5                   10                  15

Gly

<210> SEQ ID NO 64
<211> LENGTH: 11
<212> TYPE: PRT
<213> ORGANISM: Artificial Sequence
<220> FEATURE:
<223> OTHER INFORMATION: VH-CDR1

<400> SEQUENCE: 64

Trp Gly Gly Asp Gly Phe Tyr Ala Met Asp Tyr
1               5                   10

<210> SEQ ID NO 65
<211> LENGTH: 109
<212> TYPE: PRT
<213> ORGANISM: Artificial Sequence
<220> FEATURE:
<223> OTHER INFORMATION: VL

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 66
```

<211> LENGTH: 120
<212> TYPE: PRT
<213> ORGANISM: Artificial Sequence
<220> FEATURE:
<223> OTHER INFORMATION: VH

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 67
<211> LENGTH: 41
<212> TYPE: PRT
<213> ORGANISM: Artificial Sequence
<220> FEATURE:
<223> OTHER INFORMATION: HER-lm32 (MPM N10C G30C) (H)

<400> SEQUENCE: 67

Lys Ser Leu Ser Leu Ser Pro Gly Ser Gly Gly Ser Gly Gly Ala
1               5                   10                  15

Gln Thr Cys Phe Met Pro Met Asp Gln Asp Glu Ala Leu Leu Tyr Glu
            20                  25                  30

Glu Phe Ile Leu Gln Gln Cys Leu Glu
        35                  40

<210> SEQ ID NO 68
<211> LENGTH: 41
<212> TYPE: PRT
<213> ORGANISM: Artificial Sequence
<220> FEATURE:
<223> OTHER INFORMATION: HER-lm32 (MPM F11C G30C) (H

<400> SEQUENCE: 68

Lys Ser Leu Ser Leu Ser Pro Gly Ser Gly Gly Ser Gly Gly Ala
1               5                   10                  15

Gln Thr Asn Cys Met Pro Met Asp Gln Asp Glu Ala Leu Leu Tyr Glu
            20                  25                  30

Glu Phe Ile Leu Gln Gln Cys Leu Glu
        35                  40

<210> SEQ ID NO 69
<211> LENGTH: 41
<212> TYPE: PRT
<213> ORGANISM: Artificial Sequence
<220> FEATURE:
<223> OTHER INFORMATION: HER-lm32 (MPM N10C L28C) (H)

<400> SEQUENCE: 69

Lys Ser Leu Ser Leu Ser Pro Gly Ser Gly Gly Gly Ser Gly Gly Ala
1               5                   10                  15

Gln Thr Cys Phe Met Pro Met Asp Gln Asp Glu Ala Leu Leu Tyr Glu
            20                  25                  30

Glu Phe Ile Cys Gln Gln Gly Leu Glu
        35                  40

<210> SEQ ID NO 70
<211> LENGTH: 41
<212> TYPE: PRT
<213> ORGANISM: Artificial Sequence
<220> FEATURE:
<223> OTHER INFORMATION: HER-lm32 (MPM M5C G30C) (H)

<400> SEQUENCE: 70

Lys Ser Leu Ser Leu Ser Pro Gly Ser Gly Gly Gly Ser Cys Gly Ala
1               5                   10                  15

Gln Thr Asn Phe Met Pro Met Asp Gln Asp Glu Ala Leu Leu Tyr Glu
            20                  25                  30

Glu Phe Ile Leu Gln Gln Cys Leu Glu
        35                  40

<210> SEQ ID NO 71
<211> LENGTH: 7
<212> TYPE: PRT
<213> ORGANISM: Artificial Sequence
<220> FEATURE:
<223> OTHER INFORMATION: MRD

<400> SEQUENCE: 71

Ala Thr Trp Leu Pro Pro Pro
1               5

<210> SEQ ID NO 72
<211> LENGTH: 11
<212> TYPE: PRT
<213> ORGANISM: Artificial Sequence
<220> FEATURE:
<223> OTHER INFORMATION: VL-CDR1

<400> SEQUENCE: 72

Ser Ala Ser Gln Asp Ile Ser Asn Tyr Leu Asn
1               5                   10

<210> SEQ ID NO 73
<211> LENGTH: 7
<212> TYPE: PRT
<213> ORGANISM: Artificial Sequence
<220> FEATURE:
<223> OTHER INFORMATION: VL-CDR2

<400> SEQUENCE: 73

Phe Thr Ser Ser Leu His Ser
1               5

<210> SEQ ID NO 74
<211> LENGTH: 9
<212> TYPE: PRT
<213> ORGANISM: Artificial Sequence
<220> FEATURE:
<223> OTHER INFORMATION: VL-CDR3

<400> SEQUENCE: 74

Gln Gln Tyr Ser Thr Val Pro Trp Thr

<210> SEQ ID NO 75
<211> LENGTH: 10
<212> TYPE: PRT
<213> ORGANISM: Artificial Sequence
<220> FEATURE:
<223> OTHER INFORMATION: VH-CDR1

<400> SEQUENCE: 75

Gly Tyr Thr Phe Thr Asn Tyr Gly Met Asn
1               5                   10

<210> SEQ ID NO 76
<211> LENGTH: 17
<212> TYPE: PRT
<213> ORGANISM: Artificial Sequence
<220> FEATURE:
<223> OTHER INFORMATION: VH-CDR2

<400> SEQUENCE: 76

Trp Ile Asn Thr Tyr Thr Gly Glu Pro Thr Tyr Ala Ala Asp Phe Lys
1               5                   10                  15

Arg

<210> SEQ ID NO 77
<211> LENGTH: 14
<212> TYPE: PRT
<213> ORGANISM: Artificial Sequence
<220> FEATURE:
<223> OTHER INFORMATION: VH-CDR3

<400> SEQUENCE: 77

Tyr Pro His Tyr Tyr Gly Ser Ser His Trp Tyr Phe Asp Val
1               5                   10

<210> SEQ ID NO 78
<211> LENGTH: 108
<212> TYPE: PRT
<213> ORGANISM: Artificial Sequence
<220> FEATURE:
<223> OTHER INFORMATION: VL

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 79
<211> LENGTH: 123
<212> TYPE: PRT
<213> ORGANISM: Artificial Sequence

<220> FEATURE:
<223> OTHER INFORMATION: VH

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 80
<211> LENGTH: 11
<212> TYPE: PRT
<213> ORGANISM: Artificial Sequence
<220> FEATURE:
<223> OTHER INFORMATION: VL-CDR1

<400> SEQUENCE: 80

Arg Ala Ser Gln Gly Ile Arg Asn Tyr Leu Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: VL-CDR2

<400> SEQUENCE: 81

Ala Ala Ser Thr Leu Gln Ser
1               5

<210> SEQ ID NO 82
<211> LENGTH: 9
<212> TYPE: PRT
<213> ORGANISM: Artificial Sequence
<220> FEATURE:
<223> OTHER INFORMATION: VL-CDR3

<400> SEQUENCE: 82

Gln Arg Tyr Asn Arg Ala Pro Tyr Thr
1               5

<210> SEQ ID NO 83
<211> LENGTH: 5
<212> TYPE: PRT
<213> ORGANISM: Artificial Sequence
<220> FEATURE:
<223> OTHER INFORMATION: VH-CDR1

<400> SEQUENCE: 83

Asp Tyr Ala Met His

```
<210> SEQ ID NO 84
<211> LENGTH: 17
<212> TYPE: PRT
<213> ORGANISM: Artificial Sequence
<220> FEATURE:
<223> OTHER INFORMATION: VH-CDR2

<400> SEQUENCE: 84

Ala Ile Thr Trp Asn Ser Gly His Ile Asp Tyr Ala Asp Ser Val Glu
1               5                   10                  15
Gly

<210> SEQ ID NO 85
<211> LENGTH: 12
<212> TYPE: PRT
<213> ORGANISM: Artificial Sequence
<220> FEATURE:
<223> OTHER INFORMATION: VH-CDR3

<400> SEQUENCE: 85

Val Ser Tyr Leu Ser Thr Ala Ser Ser Leu Asp Tyr
1               5                   10

<210> SEQ ID NO 86
<211> LENGTH: 108
<212> TYPE: PRT
<213> ORGANISM: Artificial Sequence
<220> FEATURE:
<223> OTHER INFORMATION: VL

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg
            100                 105

<210> SEQ ID NO 87
<211> LENGTH: 121
<212> TYPE: PRT
<213> ORGANISM: Artificial Sequence
<220> FEATURE:
<223> OTHER INFORMATION: VH

<400> SEQUENCE: 87

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45
```

-continued

```
Ser Ala Ile Thr Trp Asn Ser Gly His Ile Asp Tyr Ala Asp Ser Val
        50                  55                  60
Glu Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                85                  90                  95
Ala Lys Val Ser Tyr Leu Ser Thr Ala Ser Ser Leu Asp Tyr Trp Gly
            100                 105                 110
Gln Gly Thr Leu Val Thr Val Ser Ser
            115                 120
```

<210> SEQ ID NO 88
<211> LENGTH: 40
<212> TYPE: PRT
<213> ORGANISM: Artificial Sequence
<220> FEATURE:
<223> OTHER INFORMATION: MRD expressed as a MBP fusion protein

<400> SEQUENCE: 88

```
Lys Ser Leu Ser Leu Ser Pro Gly Ser Gly Gly Ser Met Gly Ala
 1               5                  10                  15
Gln Thr Asn Phe Met Pro Met Asp Asn Asp Glu Gly Leu Leu Tyr Glu
                20                  25                  30
Gln Phe Ile Leu Gln Gln Gly Leu
            35                  40
```

<210> SEQ ID NO 89
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 89

```
Lys Ser Leu Ser Leu Ser Pro Gly Ser Gly Gly Ser Met Gly Ala
 1               5                  10                  15
Gln Thr Asn Phe Met Pro Met Asp Asn Asp Glu Leu Gly Leu Tyr Glu
                20                  25                  30
Gln Phe Ile Leu Gln Gln Gly Leu Glu
            35                  40
```

<210> SEQ ID NO 90
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 90

```
Lys Ser Leu Ser Leu Ser Pro Gly Ser Gly Gly Ser Met Gly Ala
 1               5                  10                  15
Gln Thr Asn Phe Met Pro Met Asp Asn Asp Glu Ala Leu Leu Tyr Glu
                20                  25                  30
Gln Phe Ile Leu Gln Gln Gly Leu Glu
            35                  40
```

<210> SEQ ID NO 91
<211> LENGTH: 41
<212> TYPE: PRT
<213> ORGANISM: Artificial Sequence
<220> FEATURE:

<223> OTHER INFORMATION: MRD expressed as a MBP fusion protein

<400> SEQUENCE: 91

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Leu Thr Leu Tyr Glu
            20                  25                  30

Gln Phe Ile Leu Gln Gln Gly Leu Glu
        35                  40

<210> SEQ ID NO 92
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 92

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Leu Leu Leu Tyr Glu
            20                  25                  30

Gln Phe Ile Tyr Gln Gln Gly Leu Glu
        35                  40

<210> SEQ ID NO 93
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 93

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Gly Leu Leu Tyr Glu
            20                  25                  30

Gln Phe Ile Tyr Gln Gln Gly Leu Glu
        35                  40

<210> SEQ ID NO 94
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 94

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Ala Leu Leu Tyr Glu
            20                  25                  30

Gln Phe Ile Tyr Gln Gln Gly Leu Glu
        35                  40

<210> SEQ ID NO 95
<211> LENGTH: 39
<212> TYPE: PRT
<213> ORGANISM: Artificial Sequence
<220> FEATURE:
<223> OTHER INFORMATION: MRD expressed as a MBP fusion protein

<400> SEQUENCE: 95

Lys Ser Leu Ser Leu Ser Pro Gly Ser Gly Gly Gly Ser Met Gly Ala
1               5                   10                  15

Gln Thr Asn Phe Met Pro Met Asp Asn Glu Glu Leu Thr Leu Tyr Glu
            20                  25                  30

Gln Phe Ile Phe Gln Gln Gly
        35

<210> SEQ ID NO 96
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 96

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Gly Leu Leu Tyr Glu
            20                  25                  30

Glu Phe Ile Leu Gln Gln Gly Leu Glu
        35                  40

<210> SEQ ID NO 97
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 97

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Ala Leu Leu Tyr Glu
            20                  25                  30

Glu Phe Ile Leu Gln Gln Gly Leu Glu
        35                  40

<210> SEQ ID NO 98
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 98

Lys Ser Leu Ser Leu Ser Pro Gly Ser Gly Gly Gly Ser Met Gly Ala
1               5                   10                  15

Gln Thr Asn Phe Met Pro Met Asp Asn Glu Glu Leu Thr Leu Tyr Glu
            20                  25                  30

Glu Phe Ile Leu Gln Gln Gly Leu Glu
        35                  40

<210> SEQ ID NO 99
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 99

Lys Ser Leu Ser Leu Ser Pro Gly Ser Gly Gly Gly Ser Met Gly Ala
1               5                   10                  15

Gln Thr Asn Phe Met Pro Met Asp Gln Asp Glu Leu Leu Tyr Glu
            20                  25                  30

Gln Phe Ile Leu Gln Gln Gly Leu Glu
            35                  40

<210> SEQ ID NO 100
<211> LENGTH: 41
<212> TYPE: PRT
<213> ORGANISM: Artificial Sequence
<220> FEATURE:
<223> OTHER INFORMATION: MRD expressed as a MBP fusion protein

<400> SEQUENCE: 100

Lys Ser Leu Ser Leu Ser Pro Gly Ser Gly Gly Gly Ser Met Gly Ala
1               5                   10                  15

Gln Thr Asn Phe Met Pro Met Asp Asp Asp Glu Leu Leu Leu Tyr Glu
            20                  25                  30

Gln Phe Ile Leu Gln Gln Gly Leu Glu
            35                  40

<210> SEQ ID NO 101
<211> LENGTH: 41
<212> TYPE: PRT
<213> ORGANISM: Artificial Sequence
<220> FEATURE:
<223> OTHER INFORMATION: HER-1m32 (MPM M5C L28C) (H)

<400> SEQUENCE: 101

Lys Ser Leu Ser Leu Ser Pro Gly Ser Gly Gly Gly Ser Cys Gly Ala
1               5                   10                  15

Gln Thr Asn Phe Met Pro Met Asp Gln Asp Glu Ala Leu Leu Tyr Glu
            20                  25                  30

Glu Phe Ile Cys Gln Gln Gly Leu Glu
            35                  40

<210> SEQ ID NO 102
<211> LENGTH: 105
<212> TYPE: PRT
<213> ORGANISM: Artificial Sequence
<220> FEATURE:
<223> OTHER INFORMATION: MRD containing antibody

<400> SEQUENCE: 102

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Lys Leu Gly Thr
            35                  40                  45

Asn Ser Gln Glu Ser Val Thr Glu Gln Asp Ser Lys Asp Ser Thr Tyr
        50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Leu Pro Val
                85                  90                  95

Thr Lys Ser Phe Asn Arg Gly Glu Cys
            100                 105

<210> SEQ ID NO 103
<211> LENGTH: 10

-continued

```
<212> TYPE: PRT
<213> ORGANISM: Artificial Sequence
<220> FEATURE:
<223> OTHER INFORMATION: MRD encoded sequence

<400> SEQUENCE: 103

Ser Leu Phe Val Pro Arg Pro Glu Arg Lys
1               5                   10

<210> SEQ ID NO 104
<211> LENGTH: 10
<212> TYPE: PRT
<213> ORGANISM: Artificial Sequence
<220> FEATURE:
<223> OTHER INFORMATION: MRD encoded sequence

<400> SEQUENCE: 104

Glu Ser Asp Val Leu His Phe Thr Ser Thr
1               5                   10

<210> SEQ ID NO 105
<211> LENGTH: 9
<212> TYPE: PRT
<213> ORGANISM: Artificial Sequence
<220> FEATURE:
<223> OTHER INFORMATION: MRD encoded sequence

<400> SEQUENCE: 105

Leu Arg Lys Tyr Ala Asp Gly Thr Leu
1               5

<210> SEQ ID NO 106
<211> LENGTH: 9
<212> TYPE: PRT
<213> ORGANISM: Artificial Sequence
<220> FEATURE:
<223> OTHER INFORMATION: MRD encoded sequence

<400> SEQUENCE: 106

Cys Asp Cys Arg Gly Asp Cys Phe Cys
1               5

<210> SEQ ID NO 107
<211> LENGTH: 28
<212> TYPE: PRT
<213> ORGANISM: Artificial Sequence
<220> FEATURE:
<223> OTHER INFORMATION: L17D

<400> SEQUENCE: 107

Met Gly Ala Gln Thr Asn Phe Met Pro Met Asp Asp Asp Glu Leu Leu
1               5                   10                  15

Leu Tyr Glu Gln Phe Ile Leu Gln Gln Gly Leu Glu
            20                  25

<210> SEQ ID NO 108
<211> LENGTH: 41
<212> TYPE: PRT
<213> ORGANISM: Artificial Sequence
<220> FEATURE:
<223> OTHER INFORMATION: HER-1m32 MPM A7C G30C) (H)

<400> SEQUENCE: 108

Lys Ser Leu Ser Leu Ser Pro Gly Ser Gly Gly Ser Gly Gly Cys
1               5                   10                  15

Gln Thr Asn Phe Met Pro Met Asp Gln Asp Glu Ala Leu Leu Tyr Glu
```

Glu Phe Ile Leu Gln Gln Cys Leu Glu
        35                  40

<210> SEQ ID NO 109
<211> LENGTH: 41
<212> TYPE: PRT
<213> ORGANISM: Artificial Sequence
<220> FEATURE:
<223> OTHER INFORMATION: HER-lm32 (MPM P13C G30C) (H)

<400> SEQUENCE: 109

Lys Ser Leu Ser Leu Ser Pro Gly Ser Gly Gly Gly Ser Gly Gly Ala
1               5                   10                  15

Gln Thr Asn Phe Met Cys Met Asp Gln Asp Glu Ala Leu Leu Tyr Glu
            20                  25                  30

Glu Phe Ile Leu Gln Gln Cys Leu Glu
        35                  40

<210> SEQ ID NO 110
<211> LENGTH: 41
<212> TYPE: PRT
<213> ORGANISM: Artificial Sequence
<220> FEATURE:
<223> OTHER INFORMATION: HER-lm32 (MPM M5C N10C) (H)

<400> SEQUENCE: 110

Lys Ser Leu Ser Leu Ser Pro Gly Ser Gly Gly Gly Ser Cys Gly Ala
1               5                   10                  15

Gln Thr Cys Phe Met Pro Met Asp Gln Asp Glu Ala Leu Leu Tyr Glu
            20                  25                  30

Glu Phe Ile Leu Gln Gln Gly Leu Glu
        35                  40

<210> SEQ ID NO 111
<211> LENGTH: 41
<212> TYPE: PRT
<213> ORGANISM: Artificial Sequence
<220> FEATURE:
<223> OTHER INFORMATION: HER-lm32 (MPM M5C F11C) (H)

<400> SEQUENCE: 111

Lys Ser Leu Ser Leu Ser Pro Gly Ser Gly Gly Gly Ser Cys Gly Ala
1               5                   10                  15

Gln Thr Asn Cys Met Pro Met Asp Gln Asp Glu Ala Leu Leu Tyr Glu
            20                  25                  30

Glu Phe Ile Leu Gln Gln Gly Leu Glu
        35                  40

<210> SEQ ID NO 112
<211> LENGTH: 36
<212> TYPE: PRT
<213> ORGANISM: Artificial Sequence
<220> FEATURE:
<223> OTHER INFORMATION: HER-lm32 (MPM D5 N10C G30C) (H)

<400> SEQUENCE: 112

Lys Ser Leu Ser Leu Ser Pro Gly Ser Gly Gly Gly Ser Cys Phe Met
1               5                   10                  15

Pro Met Asp Gln Asp Glu Ala Leu Leu Tyr Glu Glu Phe Ile Leu Gln
            20                  25                  30

Gln Cys Leu Glu

<210> SEQ ID NO 113
<211> LENGTH: 36
<212> TYPE: PRT
<213> ORGANISM: Artificial Sequence
<220> FEATURE:
<223> OTHER INFORMATION: HER-lm32 (MPM D5 N10C L28C) (H)

<400> SEQUENCE: 113

Lys Ser Leu Ser Leu Ser Pro Gly Ser Gly Gly Ser Cys Phe Met
1               5                   10                  15

Pro Met Asp Gln Asp Glu Ala Leu Leu Tyr Glu Glu Phe Ile Cys Gln
            20                  25                  30

Gln Gly Leu Glu
        35

<210> SEQ ID NO 114
<211> LENGTH: 35
<212> TYPE: PRT
<213> ORGANISM: Artificial Sequence
<220> FEATURE:
<223> OTHER INFORMATION: L1-7D MDD

<400> SEQUENCE: 114

Pro Gly Lys Gly Gly Gly Ser Met Gly Ala Gln Thr Asn Phe Met Pro
1               5                   10                  15

Met Asp Asp Asp Glu Gln Arg Leu Tyr Glu Gln Phe Ile Leu Gln Gln
            20                  25                  30

Gly Leu Glu
        35

<210> SEQ ID NO 115
<211> LENGTH: 35
<212> TYPE: PRT
<213> ORGANISM: Artificial Sequence
<220> FEATURE:
<223> OTHER INFORMATION: L1-7D MQD

<400> SEQUENCE: 115

Pro Gly Lys Gly Gly Gly Ser Met Gly Ala Gln Thr Asn Phe Met Pro
1               5                   10                  15

Met Gln Asp Asp Glu Gln Arg Leu Tyr Glu Gln Phe Ile Leu Gln Gln
            20                  25                  30

Gly Leu Glu
        35

<210> SEQ ID NO 116
<211> LENGTH: 35
<212> TYPE: PRT
<213> ORGANISM: Artificial Sequence
<220> FEATURE:
<223> OTHER INFORMATION: L1-7D MVD

<400> SEQUENCE: 116

Pro Gly Lys Gly Gly Gly Ser Met Gly Ala Gln Thr Asn Phe Met Pro
1               5                   10                  15

Met Val Asp Asp Glu Gln Arg Leu Tyr Glu Gln Phe Ile Leu Gln Gln
            20                  25                  30

Gly Leu Glu
        35

```
<210> SEQ ID NO 117
<211> LENGTH: 35
<212> TYPE: PRT
<213> ORGANISM: Artificial Sequence
<220> FEATURE:
<223> OTHER INFORMATION: L1-7D MHD

<400> SEQUENCE: 117

Pro Gly Lys Gly Gly Gly Ser Met Gly Ala Gln Thr Asn Phe Met Pro
1               5                   10                  15

Met His Asp Asp Glu Gln Arg Leu Tyr Glu Gln Phe Ile Leu Gln Gln
            20                  25                  30

Gly Leu Glu
        35

<210> SEQ ID NO 118
<211> LENGTH: 35
<212> TYPE: PRT
<213> ORGANISM: Artificial Sequence
<220> FEATURE:
<223> OTHER INFORMATION: L1-7D MND

<400> SEQUENCE: 118

Pro Gly Lys Gly Gly Gly Ser Met Gly Ala Gln Thr Asn Phe Met Pro
1               5                   10                  15

Met Asn Asp Asp Glu Gln Arg Leu Tyr Glu Gln Phe Ile Leu Gln Gln
            20                  25                  30

Gly Leu Glu
        35

<210> SEQ ID NO 119
<211> LENGTH: 35
<212> TYPE: PRT
<213> ORGANISM: Artificial Sequence
<220> FEATURE:
<223> OTHER INFORMATION: L1-7D MKD

<400> SEQUENCE: 119

Pro Gly Lys Gly Gly Gly Ser Met Gly Ala Gln Thr Asn Phe Met Pro
1               5                   10                  15

Met Lys Asp Asp Glu Gln Arg Leu Tyr Glu Gln Phe Ile Leu Gln Gln
            20                  25                  30

Gly Leu Glu
        35

<210> SEQ ID NO 120
<211> LENGTH: 35
<212> TYPE: PRT
<213> ORGANISM: Artificial Sequence
<220> FEATURE:
<223> OTHER INFORMATION: L1-7D MAD

<400> SEQUENCE: 120

Pro Gly Lys Gly Gly Gly Ser Met Gly Ala Gln Thr Asn Phe Met Pro
1               5                   10                  15

Met Ala Asp Asp Glu Gln Arg Leu Tyr Glu Gln Phe Ile Leu Gln Gln
            20                  25                  30

Gly Leu Glu
        35

<210> SEQ ID NO 121
<211> LENGTH: 35
<212> TYPE: PRT
```

```
<213> ORGANISM: Artificial Sequence
<220> FEATURE:
<223> OTHER INFORMATION: L1-7D MSD

<400> SEQUENCE: 121

Pro Gly Lys Gly Gly Gly Ser Met Gly Ala Gln Thr Asn Phe Met Pro
1               5                   10                  15

Met Ser Asp Asp Glu Gln Arg Leu Tyr Glu Gln Phe Ile Leu Gln Gln
            20                  25                  30

Gly Leu Glu
        35

<210> SEQ ID NO 122
<211> LENGTH: 35
<212> TYPE: PRT
<213> ORGANISM: Artificial Sequence
<220> FEATURE:
<223> OTHER INFORMATION: L1-7D MRD

<400> SEQUENCE: 122

Pro Gly Lys Gly Gly Gly Ser Met Gly Ala Gln Thr Asn Phe Met Pro
1               5                   10                  15

Met Arg Asp Asp Glu Gln Arg Leu Tyr Glu Gln Phe Ile Leu Gln Gln
            20                  25                  30

Gly Leu Glu
        35

<210> SEQ ID NO 123
<211> LENGTH: 35
<212> TYPE: PRT
<213> ORGANISM: Artificial Sequence
<220> FEATURE:
<223> OTHER INFORMATION: L1-7D MGD

<400> SEQUENCE: 123

Pro Gly Lys Gly Gly Gly Ser Met Gly Ala Gln Thr Asn Phe Met Pro
1               5                   10                  15

Met Gly Asp Asp Glu Gln Arg Leu Tyr Glu Gln Phe Ile Leu Gln Gln
            20                  25                  30

Gly Leu Glu
        35

<210> SEQ ID NO 124
<211> LENGTH: 35
<212> TYPE: PRT
<213> ORGANISM: Artificial Sequence
<220> FEATURE:
<223> OTHER INFORMATION: L1-7D MTD

<400> SEQUENCE: 124

Pro Gly Lys Gly Gly Gly Ser Met Gly Ala Gln Thr Asn Phe Met Pro
1               5                   10                  15

Met Thr Asp Asp Glu Gln Arg Leu Tyr Glu Gln Phe Ile Leu Gln Gln
            20                  25                  30

Gly Leu Glu
        35

<210> SEQ ID NO 125
<211> LENGTH: 35
<212> TYPE: PRT
<213> ORGANISM: Artificial Sequence
<220> FEATURE:
<223> OTHER INFORMATION: L1-7D MYD
```

-continued

```
<400> SEQUENCE: 125

Pro Gly Lys Gly Gly Gly Ser Met Gly Ala Gln Thr Asn Phe Met Pro
1               5                   10                  15

Met Tyr Asp Asp Glu Gln Arg Leu Tyr Glu Gln Phe Ile Leu Gln Gln
            20                  25                  30

Gly Leu Glu
        35

<210> SEQ ID NO 126
<211> LENGTH: 35
<212> TYPE: PRT
<213> ORGANISM: Artificial Sequence
<220> FEATURE:
<223> OTHER INFORMATION: L1-7D MPD

<400> SEQUENCE: 126

Pro Gly Lys Gly Gly Gly Ser Met Gly Ala Gln Thr Asn Phe Met Pro
1               5                   10                  15

Met Pro Asp Asp Glu Gln Arg Leu Tyr Glu Gln Phe Ile Leu Gln Gln
            20                  25                  30

Gly Leu Glu
        35

<210> SEQ ID NO 127
<211> LENGTH: 35
<212> TYPE: PRT
<213> ORGANISM: Artificial Sequence
<220> FEATURE:
<223> OTHER INFORMATION: L1-7D MID

<400> SEQUENCE: 127

Pro Gly Lys Gly Gly Gly Ser Met Gly Ala Gln Thr Asn Phe Met Pro
1               5                   10                  15

Met Ile Asp Asp Glu Gln Arg Leu Tyr Glu Gln Phe Ile Leu Gln Gln
            20                  25                  30

Gly Leu Glu
        35

<210> SEQ ID NO 128
<211> LENGTH: 35
<212> TYPE: PRT
<213> ORGANISM: Artificial Sequence
<220> FEATURE:
<223> OTHER INFORMATION: L1-7D MFD 14F11

<400> SEQUENCE: 128

Pro Gly Lys Gly Gly Gly Ser Met Gly Ala Gln Thr Asn Phe Met Pro
1               5                   10                  15

Met Phe Asp Asp Glu Gln Arg Leu Tyr Glu Gln Phe Ile Leu Gln Gln
            20                  25                  30

Gly Leu Glu
        35

<210> SEQ ID NO 129
<211> LENGTH: 35
<212> TYPE: PRT
<213> ORGANISM: Artificial Sequence
<220> FEATURE:
<223> OTHER INFORMATION: L1-7D MWD

<400> SEQUENCE: 129
```

```
Pro Gly Lys Gly Gly Gly Ser Met Gly Ala Gln Thr Asn Phe Met Pro
1               5                   10                  15

Met Trp Asp Asp Glu Gln Arg Leu Tyr Glu Gln Phe Ile Leu Gln Gln
            20                  25                  30

Gly Leu Glu
        35

<210> SEQ ID NO 130
<211> LENGTH: 35
<212> TYPE: PRT
<213> ORGANISM: Artificial Sequence
<220> FEATURE:
<223> OTHER INFORMATION: L1-7D MLD

<400> SEQUENCE: 130

Pro Gly Lys Gly Gly Gly Ser Met Gly Ala Gln Thr Asn Phe Met Pro
1               5                   10                  15

Met Leu Asp Asp Glu Gln Arg Leu Tyr Glu Gln Phe Ile Leu Gln Gln
            20                  25                  30

Gly Leu Glu
        35

<210> SEQ ID NO 131
<211> LENGTH: 35
<212> TYPE: PRT
<213> ORGANISM: Artificial Sequence
<220> FEATURE:
<223> OTHER INFORMATION: L1-7D MED

<400> SEQUENCE: 131

Pro Gly Lys Gly Gly Gly Ser Met Gly Ala Gln Thr Asn Phe Met Pro
1               5                   10                  15

Met Glu Asp Asp Glu Gln Arg Leu Tyr Glu Gln Phe Ile Leu Gln Gln
            20                  25                  30

Gly Leu Glu
        35

<210> SEQ ID NO 132
<211> LENGTH: 35
<212> TYPE: PRT
<213> ORGANISM: Artificial Sequence
<220> FEATURE:
<223> OTHER INFORMATION: L1-7D MMD

<400> SEQUENCE: 132

Pro Gly Lys Gly Gly Gly Ser Met Gly Ala Gln Thr Asn Phe Met Pro
1               5                   10                  15

Met Met Asp Asp Glu Gln Arg Leu Tyr Glu Gln Phe Ile Leu Gln Gln
            20                  25                  30

Gly Leu Glu
        35

<210> SEQ ID NO 133
<211> LENGTH: 35
<212> TYPE: PRT
<213> ORGANISM: Artificial Sequence
<220> FEATURE:
<223> OTHER INFORMATION: L1-7D MFD 14G4

<400> SEQUENCE: 133

Pro Gly Lys Gly Gly Gly Ser Met Gly Ala Gln Thr Asn Phe Met Pro
1               5                   10                  15
```

```
Met Phe Asp Asp Glu Gln Arg Leu Tyr Asp Gln Phe Ile Leu Gln Gln
            20                  25                  30

Gly Leu Glu
        35

<210> SEQ ID NO 134
<211> LENGTH: 35
<212> TYPE: PRT
<213> ORGANISM: Artificial Sequence
<220> FEATURE:
<223> OTHER INFORMATION: Lm32 KtoS

<400> SEQUENCE: 134

Pro Gly Ser Gly Gly Gly Ser Met Gly Ala Gln Thr Asn Phe Met Pro
1               5                   10                  15

Met Asp Asn Asp Glu Leu Leu Leu Tyr Glu Gln Phe Ile Leu Gln Gln
            20                  25                  30

Gly Leu Glu
        35

<210> SEQ ID NO 135
<211> LENGTH: 67
<212> TYPE: PRT
<213> ORGANISM: Artificial Sequence
<220> FEATURE:
<223> OTHER INFORMATION: LM32 2X

<400> SEQUENCE: 135

Pro Gly Lys Gly Gly Gly Ser Met Gly Ala Gln Thr Asn Phe Met Pro
1               5                   10                  15

Met Asp Asn Asp Glu Leu Leu Leu Tyr Glu Gln Phe Ile Leu Gln Gln
            20                  25                  30

Gly Leu Glu Gly Gly Gly Ser Met Gly Ala Gln Thr Asn Phe Met Pro
        35                  40                  45

Met Asp Asn Asp Glu Leu Leu Leu Tyr Glu Gln Phe Ile Leu Gln Gln
        50                  55                  60

Gly Leu Glu
65
```